US012134787B2

(12) United States Patent
Schulze Gronover et al.

(10) Patent No.: US 12,134,787 B2
(45) Date of Patent: Nov. 5, 2024

(54) METHOD FOR INCREASING THE YIELD OF OXIDOSQUALENE, TRITERPENES AND/OR TRITERPENOIDS AND HOST CELL THEREFORE

(71) Applicants: Fraunhofer-Gesellschaft zur Foerderung der Angewandten Forschung E.V., Munich (DE); Westfaelische Wilhelms-Universitaet Muenster, Muenster (DE)

(72) Inventors: Christian Schulze Gronover, Muenster (DE); Lowis Gerrit Boje Mueller, Rheine (DE); Nicole Van Deenen, Muenster (DE); Jan Niklas Broeker, Muenster (DE)

(73) Assignees: Fraunhofer-Gesellschaft zur Foerderung der Angewandten Forschung E.V., Munich (DE); Westfaelische Wilhelms-Universitaet Muenster, Muenster (DE)

( * ) Notice: Subject to any disclaimer, the term of this patent is extended or adjusted under 35 U.S.C. 154(b) by 968 days.

(21) Appl. No.: 17/046,207

(22) PCT Filed: Apr. 8, 2019

(86) PCT No.: PCT/EP2019/058789
§ 371 (c)(1),
(2) Date: Oct. 8, 2020

(87) PCT Pub. No.: WO2019/197327
PCT Pub. Date: Oct. 17, 2019

(65) Prior Publication Data

US 2021/0071150 A1 Mar. 11, 2021

(30) Foreign Application Priority Data

Apr. 9, 2018 (EP) .................................... 18166374

(51) Int. Cl.

| | |
|---|---|
| ***C12N 9/04*** | (2006.01) |
| ***C12N 1/16*** | (2006.01) |
| ***C12N 1/18*** | (2006.01) |
| ***C12N 9/90*** | (2006.01) |
| ***C12N 15/81*** | (2006.01) |
| ***C12P 5/00*** | (2006.01) |
| ***C12P 33/00*** | (2006.01) |

(52) U.S. Cl.
CPC ............. *C12N 9/0006* (2013.01); *C12N 1/16* (2013.01); *C12N 1/18* (2013.01); *C12N 9/90* (2013.01); *C12N 15/81* (2013.01); *C12P 5/007* (2013.01); *C12P 33/00* (2013.01); *C12Y 101/01034* (2013.01); *C12Y 504/99007* (2013.01); *C12Y 504/99041* (2013.01); *C12N 2500/20* (2013.01)

(58) Field of Classification Search
CPC .......... C12N 9/0006; C12N 1/16; C12N 1/18; C12N 9/90; C12N 15/81; C12N 2500/20; C12N 15/52; C12N 9/88; C12P 5/007; C12P 33/00; C12Y 101/01034; C12Y 504/99007; C12Y 504/99041
See application file for complete search history.

(56) References Cited

FOREIGN PATENT DOCUMENTS

| | | | |
|---|---|---|---|
| CN | 106635853 | A | 5/2017 |
| WO | 2009126623 | A2 | 10/2009 |
| WO | WO 2018120983 | A1 * | 7/2018 |

OTHER PUBLICATIONS

Yuan et al. Combinatorial engineering of mevalonate pathway for improved amorpha-4, 11-dience production in budding yeast. Biotechnology and Bioengineering (2014), 111:608-617). (Year: 2014).*
Polakowski et al. Overexpression of a cytosolic hydroxymethylglutaryl-CoA reductase leads to squalene accumulation in yeast. Appl Microbiol Biotechnol (1998) 49: 66-67. (Year: 1998).*
Alberti et al. (2007) "A suite of Gateway® cloning vectors for high-throughput genetic analysis in *Saccharomyces cerevisiae*", Yeast, 24(10):913-919.
Arendt at al. (2016) "Synthetic biology for production of natural and new-to-nature terpenoids in photosynthetic organisms", The Plant Journal, 87:16-37.
Arendt et al. (2017) "An endoplasmic reticulum-engineered yeast platform for overproduction of triterpenoids", Metabolic Engineering, 40:165-175.
Asadollahi et al. (2010) "Enhancement of farnesyl diphosphate pool as direct precursor of sesquiterpenes through metabolic engineering of the mevalonate pathway in saccharomyces cerevisiae", Biotechnology and Bloengineering, 106(1):86-96.
Broker et al. (2018) "Upregulating the mevalonate pathway and repressing sterol synthesis in *Saccharomyces cerevisiae* enhances the production of triterpenes", Applied Microbiology and Biotechnology, 102:6923-6934.
Demierre et al. (2005) "Statins and cancer prevention" Nature, 5:930-942.
Donald et al. (1997) "Effects of overproduction of the catalytic domain of 3-hydroxy-3-methylglutaryl coenzyme A reductase on squalene synthesis in *Saccharomyces cerevisiae*", Applied and Environmental Microbiology, 63(9):3341-3344.
Gietz et al. (2007) "High-efficiency yeast transformation using the LiAc/SS carrier DNA/PEG method", Nature Protocols, 2(1):31-34.
Hemmerlin et al. (2012) "A raison d'être for two distinct pathways in the early steps of plant isoprenoid biosynthesis?", Progress in Lipid Research, 51:95-148.

(Continued)

*Primary Examiner* — Iqbal H Chowdhury
(74) *Attorney, Agent, or Firm* — Kagan Binder, PLLC

(57) ABSTRACT

The present invention relates to a method of increasing the yield of at least one of oxidosqualene, triterpenes and/or triterpenoids in a specifically engineered host cell and a respective host cell as well as to the use of said host cell for manufacturing the at least one of oxidosqualene, triterpenes and/or triterpenoids.

19 Claims, 40 Drawing Sheets

Specification includes a Sequence Listing.

(56) References Cited

OTHER PUBLICATIONS

Henry et al. (2002) "ROX1 and ERG regulation in *Saccharomyces cerevisiae*: implications for antifungal susceptibility" Eukaryotic Cell, 1(6):1041-1044.
Jakoiūnas et al. (2015) "Multiplex metabolic pathway engineering using CRISPR/Cas9 in *Saccharomyces cerevisiae*", Metabolic Engineering, 28:213-222.
Jamison et al. (1999) "The yeast transcription factor Mac1 binds to DNA in a modular fashion" The Journal of Biological Chemistry, 274(38):26962-26967.
Jensen et al. (2013) "EasyClone: method for iterative chromosomal integration of multiple genes in *Saccharomyces cerevisiae*" FEMS Yeast Research, 14:238-248.
Kirby et al. (2008) "Engineering triterpene production in Saccharomyces cerevisiae—b-amyrin synthase from Artemisia annua" FEBS Journal, 275:1852-1859.
Labbe et al. (1997) "Copper-specific transcriptional repression of yeast genes encoding critical components in the copper transport pathway", The Journal of Biological Chemistry, 272:15951-15958.
Liao et al. (2016) "The potential of the mevalonate pathway for enhanced isoprenoid production" Biotechnology Advances, 34:697-713.
Lv et al. (2014) "Enhanced isoprene biosynthesis in Saccharomyces cerevisiae byengineering of the native acetyl-CoA and mevalonic acidpathways with a push-pull-restrain strategy" Journal of Biotechnology, 186:128-136.
M'Baya et al. (1989) "Regulation of squalene synthetase and squalene epoxidase activities in *Saccharomyces cerevisiae*", Lipids, 24:1020-1023.
Martin et al. (2003) "Engineering a mevalonate pathway in *Escherichia coli* for production of terpenoids", Nature Biotechnology, 21(7):796-802.
Montañés et al. (2011) "Repression of ergosterol biosynthesis is essential for stress resistance and is mediated by the Hog1 MAP kinase and the Mot3 and Rox1 transcription factors", Molecular Microbiology, 79(4), 1008-1023.
Moses et al. (2014) "Combinatorial biosynthesis of sapogenins and saponins in *Saccharomyces cerevisiae* using a C-16α hydroxylase from Bupleurum falcatum", PNAS, 111(4):1634-1639.
Moses et al. (2013) "Bioengineering of plant (tri)terpenoids: from metabolic engineering of plants to synthetic biology in vivo and in vitro", New Phytologist, 200:27-43.
Ozaydn et al. (2013) Carotenoid-based phenotypic screen of the yeast deletion collection reveals new genes with roles in is oprenoid production, Metabolic Engineering, 15:174-183.
Paddon et al. (2013) "High-level semi-synthetic production of the potent antimalarial artemisinin", Nature, 496:9 pages.
Post et al. (2012) "Laticifer-specific cis-prenyltransferase silencing affects the rubber, triterpene, and inulin content of taraxacum brevicomniculatum", Plant Physiology, 158:1406-1417.
Pütter et al. (2017) Isoprenoid biosynthesis in dandelion latexis enhanced by the overexpression of three key enzymes involved in the mevalonate pathway, BMC Plant Biology, 17(88):13 pages.
Ro et al. (2006) "Production of the antimalarial drug precursor artemisinic acid in engineered yeast", Nature, 440:940-943.
Rodriguez et al. (2014) "Production and quantification of sesquiterpenes in *Saccharomyces cerevisiae*, including extraction, detection and quantification of terpene products and key related metabolites", Nature Protocols, 9(8):1980-1996.
Sanger et al. (1977) "DNA sequencing with chain-terminating inhibitors", PNAS, 74(12):5463-5467.
Sheng et al. (2011) "Synthesis, biology and clinical significance of pentacyclic triterpenes: a multi-target approach to prevention and treatment of metabolic and vascular diseases", Natural Product Reports, 28:543-593.
Scalcinati et al. (2012) "Combined metabolic engineering of precursor and co-factor supply to increase α-santalene production by Saccharomyces cerevisiae", Microbial Cell Factories , 11(117):16 pages.
Shibuya et al. (1999) "Two branches of the lupeol synthase gene in the molecular evolution of plant oxidosqualene cyclases", European Journal of Biochemistry, 266:302-307.
Vickers et al. (2017) "Recent advances in synthetic biology for engineering isoprenoid production in yeast", Current Opinion in Chemical Biology, 40:47-56.
Veen et al. (2003) "Combined overexpression of genes of the ergosterol biosynthetic pathway leads to accumulation of sterols in *Saccharomyces cerevisiae*", FEMS Yeast Research, 4:87-95.
Westfall et al. (2012) "Production of amorphadiene in yeast, and its conversion to dihydroartemisinic acid, precursor to the antimalarial agent artemisinin", PNAS, 109(3):E111-E118.
Yamaguchi-Iwai et al. (1997) Homeostatic regulation of copper uptake in yeast via direct binding of MAC1 protein to upstream regulatory sequences of FRE1 and CTR1, The Journal of Biological Chemistry, 272:17711-17718.
Yuan et al. (2014) "Combinatorial engineering of mevalonate pathway for improved amorpha-4,11-diene production in budding yeast", Biotechnology and Bioengineering, 111(3):608-617.
Xu et al. (2004) "On the origins of triterpenoid skeletal diversity" Phytochemistry, 65:261-291.
Nakazono, Mikio (2014) "Investigation of Enzymes for Biosynthesis of Triterpenoids (Lupeol and Betulinic acid) in 1 Soybean", Soy Protein Research, 17:13-17, (English Abstract).

* cited by examiner

Figure 1

MVLTNKTVISGSKVKSLSSAQSSSSGPSSSSEEDDSRDIESLDKKIRPLEELEALLSSGNTKQLKNKEVAALVIHGKLPLYALEKKL
GDTTRAVAVRRKALSILAEAPVLASDRLPYKNYDYDRVFGACCENVIGYMPLPVGVIGPLVIDGTSYHIPMATTEGCLVASAM
RGCKAINAGGGATTVLTKDGMTRGPVVRFPTLKRSGACKIWLDSEEGQNAIKKAFNSTSRFARLQHIQTCLAGDLLFMRFRT
TTGDAMGMNMISKGVEYSLKQMVEEYGWEDMEVVSVSGNYCTDKKPAAINWIEGRGKSVVAEATIPGDVVRKVLKSDVS
ALVELNIAKNLVGSAMAGSVGGFNAHAANLVTAVFLALGQDPAQNVESSNCITLMKEVDGDLRISVSMPSIEVGTIGGGTVL
EPQGAMLDLLGVRGPHATAPGTNARQLARIVACAVLAGELSLCAALAAGHLVQSHMTHNRKPAEPTKPNNLDATDINRLK
DGSVTCIKS $P_{ERG7}$ ::$P_{CTR3}$-Konstrukt rox1::$P_{GAL1\text{-}tHMGR}$;$P_{GAL10\text{-}ERG13}$-Konstrukt rox1::$P_{GAL1}$-tHMGR;$P_{GAL10}$-ERG13-Konstrukt

Figure 3

GCGGCCGCAATCTGCTGCTATTCGTGATTACTGTTACAACCTAACGGTTTAAATGAAACCTGGTTCTGAAGGGTCATTTTA
TAACTTCAAGTTCCCTTAGCCTTTCGATTCATTTTGATTATGCCATTTCTAGACCGTGTTATAGGCGCTGGCGTTTAATTTGG
TGTAGCTTGGTTTAGTCAAGAGTTGTATTAGTGTTCCTCGATAAAGTCGATGTTTCCGGATATTGTGTTAAAATTTCAAGTA
TGCTACTAATGGGGTAAAGTTGCATGATTAGCAGAGACATATGGCTTGTTATGGTTCGGCTTCCTCATTTTTCATGCTTAGT
TTTTGTCCATCTCATTGTACATTTCTGAATCCTAATGCATGACTCCCTAACATTACTATTAAATTCTCAATAGTGAAGAATAAG
CAAAATGGGAACCATGATAATTTCTAGCTTTCTCTCCACCCCTATTTTAATTTGCAATCATATATAGTACTTTCAATAGCATCT
TTTCTAGATTTGATATCTGCGGAGAATCCTCAGCACTAGTCCTGCAGGGGTAACGCCAGGGTTTTCCCAGTCACGACGTT
GTAAAACGACGGCCAGTGAGCGCGCGTAATACGACTCACTATAGGGCGAATTGGGTGCATAGGCCACTAGTGGATCTGA
TATCACCTAATAACTTCGTATAGCATACATTATACGAAGTTATATTAAGGGTTCTCGAGAGCTCGCTGTGAAGATCCCAGCA
AAGGCTTACAAAGTGTTATCTCTTTTGAGACTTGTTGAGTTGAACACTGGTGTTTTCATCAAACTTACCAAGGACGTGTA
CCCATTGTTGAAACTTGTATCACCATATATTGTTATCGGACAACCTTCACTTGCATCTATCCGTTCTTTAATCCAAAAGAGAT
CTAGAATAATGTGGCAAAGGCCAGAAGATAAAGAACCAAAAGAGATAATCTTGAATGACAACAATATCGTTGAAGAGAA
ATTAGGTGATGAAGGTGTCATTTGTATCGAGGATATCATCCATGAGATTTCGACGTTGGGCGAAAATTTCTCGAAATGTAC
TTTCTTCCTATTACCATTCAAATTGAACAGAGAAGTCAGTGGATTCGGTGCCATCTCCCGTTTGAATAAACTGAAAATGCG
CGAACAAAACAAGAAGACTCGTCAAATTTCAAACGCTGCCACGGCTCCAGTTATCCAAGTAGATATCGACTCAATGATTT
CCAAGTTGAATTGATTAACTATAAAAGGAAAAATATCTGTACAATAGACATCGGGCTCCCATTGGCCCTACCCACATATGTAG
AAATACATTACTCTATTCACTACTGCATTTAGTTATGTTTAACATTTGATATAGCAGACTACCGCCAGGCACAATATATTCCCC
TTCCCTCTTGCCATTCGCTGTACTTGTGGTGGATTCCAATTCAGCGCAGTCACGTGCTAGTAATCACCGCATTTTTTTCTTT
TCCTTTCAGGCTAAAACCGGTTCCGGGCCTGATCCCTGCACTCATTTTCTAACGGAAAACCTTCAGAAGCATAACTACCCA
TTCCAGTTTAGAGTCATGACAGGTTCAACATCAGATGCTTCATATACTTTTATATATTGAATTATATAAATATATCTATGTACTC
TAAGTAAGTACATCTGCTTTAACGCATTCCTACATTTGCTTCGATTTATTTTTATTGTTGATACCTATTTGAAGAAGTAAAAA
GTATCCCACACTACACAGATTATACCATGTCTAAGAATATCGTTGTCCTACCGGGTGATCACGTCGGTAAAGAAGTTACTG
ACGAAGCTATTAAGGTCTTGAATGCCATTGCTGAAGTCCGTCCAGAAATTAAGTTCAATTTCCAACATCACTTGATCGGG
GGTGCTGCCATCGATGCCACTGGCACTCCTTTACCAGATGAAGCTCTAGAAGCCTCTAAGAAAGCCGATGCTGTCTTACT
AGGTGCTGTTGGTGGTCCAAAATGGGGTACGGGCGCAGTTAGACCAGAACAAGGTCTATTGAAGATCAGAAAGGAATT
GGGTCTATACGCCAACTTGAGACCATGTAACTTTGCTTCTGATTCTTTACTAGATCTTTCTCCTTTGAAGCCTGAATATGCA
AAGGGTACCGATTTCGTCGTCGTTAGAGAATTGGTTGGTGGTATCTACTTTGGTGAAAGAAAAGAAGATGAAGGTGACG
GAGTTGCTTGGGACTCTGAGAAATACAGTGTTCCTGAAGTTCAAAGAATTACAAGAATGGCTGCTTTCTTGGCATTGCA
ACAAAACCCACCATTACCAATCTGGTCTCTTGACAAGGCTAACGTGCTTGCCTCTTCCAGATTGTGGAGAAAGACTGTTG
AAGAAACCATCAAGACTGAGTTCCCACAATTAACTGTTCAGCACCAATTGATCGACTCTGCTGCTATGATTTTGGTTAAAT
CACCAACTAAGCTAAACGGTGTTGTTATTACCAACAACATGTTTGGTGATATTATCTCCGATGAAGCCTCTGTTATTCCAGG
TTCTTTGGGTTTATTACCTTCTGCATCTCTAGCTTCCCTACCTGACACTAACAAGGCATTCGGTTTGTACGAACCATGTCAT
GGTTCTGCCCCAGATTTACCAGCAAACAAGGTTAACCCAATTGCTACCATCTTATCTGCAGCTATGATGTTGAAGTTATCCT
TGGATTTGGTTGAAGAAGGTAGGGCTCTTGAAGAAGCTGTTAGAAATGTCTTGGATGCAGGTGTCAGAACCGGTGACC
TTGGTGGTTCTAACTCTACCACTGAGGTTGGCGATGCTATCGCCAAGGCTGTCAAGGAAATCTTGGCTTAAAGAGTCTTT
TGTAACGACCCCGTCTCCACCAACTTGGTATGCTTGAAATCTCAAGGCCATTACACATTCAGTTATGTGAACGAAAGGTCT
TTATTTAACGTAGCATAAACTAAATAATACAGGTTCCGGTTAGCCTGCGGATCTCTAGACCTAATAACTTCGTATAGCATACA
TTATACGAAGTTATATTAAGGGTTGTCGACCTGCAGCGGGATCCGGTATTCCAATGAGAATCGCTAGAAATGCTTTACCAG
AACTAGACTACTTGTCGCAGATCACTTTTGAACTGTATGAGAGTACGGATGCTTCTGGTCAAAAATCGCATTCCATTAGAC
TGAAAATGTCTCCTGGGTGTCATACTCAAGATCCGTTAGATGTTCAATTAGATGACAGGCATTATATTAGTTGTATTCCAAA
GATTTCCCTGACGAAGCATTTGGATATGGACTACGTTCAACAGAAATTGAGAAACAAATTTACCAGGGTCATTATGCCTCC
GAAATTTACACCAGTAAACATTACGAGCCCCAACTTGAGTTTCCAGAAACGCAAAACCAGAAGAAAGTCGGTATCTGTT
GAGAAGTTGAAGCTTCCTGCCTCGTCCGGATCTTCATCATCTACCTCCGTTAACAAG

Figure 3 (cont.)

ACATTAGATTAGTGATCACACCCAATTTTTAATTTAGCAACCCAAAATAAATAAGTATTTACTCAACTTTTTTTTAATAAAAA
AAAACTTAATTGAATTTTGCTCGCGATCTTTAGGTCCGGGGTTTTCGTTGAACCCTTAGACGAGCAAATTAGCGCCATAA
GGATATACGTCAGAGCACATTAATTAGTGACATATACCTATATAAAGAGCAACCTTCTCCGATAGACTTGTAATTTATCTTAT
TTCATTTCCTAACACTTTGGTCGAAGAAGAGGGATAAGAACAGACGAAAACACATTTAAGGGCTATACAAAGATGACAG
AATTTTATTCTGACACAATCGGTCTACCAAAGACAGATCCACGTCTTTGGAGACTGAGAACTGATGAGCTAGGCCGAGA
AAGCTGGGAATATTTAACCCCTCAGCAAGCCGCAAACGACCCACCATCCACTTTCACGCAGTGGCTTCTTCAAGATCCCA
AATTTCCTCAACCTCATCCAGAAAGAAATAAGCATTCACCAGATTTTTCAGCCTTCGATGCGTGTCATAATGGTGCATCTTT
TTTCAAACTGCTTCAAGAGCCTGACTCAGGTATTTTTCCGTGTCAATATAAAGGACCCATGTTCATGACAATCGGTTACGT
AGCCGTAAACTATATCGCCGGTATTGAAATTCCTGAGCATGAGAGAATAGAATTAATTAGATACATCGTCAATACAGCACAT
CCGGTTGATGGTGGCTGGGGTCTACATTCTGTTGACAAATCCACCGTGTTTGGTACAGTATTGAACTATGTAATCTTACGT
TTATTGGGGCGGCCGC

Figure 4

GCGGCCGCATGAATCCTAAATCCTCTACACCTAAGATTCCAAGACCCAAGAACGCATTTATTCTGTTCAGACAGCACTACC
ACAGGATCTTAATAGACGAATGGACCGCTCAAGGTGTGGAAATACCCCATAATTCAAACATTTCTAAAATTATTGGTACGA
AGTGGAAGGGCTTACAACCGGAAGATAAGGCACACTGGGAAAATCTAGCGGAGAAGGAGAAACTAGAACATAAAAGG
AAGTATCCTGAATACAAATACAAGCCGGTAAGAAAGTCTAAGAAGAAGCAACTACTTTTGAAGGAAATCGAGCAACAGC
AGCAGCAACAACAGAAAGAACAGCAGCAGCAGAAACAGTCACAACCGCAATTACAACAGCCCTTTAACAACAATATAG
TTCTTATGAAAAGAGCACATTCTCTTTCACCATCTTCCTCGGTGTCAAGCTCGAACAGCTATCAGTTCCAATTGAACAATG
ATCTTAAGAGGTTGCCTATTCCTTCTGTTAATACTTCTAACTATATGGTCTCCAGATCTTCAGCACTAGTCCTGCAGGGGTA
ACGCCAGGGTTTTCCCAGTCACGACGTTGTAAAACGACGGCCAGTGAGCGCGCGTAATACGACTCACTATAGGGCGAAT
TGGGTGCATAGGCCACTAGTGGATCTGATATCACCTAATAACTTCGTATAGCATACATTATACGAAGTTATATTAAGGGTTCT
CGAGAGCTCGTTTTATTTAGGTTCTATCGAGGAGAAAAAGCGACAAGAAGAGATAGACCATGGATAAACTGATTATGTTC
TAAACACTCCTCAGAAGCTCATCGAACTGTCATCCTGCGTGAAGATTAAAATCCAACTTAGAAATTTCGAGCTTACGGAG
ACAATCATATGGGAGAAGCAATTGGAAGATAGAAAAAAGGTACTCGGTACATAAATATATGTGATTCTGGGTAGAAGATC
GGTCTGCATTGGATGGTGGTAACGCATTTTTTTACACACATTACTTGCCTCGAGCATCAAATGGTGGTTATTCGTGGATCT
ATATCACGTGATTTGCTTAAGAATTGTCGTTCATGGTGACACTTTTAGCTTTGACATGATTAAGCTCATCTCAATTGATGTTA
TCTAAAGTCATTTCAACTATCTAAGATGTGGTTGTGATTGGGCCATTTTGTGAAAGCCAGTACGCCAGCGTCAATACACTC
CCGTCAATTAGTTGCACCATGTCCACAAAATCATATACCAGTAGAGCTGAGACTCATGCAAGTCCGGTTGCATCGAAACTT
TTACGTTTAATGGATGAAAAGAAGACCAATTTGTGTGCTTCTCTTGACGTTCGTTCGACTGATGAGCTATTGAAACTTGTT
GAAACGTTGGGTCCATACATTTGCCTTTTGAAAACACACGTTGATATCTTGGATGATTTCAGTTATGAGGGTACTGTCGTT
CCATTGAAAGCATTGGCAGAGAAATACAAGTTCTTGATATTTGAGGACAGAAAATTCGCCGATATCGGTAACACAGTCAA
ATTACAATATACATCGGGCGTTTACCGTATCGCAGAATGGTCTGATATCACCAACGCCCACGGGGTTACTGGTGCTGGTAT
TGTTGCTGGCTTGAAACAAGGTGCGCAAGAGGTCACCAAAGAACCAAGGGGATTATTGATGCTTGCTGAATTGTCTTCC
AAGGGTTCTCTAGCACACGGTGAATATACTAAGGGTACCGTTGATATTGCAAAGAGTGATAAAGATTTCGTTATTGGGTTC
ATTGCTCAGAACGATATGGGAGGAAGAGAAGAAGGGTTTGATTGGCTAATCATGACCCCAGGTGTAGGTTTAGACGAC
AAAGGCGATGCATTGGGTCAGCAGTACAGAACCGTCGACGAAGTTGTAAGTGGTGGATCAGATATCATCATTGTTGGCA
GAGGACTTTTCGCCAAGGGTAGAGATCCTAAGGTTGAAGGTGAAAGATACAGAAATGCTGGATGGGAAGCGTACCAAA
AGAGAATCAGCGCTCCCCATTAATTATACAGGAAACTTAATAGAACAAATCACATATTTAATCTAATAGCCACCTGCATTGG
CACGGTGCAACACTACTTCAACTTCATCTTACAAAAAGATCACGTGATCTGTTGTATTGGGATCTCTAGACCTAATAACTTC
GTATAGCATACATTATACGAAGTTATATTAAGGGTTGTCGACCTGCAGCGTACGAAGCTTCAGCTGACGCGATGAATGCGT
GCGATGAGCGACCTCATGCTATACCTGAGAAAGCAACCTGACCTACAGGAAAGAGTTACTCAAGAATAAGAATTTTCGTT
TTAAAACCTAAGAGTCACTTTAAAATTTGTATACACTTATTTTTTTTATAACTTATTTAATAATAAAAATCATAAATCATAAGA
AATTCGCTTATTTAGAAGTGTCAACAACGTATCTACCAACGATTTGACCCTTTTCCATCTTTTCGTAAATTTCTGGCAAGGT
AGACAAGCCGACAACCTTGATTGGAGACTTGACCAAACCTCTGGCGAAGAATTGTTAATTAAGAGCTCAGATCTTATCGT
CGTCATCCTTGTAATCCATCGATACTAGTGCGGCCGCTTATTTTTTAACATCGTAAGATCTTCTAAATTTGTCATCGATGTTG
GTCAAGTAGTAAACACCACTTTGCAAATGCTCAATGGAACCTTGAGGTTTGAAGTTCTTCTTCAAATGGGCATTTTCTCTC
AATTCGATGGCAGCTTCGTAATCCTTTGGAGTTTCGGTGATTCTCTTGGCTAATTTGTTAGTAATATCTAATTCCTTGATAAT
ATGTTGGACGTCACCAACAATTTTGCAAGAATATAGAGATGCAGCTAAACCGGAACCGTAAGAAAATAAACCAACACGC
TTGCCTTGTAAGTCGTCAGATCCAACATAGTTTAATAGAGATGCAAAGGCGGCATAAACAGATGCGGTGTACATGTTACCT
GTGTTTGTTGGAACAATCAAAGATTGGGCAACTCTCTCTTTGTGGAATGGCTTAGCAACATTAACAAAAGTTTTTTCAAT
GTTCTTATCGGTTAAAGATTCGTCATAATCGCGAGTAGCTAATTCGGCGTCAACTTCTGGGAACAATTGAGGATTGGCTCT
GAAATCGTTATATAGTAATCTACCGTATGATTTTGTGACCAATTTACAGGTTGGAACATGGAAAACGTTGTAGTCGAAATAT
TTCAAAACGTTCAAAGCATCCGAACCAGCGGGATCGCTAACCAACCCTTTAGAAATAGCCTTCTTGGAATAACTCTTGTA
AACTTGATCAAGAGCCTTGACGTAACAAGTTAATGAAAAATGACCATCGACGTAAGGATATTCGCTGGTGAAATCTGGCT
TGTAAAAATCGTAGGCGTGTTCCATGTAAGAAGCTCTTACAGAGTCAAATACAATTG

Figure 4 (cont.)

GAGCATCAGGACCGATCCACATAGCAACAGTACCGGCACCACCGGTTGGTCTTGCGGCACCCTTATCGTAGATGGCAATA
TCACCGCAAACTACAATGGCGTCTCTACCATCCCATGCGTTAGATTCAATCCAGTTCAAAGAGTTGAACAACGCGTTGGTA
CCACCGTAACAGGCATTAAGCGTGTCAATACCTTCGACGTCAGTGTTTTCACCAAACAATTGCATCAAGACAGACTTGAC
AGACTTGGACTTGTCAATCAGAGTTTCAGTACCGACTTCTAATCTACCAATTTTGTTGGTGTCGATGTTGTAACTCTTGATC
AACTTAGACAAAACAGTTAGGGACATCGAGTAGATATCTTCTCTGTCATTGACAAAAGACATGTTGGTTTGGCCCAGACC
AATTGTGTATTTACCTTGAGAAACGCCATCAAATTTCTCTAGCTCAGATTGGTTGACACATTGAGTTGGGATGTAAATTTG
GATACCTTTAATACCGACATTTTGAGGTCTGGTTTTTTGTTCAGCGGTCTTTTGTTTTTTTAGTTCAGTCATTTGCAAGTTT
GTATTGTGTAATTGTTGTTGCTTTTGCGGCCTAAGTCTTCCTTTAATACCACACCAACAAAGTTTAGTTGAGAGTTTCATAA
AAAAGAATTCGAATTTTCAAAAATTCTTACTTTTTTTTTGGATGGACGCAAAGAAGTTTAATAATCATATTACATGGCATTA
CCACCATATACATATCCATATACATATCCATATCTAATCTTACTTATATGTTGTGGAAATGTAAAGAGCCCCATTATCTTAGCCT
AAAAAAACCTTCTCTTTGGAACTTTCAGTAATACGCTTAACTGCTCATTGCTATATTGAAGTACGGATTAGAAGCCGCCGA
GCGGGTGACAGCCCTCCGAAGGAAGACTCTCCTCCGTGCGTCCTCGTCTTCACCGGTCGCGTTCCTGAAACGCAGATGT
GCCTCGCGCCGCACTGCTCCGAACAATAAAGATTCTACAATACTAGCTTTTATGGTTATGAAGAGGAAAAATTGGCAGTA
ACCTGGCCCCACAAACCTTCAAATGAACGAATCAAATTAACAACCATAGGATGATAATGCGATTAGTTTTTTAGCCTTATTT
CTGGGGTAATTAATCAGCGAAGCGATGATTTTTGATCTATTAACAGATATATAAATGCAAAAACTGCATAACCACTTTAACT
AATACTTTCAACATTTTCGGTTTGTATTACTTCTTATTCAAATGTAATAAAAGTATCAACAAAAAATTGTTAATATACCTCTAT
ACTTTAACGTCAAGGAGAAAAAACCCCGGATCCTTTTTTATGGTTTTAACCAATAAAACAGTCATTTCTGGATCGAAAGT
CAAAAGTTTATCATCTGCGCAATCGAGCTCATCAGGACCTTCATCATCTAGTGAGGAAGATGATTCCCGCGATATTGAAAG
CTTGGATAAGAAAATACGTCCTTTAGAAGAATTAGAAGCATTATTAAGTAGTGGAAATACAAAACAATTGAAGAACAAAG
AGGTCGCTGCCTTGGTTATTCACGGTAAGTTACCTTTGTACGCTTTGGAGAAAAAATTAGGTGATACTACGAGAGCGGTT
GCGGTACGTAGGAAGGCTCTTTCAATTTTGGCAGAAGCTCCTGTATTAGCATCTGATCGTTTACCATATAAAAATTATGACT
ACGACCGCGTATTTGGCGCTTGTTGTGAAAATGTTATAGGTTACATGCCTTTGCCCGTTGGTGTTATAGGCCCCTTGGTTA
TCGATGGTACATCTTATCATATACCAATGGCAACTACAGAGGGTTGTTTGGTAGCTTCTGCCATGCGTGGCTGTAAGGCAA
TCAATGCTGGCGGTGGTGCAACAACTGTTTTAACTAAGGATGGTATGACAAGAGGCCCAGTAGTCCGTTTCCCAACTTTG
AAAAGATCTGGTGCCTGTAAGATATGGTTAGACTCAGAAGAGGGACAAAACGCAATTAAAAAAGCTTTTAACTCTACATC
AAGATTTGCACGTCTGCAACATATTCAAACTTGTCTAGCAGGAGATTTACTCTTCATGAGATTTAGAACAACTACTGGTGA
CGCAATGGGTATGAATATGATTTCTAAAGGTGTCGAATACTCATTAAAGCAAATGGTAGAAGAGTATGGCTGGGAAGATA
TGGAGGTTGTCTCCGTTTCTGGTAACTACTGTACCGACAAAAAACCAGCTGCCATCAACTGGATCGAAGGTCGTGGTAA
GAGTGTCGTCGCAGAAGCTACTATTCCTGGTGATGTTGTCAGAAAAGTGTTAAAAAGTGATGTTTCCGCATTGGTTGAGT
TGAACATTGCTAAGAATTTGGTTGGATCTGCAATGGCTGGGTCTGTTGGTGGATTTAACGCACATGCAGCTAATTTAGTG
ACAGCTGTTTTCTTGGCATTAGGACAAGATCCTGCACAAAATGTTGAAAGTTCCAACTGTATAACATTGATGAAAGAAGT
GGACGGTGATTTGAGAATTTCCGTATCCATGCCATCCATCGAAGTAGGTACCATCGGTGGTGGTACTGTTCTAGAACCAC
AAGGTGCCATGTTGGACTTATTAGGTGTAAGAGGCCCGCATGCTACCGCTCCTGGTACCAACGCACGTCAATTAGCAAGA
ATAGTTGCCTGTGCCGTCTTGGCAGGTGAATTATCCTTATGTGCTGCCCTAGCAGCCGGCCATTTGGTTCAAAGTCATATG
ACCCACAACAGGAAACCTGCTGAACCAACAAAACCTAACAATTTGGACGCCACTGATATAAATCGTTTGAAAGATGGGT
CCGTCACCTGCATTAAATCCTAGTCGACATGGAACAGAAGTTGATTTCCGAAGAAGACCTCGAGTAAGCTTGGTACCGC
GGCTAGCTAAGATCCGCTCTAACCGAAAAGGAAGGAGTTAGACAACCTGAAGTCTAGGTCCCTATTTATTTTTTTATAGTT
ATGTTAGTATTAAGAACGTTATTTATATTTCAAATTTTTCTTTTTTTTCTGTACAGACGCGTGTACGCATGTAACATTATACTG
AAAACCTTGCTTGAGAAGGTTTTGGGACGCTCGAAGCGCGTGCATTCTTATTCTTGAGTAACTCTTTCCTGTAGGTCAGG
TTGCTTTCTCAGGTATAGCATGAGGTCGCTCATCGCACGCATTCCATGCGAGCTCGCTGAGGACTTAAAGATCTTTAAGTG
GACTACCTTTGACGCATGATAAGACGGCAAGAGACCTACCACAGCTGTCATCTCAACTAAATTCTATTCCATATTACTCAGC
TCCACACGACCCTTCAACGAGACATCATTACCTCAACGTCGCTCAAGCTCAACCAAGGGCTAACTCGACCCCTCAATTGC
CCTTTATTTCATCCATTATCAACAACAGCAGTCAAACACCGGTAACTACAACTA

Figure 4 (cont.)

CCACATCCACAACAACTGCGACATCTTCTCCTGGGAAATTCTCCTCTTCTCCGAACTCCTCTGTACTGGAGAACAACAGAT
TAAACAGTATCAACAATTCAAATCAATATTTACCTCCCCCTCTATTACCTTCTCTGCAAGATTTTCAACTGGATCAGTACCAG
CAGCTAAAGCAGATGGGACCAACTTATATTGTCAAACCACTGTCTCACACCAGGAACAATCTATTGTCCACAACTACCCCT
ACGCATCATCACATTCCTCATATACCAAACCAAAACATTCCTCTACATCAAATTATAAACTCAAGCAACACTGAGGTCACCG
CTAAAACTAGCCTAGTTTCTCCGAAATGAGCGGCCGC

Figure 5

ATGTGGAAGCTGAAAATAGCAGAAGGTAGTGATGATGAGTGGCTGACCACCACCAACAACCACGTCGGCCGTCAGCAC
TGGCAGTTTGATCCGGATGCTGGAACCGAAGAGGAACGTGCTCAGATTGAAAAGATTCGTCTCAACTTCAAACTTAATC
GTTTTCAATTCAAACAAAGTGCCGACTTGTTAATGCGTACTCAACTAAGAAAAGAGAACCCAATCAATAAAATACCGGAT
GCAATAAAATTGAATGAAACAGAAGAAGTGACAAATGACGCAGTGTCAACTACACTCAAAAGAGCCATTAGCTTTTACT
CCACCATTCAAGCCCATGATGGGCACTGGCCAGCTGAGTCTGCTGGCCCTTTGTTCTTCCTTCCTCCATTGGTAATAGCAC
TATATGTGACTGGAGCAATGAATGATATTCTAACACCCGCACATCAGCTAGAAATAAAACGTTACATATACAATCATCAGAA
TGAAGATGGAGGTTGGGGATTACATATAGAGGGTCATAGCACAATATTTGGATCAGTACTTAGTTACATAACTTTAAGATT
ACTTGGGGAAGAAGCTGATAGTGTTGCAGAGGACATGGCTTTGGTTAAGGGGCGTAAATGGATCCTTGACCATGGTGG
TGCAGTTGGGATTCCTTCGTGGGGAAAGTTTTGGCTTACGATACTTGGAGTATACGAATGGGGAGGCTGTAATCCTATGC
CACCCGAATTTTGGCTCATGCCTAAGTTTTTCCCAATTCATCCAGGCAAAATGTTGTGTTATTGTCGCTTAGTTTACATGCC
CATGTCGTACTTATACGGCAAAAGATTTGTGGGAAAAATAACCGAGTTGGTTCGCGACCTAAGGCAAGAGCTTTATACAG
ACCCTTATGATGAGATTAATTGGAATAAAGCACGAAACACGTGTGCAAAGGAAGATCTCTACTATCCACACCCTTTTGTTC
AAGATATGGTATGGGGTGTACTTCATAATGTTTTTGAACCTGTATTAACAAGTCGTCCGCTTTCCACACTAAGAGAAAAGG
CTTTGAAAGTCGCAATGGATCATGTTCACTATGAAGATAAGAGTAGTAGATATCTTTGCATTGGATGTGTGGAAAAGGTG
TTATGCTTGATTGCAACGTGGGTGGAAGATCCAAATGGTGATGCATATAAACGTCATCTTGCTAGAATTCCTGACTACTTTT
GGGTTGCTGAAGATGGGATGAAAATGCAGAGTTTTGGATGTCAAATGTGGGATGCGGCCTTTGCTATTCAAGCTATTTTA
TCTAGTAATCTAGCCGAAGAATACGGCCCGACTCTTAAAAAAGCACACGAGTTTGTAAAAGCATCACAGGTTCGTGATAA
TCCGCCGGGAGATTTCAGTAAAATGTACAGACACACTTCTAAGGGTGCATGGACATTTTCCATACAAGATCATGGTTGGC
AAGTCTCTGATTGTACGGCTGAAGGCTTGAAGGTTGCACTTTTGTACTCCCAAATGAGCCCAGAACTTGTGGGCGAAAA
ACTTGAAACTGAGCATCTCTACGATGCTGTCAATGTCATTCTTTCATTACAAAGTGAAAACGGTGGCTTTCCTGCTTGGGA
ACCACAAAGGGCGTATGCTTGGTTGGAGAAATTCAACCCGACTGAATTCTTTGAAGATGTGTTGATCGAACGAGAGTAT
GTTGAATGCACTTCATCTGCAATCCAAGGTTTGACACTCTTCAAGAAGTTGCACCCAGGGCACAGAACCAAGGAGATCG
AGCATTGTATATCAAGAGCTATAAAGTACGTCGAAGACACACAAGAAAGTGATGGTTCATGGTATGGTTGTTGGGGAATT
TGCTACACCTATGGTACATGGTTTGCGGTAGATGCGCTAGTAGCTTGTGGTAAGAACTATCATAACTCTCCCGCCCTTCAA
AAAGCATGCAAATTTCTGTTATCCAAACAACTTCCGGATGGTGGATGGGGAGAAAGTTATCTTTCGAGCTCAAATAAGGT
GTATACGAATTTGGAGGGAAATCGTTCGAATTTAGTGCATACATCATGGGCTTTAATATCACTTATTAAAGCGGGACAGGC
TGAAATTGATCCTACACCAATATCTAATGGCGTACGGCTTCTCATCAATTCACAAATGGAAGAAGGGGACTTTCCTCAACA
GGAAATCACAGGAGTGTTCATGAAGAACTGTAACCTCAATTACTCATCATATCGAAATATTTTTCCCATATGGGCACTTGGT
GAATATCGTCGTATTGTTCAAAATATATGA a

C

Figur 7 (cont.)
C
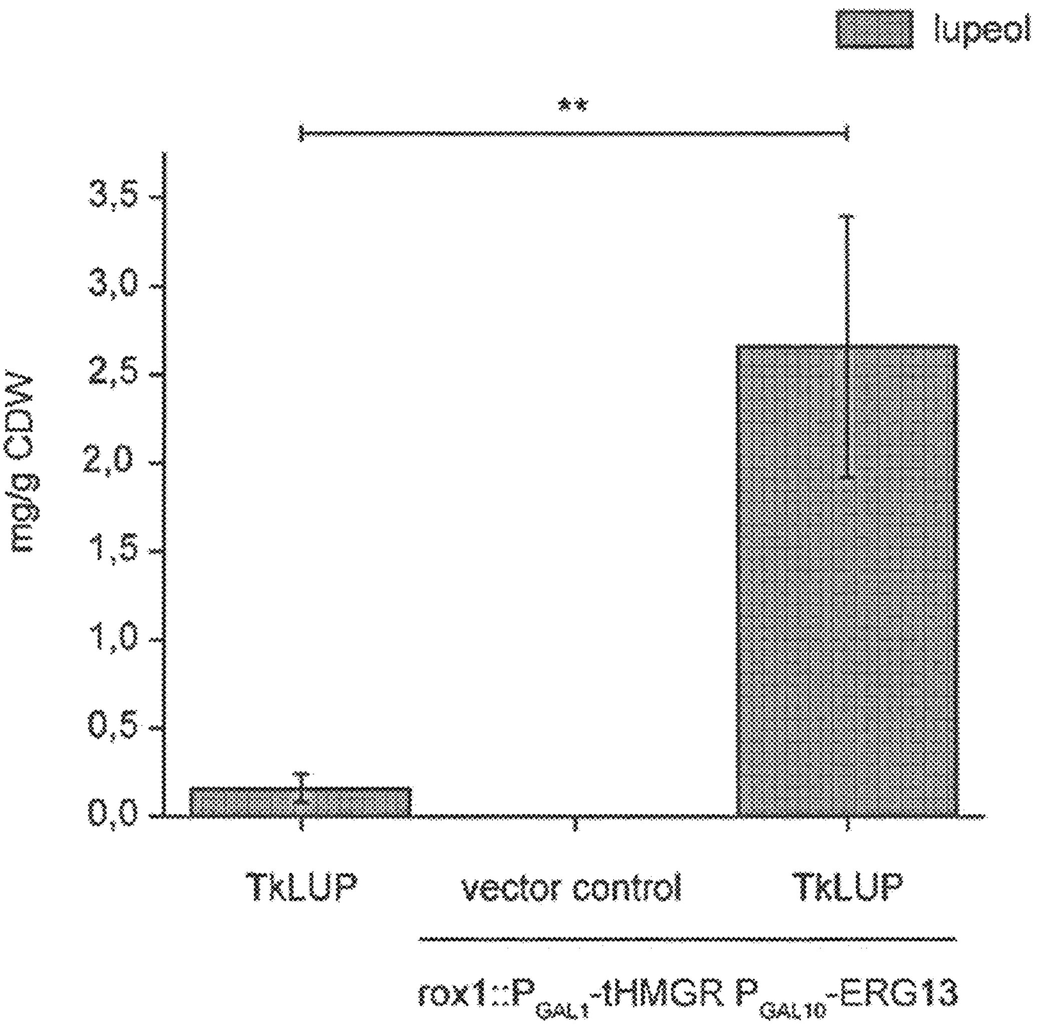

d

Figur 7 (cont.)
e
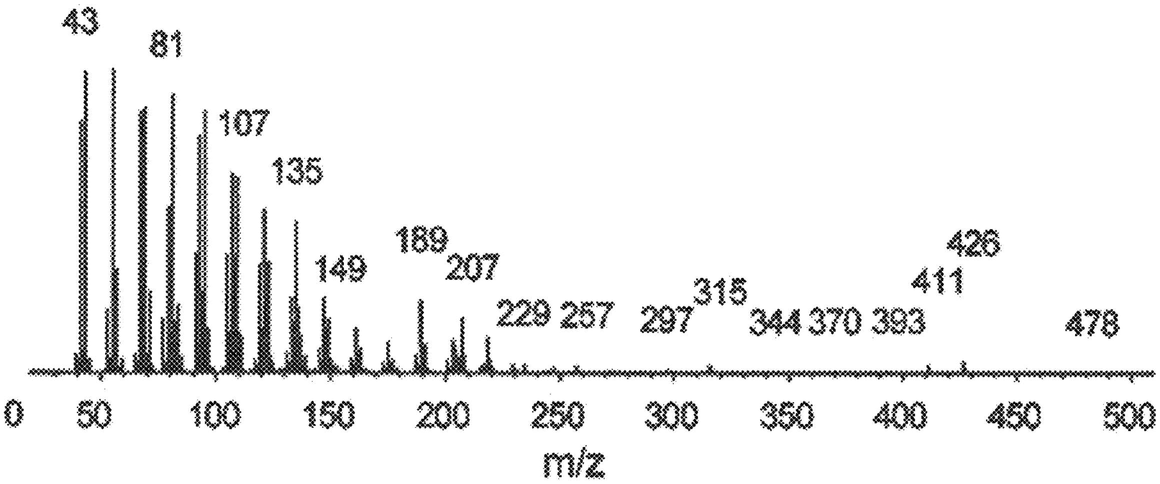

Figure 13:
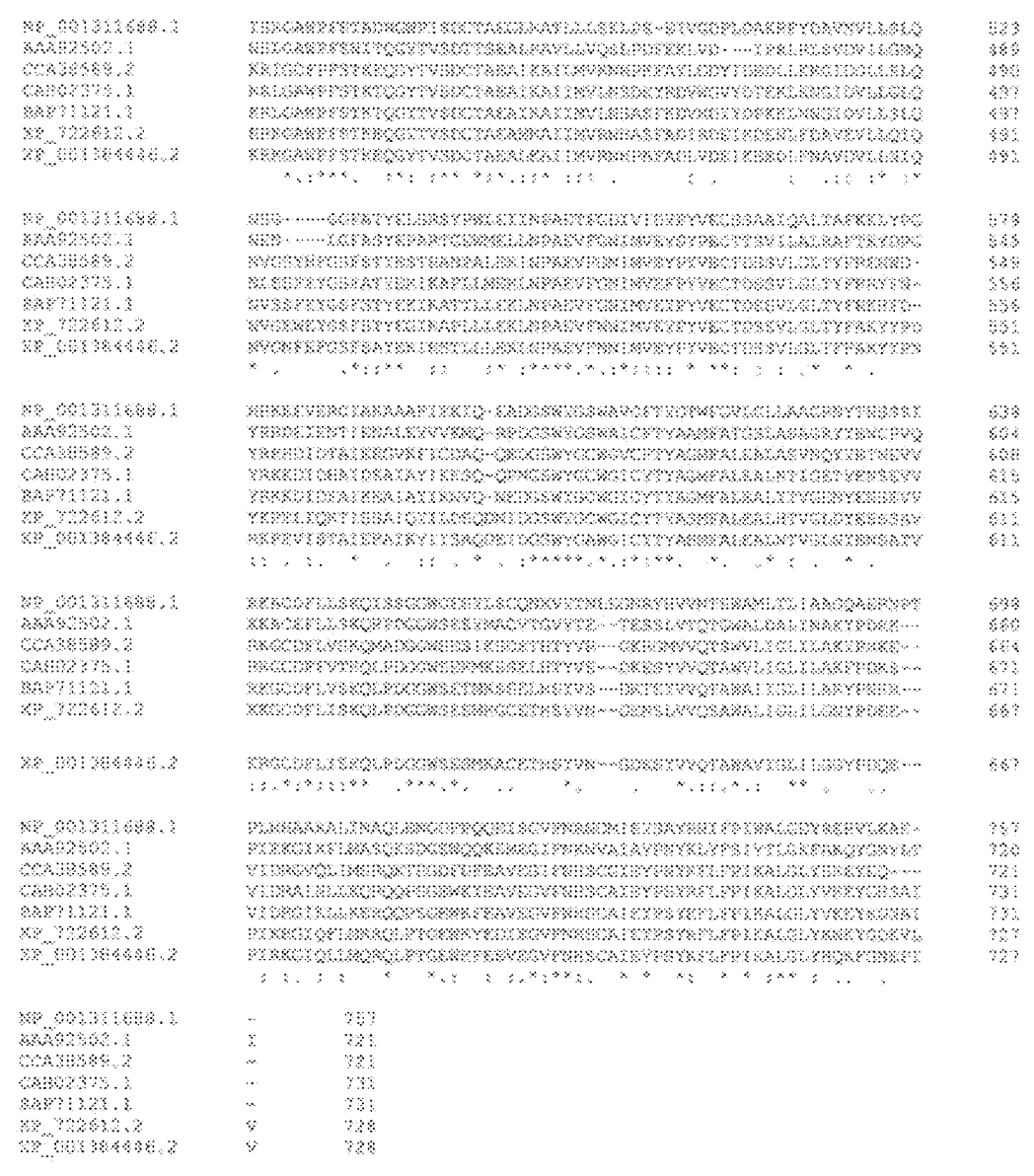

```
NP_001311688.1      IDDGAWPFSTADKGWPISDCTAEGLKAVLLLSELPS-EIVGDPLDAKRFYDAVNVLLSLQ     523
AAA92502.1          NDLGAWPFSNITQGYTVSDCTAEALKAVLLVQSLPDFKKLVD----IPKLRLSVDILGMQ     489
CCA38589.2          KKIGGFPFSTKEQGYTVSDCTAEAIKAILMVRKMPFFAYLCDYTEEDLLKKGIDDLLSLQ     490
CAB02375.1          NKIGAWPFSTKTQGYTVSDCTAEAIKAIIMVLKSDKYRDVKGVYDTEKLKNGIDVLLSLQ     497
BAF71121.1          KNLGAWPFSTKTQGYTVSDCTAEAIKAIIMVLKDASFKDVKGIYDPKKLNNGIDVLLSLQ     497
XP_722612.2         KNDGAWPFSTKEQGYTVSDCTAEAMKAIIMVRNHASFADINDEIKDENLFDAVEVLLQIQ     491
XP_001384446.2      KKKGAWPFSTKEQGYTVSDCTAEALKAIIMVRNNPAFAGLVDEIKEEGLFNAVDVLLSIQ     491
                       *.:***.  :*: :** *:*.::* ::: .      : .        :   .:: :* :*

NP_001311688.1      NEG------GGFATYELGRSYPWLGIINPAETFGDIVIDYPYVECSSAAIQALTAFKKLYPG     578
AAA92502.1          NED------LGFASYEPARTGSWMELLNPAEVFGNIMVEYQYPECTTSVLLALRAFTKYDPG     545
CCA38589.2          NVGSYNFGSFSTYKSTSANPALSKINPAEVFGNIMVEYPYVECTDSSVLGLTYFRKKND-     549
CAB02375.1          NLGGFKYGSFATYEKIKAPLLMEKLNPAEVFGNIMVEYPYVECTDSSVLGLTYFRKYYN-     556
BAF71121.1          NVSSFKYGSFSTYEKIKAPLLLEKLNPAEVFGNIMVEYPYVECTDSGVLGLTYFKKHYD-     556
XP_722612.2         NVGEWEYGSFSTYEGIKAPLLLEKLNPAEVFNNIMVEYPYVECTDSSVLGLTYFAKYYPD     551
XP_001384446.2      NVGNFKFGSFSAYEKIKSTLLLEKLNPAEVFNNIMVEYPYVECTDSSVLGLTFFAKYYPN     551
                    * .       .*::**  ::   :* :****.*.:*::: * **: : : .:*  * .

NP_001311688.1      HRKEEVERCISKAAAFIEKIQ-EADGSWYGSWAVCFTYGTWFGVLGLLAAGPNYTNDSSI     638
AAA92502.1          YRRDEIENTIKEALEVVVKMQ-RPDGSWYGSWAICFTYAAMFATGSLASAGRTYENCPVQ     604
CCA38589.2          YRKHDIDTAIKKGVKFICDAQ-QEDGSWYGSWGVCFTYAGMFALEALASVGQTYENGEVV     608
CAB02375.1          YRKKDIDEAIDKAIAYIKKSQ-QPDGSWYGSWGICYTYAGMFALEALHTIGETYENSEVV     615
BAF71121.1          YRKKDIDYAIKKAIAYIKNVQ-NEDGSWYGSWGICYTYAGMFALEALYTVGENYENSEVV     615
XP_722612.2         YKPELIQKTIESAIQYILKSQDNIDGSWYGSWGICYTYASMFALEALHTVGLDYESSGRV     611
XP_001384446.2      HKPEVISTAIEPAIKYIISAQDEIDGSWYGAWGICYTYAGMFALEALNTVGLGYENSATV     611
                    :: . :.  *  .  :: . * . :*****.*.:*:**.  *.   *. .* .   .

NP_001311688.1      KKACDFLLSKQLSSGGWGESYLSCQNKVYTNLEGNRSHVVNTGWAMLALIKAGQAERDPT     698
AAA92502.1          KKACEFLLSKQRPGGGWSESYKACVTGVYTE--TESSLVYQTGWALLALIRAKYPDAK---     660
CCA38589.2          RKGCDFLVSKQMADGGWSEDIKSCETETYVE---GEKSMVVQTSWVLIGLILAKDPNKE--     664
CAB02375.1          RKGCDFLVSKQLPDGGWSEPMKSCELHTYVS---DKESYVVQTAWVLIGLILAEYPDKS--     671
BAF71121.1          KKGCDFLVSKQLPDGGWSETMKSCELHSYVS---DKTSYVVQTAWAIIGLILAEYPEEK--     671
XP_722612.2         KKGCDFLISKQLPDGGWSESMKGCETHSYVN--GEPSLVVQSAWALIGLILGKYPDEE--     667

XP_001384446.2      KKGCDFLISKQLPDGGWSESMKACETHSYVN--GDKSYVVQTAWAVIGLILSEYPNQE--     667
                    :*.*:*::***  .***.*.  .*     *.      .    *. :**.: *  **  .

NP_001311688.1      PLHRAAKALINAQLENGDFPQQEISCVFNRNCMISYAAYRNIFPIWALGDYRSRVLKAP-     757
AAA92502.1          PIKKGIKFLMASQENGKWSQQGKMGIFWKNVAIAYPNYKLYFSIYTLGKFRNQYRRVLT     720
CCA38589.2          VIDRGVQLIMGRQLTNGDFNFEAVEGIFNHSCGIEYPNYRFLFPIKALGLYSRKYEQ---     721
CAB02375.1          VIERALELLKGRQLPNGDWKYEAVEGVFNHSCAIEYPSYRFLFPIKALGLYVNKYGDAI     731
BAF71121.1          VIDRGIKLLMSRQLPNGEWKYEAVEGVFNHSCAIEYPSYRFLFPIKALGLYVRKYKNNI     731
XP_722612.2         PIERGIQFIMKAQLPTGEWKYEDIEGVFNHSCAIEYPSYRFLFPIKALGLYKNKYGDKVL     727
XP_001384446.2      PIKKGIQLIMQRQLPTGEWKFEEVEGVFNHSCAIEYPSYRFLFPIKALGLFHQKFGNEFI     727
                     : :. : :    *     *.:   : :.*:**:.  * *  *:  * * :** : ..   .

NP_001311688.1      -       757
AAA92502.1          I       721
CCA38589.2          -       721
CAB02375.1          -       731
BAF71121.1          -       731
XP_722612.2         V       728
XP_001384446.2      V       728
```

Figure 14

| | 1 | 2 | 3 | 4 | 5 | 6 | 7 |
|---|---|---|---|---|---|---|---|
| 1: NP_001311698.1 | 100.00 | 39.94 | 36.49 | 34.83 | 35.52 | 35.92 | 37.18 |
| 2: AAA92502.1 | 39.94 | 100.00 | 43.48 | 41.90 | 43.02 | 45.28 | 45.98 |
| 3: CCA38588.2 | 36.49 | 43.48 | 100.00 | 62.97 | 63.25 | 61.34 | 63.14 |
| 4: CAR02375.1 | 34.83 | 41.90 | 62.97 | 100.00 | 83.58 | 64.68 | 63.43 |
| 5: BAP71121.1 | 35.52 | 43.02 | 63.25 | 83.58 | 100.00 | 65.79 | 64.96 |
| 6: XP_722612.2 | 35.92 | 45.28 | 61.34 | 64.68 | 65.79 | 100.00 | 76.79 |
| 7: XP_001384446.2 | 37.18 | 45.98 | 63.14 | 63.43 | 64.96 | 76.79 | 100.00 |

METHOD FOR INCREASING THE YIELD OF OXIDOSQUALENE, TRITERPENES AND/OR TRITERPENOIDS AND HOST CELL THEREFORE

PRIORITY CLAIM

This application claims priority to International Application No. PCT/EP2019/058789, filed Apr. 8, 2019, which claims priority to European Application No. 18166374.1, filed Apr. 9, 2018, wherein the contents of said applications are incorporated herein by reference in their entireties. Also, the entire contents of the ASCII text file entitled "IPM0105US_Sequence_Listing.txt" created on Oct. 2, 2020, having a size of 152 kilobytes.

TECHNICAL FIELD OF THE INVENTION

The present invention is in the field of recombinant biotechnology, in particular in the field of metabolic engineering. The present invention generally relates to a method of increasing the yield of at least one of oxidosqualene, triterpenes and/or triterpenoids in a host cell and purification thereof. The invention also relates to the respective host cell for manufacturing at least one of oxidosqualene, triterpenes and/or terpenoids, wherein the host cell's capacity to produce at least one of oxidosqualene, triterpenes and/or triterpenoids is improved. Further, the present invention relates to the use of the host cell for manufacturing at least one of oxidosqualene, triterpenes and/or triterpenoids.

BACKGROUND ART

Pentacyclic triterpenes are a class of plant secondary metabolites that derive from the mevalonate (MVA) pathway and show high economical and pharmaceutical potential. As the production of these substances in heterologous systems—such as *Saccharomyces cerevisiae*—is favourable, research in and design of such systems raised in the last years.

Isoprenoids are the largest group of natural compounds found in all living organisms and show a diversity of at least 50.000 different structures, known so far (Hemmerlin et al., 2012; Liao et al., 2016). These structures mainly derive from the highly regulated mevalonate pathway (MVA-pathway), where acetyl-CoA is converted into the isoprenoid precursor isopentenyl diphosphate (IPP). To convert acetyl-CoA into IPP six enzymes are needed, whereas the 3-hydroxy-3-methylglutaryl-coenzyme A reductase (HMGR) is known to be the rate limiting step of the pathway (Demierre et al., 2005). After isomerization to dimethylallyl pyrophosphate (DMAPP), IPP and DMAPP can enter different isoprenoid pathways. After the reaction of two IPPs and one DMAPP molecules farnesyl pyrophosphate (FPP) is build up and converted to squalene via squalene synthase. Squalene is used—in its oxidized form 2,3-oxidosqualene—to synthesize sterol precursors (e.g. lanosterol in fungi and animals or cycloartenol in plants) or pentacyclic triterpenes via different oxidosqualene cyclases (OSCs) such as lupeol synthase from *Taraxacum officinale* or β-amyrin synthase from *Artemisia annua* (Shibuya et al., 1999; Kirby et al., 2008). Furthermore, other modifications of FPP lead to the synthesis of sesquiterpenes such as farnesene or amorpha-4,11-diene, a precursor of the anti-malaria drug artemisinin (Martin et al., 2003).

Due to their economical and pharmaceutical potential, a lot of studies dealt with the production of isoprenoids in heterologous systems, such as *Saccharomyces cerevisiae* (reviewed in Liao et al., 2016 and Vickers et al., 2017). Starting to highlight the potential of yeast MVA pathway for the production of isoprenoids in 1997, Donald et al. reported the overexpression of the catalytic domain of HMGR in yeast, resulting in an increase of the triterpene squalene. Further reports on the deregulation of the MVA pathway came up in CRISPR/Cas9 experiments that provided a set of loci triggering the accumulation of mevalonate and triterpenes when knocked out (Jakočiūnas et al., 2015; Ahrend et al., 2017). This set included ROX1, a transcriptional regulator reported to repress genes in the MVA pathway and sterol biosynthesis (Henry et al., 2002; Montañés et al., 2011; Özaydin et al., 2013; Jakočiūnas et al., 2015). Additionally, several studies report on the insertion of specific promoters into the yeast genome to regulate genes involved in endogenous but competitive isoprenoid pathways (e.g. sterol biosynthesis vs. pentacyclic triterpene biosynthesis) to redirect the metabolic flux in a precise and wanted manner.

Therefore, Kirby et al. used the methionine sensitive MET3 promoter to downregulate the expression of the yeasts lanosterol synthase (ERG7), which catalyzes the first step of late sterol biosynthesis, for the production of β-amyrin. Furthermore, the MET3 promoter was used in the production of artemisinin for the repression of the yeast squalene synthase gene (ERG9) (Ro et al., 2006; Westfall et al., 2012).

US 2017/0130233 describes a yeast strain and a method for microbial production of pentacyclic triterpenes and/or triterpenoids in yeast. In particular, the said modified yeast strain is for production of pentacyclic triterpenoids comprising at least one copy of a gene for encoding an oxidosqualene cyclase, at least one copy of a gene for encoding an NADPH-cytochrome P450 reductase and/or at least one copy of a gene for encoding a cytochrome P450 monooxygenease.

U.S. Pat. No. 5,460,948 describes a method of increasing the accumulation of squalene and specific sterols in yeast comprising increasing the expression level of a structural gene encoding a polypeptide having HMG-CoA-reductase activity in a mutant yeast having single or double defects in the expression of sterol biosynthetic enzymes.

Pentacyclic triterpenes and triterpenoids exhibit an enormous potential for industrial and pharmaceutical applications (Sheng and Sun, 2010). However, extraction often proves economically nonviable as overall amounts in planta are low and biotechnological production in heterologous hosts faces several constraints such as low efficiency of the corresponding enzymes or lacking post-translational modifications (Moses and Pollier, 2013; Arendt et al., 2016).

Consequently, though the production and extraction of oxidosqualene, triterpenes and/or triterpenoids with organic extraction from plants and subsequent purification is possible, this has led up to now to high costs for gaining pure endproducts and to high differences in the quality of the endproducts as the concentration and composition of triterpenes in plants can vary in wide ranges.

Thus, there is a need for a cost reduced and reliable method for gaining a high yield of oxidosqualene, triterpenes and/or triterpenoids.

SUMMARY OF THE INVENTION

According to the present invention, the inventors designed a new heterologous platform for the production of oxidosqualene, triterpenes and/or triterpenoids, which is cost-effective, reliable and allows the production of oxidosqualene, triterpenes and/or triterpenoids in a high purity.

The present invention provides a method of increasing the yield of at least one of oxidosqualene, triterpenes and/or triterpenoids in a host cell comprising:

engineering the host cell to overexpress a 3-hydroxy-3-methylglutaryl-coenzyme A reductase comprising an amino acid sequence as shown in SEQ ID NO: 1 or to overexpress a protein having at least 44% sequence identity with the amino acid sequence as shown in SEQ ID NO: 1, with the proviso that said protein is capable to produce mevalonic acid, and to overexpress a protein comprising at least one amino acid sequence selected from the group consisting of SEQ ID NOs: 2, 3, 4, 5, 6, 7 and 8 or comprising at least one amino acid sequence having at least 44% sequence identity with an amino acid sequence selected from the group consisting of SEQ ID NOs: 2, 3, 4, 5, 6, 7 and 8, with the proviso that said protein is capable to produce at least one of acetoacetyl-CoA, 3-hydroxy-3-methylglutaryl-CoA, mevalonate-5-phosphate, mevalonate-5-pyrophosphate, isopentenyl-5-pyrophosphat, farnesyl-pyrophosphate or dimethylallyl-pyrophosphate, engineering the host cell to express at least one heterologous protein producing at least one of oxidosqualene, triterpenes and/or triterpenoids, culturing said host cell under suitable conditions to express the at least one of oxidosqualene, triterpenes and/or triterpenoids, and purifying the at least one of oxidosqualene, triterpenes and/or triterpenoids, thereby increasing the yield of the at least one of oxidosqualene, triterpenes and/or triterpenoids in comparison to the host cell prior to engineering.

In a preferred embodiment, in the method according to the present invention, the host cell is engineered to overexpress a protein comprising the amino acid sequence of SEQ ID NO: 3 or comprising an amino acid sequence having at least 44% sequence identity with the SEQ ID NO: 3, with the proviso that said protein is capable to produce 3-hydroxy-3-methylglutaryl-CoA.

In a preferred embodiment, the method according to the present invention additionally comprises engineering the host cell to knock out at least one locus selected from the group consisting of ROX1 (SEQ ID NO: 25), BTS1 (SEQ ID NO: 54), YPL062W (SEQ ID NO: 55), DOS2 (SEQ ID NO: 56), YER134C (SEQ ID NO: 57), VBA5 (SEQ ID NO: 58), YNR063W (SEQ ID NO: 59), YJL064W (SEQ ID NO: 60) and YGR259C (SEQ ID NO: 61).

In a further embodiment, the method according to the present invention additionally comprises engineering the host cell to repress the lanosterolsynthase (ERG7) comprising an amino acid sequence as shown in SEQ ID NO: 9 or to repress a protein comprising an amino acid sequence having at least 34% sequence identity with the SEQ ID NO: 9, with the proviso that said protein is capable to produce lanosterol. Preferably said repression is carried out by the insertion of the CTR3-promoter and/or the addition of coppersulfate $CuSO_4$.

In this preferred embodiment, the added amount of coppersulfate may be at least 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370 or 375 mM $CuSO_4$, preferably at least 150 mM $CuSO_4$.

In the method of the present invention, the at least one heterologous protein which produces the at least one of oxidosqualene, triterpenes and/or triterpenoids may be selected from the group consisting of lupeol synthases, preferably the lupeol synthase from *Taraxacum koksaghyz*, oxidosqualene cyclases (OSC), preferably the oxidosqualene cyclases TkOSC1-6 from *Taraxacum koksaghyz*, β-amyrin synthase, preferably the β-amyrin synthase from *Arabidopsis thaliana* or from *Artemisia annua*, terpene cyclase, preferably the terpene cyclase from *Glycyrrhiza uralensis* (GuLUP1).

According to the method of the present invention, the at least one of oxidosqualene, triterpenes and/or triterpenoids is extracted from a plant.

In a further embodiment of the method of the present invention, the purification of the at least one of oxidosqualene, triterpenes and/or triterpenoids is carried out by at least two chromatography steps, preferably by using a C18 column for the first chromatography step and a biphenyl column for the second chromatography step.

In one embodiment of the method of the present invention, the yield of more than one oxidosqualene, triterpenes and/or triterpenoids may be increased.

The invention further provides a recombinant host cell for manufacturing at least one of oxidosqualene, triterpenes and/or triterpenoids, wherein the host cell is engineered to overexpress a 3-hydroxy-3-methylglutaryl-coenzyme A reductase comprising an amino acid sequence as shown in SEQ ID NO: 1 or to overexpress a protein having at least 44% sequence identity with the amino acid sequence as shown in SEQ ID NO: 1, with the proviso that said protein is capable to produce mevalonic acid, and to overexpress a protein comprising at least one amino acid sequence selected from the group consisting of SEQ ID NOs: 2, 3, 4, 5, 6, 7 and 8 or comprising at least one amino acid sequence having at least 44% sequence identity with an amino acid sequence selected from the group consisting of SEQ ID NOs: 2, 3, 4, 5, 6, 7 and 8, with the proviso that said protein is capable to produce at least one of acetoacetyl-CoA, 3-hydroxy-3-methylglutaryl-CoA, mevalonate-5-phosphate, mevalonate-5-pyrophosphate, isopentenyl-5-pyrophosphat, farnesyl-pyrophosphate or dimethylallyl-pyrophosphate.

According to the present invention, the host cell may be selected from the group consisting of *Saccharomyces cerevisiae, Nicotiana benthamiana, Pichia pastoris, Pichia methanolica, Schizosaccharomyces pombe, Kluyveromyces lactis, Kluyveromyces marxianus, Pichia stipitis, Candida albicans, Candida utilis* and BY2 cells.

The host cell may further be engineered to overexpress the protein comprising the SEQ ID NO: 3 or comprising an amino acid sequence having at least 44% sequence identity with SEQ ID NO: 3, with the proviso that said protein is capable to produce 3-hydroxy-3-methylglutaryl-CoA.

The host cell of the present invention may further be engineered to repress the lanosterolsynthase (ERG7) comprising an amino acid sequence as shown in SEQ ID NO: 9 or to repress an amino acid sequence having at least 34% sequence identity with the SEQ ID NO: 9, with the proviso that said protein is capable to produce lanosterol, preferably by the insertion of the CTR3-promoter and/or the addition of coppersulfate $CuSO_4$. Preferably, the lanosterolsynthase (ERG7), which is repressed according to the present invention, is from *Saccharomyces cerevisiae, Pichia pastoris, Pichia methanolica, Schizosaccharomyces pombe, Kluyveromyces lactis, Kluyveromyces marxianus, Pichia stipitis, Candida albicans* or *Candida utilis*.

It is preferred that the host cell is further engineered to knock out at least one locus selected from the group consisting of ROX1 (SEQ ID NO: 25), BTS1 (SEQ ID NO: 54), YPL062W (SEQ ID NO: 55), DOS2 (SEQ ID NO: 56), YER134C (SEQ ID NO: 57), VBA5 (SEQ ID NO: 58), YNR063W (SEQ ID NO: 59), YJL064W (SEQ ID NO: 60) and YGR259C (SEQ ID NO: 61).

It is preferred for the host cell of the present invention that the at least one of oxidosqualene, triterpenes and/or triterpenoids is an oxidosqualene, preferably 2,3-oxidosqualene, a sterol, preferably sigmasterol or sitosterol, a triterpene, preferably a pentacyclic triterpene, more preferably lupeol, such as, but not limited to, lup-19(21)-en-3-ol and lup-20(29)-en-3-ol, β-amyrin, α-amyrin, taraxasterol, triterpene acetates, acylated triterpenes, saponines, sapogenines, lup-19(21)-en-3-one, lup-20(29)-en-3-one, taraxerol, taraxerone, α-amyrone, β-amyrone, taraxasterone, friedelin, betulin, betulinic acid, cholesterol, ergosterol, lanosterol, glucocorticoids, mineralocorticoids, estrogens, gestagens, cardenolides, bufadienolides, steroid alkaloides, saponins, sapogenins or acylated triterpenes.

The present invention also provides the use of the host cell of the present invention for manufacturing at least one of oxidosqualene, triterpenes and/or triterpenoids.

Thus, the inventors have found a combinatorial engineering strategy, which comprises the overexpression of mevalonate pathway genes and/or proteins. Additionally, in one embodiment, the method of the present invention comprises the knock out of negative regulators and the knock down of a competitive pathway of the mevalonate pathway.

BRIEF DESCRIPTION OF THE FIGURES

FIG. 1 shows the amino acid sequence of 3-hydroxy-3-methylglutaryl-coenzyme A reductase having an amino acid sequence as shown in SEQ ID NO: 1.

FIG. 3 shows the nucleotide sequence of the $P_{erg7}$:$P_{CTR3}$-construct (SEQ ID NO: 10).

FIG. 4 shows the nucleotide sequence of the rox1::$P_{Gal1\text{-}tHMGR}$; $P_{GAL10\text{-}ERG13}$-construct (SEQ ID NO: 11).

FIG. 5 shows the nucleotide sequence of the enzyme LUP of *Taraxacum koksaghyz* (TkLUP) (SEQ ID NO: 12).

FIG. 6*a* shows the schematic representation of the TkLUP coding sequence (SEQ ID NO: 12) under the control of the GAL1 promoter (GAL1-P) and CYC1 terminator (CYC1-T). FIG. 6*b* shows two additional peaks in the GC-MS spectra of yeast cells carrying the TkLUP coding sequence (SEQ ID NO: 12) (arrows; m/z=218), most likely, representing β-amyrin (ret. time 17.95 min) and lupeol (ret. time 18.25 min) as they share the same retention time with the corresponding standards. FIG. 6*c* shows the yeasts harboring the TkLUP coding sequence (SEQ ID NO: 12) accumulated 0.16 mg/g CDW of the putative lupeol, whereas a quantification of the β-amyrin peak was not possible. Untransformed (WT) and pAG424GAL1-ccdb transformed (vector control) CEN.PK2-1C cells served as controls. Standard deviation was calculated from n=3 individual transformants; CDW=cell dry weight.

FIG. 7*a* shows the schematic representation of the construct for the deletion of ROX1 (SEQ ID NO: 25) and overexpression of tHMGR (SEQ ID NO: 32) and ERG13 (SEQ ID NO: 14). The coding sequences of tHMGR and ERG13 were cloned under the control of a bidirectional GAL1/GAL10 promoter (GAL1-P; GAL10-P). KlUra3 was used to complement the uracil-auxotrophie during integration of the construct into the yeast genome. The locus for integration was defined by sequences flanking the construct (target-up; target-down) and being homologous to the genome target site (ROX1, SEQ ID NO: 25). Transformation of the NotI-linearized construct lead to the knock out of ROX1 (SEQ ID NO: 25) by homologous recombination. FIGS. 7*b* and 7*c* shows yeast strains carrying the integrated construct in addition to the TkLUP (SEQ ID NO: 12) coding sequence (rox1::$P_{GAL1}$-tHMGR $P_{GAL10}$-ERG13 TkLUP) showed an enhanced accumulation of the lupeol precursor squalene in contrast to yeasts carrying only the TkLup containing plasmid (TkLUP; p=0.0137). Cells containing the empty vector pAG424GALI_ccdB served as control (rox1::$P_{GAL1}$-tHMGR $P_{GAL10}$-ERG13 vector control). Furthermore, the deletion of ROX1 (SEQ ID NO: 25) and overexpression of tHMGR (SEQ ID NO: 32) and ERG13 (SEQ ID NO: 14) resulted in a 16.5-fold enhanced accumulation of lupeol (p=0.00893). FIG. 7*d* shows the MS spectrum of the designated lupeol peak and FIG. 7*e* shows the MS spectrum of the measured external lupeol standard. Standard deviation was calculated from n=3 individual transformants. CDW=cell dry weight; *=p≤0.05; **=p≤0.01.

FIG. 8*a* is the schematic representation of the construct for the integration of the copper sensitive CTR3 promoter (CTR3-P) (SEQ ID NO: 42). To introduce the promoter into the yeast genome the leucine auxotrophie was complemented by the KlLeu2 gene. The construct was flanked by sequences homologous to the ERG7 promoter (target-up; ERG7-P) and the ERG7 coding sequence (target-down; ERG7, SEQ ID NO: 42) to target the CTR3 promoter (SEQ ID NO: 42) infront of endogenous ERG7 coding sequence (SEQ ID NO: 20) to repress sterol biosynthesis. FIGS. 8*b* and 8*c* show that a yeast strain carrying the CTR3 promoter construct (SEQ ID NO: 42) shows a reduction in squalene levels (8*b*) and accumulation of 2,3-oxidosqualene (8*c*) even without being exposed to $CuSO_4$ (rox1::$P_{GAL1}$-tHMGR $P_{GAL10}$-ERG13 $P_{ERG7}$Δ::$P_{CTR3}$, 0 μM $CuSO_4$). This effect could be significantly enhanced by applying 150 μM $CuSO_4$ to the growth media (rox1::$P_{GAL1}$-tHMGR $P_{GAL10}$-ERG13 $P_{ERG7}$Δ::$P_{CTR3}$, 150 μM $CuSO_4$; p=0.00613 for the reduction of squalene; p=0.00507 for the accumulation of 2,3-oxidosqualene). The addition of a 2,5-fold copper concentration showed a further significant decrease in squalene levels and a further enhanced 2,3-oxidosqualene content (rox1::$P_{GAL1}$-tHMGR $P_{GAL10}$-ERG13 $P_{ERG7}$Δ::$P_{CTR3}$, 375 μM $CuSO_4$). Standard deviation was calculated from n=3 individual transformants. CDW=cell dry weight; *=p≤0.05; =p≤0.01;*=p≤0.001.

Figure 10:
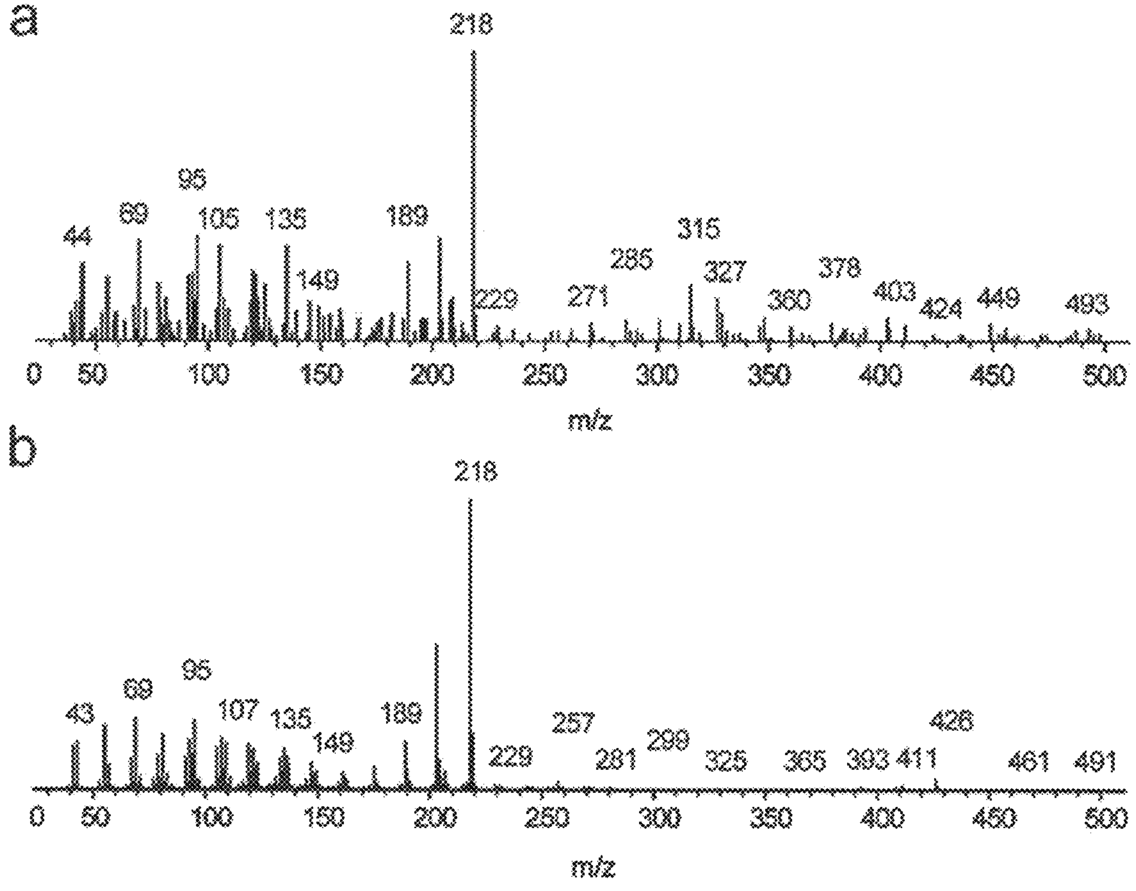

FIG. 10 shows the identification of β-amyrin in yeast after repression of ERG7 (SEQ ID NO: 20). FIG. 10*a* shows the MS spectrum of the designated β-amyrin peak from the engineered yeast strain (rox1::$P_{GAL1}$-tHMGR $P_{GAL10}$-ERG13 $P_{erg7}$Δ::$P_{CTR3}$ TkLUP) and FIG. 10*b* shows the MS spectrum of the measured external β-amyrin standard.

Figure 11:
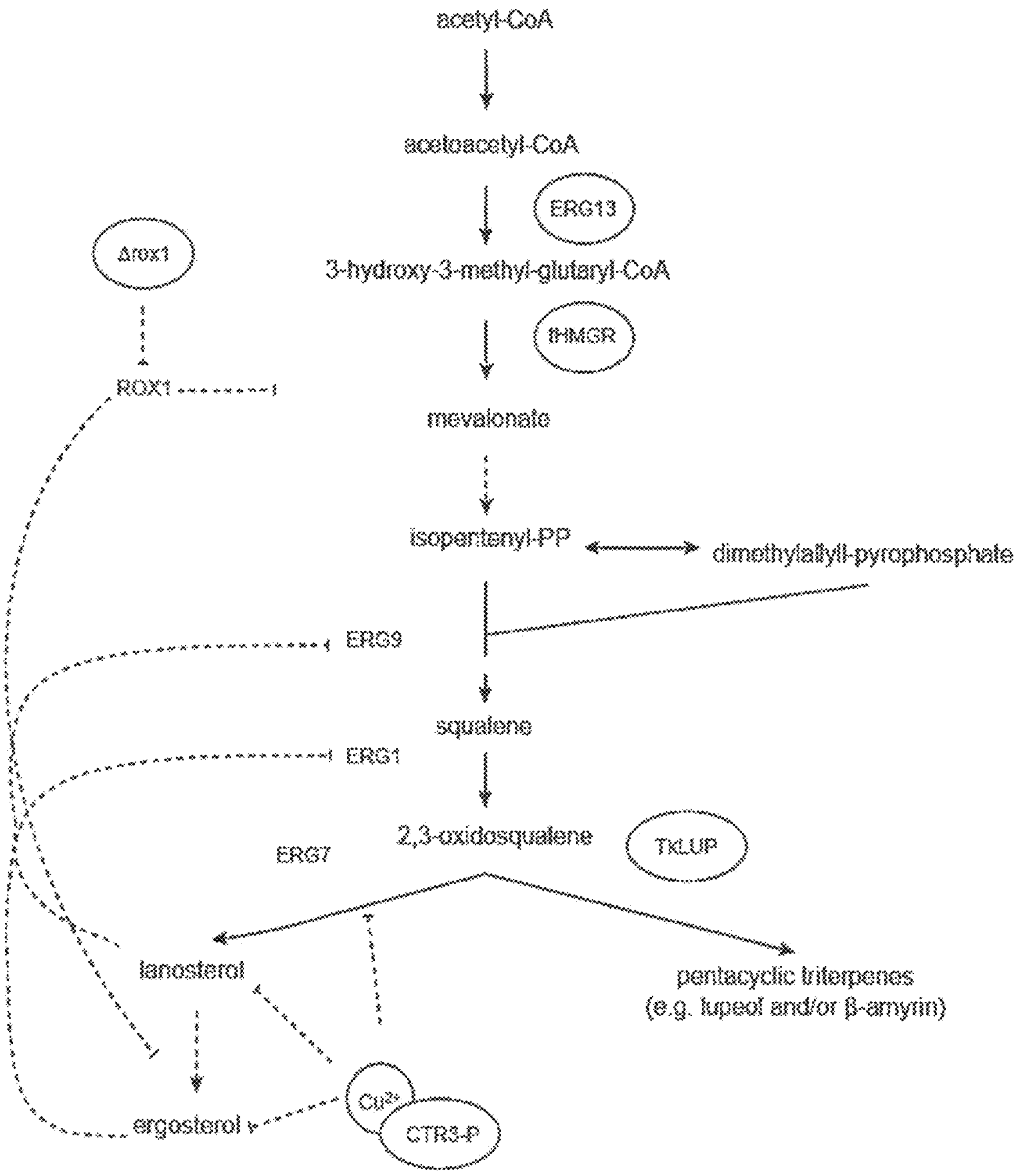

FIG. 11 shows a schematic excerpt of the mevalonate pathway.

Figure 12:
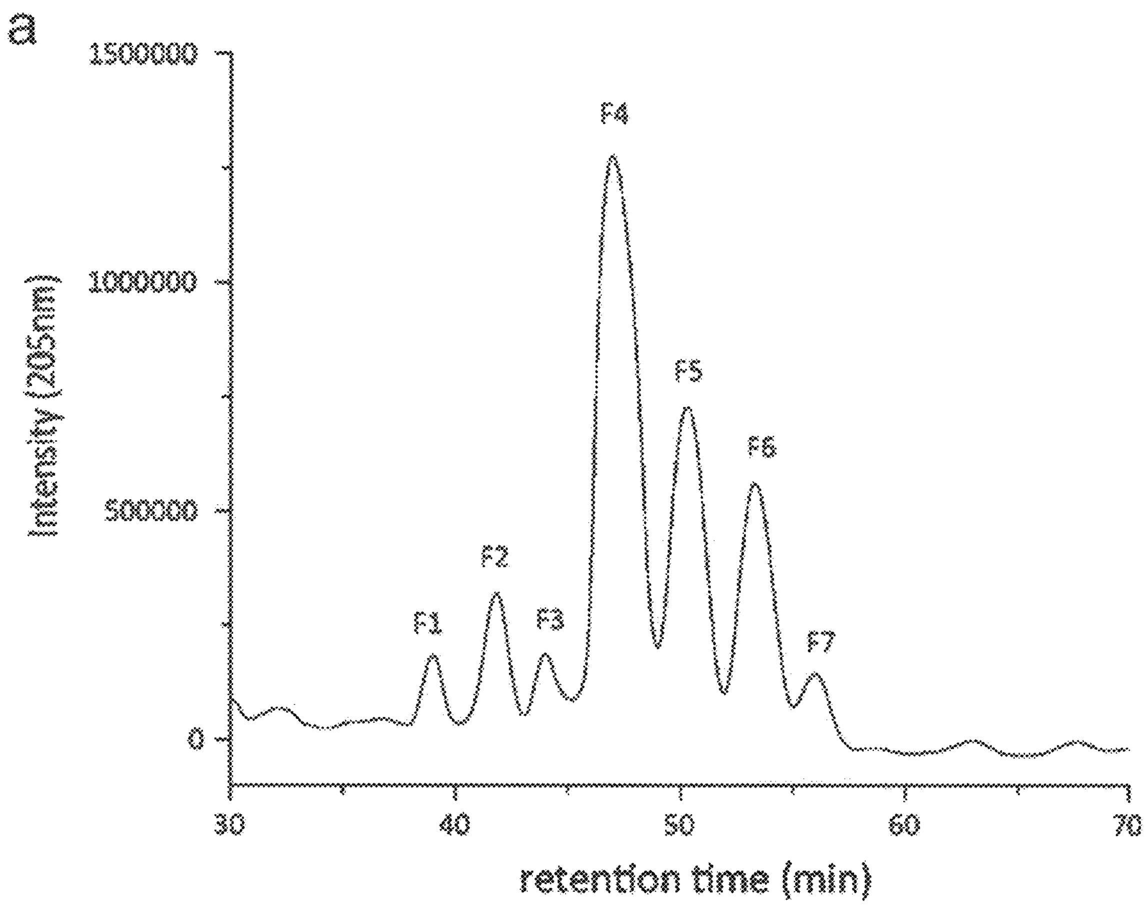
Figure 12:
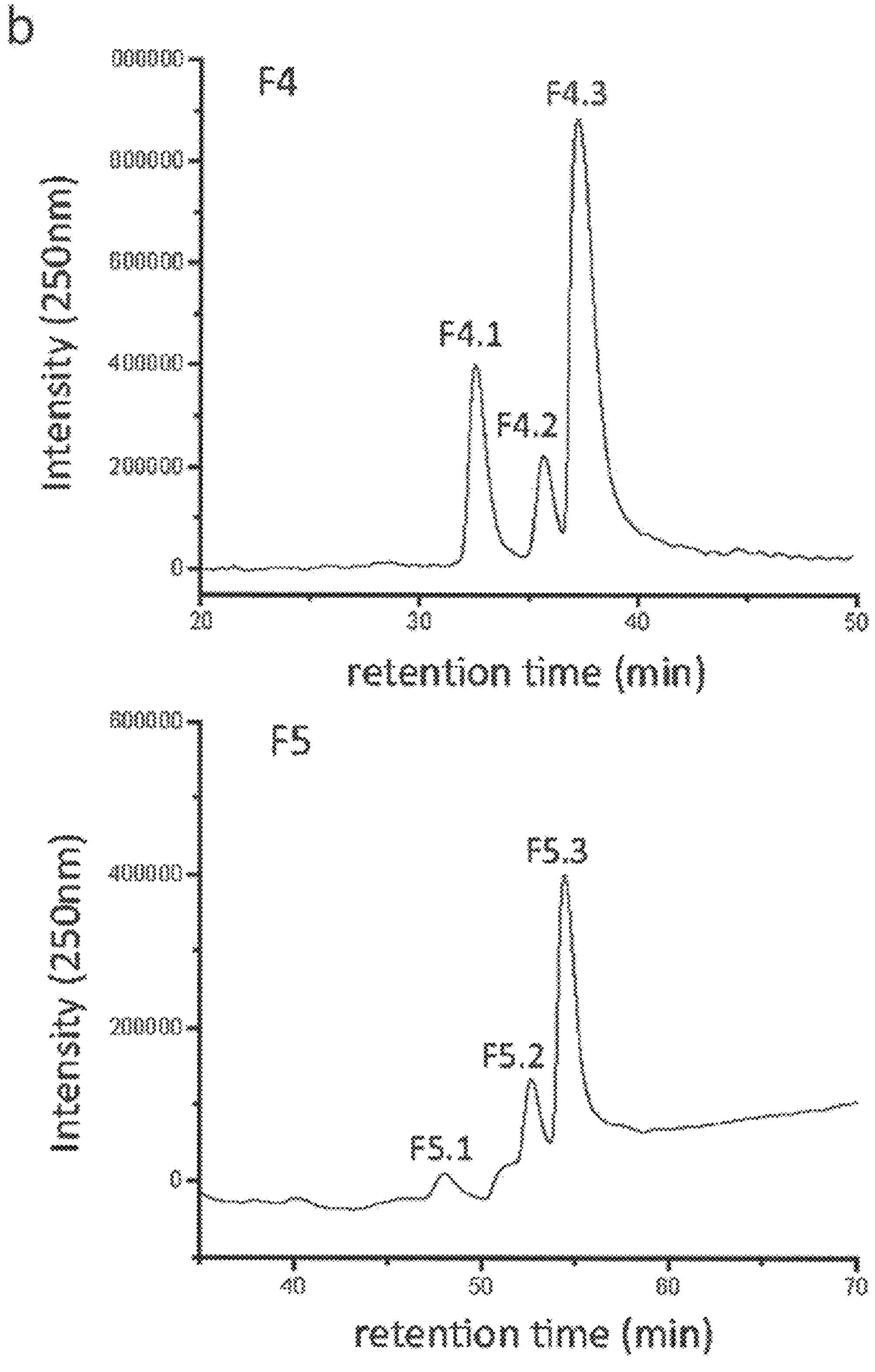
Figure 12:
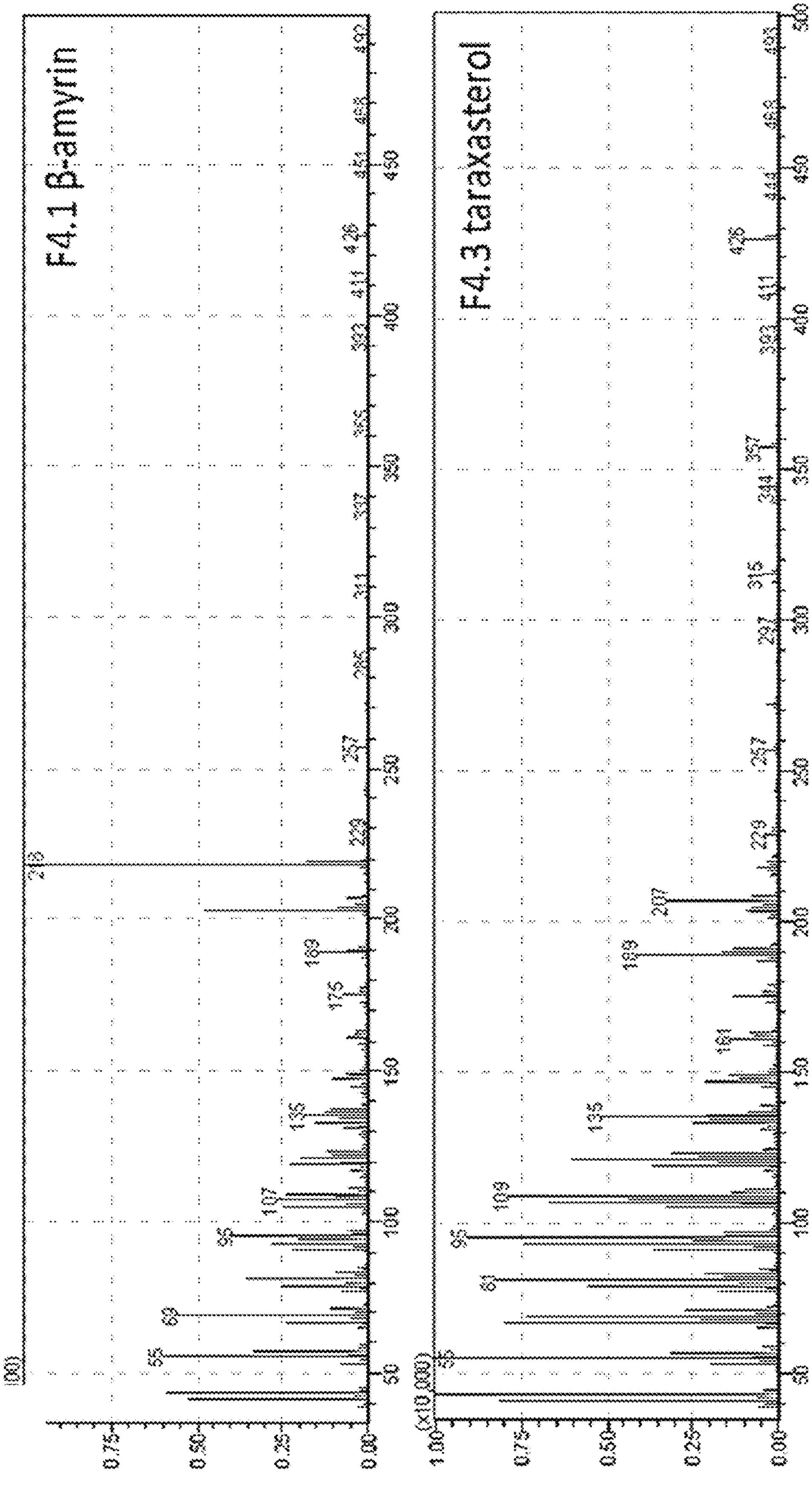
Figure 12C:
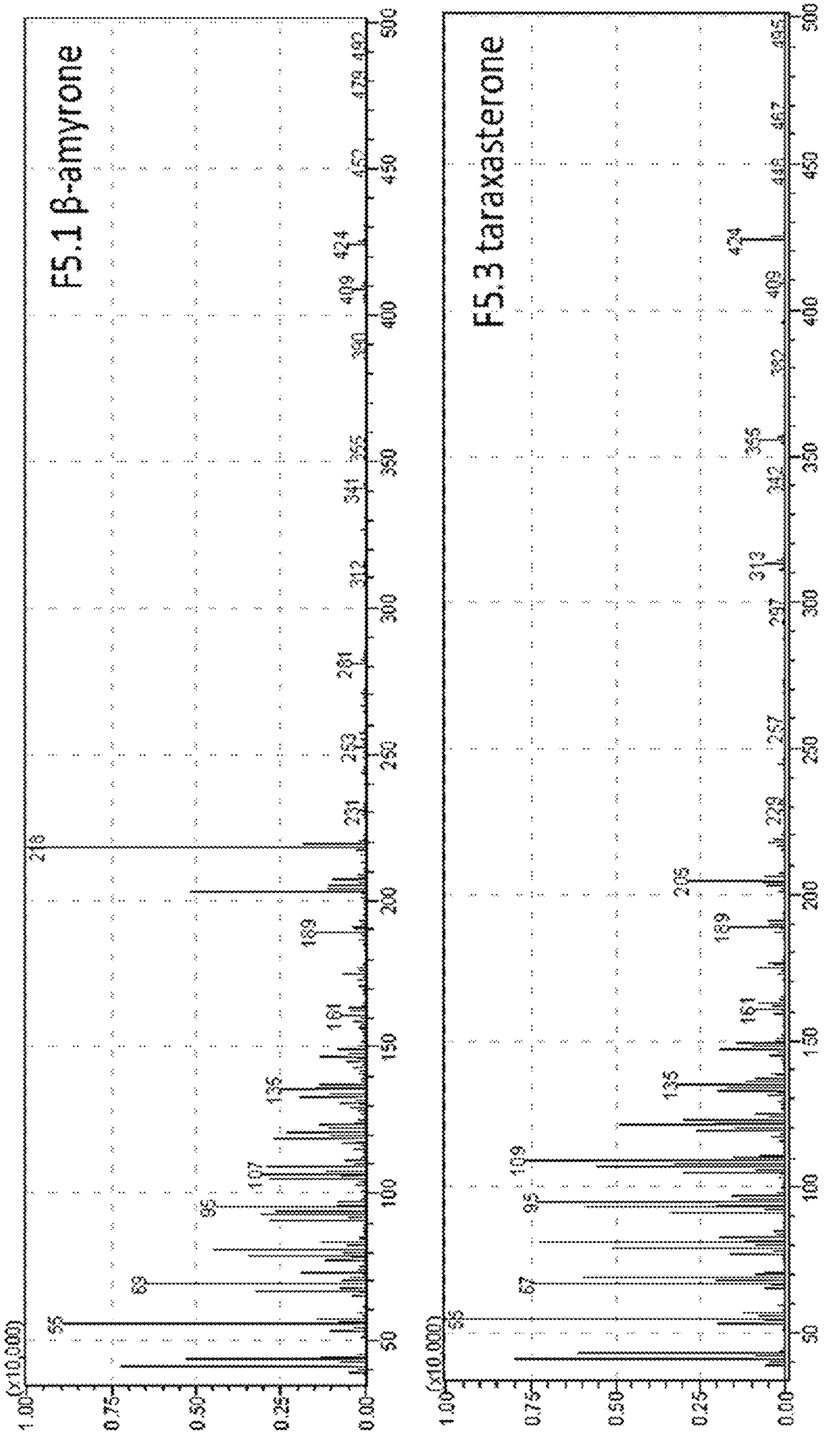
Figure 12:
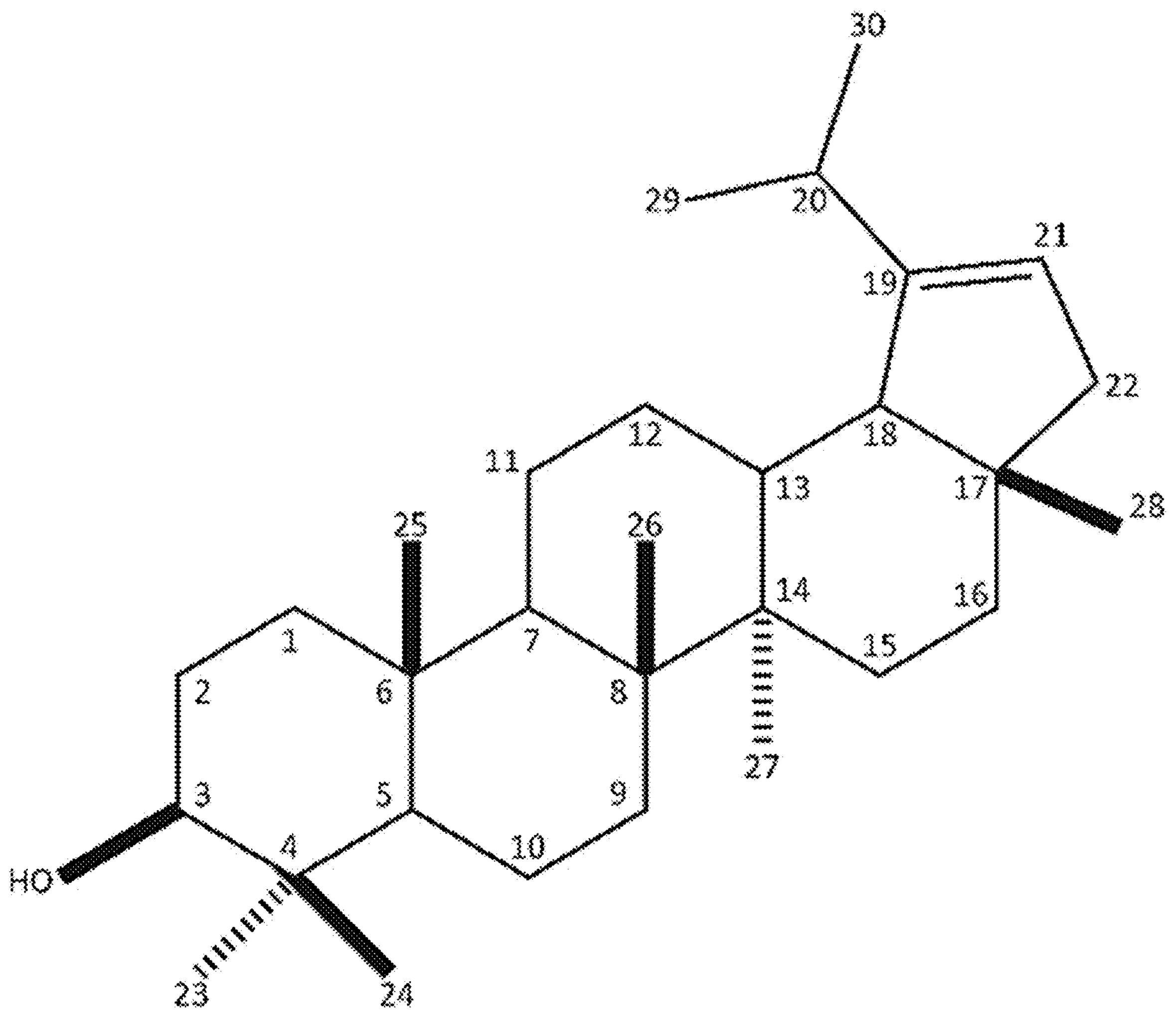
Figure 12D:
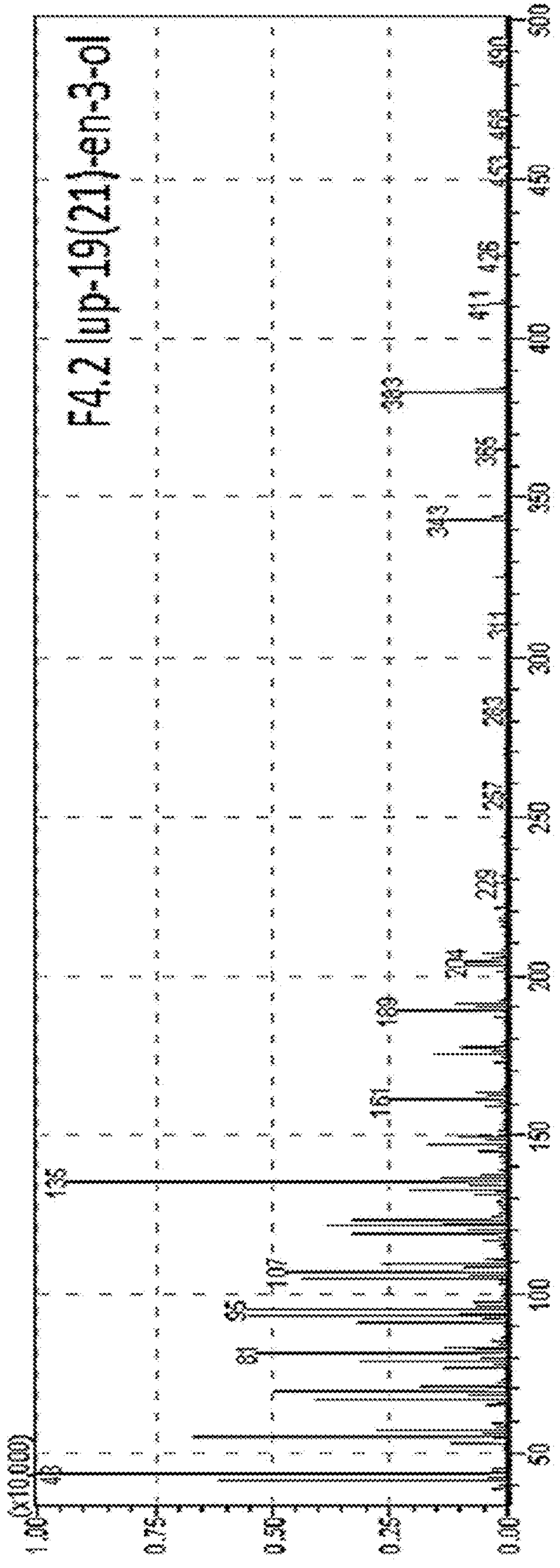
Figure 12:
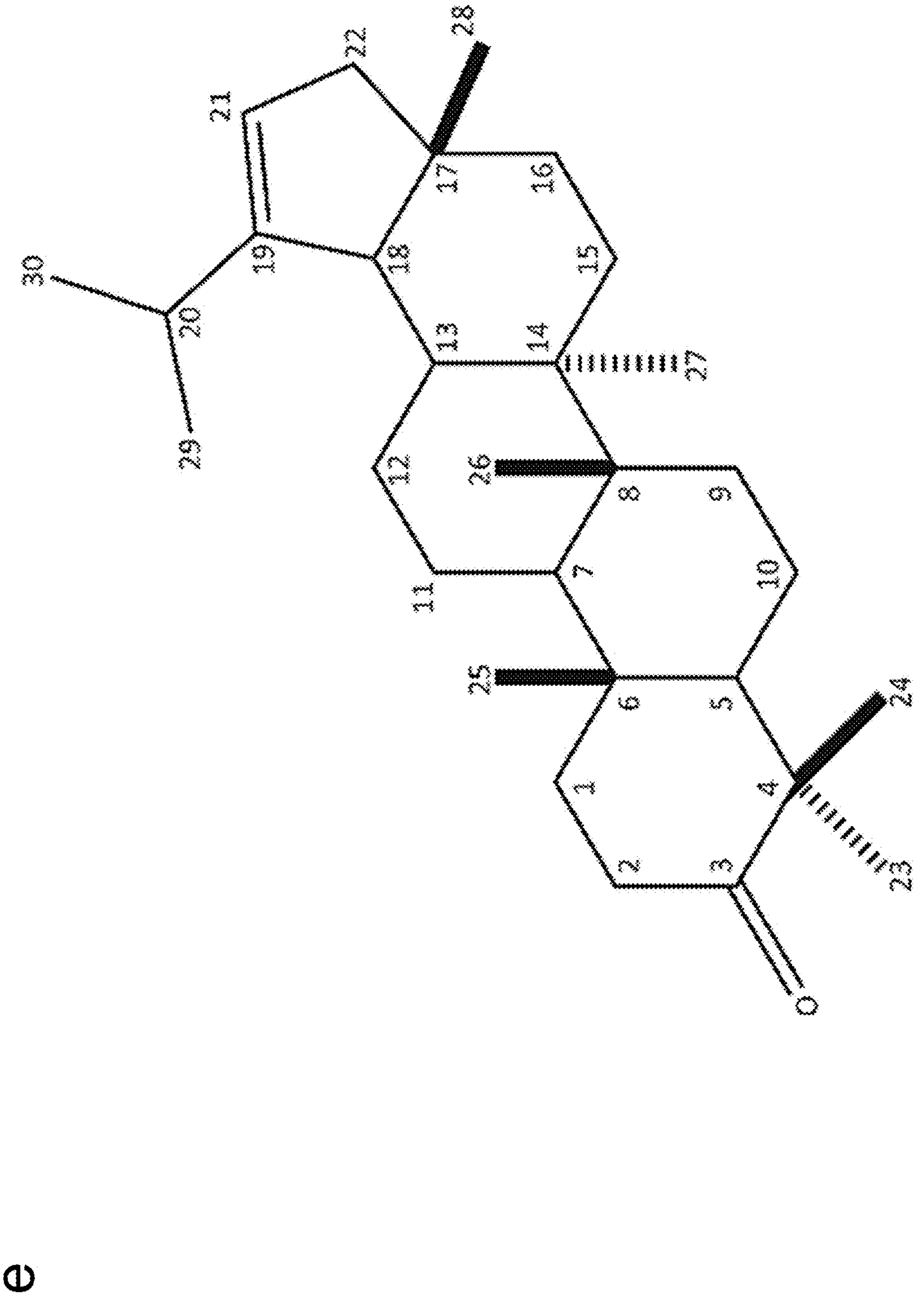
Figure 12E:
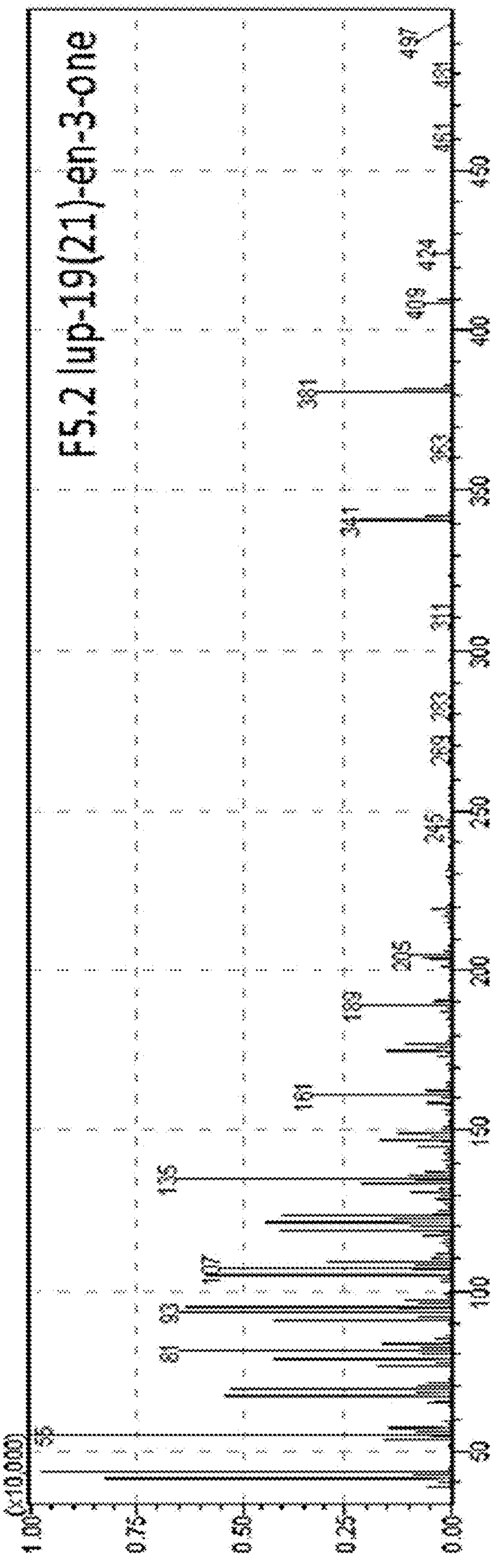

FIG. 12 shows triterpene purification by HPLC. Single triterpenes were separated using an Ultra C18 column (FIG. 12*a*) followed by an Ultra biphenyl column (FIG. 12*b*). FIG. 12*c* shows the MS spectra of β-amyrin and taraxasterol and their ketone derivatives purified from fraction 4 (F4) and 5 (F5), respectively (see Example 7). FIGS. 12*c* to 12*e* show the molecular structure and MS spectra of the newly identified lup-19(21)-en-3-ol and its ketone derivative lup-19 (21)-en-3-one purified from F4 and F5, respectively (see Example 7).

Figure 13:
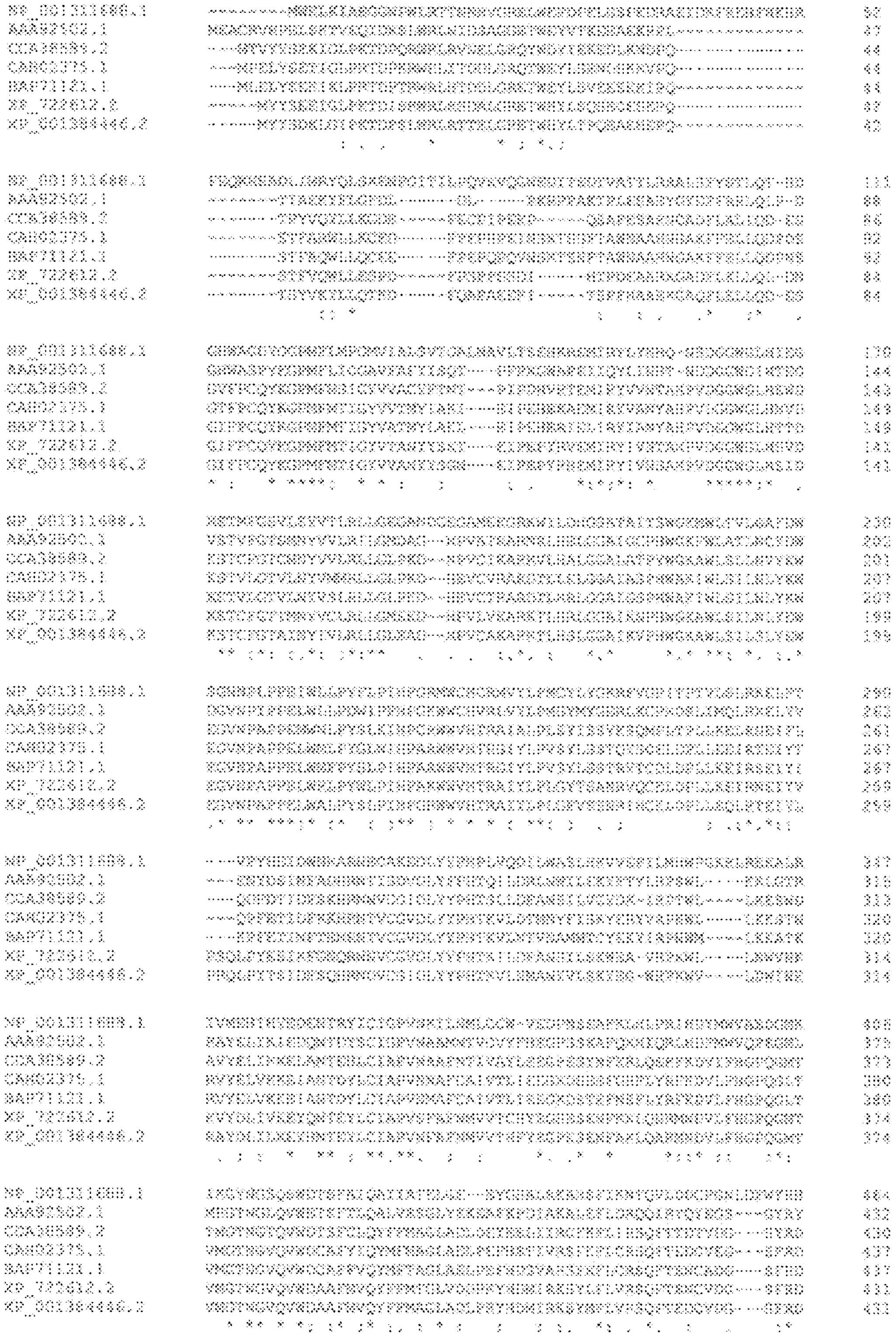

FIG. 13 shows the sequence alignment of the cycloartenol synthase-like from *Nicotiana tabacum* (SEQ ID NO: 21, NP_001311688.1), the lanosterol synthase from *Schizosaccharomyces pombe* (SEQ ID NO: 63, AAA92502.1), the lanosterol synthase from *Pichia pastoris* (SEQ ID NO: 64, CCA38589.2), the lanosterol synthase from *Kluyveromyces lactis* (SEQ ID NO: 65, CAH02375.1), the lanosterol synthase from *Kluyveromyces marxianus* (SEQ ID NO: 66, BAP71121.1), the lanosterol synthase from *Candida albicans* SC5314 (SEQ ID NO: 67, XP_722612.2), and the lanosterol synthase (Oxidosqualene-lanosterol cyclase) (2,3-epoxysqualene-lanosterol cyclase) (OSC) from *Pichia stipitis* (SEQ ID NO: 62: XP_001384446.2). The conditions for this alignment are given further below.

FIG. 14 shows the respective percent identity matrix created from the alignment of FIG. 13.

DETAILED DESCRIPTION OF THE INVENTION

The present invention provides a method of increasing the yield of at least one of oxidosqualene, triterpenes and/or triterpenoids in a host cell comprising:

engineering the host cell to overexpress a 3-hydroxy-3-methylglutaryl-coenzyme A reductase comprising an amino acid sequence as shown in SEQ ID NO: 1 or to overexpress a protein having at least 44% sequence identity with the amino acid sequence as shown in SEQ ID NO: 1, with the proviso that said protein is capable to produce mevalonic acid, and to overexpress a protein comprising at least one amino acid sequence selected from the group consisting of SEQ ID NOs: 2, 3, 4, 5, 6, 7 and 8 or comprising at least one amino acid sequence having at least 44% sequence identity with an amino acid sequence selected from the group consisting of SEQ ID NOs: 2, 3, 4, 5, 6, 7 and 8, with the proviso that said protein is capable to produce at least one of acetoacetyl-CoA, 3-hydroxy-3-methylglutaryl-CoA, mevalonate-5-phosphate, mevalonate-5-pyrophosphate, isopentenyl-5-pyrophosphat, farnesyl-pyrophosphate or dimethylallyl-pyrophosphate, engineering the host cell to express at least one heterologous protein producing the at least one of oxidosqualene, triterpenes and/or triterpenoids, culturing said host cell under suitable conditions to express the at least one of oxidosqualene, triterpenes and/or triterpenoids, and purifying the at least one of oxidosqualene, triterpenes and/or triterpenoids, thereby increasing the yield of the at least one of oxidosqualene, triterpenes and/or triterpenoids in comparison to the host cell prior to engineering.

According to the present invention, the at least one of oxidosqualene, triterpenes and/or triterpenoids is an oxidosqualene, preferably 2,3-oxidosqualene, a sterol, preferably sigmasterol or sitosterol, a triterpene, preferably a pentacyclic triterpene, more preferably lupeol, such as but not limited to, lup-19(21)-en-3-ol and lup-20(29)-en-3-ol, β-amyrin, α-amyrin, taraxasterol, triterpene acetates, acylated triterpenes, saponines, sapogenines, lup-19(21)-en-3-one, lup-20(29)-en-3-one, taraxerol, taraxerone, α-amyrone, β-amyrone, taraxasterone, friedelin, betulin, betulinic acid, cholesterol, ergosterol, lanosterol, glucocorticoids, mineralocorticoids, estrogens, gestagens, cardenolides, bufadienolides, steroid alkaloides, saponins, sapogenins or acylated triterpenes.

This means that in one embodiment, the present invention provides a method of increasing the yield of at least one oxidosqualene, preferably 2,3-oxidosqualene, in a host cell comprising:

engineering the host cell to overexpress a 3-hydroxy-3-methylglutaryl-coenzyme A reductase comprising an amino acid sequence as shown in SEQ ID NO: 1 or to overexpress a protein having at least 44% sequence identity with the amino acid sequence as shown in SEQ ID NO: 1, with the proviso that said protein is capable to produce mevalonic acid, and to overexpress a protein comprising at least one amino acid sequence selected from the group consisting of SEQ ID NOs: 2, 3, 4, 5, 6, 7 and 8 or comprising at least one amino acid sequence having at least 44% sequence identity with an amino acid sequence selected from the group consisting of SEQ ID NOs: 2, 3, 4, 5, 6, 7 and 8, with the proviso that said protein is capable to produce at least one of acetoacetyl-CoA, 3-hydroxy-3-methylglutaryl-CoA, mevalonate-5-phosphate, mevalonate-5-pyrophosphate, isopentenyl-5-pyrophosphate, farnesyl-pyrophosphate or dimethylallyl-pyrophosphate, engineering the host cell to express at least one heterologous protein producing the at least one oxidosqualene, preferably 2,3-oxidosqualene, culturing said host cell under suitable conditions to express the at least one oxidosqualene, preferably 2,3-oxidosqualene, and purifying the at least one oxidosqualene, preferably 2,3-oxidosqualene, thereby increasing the yield of the at least one oxidosqualene, preferably 2,3-oxidosqualene, in comparison to the host cell prior to engineering.

This means that in one embodiment, the present invention provides a method of increasing the yield of 2,3-oxidosqualene, in a host cell comprising:

engineering the host cell to overexpress a 3-hydroxy-3-methylglutaryl-coenzyme A reductase comprising an amino acid sequence as shown in SEQ ID NO: 1 or to overexpress a protein having at least 44% sequence identity with the amino acid sequence as shown in SEQ ID NO: 1, with the proviso that said protein is capable to produce mevalonic acid, and to overexpress a protein comprising at least one amino acid sequence selected from the group consisting of SEQ ID NOs: 2, 3, 4, 5, 6, 7 and 8 or comprising at least one amino acid sequence having at least 44% sequence identity with an amino acid sequence selected from the group consisting of SEQ ID NOs: 2, 3, 4, 5, 6, 7 and 8, with the proviso that said protein is capable to produce at least one of acetoacetyl-CoA, 3-hydroxy-3-methyl-glutaryl-CoA, mevalonate-5-phosphate, mevalonate-5-pyrophosphate, isopentenyl-5-pyrophosphate, farnesyl-pyrophosphate or dimethylallyl-pyrophosphate, engineering the host cell to express at least one heterologous protein producing 2,3-oxidosqualene, culturing said host cell under suitable conditions to express 2,3-oxidosqualene, and purifying 2,3-oxidosqualene, thereby increasing the yield of 2,3-oxidosqualene in comparison to the host cell prior to engineering.

In one embodiment, the present invention provides a method of increasing the yield of lupeol, in a host cell comprising:

engineering the host cell to overexpress a 3-hydroxy-3-methylglutaryl-coenzyme A reductase comprising an amino acid sequence as shown in SEQ ID NO: 1 or to overexpress a protein having at least 44% sequence identity with the amino acid sequence as shown in SEQ ID NO: 1, with the proviso that said protein is capable to produce mevalonic acid, and to overexpress a protein comprising at least one amino acid sequence selected from the group consisting of SEQ ID NOs: 2, 3, 4, 5, 6, 7 and 8 or comprising at least one amino acid sequence having at least 44% sequence identity with an amino acid sequence selected from the group consisting of SEQ ID NOs: 2, 3, 4, 5, 6, 7 and 8, with the proviso that said protein is capable to produce at least one of acetoacetyl-CoA, 3-hydroxy-3-methyl-glutaryl-CoA, mevalonate-5-phosphate, mevalonate-5-pyrophosphate, isopentenyl-5-pyrophosphate, farnesyl-pyrophosphate or dimethylallyl-pyrophosphate, engineering the host cell to express at least one heterologous protein producing lupeol, culturing said host cell under suitable conditions to express lupeol, and purifying lupeol, thereby increasing the yield of lupeol in comparison to the host cell prior to engineering.

This means that in one embodiment, the present invention provides a method of increasing the yield of at least one of squalene, lanosterol and/or ergosterol, in a host cell comprising:

engineering the host cell to overexpress a 3-hydroxy-3-methylglutaryl-coenzyme A reductase comprising an amino acid sequence as shown in SEQ ID NO: 1 or to overexpress a protein having at least 44% sequence identity with the amino acid sequence as shown in SEQ ID NO: 1, with the proviso that said protein is capable to produce mevalonic acid, and to overexpress a protein comprising at least one amino acid sequence selected from the group consisting of SEQ ID NOs: 2, 3, 4, 5, 6, 7 and 8 or comprising at least one amino acid sequence having at least 44% sequence identity with an amino acid sequence selected from the group consisting of SEQ ID NOs: 2, 3, 4, 5, 6, 7 and 8, with the proviso that said protein is capable to produce at least one of acetoacetyl-CoA, 3-hydroxy-3-methyl-glutaryl-CoA, mevalonate-5-phosphate, mevalonate-5-pyrophosphate, isopentenyl-5-pyrophosphate, farnesyl-pyrophosphate or dimethylallyl-pyrophosphate, engineering the host cell to express at least one heterologous protein producing the at least one of squalene, lanosterol and/or ergosterol, culturing said host cell under suitable conditions to express the at least one of squalene, lanosterol and/or ergosterol, and purifying the at least one of squalene, lanosterol and/or ergosterol, thereby increasing the yield of at least one of squalene, lanosterol and/or ergosterol in comparison to the host cell prior to engineering.

The present invention provides a method of increasing the yield of at least one of oxidosqualene, triterpenes and/or triterpenoids in a host cell comprising:

engineering the host cell to overexpress a 3-hydroxy-3-methylglutaryl-coenzyme A reductase comprising an amino acid sequence as shown in SEQ ID NO: 1 or to overexpress a protein having at least 44% sequence identity with the amino acid sequence as shown in SEQ ID NO: 1, with the proviso that said protein is capable to produce mevalonic acid, and to overexpress a protein comprising at least one amino acid sequence selected from the group consisting of SEQ ID NOs: 2, 3, 4, 5, 6, 7 and 8 or comprising at least one amino acid sequence having at least 44% sequence identity with an amino acid sequence selected from the group consisting of SEQ ID NOs: 2, 3, 4, 5, 6, 7 and 8, with the proviso that said protein is capable to produce at least one of acetoacetyl-CoA, 3-hydroxy-3-methyl-glutaryl-CoA, mevalonate-5-phosphate, mevalonate-5-pyrophosphate, isopentenyl-5-pyrophosphate, farnesyl-pyrophosphate or dimethylallyl-pyrophosphate, engineering the host cell to express at least one heterologous protein producing the at least one of oxidosqualene, triterpenes and/or triterpenoids, culturing said host cell under suitable conditions to express the at least one of oxidosqualene, triterpenes and/or triterpenoids, and purifying the at least one of oxidosqualene, triterpenes and/or triterpenoids, thereby increasing the yield of the at least one of oxidosqualene, triterpenes and/or triterpenoids in comparison to the host cell prior to engineering, wherein the at least one of oxidosqualene, triterpenes and/or triterpenoids is not glycyrrhetinic acid. Glycyrrhetinic acid is also known as glycyrrhetic acid or enoxolone and is a pentacyclic triterpenoid derivative of the β-amyrin type obtained from the hydrolysis of glycyrrhizic acid.

The terpenoids, sometimes called isoprenoids, are a large and diverse class of naturally occurring organic chemicals similar to terpenes, derived from five-carbon isoprene units.

Plant terpenoids are used extensively for their aromatic qualities and play a role in traditional herbal remedies.

Terpenoids contribute to the scent of eucalyptus, the flavors of cinnamon, cloves, and ginger, the yellow color in sunflowers, and the red color in tomatoes. Well-known terpenoids include citral, menthol, camphor, salvinorin A in the plant *Salvia divinorum*, the cannabinoids found in cannabis, ginkgolide and bilobalide found in *Ginkgo biloba*, and the curcuminoids found in turmeric and mustard seed.

The steroids and sterols in animals are biologically produced from terpenoid precursors. Sometimes terpenoids are added to proteins, e.g., to enhance their attachment to the cell membrane; this is known as isoprenylation.

Further, triterpenoids are, for example, but are not limited to, saponines, sapogenines, acylated triterpenes, keto derivatives of triterpenes, such as α-amyrone, β-amyrone, taraxasterone and carboxylic acidic derivatives, such as betulinic acid, glycyrrhetinic and boswellic acid.

Triterpenes are a class of chemical compounds composed of three terpene units with the molecular formula $C_{30}H_{48}$. They may also be thought of as consisting of six isoprene units. The triterpenes are subdivided into linear, tetracyclic and pentacyclic triterpenes. Animals, plants and fungi all create triterpenes, with arguably the most important example being squalene as it forms the basis of almost all steroids. Additional examples for triterpenes are certain steroids and cardiac glycosides. Further triterpenes according to the present invention are, for example, but are not limited to, lupeol, lup-19(21)-en-3-ol, lup-20(29)-en-3-ol, β-amyrin, α-amyrin and taraxasterol. Additionally, for example, the triterpenoids saponins are triterpenes, which belong to the saponin group of this class of chemical compounds.

Oxidosqualene, are, for example, but are not limited to, 2,3-oxidosqualene.

According to the present invention, increasing the yield of the at least one of oxidosqualene, triterpenes and/or triterpenoids means in comparison to a host cell which does not overexpress a 3-hydroxy-3-methylglutaryl-coenzyme A reductase comprising an amino acid sequence as shown in SEQ ID NO: 1 or which does not overexpress a protein having at least 44% sequence identity with the amino acid sequence as shown in SEQ ID NO: 1, with the proviso that said protein is capable to produce mevalonic acid, and wherein the host cell does not overexpress a protein comprising at least one amino acid sequence selected from the group consisting of SEQ ID NOs: 2, 3, 4, 5, 6, 7 and 8 or comprising at least one amino acid sequence having at least 44% sequence identity with an amino acid sequence selected from the group consisting of SEQ ID NOs: 2, 3, 4, 5, 6, 7 and 8, with the proviso that said protein is capable to produce at least one of acetoacetyl-CoA, 3-hydroxy-3-methylglutaryl-CoA, mevalonate-5-phosphate, mevalonate-5-pyrophosphate, isopentenyl-5-pyrophosphat, farnesyl-pyrophosphate or dimethylallyl-pyrophosphate.

In a preferred embodiment of the present invention, the method of the present invention comprises engineering the host cell to overexpress 3-hydroxy-3-methylglutaryl-coenzyme A reductase comprising an amino acid sequence as shown in SEQ ID NO: 1. Said 3-hydroxy-3-methylglutaryl-coenzyme A reductase can be abbreviated with tHMGR. It is also known as the catalytic domain of the enzyme HMGR. In a preferred embodiment, the enzyme tHMGR consists of the amino acid sequence as shown in SEQ ID NO: 1.

In a preferred embodiment, in the method according to the present invention the host cell is engineered to overexpress a protein comprising the amino acid sequence of SEQ ID NO: 3 or comprising an amino acid sequence having at least 44% sequence identity with the SEQ ID NO: 3, with the proviso that said protein is capable to produce 3-hydroxy-3-methylglutaryl-CoA.

In a preferred embodiment, in the method according to the present invention, the host cell is engineered to overexpress a protein comprising the amino acid sequence of SEQ ID NO: 2 or comprising an amino acid sequence having at least 44% sequence identity with the SEQ ID NO: 2, with the proviso that said protein is capable to produce acetoacetyl-CoA.

In a preferred embodiment, in the method according to the present invention, the host cell is engineered to overexpress a protein comprising the amino acid sequence of SEQ ID NO: 4 or comprising an amino acid sequence having at least 44% sequence identity with the SEQ ID NO: 4, with the proviso that said protein is capable to produce mevalonate-5-phosphate.

In a preferred embodiment, in the method according to the present invention, the host cell is engineered to overexpress a protein comprising the amino acid sequence of SEQ ID NO: 5 or comprising an amino acid sequence having at least 44% sequence identity with the SEQ ID NO: 5, with the proviso that said protein is capable to produce mevalonate-5-pyrophosphate.

In a preferred embodiment, in the method according to the present invention, the host cell is engineered to overexpress a protein comprising the amino acid sequence of SEQ ID NO: 5 or comprising an amino acid sequence having at least 44% sequence identity with the SEQ ID NO: 6, with the proviso that said protein is capable to produce isopentenyl-5-pyrophosphate.

In a preferred embodiment, in the method according to the present invention, the host cell is engineered to overexpress a protein comprising the amino acid sequence of SEQ ID NO: 7 or comprising an amino acid sequence having at least 44% sequence identity with the SEQ ID NO: 7, with the proviso that said protein is capable to produce farnesyl-pyrophosphate.

In a preferred embodiment, in the method according to the present invention the host cell is engineered to overexpress a protein comprising the amino acid sequence of SEQ ID NO: 8 or comprising an amino acid sequence having at least 44% sequence identity with the SEQ ID NO: 8, with the proviso that said protein is capable to produce dimethylallyl-pyrophosphate.

The present invention also provides a method of increasing the yield of at least one of oxidosqualene, triterpenes and/or triterpenoids in a host cell comprising:

engineering the host cell to overexpress a 3-hydroxy-3-methylglutaryl-coenzyme A reductase comprising an amino acid sequence as shown in SEQ ID NO: 1 and to overexpress a protein comprising at least one amino acid sequence selected from the group consisting of SEQ ID NOs: 2, 3, 4, 5, 6, 7 and 8 or comprising at least one amino acid sequence having at least 44% sequence identity with an amino acid sequence selected from the group consisting of SEQ ID NOs: 2, 3, 4, 5, 6, 7 and 8, with the proviso that said protein is capable to produce at least one of acetoacetyl-CoA, 3-hydroxy-3-methylglutaryl-CoA, mevalonate-5-phosphate, mevalonate-5-pyrophosphate, isopentenyl-5-pyrophosphat, farnesyl-pyrophosphate or dimethylallyl-pyrophosphate, engineering the host cell to express at least one heterologous protein producing the at least one of oxidosqualene, triterpenes and/or triterpenoids, culturing said host cell under suitable conditions to express the at least one of oxidosqualene, triterpenes and/or triterpenoids, and purifying the at least one of oxidosqualene, triterpenes and/or triterpenoids, thereby increasing the yield of the at least one of oxidosqualene, triterpenes and/or triterpenoids in comparison to the host cell prior to engineering.

```
SEQ ID NO: 1:
MVLTNKTVISGSKVKSLSSAQSSSSGPSSSSEEDDSRDIESLDKKIRP

LEELEALLSSGNTKQLKNKEVAALVIHGKLPLYALEKKLGDTTRAVAV

RRKALSILAEAPVLASDRLPYKNYDYDRVFGACCENVIGYMPLPVGVI

GPLVIDGTSYHIPMATTEGCLVASAMRGCKAINAGGGATTVLTKDGMT

RGPVVRFPTLKRSGACKIWLDSEEGQNAIKKAFNSTSRFARLQHIQTC

LAGDLLFMRFRTTTGDAMGMNMISKGVEYSLKQMVEEYGWEDMEVVSV

SGNYCTDKKPAAINWIEGRGKSVVAEATIPGDVVRKVLKSDVSALVEL

NIAKNLVGSAMAGSVGGFNAHAANLVTAVFLALGQDPAQNVESSNCIT

LMKEVDGDLRISVSMPSIEVGTIGGGTVLEPQGAMLDLLGVRGPHATA

PGTNARQLARIVACAVLAGELSLCAALAAGHLVQSHMTHNRKPAEPTK

PNNLDATDINRLKDGSVTCIKS
```

3-Hydroxy-3-methyl-glutaryl-coenzyme A reductase is the rate-controlling enzyme of the mevalonate pathway, the metabolic pathway that produces cholesterol and other isoprenoids. Normally, in mammalian cells this enzyme is suppressed by cholesterol derived from the internalization and degradation of low density lipoprotein (LDL) via the LDL receptor as well as oxidized species of cholesterol. Competitive inhibitors of the reductase induce the expression of LDL receptors in the liver, which in turn increases the catabolism of plasma LDL and lowers the plasma concentration of cholesterol, an important determinant of atherosclerosis. This enzyme is thus the target of the widely available cholesterol-lowering drugs known collectively as the statins.

According to the present invention, overexpression can be achieved in any ways known to a skilled person in the art. In general, it can be achieved by increasing transcription/translation of the gene, e.g. by increasing the copy number of the gene or altering or modifying regulatory sequences or sites associated with expression of a gene. For example, overexpression can be achieved by introducing one or more copies of the polynucleotide encoding the respective protein, or a functional homologue operably linked to the respective regulatory sequences (e.g. a promoter) thereof. For example, the gene can be operably linked to a strong constitutive promoter and/or strong ubiquitous promoter in order to reach high expression levels. Such promoters can be endogenous promoters or recombinant promoters. Alternatively, it is possible to remove regulatory sequences such that expression becomes constitutive. One can substitute the native promoter of a given gene with a heterologous promoter which increases expression of the gene or leads to constitutive expression of the gene. For example, the tHMGR (SEQ ID NO: 32) and/or the respective protein tHMGR comprising the amino acid sequence of SEQ ID NO: 1 may be overexpressed by more than 10%, 20%, 30%, 40%, 50%, 60%, 70%, 80%, 90%, 100%, 200%, or more than 300% by the host cell according to the present invention compared to the host cell prior to engineering and cultured under the same conditions. For example, the at least one protein comprising at least one amino acid sequence selected from the group consisting of SEQ ID NOs: 2, 3, 4, 5, 6, 7 and 8 may be overexpressed by more than 10%, 20%, 30%, 40%, 50%, 60%, 70%, 80%, 90%, 100%, 200%, or more than 300% by the host cell compared to the host cell prior to engineering and cultured under the same conditions. Using inducible promoters additionally makes it possible to increase the expression in the course of host cell cultivation. Furthermore, overexpression can also be achieved by, for example, modifying the chromosomal location of a particular gene, altering nucleic acid sequences adjacent to a particular gene such as a ribosome binding site or transcription terminator, modifying proteins (e.g., regulatory proteins, suppressors, enhancers, transcriptional activators and the like) involved in the transcription of the gene and/or the translation of the gene product, or any other conventional means of deregulating expression of a particular gene routine in the art including, but not limited to, the use of antisense nucleic acid molecules, for example, to block the expression of repressor proteins or deleting or mutating the gene for a transcriptional factor which normally represses expression of the gene desired to be overexpressed. Prolonging the life of the mRNA may also improve the level of expression. For example, certain terminator regions may be used to extend the half-lives of mRNA (Yamanishi et al., Biosci. Biotechnol. Biochem. (2011) 75:2234 and US 2013/0244243). If multiple, copies of genes are included, the genes can either be located in plasmids of variable copy number or be integrated and amplified in the chromosome. If the host cell does not comprise the gene encoding the respective protein for overexpression, it is possible to introduce the gene into the host cell for expression. In this case, "overexpression" means expressing the gene product using any methods known to a skilled person in the art.

According to the present invention, "ERG10" is the gene that encodes the protein acetyl-CoA-acetyltransferase (SEQ ID NO: 2) (also called acetoacetyl-CoA thiolase, ERG10), which catalyzes the formation of acetoacetyl-CoA in the biosynthesis of mevalonate, an intermediate required for the biosynthesis of sterols and non-sterol isoprenoids. Thus, it encodes the cytosolic enzyme that transfers an acetyl group from one acetyl-CoA molecule to another, forming acetoacetyl-CoA and is involved in the first step in mevalonate biosynthesis. The nucleotide sequence of "ERG10" is additionally herein given as SEQ ID NO: 13.

According to the present invention, the term "ERG13" means the gene encoding the enzyme 3-hydroxy-3-methylglutaryl-CoA (HMG-CoA) synthase (ERG13) (SEQ ID NO: 3) that catalyzes the condensation of acetyl-CoA with acetoacetyl-CoA to form 3-hydroxy-3-methylglutaryl-CoA (HMG-CoA), which is the substrate for HMG-CoA reductase. Thus, it is involved in the second step of the mevalonate biosynthesis. The nucleotide sequence of "ERG13" is herein additionally given as SEQ ID NO: 14.

In the context of the present invention, the term "ERG12" means the gene encoding the protein mevalonate kinase (ERG12) (SEQ ID NO: 4), which catalyzes the reaction of mevalonic acid with ATP to create mevalonate-5-phosphate. The nucleotide sequence of "ERG12" is herein additionally given as SEQ ID NO: 15.

In the present invention, the term "ERG8" means the gene encoding the protein phosphomevalonate kinase (ERG8) (SEQ ID NO: 5), which is an essential cytosolic enzyme that acts in the biosynthesis of isoprenoids and sterols, including ergosterol, from mevalonate. This protein catalyzes the reaction of mevalonate-5-phosphate with ATP to create mevalonate-5-pyrophosphate. The nucleotide sequence of "ERG8" is herein additionally given as SEQ ID NO: 16.

In the context of the present invention, the term "ERG19" means the gene encoding the protein mevalonate-5-pyrophosphate decarboxylase (ERG19) (SEQ ID NO: 6), which is an essential enzyme involved in the biosynthesis of isoprenoids and sterols, including ergosterol and acts as a homodimer. The reaction, which is catalysed by the mevalonate-5-pyrophosphate decarboxylase, forms isopentenyl-5-pyrophosphate. The gene "ERG19" is also known under the name "mvd1". The nucleotide sequence of "ERG19" is herein additionally given as SEQ ID NO: 17.

According to the present invention, the term "ERG20" means the gene encoding the protein farnesyl pyrophosphate synthetase (ERG20) (SEQ ID NO: 7). This enzyme has both dimethylallyltranstransferase and geranyltranstransferase activities and catalyzes the formation of C15 farnesyl pyrophosphate units for isoprenoid and sterol biosynthesis. Said gene ERG20 is also known under the expressions "bot3", "fds1" and "fpp1". The nucleotide sequence of "ERG20" is herein additionally given as SEQ ID NO: 18.

The term "ID11" as used in the present invention is the gene encoding the isopentenylpyrophosphate isomerase (ID11) (SEQ ID NO: 8), an isomerase that catalyzes the conversion of the relatively un-reactive isopentenyl pyrophosphate (IPP) to the more-reactive electrophile dimethylallyl pyrophosphate (DMAPP) This isomerization is a key step in the biosynthesis of isoprenoids through the mevalonate pathway. The nucleotide sequence of "ID11" is herein additionally given as SEQ ID NO: 19.

According to the present invention, genes are always marked herein with capital letters, while mutated/knockout alleles are marked in small letters.

In a preferred embodiment of the present invention, the method comprises engineering the host cell to overexpress a protein having at least 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% sequence identity with the amino acid sequence of the 3-hydroxy-3-methylglutaryl-coenzyme A reductase as shown in SEQ ID NO: 1. Said protein is capable to produce mevalonic acid.

"Sequence identity" or "% identity" as used in the context of the present invention refers to the percentage of residue matches between at least two polypeptide or polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences. For purposes of the present invention, the sequence identity between two amino acid sequences or nucleotide sequences is determined using the default settings of Clustal Omega (www.ebi.ac.uk/Tools/msa/clustalo/). Input parameters were: program: clustalo; version 1.2.4; output guide tree: false; output distance matrix: false; dealign input sequences: false; mBed-like clustering guide tree: true; mBed-like clustering iteration: true; number of iterations: 0; maximum guide tree iterations:-1; maximum HMM iterations:-1; output alignment format: clustal_num; output order: aligned; sequence type: protein.

Accordingly, in a further aspect of the present invention is provided a method of increasing the yield of at least one of oxidosqualene, triterpenes and/or triterpenoids in a host cell comprising:

engineering the host cell to overexpress a protein having at least 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% sequence identity with the amino acid sequence as shown in SEQ ID NO: 1, with the proviso that said protein is capable to produce mevalonic acid, and to overexpress a protein comprising at least one amino acid sequence selected from the group consisting of SEQ ID NOs: 2, 3, 4, 5, 6, 7 and 8 or comprising at least one amino acid sequence having at least 44% sequence identity with an amino acid sequence selected from the group consisting of SEQ ID NOs: 2, 3, 4, 5, 6, 7 and 8, with the proviso that said protein is capable to produce at least one of acetoacetyl-CoA, 3-hydroxy-3-methylglutaryl-CoA, mevalonate-5-phosphate, mevalonate-5-pyrophosphate, isopentenyl-5-pyrophosphat, farnesyl-pyrophosphate or dimethylallyl-pyrophosphate, engineering the host cell to express at least one heterologous protein producing the at least one of oxidosqualene, triterpenes and/or triterpenoids, culturing said host cell under suitable conditions to express the at least one of oxidosqualene, triterpenes and/or triterpenoids, and purifying the at least one of oxidosqualene, triterpenes and/or triterpenoids, thereby increasing the yield of the at least one of oxidosqualene, triterpenes and/or triterpenoids in comparison to the host cell prior to engineering.

Increasing the yield of the at least one of oxidosqualene, triterpenes and/or triterpenoids means here in comparison to a host cell, which does not overexpress a protein having at least 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% sequence identity with the amino acid sequence as shown in SEQ ID NO: 1, with the proviso that said protein is capable to produce mevalonic acid, and which does not overexpress a protein comprising at least one amino acid sequence selected from the group consisting of SEQ ID NOs: 2, 3, 4, 5, 6, 7 and 8 or comprising at least one amino acid sequence having at least 44% sequence identity with an amino acid sequence selected from the group consisting of SEQ ID NOs: 2, 3, 4, 5, 6, 7 and 8, with the proviso that said protein is capable to produce at least one of acetoacetyl-CoA, 3-hydroxy-3-methylglutaryl-CoA, mevalonate-5-phosphate, mevalonate-5-pyrophosphate, isopentenyl-5-pyrophosphat, farnesyl-pyrophosphate or dimethylallyl-pyrophosphate.

In a preferred embodiment of the present invention, the method comprises engineering the host cell to overexpress a protein comprising at least one amino acid sequence having at least 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% sequence identity with an amino acid sequence selected from the group consisting of SEQ ID NOs: 2, 3, 4, 5, 6, 7 and 8, with the proviso that said protein is capable to produce at least one of acetoacetyl-CoA, 3-hydroxy-3-methylglutaryl-CoA, mevalonate-5-phosphate, mevalonate-5-pyrophosphate, isopentenyl-5-pyrophosphat, farnesyl-pyrophosphate or dimethylallyl-pyrophosphate.

This means, a further aspect of the present invention provides a method of increasing the yield of at least one of oxidosqualene, triterpenes and/or triterpenoids in a host cell comprising:

engineering the host cell to overexpress 3-hydroxy-3-methylglutaryl-coenzyme A reductase comprising an amino acid sequence as shown in SEQ ID NO: 1 or to overexpress a protein comprising at least 44% sequence identity with the amino acid sequence as shown in SEQ ID NO: 1, with the proviso that said protein is capable to produce mevalonic acid, and to overexpress a protein comprising at least one amino acid sequence having at least 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% sequence identity with an amino acid sequence selected from the group consisting of SEQ ID NOs: 2, 3, 4, 5, 6, 7 and 8, with the proviso that said protein is capable to produce at least one of acetoacetyl-CoA, 3-hydroxy-3-methylglutaryl-CoA, mevalonate-5-phosphate, mevalonate-5-pyrophosphate, isopentenyl-5-pyrophosphat, farnesyl-pyrophosphate or dimethylallyl-pyrophosphate, engineering the host cell to express at least one heterologous protein producing the at least one of oxidosqualene, triterpenes and/or triterpenoids, culturing said host cell under suitable conditions to express the at least one of oxidosqualene, triterpenes and/or triterpenoids, and purifying the at least one of oxidosqualene, triterpenes and/or triterpenoids, thereby increasing the yield of the at least one of oxidosqualene, triterpenes and/or triterpenoids in comparison to the host cell prior to engineering.

Increasing the yield of the at least one of oxidosqualene, triterpenes and/or triterpenoids means in this embodiment in comparison to a host cell which does not overexpress 3-hydroxy-3-methylglutaryl-coenzyme A reductase comprising an amino acid sequence as shown in SEQ ID NO: 1 or which does not overexpress a protein comprising at least 44% sequence identity with the amino acid sequence as shown in SEQ ID NO: 1, with the proviso that said protein is capable to produce mevalonic acid, and which does not overexpress a protein comprising at least one amino acid sequence having at least 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% sequence identity with an amino acid sequence selected from the group consisting of SEQ ID NOs: 2, 3, 4, 5, 6, 7 and 8, with the proviso that said protein is capable to produce at least one of acetoacetyl-CoA, 3-hydroxy-3-methylglutaryl-CoA, mevalonate-5-phosphate, mevalonate-5-pyrophosphate, isopentenyl-5-pyrophosphat, farnesyl-pyrophosphate or dimethylallyl-pyrophosphate.

In a further preferred embodiment, the invention provides a method of increasing the yield of at least one of oxidosqualene, triterpenes and/or triterpenoids in a host cell comprising:

engineering the host cell to overexpress a protein having at least 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% sequence identity with the amino acid sequence of the 3-hydroxy-3-methylglutaryl-coenzyme A reductase as shown in SEQ ID NO: 1, with the proviso that said protein is capable to produce mevalonic acid, and to overexpress a protein comprising at least one amino acid sequence having at least 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% sequence identity with an amino acid sequence selected from the group consisting of SEQ ID NOs: 2, 3, 4, 5, 6, 7 and 8, with the proviso that said protein is capable to produce at least one of acetoacetyl-CoA, 3-hydroxy-3-methylglutaryl-CoA, mevalonate-5-phosphate, mevalonate-5-pyrophosphate, isopentenyl-5-pyrophosphat, farnesyl-pyrophosphate or dimethylallyl-pyrophosphate, engineering the host cell to express at least one heterologous protein producing the at least one of oxidosqualene, triterpenes and/or triterpenoids, culturing said host cell under suitable conditions to express the at least one of oxidosqualene, triterpenes and/or triterpenoids, and purifying the at least one of oxidosqualene, triterpenes and/or triterpenoids, thereby increasing the yield of the at least one of oxidosqualene, triterpenes and/or triterpenoids in comparison to the host cell prior to engineering.

Increasing the yield of the at least one of oxidosqualene, triterpenes and/or triterpenoids means in this specific embodiment an increase in comparison to a host cell which does not overexpress a protein having at least 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% sequence identity with the amino acid sequence of the 3-hydroxy-3-methylglutaryl-coenzyme A reductase as shown in SEQ ID NO: 1, with the proviso that said protein is capable to produce mevalonic acid, and which does not overexpress a protein comprising at least one amino acid sequence having at least 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% sequence identity with an amino acid sequence selected from the group consisting of SEQ ID NOs: 2, 3, 4, 5, 6, 7 and 8, with the proviso that said protein is capable to produce at least one of acetoacetyl-CoA, 3-hydroxy-3-methylglutaryl-CoA, mevalonate-5-phosphate, mevalonate-5-pyrophosphate, isopentenyl-5-pyrophosphat, farnesyl-pyrophosphate or dimethylallyl-pyrophosphate.

In a preferred embodiment of the method according to the present invention, the host cell is engineered to overexpress the protein comprising the amino acid sequence of SEQ ID NO: 3 or comprising an amino acid sequence having at least 44% sequence identity with the SEQ ID NO: 3, with the proviso that said protein is capable to produce 3-hydroxy-3-methyl-glutaryl-CoA.

In a preferred embodiment of the method according to the present invention, the method additionally comprises engineering the host cell to knock out at least one locus selected from the group consisting of ROX1 (SEQ ID NO: 25), BTS1 (SEQ ID NO: 54), YPL62W (SEQ ID NO: 55), DOS2 (SEQ ID NO: 56), YER134C (SEQ ID NO: 57), VBA5 (SEQ ID NO: 58), YNR063W (SEQ ID NO: 59), YJL064W (SEQ ID NO: 60) and YGR259C (SEQ ID NO: 61).

In a preferred embodiment of the method according to the present invention, the method additionally comprises engineering the host cell to knock out at least one locus selected from the group consisting of ROX1 (SEQ ID NO: 25), YPL062W (SEQ ID NO: 55), DOS2 (SEQ ID NO: 56), YER134C (SEQ ID NO: 57), VBA5 (SEQ ID NO: 58), YNR063W (SEQ ID NO: 59), YJL064W (SEQ ID NO: 60) and YGR259C (SEQ ID NO: 61).

Particularly, it is even more preferred that the method additionally comprises engineering the host cell to knock out the ROX1 (SEQ ID NO: 25) locus.

A particularly preferred method according to the present invention comprises:

engineering the host cell to overexpress a 3-hydroxy-3-methylglutaryl-coenzyme A reductase comprising an amino acid sequence as shown in SEQ ID NO: 1 or to overexpress a protein comprising at least 44% sequence identity with the amino acid sequence as shown in SEQ ID NO: 1, with the proviso that said protein is capable to produce mevalonic acid, and to overexpress a protein comprising at least one amino acid sequence selected from the group consisting of SEQ ID NOs: 2, 3, 4, 5, 6, 7 and 8 or comprising at least one amino acid sequence with at least 44% sequence identity with an amino acid sequence selected from the group consisting of SEQ ID NOs: 2, 3, 4, 5, 6, 7 and 8, with the proviso that said protein is capable to produce at least one of acetoacetyl-CoA, 3-hydroxy-3-methyl-glutaryl-CoA, mevalonate-5-phosphate, mevalonate-5-pyrophosphate, isopentenyl-5-pyrophosphat, farnesyl-pyrophosphate or dimethylallyl-pyrophosphate, and engineering the host cell to knock out the ROX1 (SEQ ID NO: 25) locus, engineering the host cell to express at least one heterologous protein producing the at least one of oxidosqualene, triterpenes and/or triterpenoids, culturing said host cell under suitable conditions to express the at least one of oxidosqualene, triterpenes and/or triterpenoids, and purifying the at least one of oxidosqualene, triterpenes and/or triterpenoids, thereby increasing the yield of the at least one of oxidosqualene, triterpenes and/or triterpenoids in comparison to the host cell prior to engineering.

Increasing the yield of the at least one of oxidosqualene, triterpenes and/or triterpenoids means in this specific embodiment an increase in comparison to a host cell which does not overexpress a 3-hydroxy-3-methylglutaryl-coenzyme A reductase comprising an amino acid sequence as shown in SEQ ID NO: 1 or which does not overexpress a protein comprising at least 44% sequence identity with the amino acid sequence as shown in SEQ ID NO: 1, with the proviso that said protein is capable to produce mevalonic acid, and wherein the host cell does not overexpress a protein comprising at least one amino acid sequence selected from the group consisting of SEQ ID NOs: 2, 3, 4, 5, 6, 7 and 8 or comprising at least one amino acid sequence with at least 44% sequence identity with an amino acid sequence selected from the group consisting of SEQ ID NOs: 2, 3, 4, 5, 6, 7 and 8, with the proviso that said protein is capable to produce at least one of acetoacetyl-CoA, 3-hydroxy-3-methylglutaryl-CoA, mevalonate-5-phosphate, mevalonate-5-pyrophosphate, isopentenyl-5-pyrophosphate, farnesyl-pyrophosphate or dimethylallyl-pyrophosphate, and which does not knock out the ROX1 (SEQ ID NO: 25) locus.

The present invention also provides in one embodiment a method of increasing the yield of at least one of squalene, lanosterol and/or ergosterol in a host cell comprising:

engineering the host cell to overexpress a 3-hydroxy-3-methylglutaryl-coenzyme A reductase comprising an amino acid sequence as shown in SEQ ID NO: 1 or to overexpress a protein having at least 44% sequence identity with the amino acid sequence as shown in SEQ ID NO: 1, with the proviso that said protein is capable to produce mevalonic acid, and to overexpress a protein comprising at least one amino acid sequence selected from the group consisting of SEQ ID NOs: 2, 3, 4, 5, 6, 7 and 8 or comprising at least one amino acid sequence having at least 44% sequence identity with an amino acid sequence selected from the group consisting of SEQ ID NOs: 2, 3, 4, 5, 6, 7 and 8, with the proviso that said protein is capable to produce at least one of acetoacetyl-CoA, 3-hydroxy-3-methyl-glutaryl-CoA, mevalonate-5-phosphate, mevalonate-5-pyrophosphate, isopentenyl-5-pyrophosphate, farnesyl-pyrophosphate or dimethylallyl-pyrophosphate, and engineering the host cell to knock out the ROX1 (SEQ ID NO: 25) locus, engineering the host cell to express at least one heterologous protein producing the at least one of squalene, lanosterol and/or ergosterol, culturing said host cell under suitable conditions to express the at least one of squalene, lanosterol and/or ergosterol, and purifying the at least one of squalene, lanosterol and/or ergosterol, thereby increasing the yield of the at least one of squalene, lanosterol or ergosterol in comparison to the host cell prior to engineering.

Increasing the yield of the at least one of squalene, lanosterol or ergosterol means in this specific embodiment an increase in comparison to a host cell which does not overexpress a 3-hydroxy-3-methylglutaryl-coenzyme A reductase comprising an amino acid sequence as shown in SEQ ID NO: 1 or which does not overexpress a protein comprising at least 44% sequence identity with the amino acid sequence as shown in SEQ ID NO: 1, with the proviso that said protein is capable to produce mevalonic acid, and wherein the host cell does not overexpress a protein comprising at least one amino acid sequence selected from the group consisting of SEQ ID NOs: 2, 3, 4, 5, 6, 7 and 8 or comprising at least one amino acid sequence with at least 44% sequence identity with an amino acid sequence selected from the group consisting of SEQ ID NOs: 2, 3, 4, 5, 6, 7 and 8, with the proviso that said protein is capable to produce at least one of acetoacetyl-CoA, 3-hydroxy-3-methylglutaryl-CoA, mevalonate-5-phosphate, mevalonate-5-pyrophosphate, isopentenyl-5-pyrophosphate, farnesyl-pyrophosphate or dimethylallyl-pyrophosphate, and which does not knock out the ROX1 (SEQ ID NO: 25) locus.

In a preferred embodiment, the method according to the present invention comprises additionally engineering the host cell to repress a lanosterolsynthase (ERG7) comprising an amino acid sequence as shown in SEQ ID NO: 9 having at least 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% sequence identity with the amino acid sequence as shown in SEQ ID NO: 9. The respective nucleotide sequence of the lanosterolsynthase is further given herein as shown in SEQ ID NO: 20. Preferably, said repression of the polynucleotide encoding the lanosterolsynthase (ERG7) or the repression of the protein lanosterolsynthase itself is carried out by the insertion of the CTR3-promoter (SEQ ID NO: 42) and/or the addition of coppersulfate $CuSO_4$.

In this preferred embodiment, the added amount of coppersulfate for repressing the lanosterolsynthase (ERG7) may be at least 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370 or 375 mM $CuSO_4$, preferably at least 150 mM $CuSO_4$.

Lanosterol synthase is an oxidosqualene cyclase (OSC) enzyme that converts (S)-2,3-oxidosqualene to a protosterol cation and finally to lanosterol. Lanosterol is a key four-ringed intermediate in cholesterol biosynthesis. In humans, lanosterol synthase is encoded by the LSS gene.

Preferably, the repressed lanosterol synthase (or the homologous cycloartenol synthase in plants) according to the present invention is from *Saccharomyces cerevisiae, Nicotiana benthamiana, Pichia pastoris, Pichia methanolica, Schizosaccharomyces pombe, Kluyveromyces lactis, Kluyveromyces marxianus, Pichia stipitis, Candida albicans, Candida utilis* and BY2 cells.

In a preferred embodiment, the method according to the present invention comprises additionally engineering the host cell to repress a cycloartenolsynthase comprising an amino acid sequence as shown in SEQ ID NO: 21 or an amino acid sequence having at least 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100% sequence identity with the amino acid sequence as shown in SEQ ID NO: 21. The nucleotide sequence of the cycloartenolsynthase is further given herein as shown in SEQ ID NO: 22.

Consequently, a particularly preferred method according to the present invention comprises:

engineering the host cell to overexpress a 3-hydroxy-3-methylglutaryl-coenzyme A reductase comprising an amino acid sequence as shown in SEQ ID NO: 1 or to overexpress a protein comprising at least 44% sequence identity with the amino acid sequence as shown in SEQ ID NO: 1, with the proviso that said protein is capable to produce mevalonic acid, and to overexpress a protein comprising at least one amino acid sequence selected from the group consisting of SEQ ID NOs: 2, 3, 4, 5, 6, 7 and 8 or comprising at least one amino acid sequence having at least 44% sequence identity with an amino acid sequence selected from the group consisting of SEQ ID NOs: 2, 3, 4, 5, 6, 7 and 8, with the proviso that said protein is capable to produce at least one of acetoacetyl-CoA, 3-hydroxy-3-methylglutaryl-CoA, mevalonate-5-phosphate, mevalonate-5-pyrophosphate, isopentenyl-5-pyrophosphate, farnesyl-pyrophosphate or dimethylallyl-pyrophosphate, and engineering the host cell to knock out the ROX1 (SEQ ID NO: 25) locus, and engineering the host cell to repress a lanosterolsynthase (ERG7) having an amino acid sequence as shown in SEQ ID NO: 9 or an amino acid sequence having at least 34% sequence identity with the SEQ ID NO: 9, with the proviso that said protein is capable to produce lanosterol, engineering the host cell to express at least one heterologous protein producing the at least one of oxidosqualene, triterpenes and/or triterpenoids, culturing said host cell under suitable conditions to express the at least one of oxidosqualene, triterpenes and/or triterpenoids, and purifying the at least one of oxidosqualene, triterpenes and/or triterpenoids, thereby increasing the yield of the at least one of oxidosqualene, triterpenes and/or triterpenoids in comparison to the host cell prior to engineering.

Increasing the yield of the protein of the mevalonate pathway means in this specific embodiment an increase in comparison to a host cell which does not overexpress a 3-hydroxy-3-methylglutaryl-coenzyme A reductase comprising an amino acid sequence as shown in SEQ ID NO: 1 or which does not overexpress a protein comprising at least 44% sequence identity with the amino acid sequence as shown in SEQ ID NO: 1, with the proviso that said protein is capable to produce mevalonic acid, and which does not overexpress a protein comprising at least one amino acid sequence selected from the group consisting of SEQ ID NOs: 2, 3, 4, 5, 6, 7 and 8 or comprising at least one amino acid sequence with at least 44% sequence identity with an amino acid sequence selected from the group consisting of SEQ ID NOs: 2, 3, 4, 5, 6, 7 and 8, with the proviso that said protein is capable to produce at least one of acetoacetyl-CoA, 3-hydroxy-3-methylglutaryl-CoA, mevalonate-5-phosphate, mevalonate-5-pyrophosphate, isopentenyl-5-pyrophosphate, farnesyl-pyrophosphate or dimethylallyl-pyrophosphate, and which does not knock out the ROX1 (SEQ ID NO: 25) locus and which does not repress a lanosterolsynthase (ERG7) having an amino acid sequence as shown in SEQ ID NO: 9 or an amino acid sequence having at least 34% sequence identity with the SEQ ID NO: 9, with the proviso that said protein is capable to produce lanosterol.

This means that in one embodiment, the present invention provides a method of increasing the yield of 2,3-oxidosqualene, in a host cell comprising:

engineering the host cell to overexpress a 3-hydroxy-3-methylglutaryl-coenzyme A reductase comprising an amino acid sequence as shown in SEQ ID NO: 1 or to overexpress a protein comprising at least 44% sequence identity with the amino acid sequence as shown in SEQ ID NO: 1, with the proviso that said protein is capable to produce mevalonic acid, and to overexpress a protein comprising at least one amino acid sequence selected from the group consisting of SEQ ID NOs: 2, 3, 4, 5, 6, 7 and 8 or comprising at least one amino acid sequence having at least 44% sequence identity with an amino acid sequence selected from the group consisting of SEQ ID NOs: 2, 3, 4, 5, 6, 7 and 8, with the proviso that said protein is capable to produce at least one of acetoacetyl-CoA, 3-hydroxy-3-methylglutaryl-CoA, mevalonate-5-phosphate, mevalonate-5-pyrophosphate, isopentenyl-5-pyrophosphate, farnesyl-pyrophosphate or dimethylallyl-pyrophosphate, and engineering the host cell to knock out the ROX1 (SEQ ID NO: 25) locus, and engineering the host cell to repress a lanosterolsynthase (ERG7) having an amino acid sequence as shown in SEQ ID NO: 9 or an amino acid sequence having at least 34% sequence identity with the SEQ ID NO: 9, with the proviso that said protein is capable to produce lanosterol, engineering the host cell to express at least one heterologous protein producing 2,3-oxidosqualene, culturing said host cell under suitable conditions to express 2,3-oxidosqualene, and purifying 2,3-oxidosqualene, thereby increasing the yield of 2,3-oxidosqualene in comparison to the host cell prior to engineering.

Increasing the yield of 2,3-oxidosqualene means in this specific embodiment an increase in comparison to a host cell which does not overexpress a 3-hydroxy-3-methylglutaryl-coenzyme A reductase comprising an amino acid sequence as shown in SEQ ID NO: 1 or which does not overexpress a protein comprising at least 44% sequence identity with the amino acid sequence as shown in SEQ ID NO: 1, with the proviso that said protein is capable to produce mevalonic acid, and which does not overexpress a protein comprising at least one amino acid sequence selected from the group consisting of SEQ ID NOs: 2, 3, 4, 5, 6, 7 and 8 or comprising at least one amino acid sequence with at least 44% sequence identity with an amino acid sequence selected from the group consisting of SEQ ID NOs: 2, 3, 4, 5, 6, 7 and 8, with the proviso that said protein is capable to produce at least one of acetoacetyl-CoA, 3-hydroxy-3-methylglutaryl-CoA, mevalonate-5-phosphate, mevalonate-5-pyrophosphate, isopentenyl-5-pyrophosphate, farnesyl-pyrophosphate or dimethylallyl-pyrophosphate, and which does not knock out the ROX1 (SEQ ID NO: 25) locus and which does not repress a lanosterolsynthase (ERG7) having an amino acid sequence as shown in SEQ ID NO: 9 or an amino acid sequence having at least 34% sequence identity with the SEQ ID NO: 9, with the proviso that said protein is capable to produce lanosterol.

In the method of the present invention, the at least one heterologous protein which encodes the at least one of oxidosqualene, triterpenes and/or triterpenoids may be selected from the group consisting of lupeol synthases, preferably the lupeol synthase from *Taraxacum koksaghyz*, oxidosqualene cyclases (OSC), preferably the oxidosqualene cyclases TkOSC1-6 from *Taraxacum koksaghyz*, β-amyrin synthase, preferably the β-amyrin synthase from *Arabidopsis thaliana* or from *Artemisia annua*, terpene cyclase, preferably terpene cyclase from *Glycyrrhiza uralensis* (GuLUP1).

According to the method of the present invention, culturing said host cell is carried out under suitable conditions. Such conditions are preferably, incubation of the freeze-dried yeast cells at at least 50° C., 60° C., 70° C., 80° C., more preferably at about 80° C., for 2-6 min, more preferably for about 5 min. KOH in methanol and cholesterol as an internal standard is preferably added to each sample. For extraction of the at least one of oxidosqualene, triterpenes and/or triterpenoids n-hexane is preferably added. The upper extraction phase thereof is preferably used, for example. Afterwards, the samples are, for example, re-solubilized in acetone and subjected to GC-MS. GC-MS analysis is preferably performed on a GC-MS-QP 2010 Ultra and with a temperature gradient.

In another embodiment of the method of the present invention, the at least one of oxidosqualene, triterpenes and/or triterpenoids is extracted from a plant. This means, according to the present invention, the at least one of oxidosqualene, triterpenes and/or triterpenoids can be extracted from a host cell as described herein or alternatively extracted from a plant, in each of the embodiments described herein.

In another embodiment, the at least one of oxidosqualene, triterpenes and/or terpenoids are purified from a plant extract preferably by using a C18 column in the first chromatography step and a biphenyl column in the second chromatography step.

The present invention also provides a method of increasing the yield of at least one of oxidosqualene, triterpenes and/or triterpenoids from a plant comprising:

engineering the plant to overexpress a 3-hydroxy-3-methylglutaryl-coenzyme A reductase comprising an amino acid sequence as shown in SEQ ID NO: 1 or to overexpress a protein having at least 44% sequence identity with the amino acid sequence as shown in SEQ ID NO: 1, with the proviso that said protein is capable to produce mevalonic acid, and to overexpress a protein comprising at least one amino acid sequence selected from the group consisting of SEQ ID NOs: 2, 3, 4, 5, 6, 7 and 8 or comprising at least one amino acid sequence having at least 44% sequence identity with an amino acid sequence selected from the group consisting of SEQ ID NOs: 2, 3, 4, 5, 6, 7 and 8, with the proviso that said protein is capable to produce at least one of acetoacetyl-CoA, 3-hydroxy-3-methylglutaryl-CoA, mevalonate-5-phosphate, mevalonate-5-pyrophosphate, isopentenyl-5-pyrophosphate, farnesyl-pyrophosphate or dimethylallyl-pyrophosphate, and purifying the at least one of oxidosqualene, triterpenes and/or triterpenoids from the respective plant extract under suitable conditions, thereby increasing the yield of the at least one of oxidosqualene, triterpenes and/or triterpenoids in comparison to the plant prior to engineering.

Herein, the plant is preferably selected from the group consisting of *Taraxacum koksaghyz, Adiantum capillus-veneris, Ajuga reptans, Aquilegia coerulea, Arabidopsis thaliana, Arachis hypogaea, Artemisia annua, Aster sedifo-*

*lius, Aster tataricus, Avena strigose, Barbarea vulgaris, Betula platyphylla, Bruguiera gymnorhiza, Bupleurum falcatum, Catharanthus roseus, Cicer arietinum, Centella asiatica, Chenopodium quinoa, Citrullus lanatus, Citrullus colocynthis, Costus speciosus, Cucumis melo, Cucumis sativus, Cucurbita pepo, Eleutherococcus senticosus, Euphorbia tirucalli, Gentiana straminea, Glycine max, Glycyrrhiza glabra, Glycyrrhiza uralensis, Ilex asprella, Kalanchoe daigremontiana, Kandelia candel, Laurencia dendroidea, Lens culinaris, Luffa cylindrica, Lotus japonicus, Maesa lanceolata, Malus domestica, Maytenus ilicifolia, Medicago truncatula, Nicotiana benthamiana, Nicotiana tabacum, Nigella sativa, Ocimum basilicum, Olea europaea, Oryza sativa, Phaeodactylum tricornutum, Phaseolus vulgaris, Pisum sativum, Platycodon grandifloras, Polygala tenuifolia, Polypodiodes niponica, Panax ginseng, Pisum sativum, Rhizophora stylosa, Ricinus communis, Saponaria vaccaria, Siraitia grosvenorii, Stevia rebaudiana, Solanum aculeatissimum, Solanum chacoense, Solanum tuberosum, Solanum lycopersicum, Sorghum bicolor, Taraxacum officinale, Taraxacum brevicorniculatum, Taraxacum mongolicum, Taraxacum platycarpum, Tniticum aestivum, Vaccaria hispanica, Veratrum californicum, Vitis vinifera, Withania somnifera* and *Zea mays.*

Further, according to the method of the present invention, the purification of the at least one of oxidosqualene, triterpenes and/or triterpenoids may be carried out by at least two chromatography steps. In this embodiment, it is preferred to use a C18 column for the first chromatography step. It is further preferred in this embodiment to use a biphenyl column for the second chromatography step. It is even more preferred to use a C18 column for the first chromatography step and a biphenyl column for the second chromatography step.

C18 columns are HPLC (high performance liquid chromatography) columns that use a C18 substance as the stationary phase. C18 HPLC columns are used in environmental sciences and chemical analysis, as well as industries such as pharmaceutical and environmental sciences, to analyze individual parts of chemical mixtures. C18 stationary phases are not identical from one C18 HPLC column to another. C18 simply means that the molecules contain 18 carbon atoms, so the other atoms in the molecule can vary, leading to significantly different substances. However, when the person skilled in the art knows the characteristics of the compounds that will be run through the C18 column, he will be able to choose the column to achieve the desired result. A C18 column can have many sizes, can be with or without an end cap, with different particle and pore sizes, varying degrees of hydrophobicity, and differing abilities to separate acidic and/or basic components. Such a chromatography step according to the present invention with a C18 column is preferably carried out by using methanol as a solvent phase.

A biphenyl column as used in the present invention comprises a biphenyl-residue as a ligand type. Such a chromatography step with a biphenyl column is preferably carried out according to the present invention by using a gradient of methanol and water as a solvent phase.

By applying the method of the present invention, the respective at least one of oxidosqualene, triterpenes and/or triterpenoids can be obtained in a high purity of at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or even 100%.

In the methods of the present invention, the yield of even more than one oxidosqualene, triterpenes and/or triterpenoids may be increased.

The term "yield" refers to the amount of at least one of oxidosqualene, triterpenes and/or triterpenoids as described herein, respectively, which is, for example, harvested from the engineered host cell or from a plant extract, and increased yields can be due to increased amounts of production or secretion of the at least one of oxidosqualene, triterpenes and/or triterpenoids by the host cell. Yield may be presented by g protein of the mevalonate pathway/g biomass (measured as dry cell weight or wet cell weight) of a host cell. An increase in yield can according to the present invention in general be determined when the yield obtained from an engineered host cell is compared to the yield obtained from a host cell prior to engineering, i.e., from a non-engineered host cell.

The invention further provides in a further embodiment an extract, preferably a plant extract, obtainable by any of the methods described herein.

The invention additionally provides a recombinant host cell for manufacturing at least one of oxidosqualene, triterpenes and/or triterpenoids, wherein the host cell is engineered to overexpress a 3-hydroxy-3-methylglutaryl-coenzyme A reductase comprising an amino acid sequence as shown in SEQ ID NO: 1 or to overexpress a protein having at least 44% sequence identity with the amino acid sequence as shown in SEQ ID NO: 1, with the proviso that said protein is capable to produce mevalonic acid, and to overexpress a protein comprising at least one amino acid sequence selected from the group consisting of SEQ ID NOs: 2, 3, 4, 5, 6, 7 and 8 or comprising at least one amino acid sequence having at least 44% sequence identity with an amino acid sequence selected from the group consisting of SEQ ID NOs: 2, 3, 4, 5, 6, 7 and 8, with the proviso that said protein is capable to produce at least one of acetoacetyl-CoA, 3-hydroxy-3-methylglutaryl-CoA, mevalonate-5-phosphate, mevalonate-5-pyrophosphate, isopentenyl-5-pyrophosphate, farnesyl-pyrophosphate or dimethylallyl-pyrophosphate.

As used herein, a "host cell" refers to a cell which is capable of protein expression and optionally protein secretion. Such host cell is applied in the methods of the present invention. For that purpose, for the host cell to over- or underexpress a polypeptide which is involved in the mevalonate pathway, a nucleotide sequence encoding said polypeptide is present or introduced in the host cell. Host cells provided by the present invention can be eukaryotic or prokaryotic host cells. Preferred host cells according to the present invention are eukaryotic cells. More preferred are non-mammalian eukaryotic host cells. Also preferred are fungal host cells or yeast cells. As will be appreciated by one of skill in the art, a prokaryotic cell lacks a membrane-bound nucleus, while an eukaryotic cell has a membrane-bound nucleus. Examples of eukaryotic cells include, but are not limited to, vertebrate cells, mammalian cells, human cells, animal cells, invertebrate cells, plant cells, nematodal cells, insect cells, stem cells, fungal cells or yeast cells.

As used herein, "engineered" host cells are host cells which have been manipulated using genetic engineering, i.e. by human intervention. When a host cell is "engineered to overexpress" a given protein, the host cell is manipulated such that the host cell has the capability to modulate gene expression, preferably overexpress a gene and/or protein of the mevalonate pathway or functional homologue thereof, thereby expression of a given protein is increased compared to the host cell under the same condition prior to manipulation.

The host cell of the invention may be a host cell selected from the group consisting of *Saccharomyces cerevisiae, Nicotiana benthamiana, Pichia pastoris, Pichia methanolica, Schizosaccharomyces pombe, Kluyveromyces lactis, Kluyveromyces marxianus, Pichia stipitis, Candida albicans, Candida utilis* and BY2 cells.

The host cell of the present invention may further be engineering to overexpress the protein comprising the SEQ ID NO: 3 or comprising an amino acid sequence having at least 44% sequence identity with SEQ ID NO: 3, with the proviso that said protein is capable to produce 3-hydroxy-3-methylglutaryl-CoA.

The host cell of the present invention may further be engineering to repress the lanosterolsynthase (ERG7) having an amino acid sequence as shown in SEQ ID NO: 9 or to repress a protein comprising an amino acid sequence having at least 34% sequence identity with the SEQ ID NO: 9, with the proviso that said protein is capable to produce lanosterol, preferably by the insertion of the CTR3-promoter and/or the addition of coppersulfate $CuSO_4$. In a preferred embodiment, a sequence including the palindrome TTTGCTC(A/G) . . . (T/C)GAGCAAA is necessary for the copper transcriptional regulation (Yamaguchi-Iwai et al., 1997; Jamison McDaniels et al., 1999; Labbé et al., 1997).

It is preferred that the host cell is further engineered to knock out at least one locus selected from the group consisting of ROX1 (SEQ ID NO: 25), BTS1 (SEQ ID NO: 54), YPL062W (SEQ ID NO: 55), DOS2 (SEQ ID NO: 56), YER134C (SEQ ID NO: 57), VBA5 (SEQ ID NO: 58), YNR063W (SEQ ID NO: 59), YJL064W (SEQ ID NO: 60) and YGR259C (SEQ ID NO: 61). It is further preferred that the host cell is further engineered to knock out at least one locus selected from the group consisting of ROX1 (SEQ ID NO: 25), YPL062W (SEQ ID NO: 55), DOS2 (SEQ ID NO: 56), YER134C (SEQ ID NO: 57), VBA5 (SEQ ID NO: 58), YNR063W (SEQ ID NO: 59), YJL064W (SEQ ID NO: 60) and YGR259C (SEQ ID NO: 61).

It is preferred for the host cell of the present invention that the at least one of oxidosqualene, triterpenes and/or triterpenoids is an oxidosqualene, preferably 2,3-oxidosqualene, a sterol, preferably, sigmasterol or sitosterol, a triterpene, preferably a pentacyclic triterpene, more preferably lupeol, such as, but not limited to, lup-19(21)-en-3-ol and lup-20(29)-en-3-ol, β-amyrin, α-amyrin, taraxasterol, triterpene acetates, acylated triterpenes, saponines, sapogenines, lup-19(21)-en-3-one, lup-20(29)-en-3-one, taraxerol, taraxerone, α-amyrone, β-amyrone, taraxasterone, friedelin, betulin, betulinic acid, cholesterol, ergosterol, lanosterol, glucocorticoids, mineralocorticoids, estrogens, gestagens, cardenolides, bufadienolides, steroid alkaloides, saponins, sapogenins or acylated triterpenes. In one specific embodiment of the host cell of the present invention, the at least one of oxidosqualene, triterpenes and/or triterpenoids is not glycyrrhetinic acid as defined above.

All embodiments described herein concerning the method of the present invention are also embodiments which apply to the host cell, and vice versa.

The present invention also provides the use of the host cell of the present invention for manufacturing at least one of oxidosqualene, triterpenes and/or triterpenoids.

By the use of the CTR3 promoter (SEQ ID NO: 42), for the transcriptional repression via $CuSO_4$, for repressing the lanosterolsynthase (ERG7), the inventors were able to lower the costs compared to industrial processes (Paddon et al., 2013).

Consequently, the inventors provide herein a new platform for the synthesis of at least one of oxidosqualene, triterpenes and/or triterpenoids. For example, they have combined the overexpression of the MVA-pathway genes ERG13 (SEQ ID NO: 14) and tHMGR (SEQ ID NO: 32) leading to the overexpression of the proteins, which are encoded by these genes, gene disruption of ROX1 (SEQ ID NO: 25) and the copper regulated repression of ERG7 (SEQ ID NO: 20) via CTR3 promoter. With this platform the inventors of the present invention were able to enhance the productivity of the MVA-pathway and redirect the metabolic flux from late sterol-biosynthesis, resulting in an enhanced production of up to 127-fold of at least one of oxidosqualene, triterpenes and/or triterpenoids.

For example, the inventors overexpressed in yeast ERG13 (SEQ ID NO: 14) and a HMG-CoA reductase 1 (tHMGR) (SEQ ID NO: 1), the key enzyme of the MVA pathway. In the same engineering step, for example, the inventors deleted a negative regulator of the pathway and sterol biosynthesis (ROX1) resulting in a push and pull strategy to enhance the metabolic flux through the system. In a second step, for example, the inventors have redirected this enhanced metabolic flux from late sterol biosynthesis towards the production of 2,3-oxidosqualene, the direct precursor of pentacyclic triterpenes. With this strategy the inventors were able to produce the up to 127-fold amount of pentacyclic triterpenes and were able to detect a second product of the model enzyme TkLUP, the lupeol synthase of the Russian dandelion *Taraxacum koksaghyz.*

This means that in one embodiment, the present invention provides a method of increasing the yield of lupeol, in a host cell comprising:

engineering the host cell to overexpress a 3-hydroxy-3-methylglutaryl-coenzyme A reductase comprising an amino acid sequence as shown in SEQ ID NO: 1 or to overexpress a protein comprising at least 44% sequence identity with the amino acid sequence as shown in SEQ ID NO: 1, with the proviso that said protein is capable to produce mevalonic acid, and to overexpress a protein comprising at least one amino acid sequence selected from the group consisting of SEQ ID NOs: 2, 3, 4, 5, 6, 7 and 8 or comprising at least one amino acid sequence with at least 44% sequence identity with an amino acid sequence selected from the group consisting of SEQ ID NOs: 2, 3, 4, 5, 6, 7 and 8, with the proviso that said protein is capable to produce at least one of acetoacetyl-CoA, 3-hydroxy-3-methylglutaryl-CoA, mevalonate-5-phosphate, mevalonate-5-pyrophosphate, isopentenyl-5-pyrophosphate, farnesyl-pyrophosphate or dimethylallyl-pyrophosphate, and engineering the host cell to knock out the ROX1 (SEQ ID NO: 25) locus, and engineering the host cell to repress a lanosterolsynthase (ERG7) having an amino acid sequence as shown in SEQ ID NO: 9 or an amino acid sequence having at least 34% sequence identity with the SEQ ID NO: 9, with the proviso that said protein is capable to produce lanosterol, and engineering the host cell to express the *T. koksaghyz* lupeol synthase TkLUP (SEQ ID NO: 12), engineering the host cell to express at least one heterologous protein producing lupeol, culturing said host cell under suitable conditions to express lupeol, and purifying lupeol, thereby increasing the yield of lupeol in comparison to the host cell prior to engineering.

Consequently, in an embodiment of the present invention an engineered platform for enhanced production of, for example, pentacyclic triterpene is provided. For example, a yeast platform is provided, wherein the overexpression of tHMGR (SEQ ID NO: 32) and ERG13 (SEQ ID NO: 14) was carried out. Additionally, for example, ROX1 (SEQ ID NO: 25) was knocked out to enhance the productivity of the at least one of oxidosqualene, triterpenes and/or triterpenoids and late sterol biosynthesis. In a specific embodiment, the metabolic flux from late sterol biosynthesis into the synthesis of pentacyclic triterpenes by the *T. koksaghyz* lupeol synthase (TkLUP, SEQ ID NO: 12) is directed. Therefore, for example, the CTR3 promoter (CTR3-P) (SEQ ID NO: 42) was used to decrease the expression of ERG7 (SEQ ID NO: 20) upon addition of copper ($Cu^{2+}$). An additional effect on 2,3-oxidosqualene accumulation could be obtained by the missing repression of ERG9 (SEQ ID NO: 49) and ERG1 (SEQ ID NO: 51) due to decreased sterol contents (lanosterol and ergosterol) in this embodiment.

It is noted that as used herein, the singular forms “a”, “an”, and “the”, include plural references unless the context clearly indicates otherwise. Thus, for example, reference to “a reagent” includes one or more of such different reagents and reference to “the method” includes reference to equivalent steps and methods known to those of ordinary skill in the art that could be modified or substituted for the methods described herein. Additionally, for example, a reference to “a host cell” includes one or more of such host cells, respectively. Similarly, for example, a reference to “methods” or “host cells” includes “a host cell” or “a method”, respectively.

Unless otherwise indicated, the term “at least” preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term “and/or” wherever used herein includes the meaning of “and”, “or” and “all or any other combination of the elements connected by said term”. For example, A, B and/or C means A, B, C, A+B, A+C, B+C and A+B+C.

Throughout this specification and the claims which follow, unless the context requires otherwise, the word “comprise”, and variations such as “comprises” and “comprising”, will be understood to imply the inclusion of a stated integer or step or group of integers or steps but not the exclusion of any other integer or step or group of integer or step. When used herein the term “comprising” can be substituted with the term “containing” or “including” or sometimes when used herein with the term “having”. When used herein “consisting of” excludes any element, step, or ingredient not specified.

The term “including” means “including but not limited to”. “Including” and “including but not limited to” are used interchangeably.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications cited throughout the text of this specification (including all patents, patent application, scientific publications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

The term “about” or “approximately” as used herein means within 20%, preferably within 10%, and more preferably within 5% of a given value or range. It includes also the concrete number, e.g., about 20 includes 20.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

A better understanding of the present invention and of its advantages will be gained from the following examples, offered for illustrative purposes only. The examples are not intended to limit the scope of the present invention in any way.

EXAMPLES OF THE INVENTION

Hereinafter, the present invention is explained in detail through examples. The following examples are intended merely to illustrate the present invention, to which the scope of the present invention is not restricted.

Material and Methods

Example 1: Cloning of Constructs

To generate pAG424Gal-TkLUP the coding sequence of TkLUP (SEQ ID NO: 12) (GenBank MG646375) was PCR amplified on *T. koksaghyz* cDNA with fw-primer 5'-AAA GTC GAC TAA AAA AAT GTG GAA GCT GAA AAT AGC-3' (SEQ ID NO: 23) and bw-primer 5'-AAA CTC GAG ATA TAT TTT GAA CAA TAC GA-3' (SEQ ID NO: 24), purified, digested and ligated into pENTR3c™ (Invitrogen, Carlsbad, USA). Afterwards the TkLup coding sequence (SEQ ID NO: 12) was introduced into pAG424Gal1-ccdB (Alberti et al. 2007; Addgene, Cambridge, USA) via recombination.

To generate pESC-rox1-KIUra3_tHMGR/ERG13 the ROX1 coding sequence (SEQ ID NO: 25) was PCR amplified from yeast DNA template with the fw-primer

```
                                    (SEQ ID NO: 26)
5'-AAA GCG GCC GCA TGA ATC CTA AAT CCT CTAC-3'
```

and bw-primer

```
                                    (SEQ ID NO: 27)
5'-AAA GCG GCC GCT CAT TTC GGA GAA ACT AGG-3'
```

(restriction sites are underlined). Furthermore, pESC-Ura (Agilent Technologies, Santa Clara, USA) was used as a template to amplify a pESC-Ura vector backbone containing NotI restriction sites using fw-primer (SEQ ID NO: 28)
5'-AAA GCG GCC GCC CAG CTG CAT TAA TGA ATC G, bw-primer (SEQ ID NO: 29)
5'-AAA GCG GCC GCG AAG TTC CTA TTC TCT AGA AA.

Both NotI digested fragments were ligated to obtain pESC-rox1. This vector was digested with BglII and a synthesized DNA-fragment (Invitrogen, Carlsbad, USA), consisting of a KIUra3 marker cassette (SEQ ID NO: 30) (Gueldener et al., 2002) and an AsiSI/Nb.BsmI USER cassette (SEQ ID NO: 31) (Hansen et al., 2012), was inserted to obtain pESC-rox1-KIUra3. In a parallel approach the coding sequences of tHMGR (SEQ ID NO: 32) and ERG13 (SEQ ID NO: 14) were PCR amplified from yeast DNA template using fw-primer 5'-AAA GGA TCC AAA AAA ATG GTT TTA ACC AAT AAA AC-3' (SEQ ID NO: 33) and bw-primer 5'-AAA GTC GAC TTA GGA TTT AAT GCA GGT GAC (SEQ ID NO: 34) for tHMGR and fw-primer 5'-AAA GAA TTC AAA AAA ATG AAA CTC TCA ACT AAA CTT TG-3' SEQ ID NO: 35 and bw-primer (SEQ ID NO: 36)
5'-AAA GCG GCC GCT TAT TTT TTA ACA TCG TAA GAT C-3' for ERG13. The obtained fragments were digested with BamHI/SalI and EcoRI/NotI and ligated into pESC-Ura to generate pESC-Ura_tHMGR/ERG13. The NotI restriction site was removed via QuikChange Lightning Site-Directed Mutagenesis Kit (Agilent Technologies, Santa Clara, USA) sticking to the manufactures protocol. In the final step the expression cassette, containing the tHMGR (SEQ ID NO: 32) and ERG13 (SEQ ID NO: 14) coding sequences as well as the bidirectional Gal1/Gal10-promoter and the ADH-1/CYC-1 terminators, was PCR amplified using fw-primer 5'-CGT GCG AUT CAG AGC GAC CTC ATG CTA TAC-3' (SEQ ID NO: 37) and bw-primer 5'-CAC GCG AUC TTC GAG CGT CCC AAA ACC-3' (SEQ ID NO: 38) (uracil-base for USER™-cloning in bald letters) and cloned into AsiSI digested pESC-rox1-KIUra3 via uracil-specific excision reaction (USER)-based cloning.

To generate pESC_ERG7-P_KILeu2_CTR3-P_ERG7 in a first step an ERG7 fragment (SEQ ID NO: 39) was amplified on yeast DNA using fw-primer 5'-CAC ATT TAA GGG CTA TAC AAA GAT GAC AGA ATT TTA TTC TGA CA-3' (SEQ ID NO: 40) (italic letters indicate overlapping region) and bw-primer (SEQ ID NO: 41)
5'-AAA GCG GCC GCC CCA ATA AAC GTA AGA TTA CA-3' and a CTR3-promoter fragment (SEQ ID NO: 42) was amplified using fw-primer (SEQ ID NO: 43)
5'-AAA GCG GCC GCC AGC TGA AGG ATC CGG TAT TCC AAT GAG AAT CGC-3' and bw-primer 5'-TGT CAG AAT AAA ATT CTG TCA TCT TTG TAT AGC TAA ATG T-3' (SEQ ID NO: 44), respectively. Both fragments were fused via overlapping-PCR with CTR3 promoter fw-primer (SEQ ID NO: 43) and ERG7-bw primer (SEQ ID NO: 41), NotI digested and ligated into NotI digested pESC-Ura vector backbone to obtain pESC_CTR3-P_ERG7. In a second step the upstream ERG7-promoter fragment (SEQ ID NO: 45) was PCR amplified on yeast DNA using fw-primer 5'-AAA CAG CTG AAT CTG CTG CTA TTC GTG-3' (SEQ ID NO: 46) and bw-primer (SEQ ID NO: 47)
5'-AAA GGA TCC CCT GCA GGC GCT GCA GGT CGA CAA C-3' and ligated via PvuII/BamHI restriction sites to obtain pESC_ERG7-P_CTR3-P_ERG7. In the last step a synthesised DNA fragment (Invitrogen, Carlsbad, USA) containing a KILeu2 auxotrophy cassette (SEQ ID NO: 48) (Gueldener et al., 2002) was ligated into SbfI/BamHI restriction sites to obtain pESC_ERG7-P_KILeu2_CTR3-P_ERG7.

All constructs were verified by sequencing (Sanger et al. 1977) on an ABI PRISM® 3100 Genetic Analyzer (Applied Biosystems, Foster City, USA). Yeast strain CEN.PK2-1C was obtained from EUROSCARF (Oberursel, Germany). Restriction enzymes were obtained from New England Biolabs GmbH (Frankfurth a.M., Germany).

Example 2: Strain Construction and Culture Conditions

The *S. cerevisiae* strain CEN-PK2-1C was transformed by lithium acetate method (Gietz 2007) using uracil (pCFB255_rox1_KIUra3_tHMGR/ERG13, SEQ ID NO: 11), leucine (pCFB255_ERG7-P_KILeu2_CTR3-P_ERG7, SEQ ID NO: 10) and tryptophan (pAG424Gal-TkLup) as selectable markers. For the stable integration into the yeast genome pCFB255_rox1_KIUra3_tHMGR/ERG13 (SEQ ID NO: 11) and pCFB255_ERG7-P_KILeu2_CTR3-P_ERG7 (SEQ ID NO: 10) were NotI digested to remove the backbone of the plasmid. The cells were plated on minimal synthetic defined medium (SD medium, Clontech, Mountain View, USA) and grown at 30° C. Clones were checked for integrity via colony-PCR using primers spanning both sides of the integrated construct if needed.

For expression of galactose-inducible genes a single colony was picked, inoculated in 5 mL SD medium and cultivated over night at 30° C. while rolling. From this culture, 50 mL of fresh SD medium (containing 150 μM $CuSO_4$ when repressing the expression of ERG7, SEQ ID NO: 20) where inoculated to a final cell density of $10^5$ cells/mL and grown at 30° C. and 140 rpm in an 250 mL Erlenmeyer flask. When the culture reached a cell density of $0.4\times10^6$ cells/mL the medium was changed to SD medium containing galactose instead of glucose to induce gene expression. The yeasts were grown until a cell density of $4\times10^6$ cells/mL was reached and harvested by centrifugation (10 min., 1000×g).

Example 3: Squalene and Triterpene Extraction and Measurements

The extraction of yeast metabolites sticked to the protocol of Rodriguez et al., 2014. In short, the freeze-dried yeast cells were incubated in a 80° C. waterbath for 5 min. After adding 1 mL 6% [w/v] KOH in methanol (Roth, Karlsruhe, Germany) and 100 μg cholesterol (as an internal standard; Sigma, St. Luis, USA) to each sample. To extract the metabolites from the methanol mixture 2 ml of n-hexane (Roth, Karlsruhe, Germany) were added in three steps and after vortexing. The upper phase was transferred to a new vial and the n-hexane was removed by evaporation. Afterwards, the samples were re-solubilized in 1 mL acetone (Roth, Karlsruhe, Germany) and subjected to GC-MS. GC-MS analysis was performed on a GC-MS-QP 2010 Ultra (Shimadzu, Duisburg, Germany) equipped with a 30 m Rtx-5MS column and a temperature gradient (120-330° C.; 21° C. per min; pressure: 58.8 kPa) was used after a 1 min hold at 120° C. and followed by a hold of 330° C. for 10 min. Molecules were detected by the ion masses 43 m/z, 55 m/z, 69 m/z, 95 m/z, 109 m/z and 189 m/z, 204 m/z, 207 m/z, 218 m/z, 271 m/z, 285 m/z, 411 m/z. Peak integration and identification was done with LabSolution software (Shimadzu, Duisburg, Germany) and NIST library, respectively. Total ion current (TIC) of the detected substances was normalized against cholesterol derived from the internal standard and dry weight of the used sample. The statistical significance of the results was confirmed by using two sample t-test at $p<0.05$.

Example 4: Identification of TkLUP as a Lupeol Synthase from *T. koksaghyz*

Figure 2:
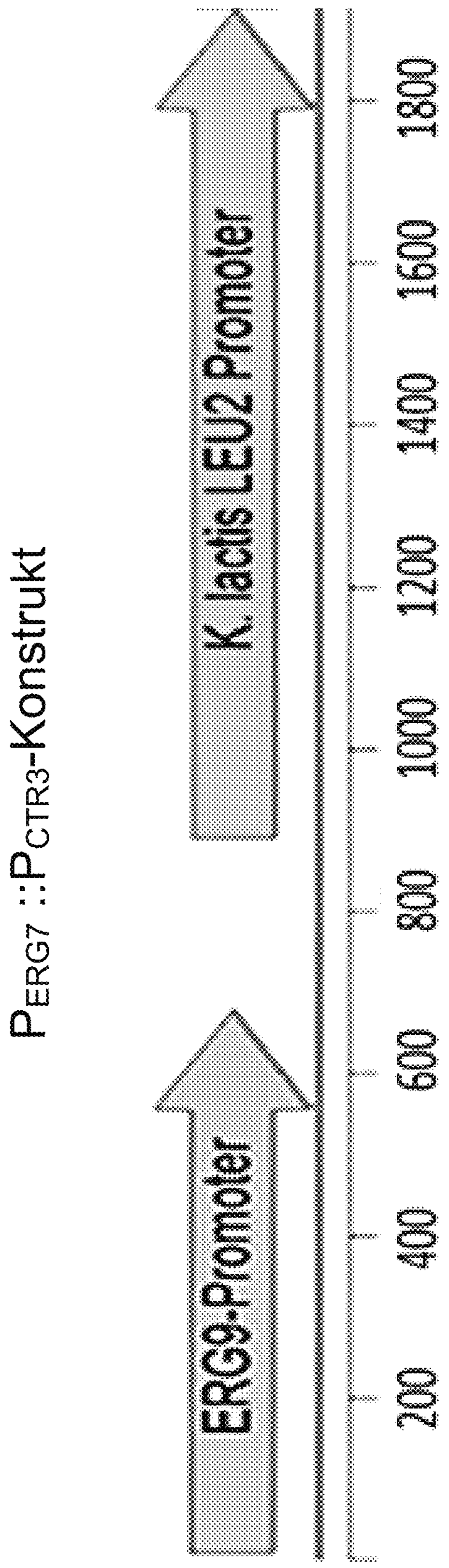
FIG. 2 schematically shows the $P_{erg7}$::$P_{CTR3}$-construct (SEQ ID NO: 10) and the rox1::$P_{Gal1\text{-}tHMGR}$; $P_{GAL19\text{-}ERG13}$-construct (SEQ ID NO: 11) used in one embodiment of the invention.
Figure 2:
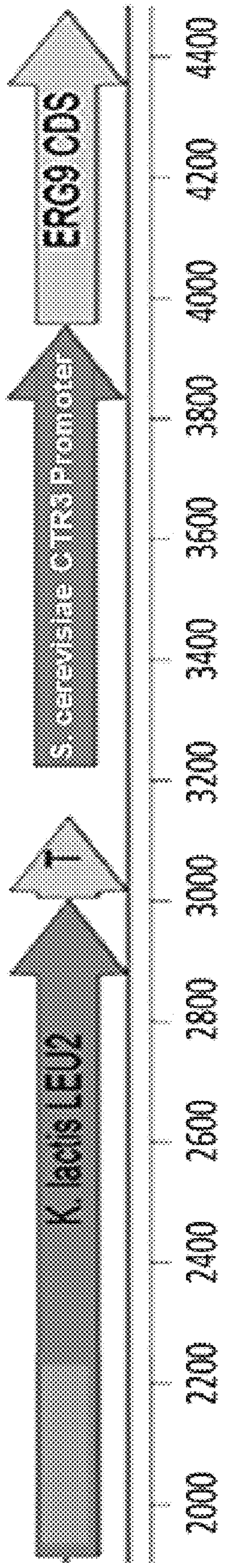
Figure 2:
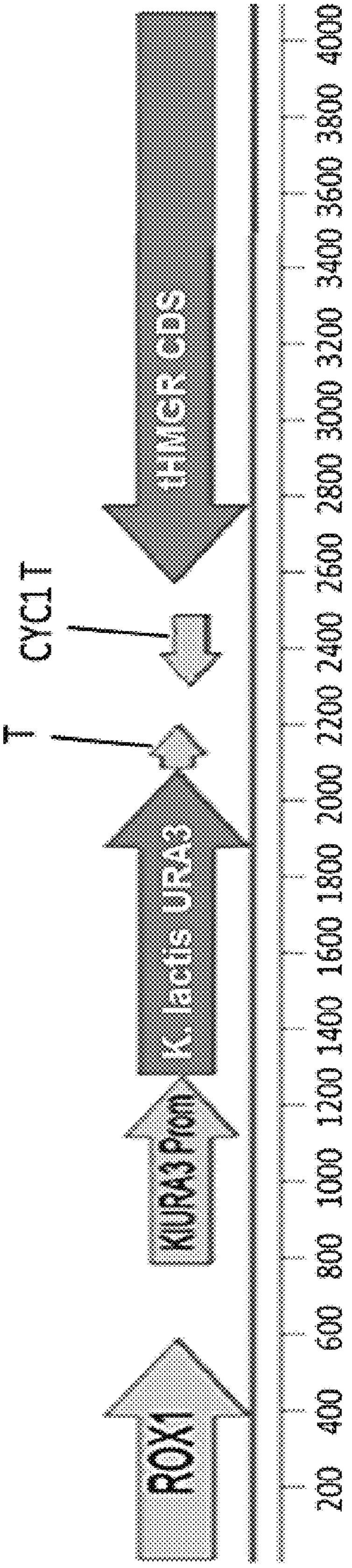
Figure 2:
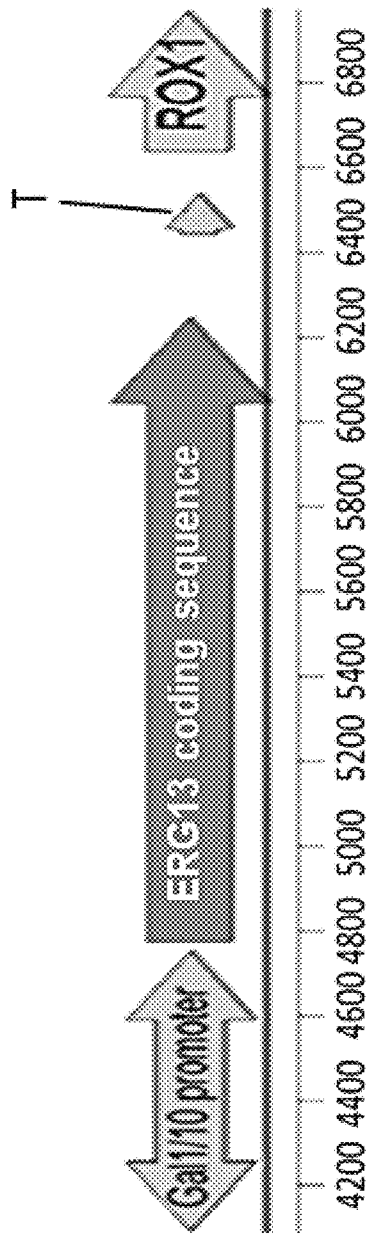
Figure 6:
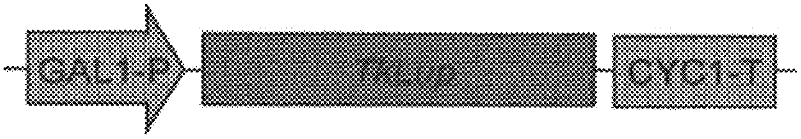
FIG. 6 shows the triterpene accumulation in TkLUP expressing yeast.
Figure 6:
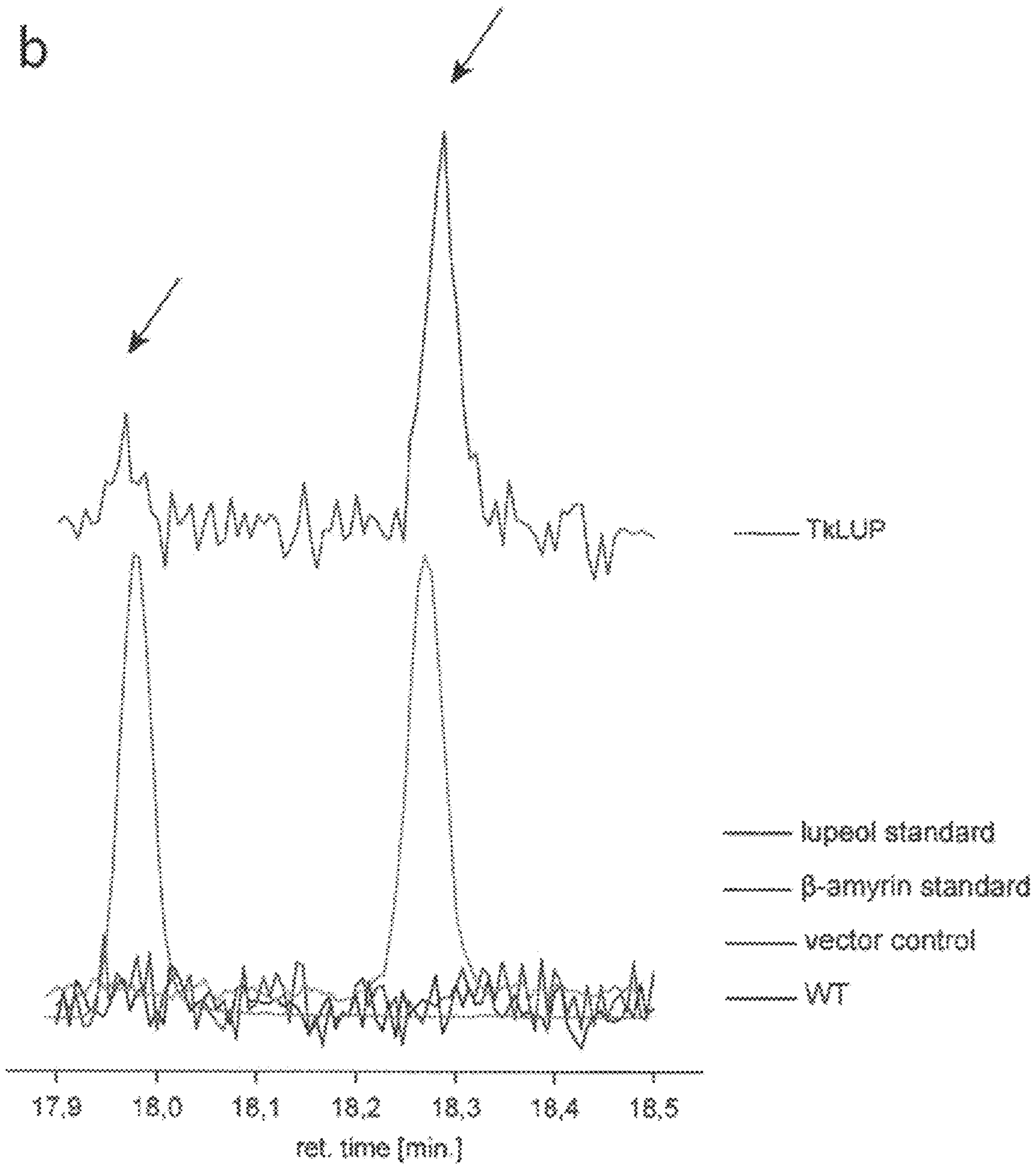
Figure 6:
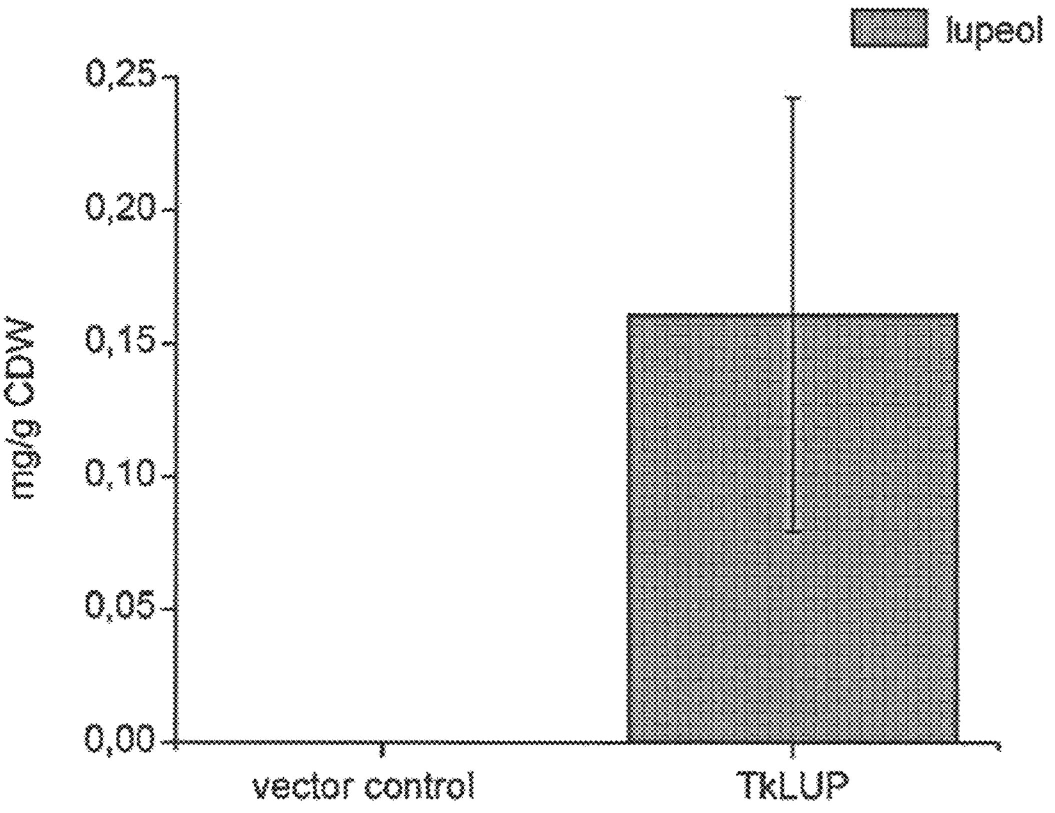

As a model enzyme for the presented yeast system we chose a lupeol synthase derived from the rubber producing dandelion *Taraxacum koksaghyz* (see FIG. 6). With primers used for the amplification of TRX, a lupeol synthase from *T. officinale* (Shibuya et al., 1999), we were able to amplify an ORF of 2277 bp from *T. koksaghyz* cDNA (GenBank accession number MG646375), coding for 759 amino acids (SEQ ID NO: 12). This sequence shared an amino acid sequence similarity of 99.3% to the described lupeol synthase and therefore, was cloned into pENTR3c™ via SalI/XhoI restriction sites. For the expression in CEN.PK2-1C yeast strain (WT) we used the advanced gateway destination vector system (pAG-vector system) and the obtained sequence was recombined into pAG424GAL1-ccdB that allows the expression under the control of GAL1 promoter. A schematic representation of the construct is shown in FIG. 6*a*. The empty vector pAG424GAL1_ccdB served as the vector control in expression experiments. After cultivation and triterpene extraction, two additional m/z 218 fragments could be detected in GC-MS measurements of the extracts from three independent transformants, harboring the putative lupeol synthase sequence (SEQ ID NO: 12) (see FIG. 6*b*). These peaks could neither be identified in the WT nor in the vector control samples. As the retention times of the detected fragments matched with the retention times measured for a β-amyrin and lupeol standard (Extrasynthese, Genay, France; FIG. 1*b*) we assumed that the obtained fragments represent the accumulation of a small trace and not quantifiable amount of β-amyrin as well as the accumulation of 0.16 mg/g CDW of lupeol (FIG. 6*c*). Due to the sequence homologies and the major detected peak that most likely represents lupeol, we conclude that the obtained sequence encodes for the lupeol synthase from *T. koksaghyz*, named TkLUP (SEQ ID NO: 12).

Figure 7:
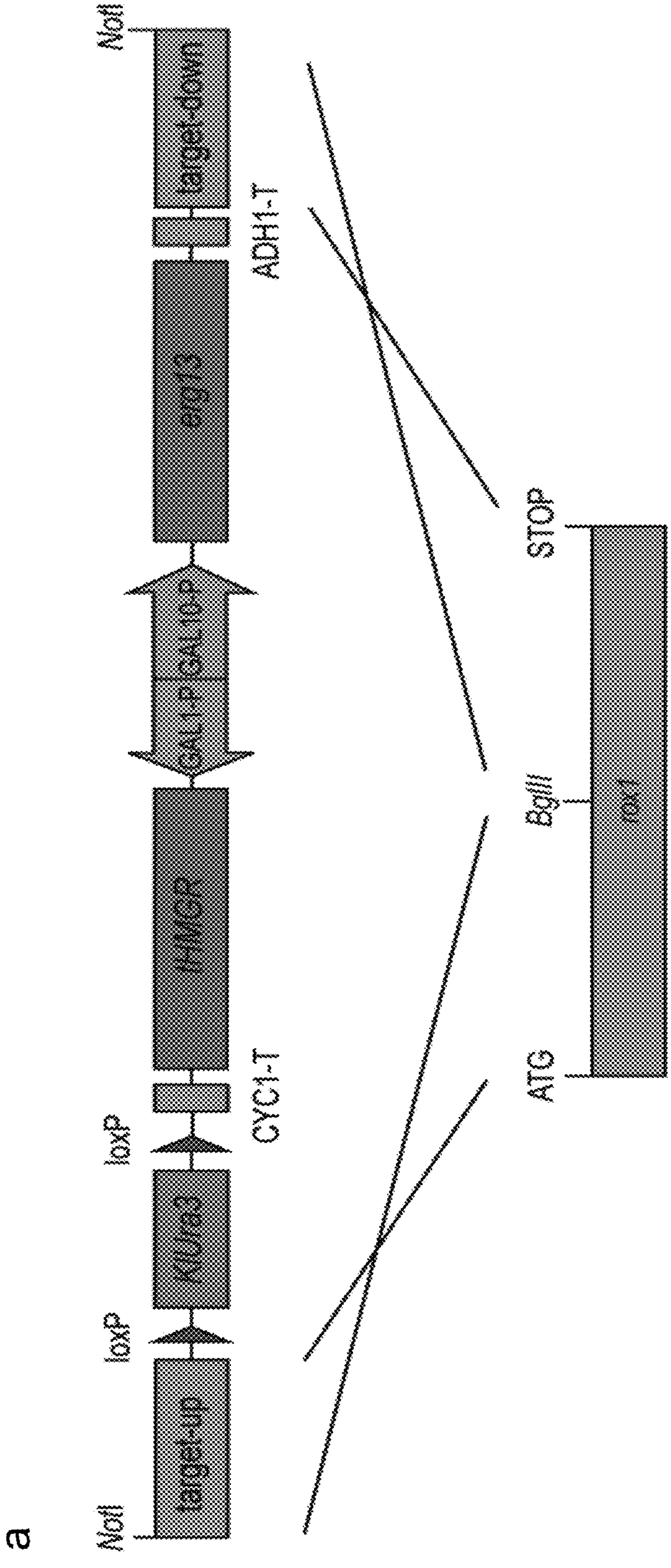
FIG. 7 shows the accumulation of squalene and lupeol after deletion of ROX1 (SEQ ID NO: 25) and overexpression of MVA pathway genes.
Figure 7:
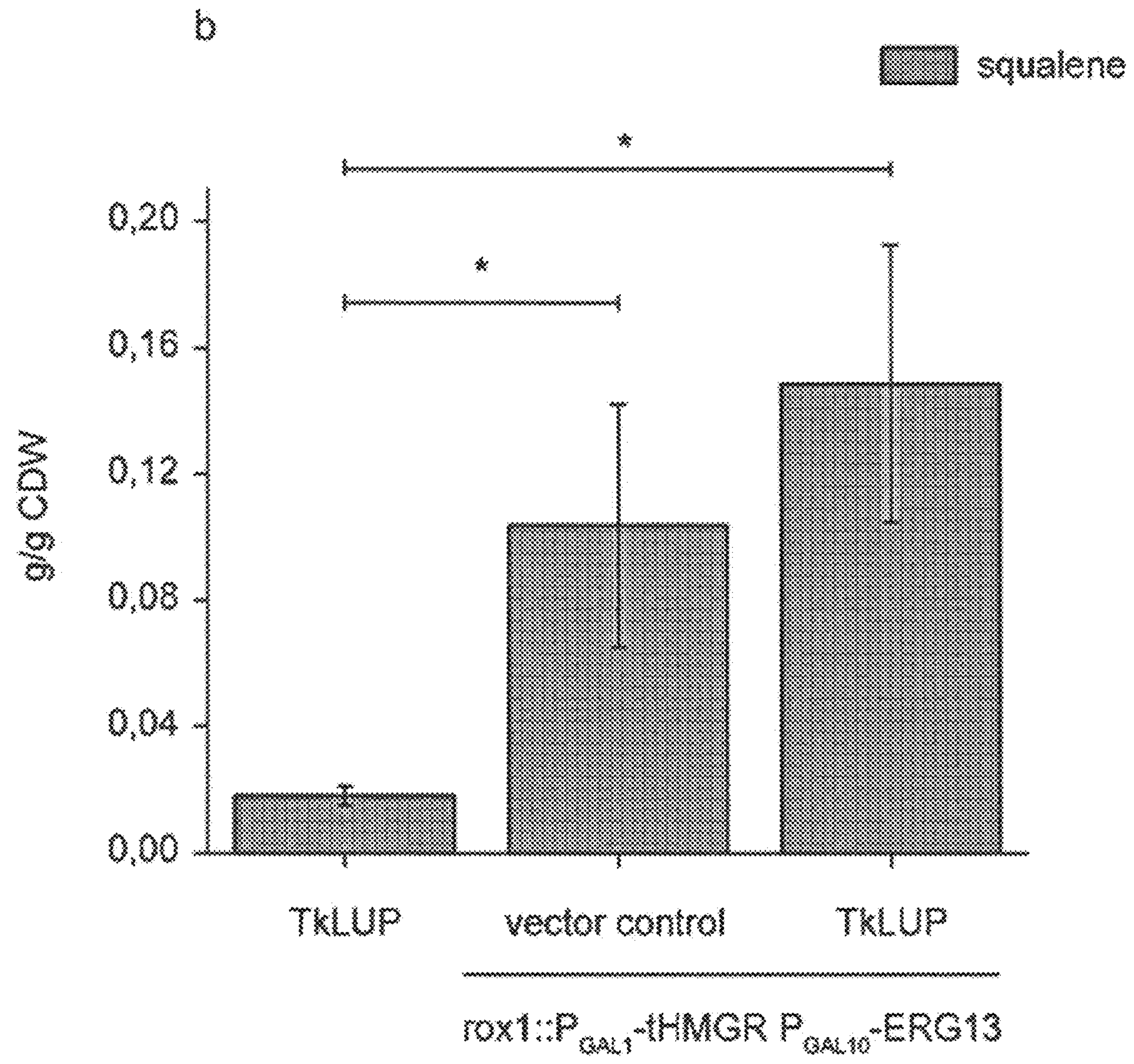
Figure 7:
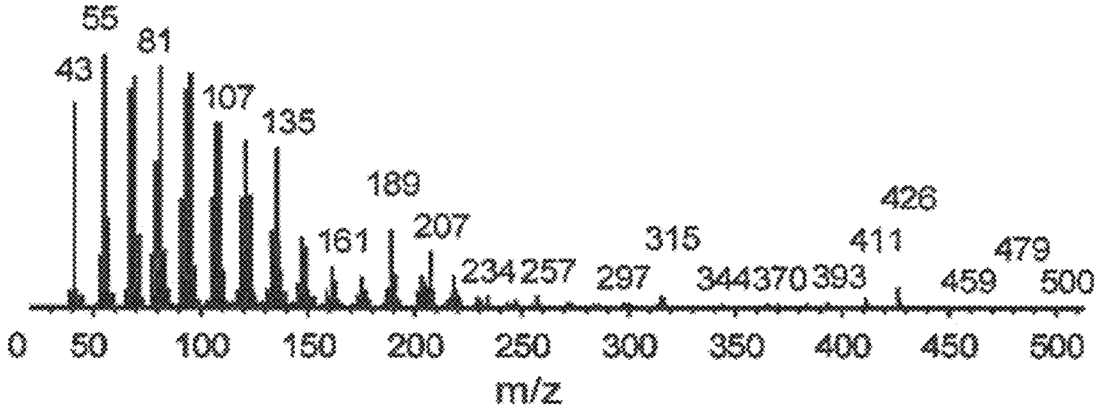

Example 5: Deletion of ROX1 and Overexpression of tHMGR and ERG13 Results in 16.5-Fold Enhanced Iupeol Accumulation To further enhance the production of the putative lupeol in yeast we decided to overexpress yeast mevalonate pathway genes that have been shown to enhance isoprenoid yield in heterologous yeast systems before (Kirby et al., 2008; Asadollahi et al., 2010; Paddon et al., 2013). As HMG1 is the key enzyme of the pathway and underlies a strict control by a feedback mechanism, we overexpressed the truncated form (referred to as tHMGR) (SEQ ID NO: 32) that does not underlie the feedback mechanism due to a missing ubiquitination signal (DeBose-Boyd, 2008). On the other hand, we chose to overexpress ERG13 (SEQ ID NO: 14) which has also been shown to have a positive effect on isoprenoid biosynthesis (Yuan et al., 2014). To further de-/upregulate the pathway the inventors considered to knock out ROX1 (SEQ ID NO: 25), which is described as a negative regulator of the mevalonate pathway and late sterol biosynthesis (Henry et al., 2002; Montañés et al., 2011; Özaydin et al., 2013; Jakočiūnas et al., 2015), aiming at an enhanced flux through the pathway by the deregulation of the pathway itself, as to an enhanced downgrade of squalene caused by an enhanced late sterol biosynthesis. To combine these steps we chose to express tHMGR (SEQ ID NO: 32) and ERG13 (SEQ ID NO: 14) under the control of the bidirectional GAL1/GAL10 promoter and integrated the overexpression cassette into the rox1 (SEQ ID NO: 25) locus resulting in its knock out. Therefore, a fragment resulting from a NotI digested pCFB255_rox1_KIUra3_tHMGR/ERG13 (SEQ ID NO: 11) was transformed into CEN.PK2-1C yeast cells (FIG. 7*a*). As expected, after expression of the integrated genes and the knock out of rox1 (SEQ ID NO: 25) a significant 8.2-fold enhanced accumulation of squalene could be detected in yeast harboring the construct and the TkLUP sequence (SEQ ID NO: 12) compared to cells only carrying the TkLUP sequence (SEQ ID NO: 12) (FIG. 7*b*). Furthermore, a 16.5-fold increase was shown for the accumulation of the designated lupeol (FIG. 7*b*), as well as a 3.6-fold increase of lanosterol content could be observed (see Table 1 below).

In accordance to previously described data, yeast cells showed a slightly reduced growth as they needed a longer time to reach the cell density (described in the material and method section) after induction and before harvesting the cells, that may occur as a result for high squalene levels being toxic to the cells (Donald et al., 1997; Asadollahi et al., 2010). However, this engineering step allowed the comparison of the mass spectra of the putative lupeol peak (FIG. 7*c*) to the mass spectra of the measured lupeol standard (FIG. 7*d*). The comparable masses of the peaks underline the assumption of the inventors of the present invention that the observed coding sequence codes for the lupeol synthase from *T. koksaghyz*. The putative β-amyrin peak was still too weak for detailed mass analysis.

Since we could observe the accumulation of the pentacyclic triterpene precursor squalene, but not of 2,3-oxidosqualene—the substrate of the TkLUP (SEQ ID NO: 12)—a bottleneck at this point of the pathway was observed. This bottleneck may occur due to lower capacity of ERG1 compared to ERG9 (as suggested by Asadohalli et al., 2010) as well as to the high activity towards 2,3-oxidosqualene of the TkLUP itself, or due the activity of the endogenous late sterol biosynthesis. To overcome this limiting factor, the overexpression of ERG1 (coding for yeast squalene epoxidase, catalizing the reaction from squalene to 2,3-oxidosqualene) would be likely, however, not successful for an enhanced pentacyclic triterpene production as an accumulation of 2,3-oxidosqualene could not be observed in a yeast strain overexpressing ERG1 (Veen et al., 2003). Therefore, the inventors downregulated ERG7 (SEQ ID NO: 20), the starting point of late sterol biosynthesis to influence the endogenous but competitive late sterol biosynthesis.

Figure 8:
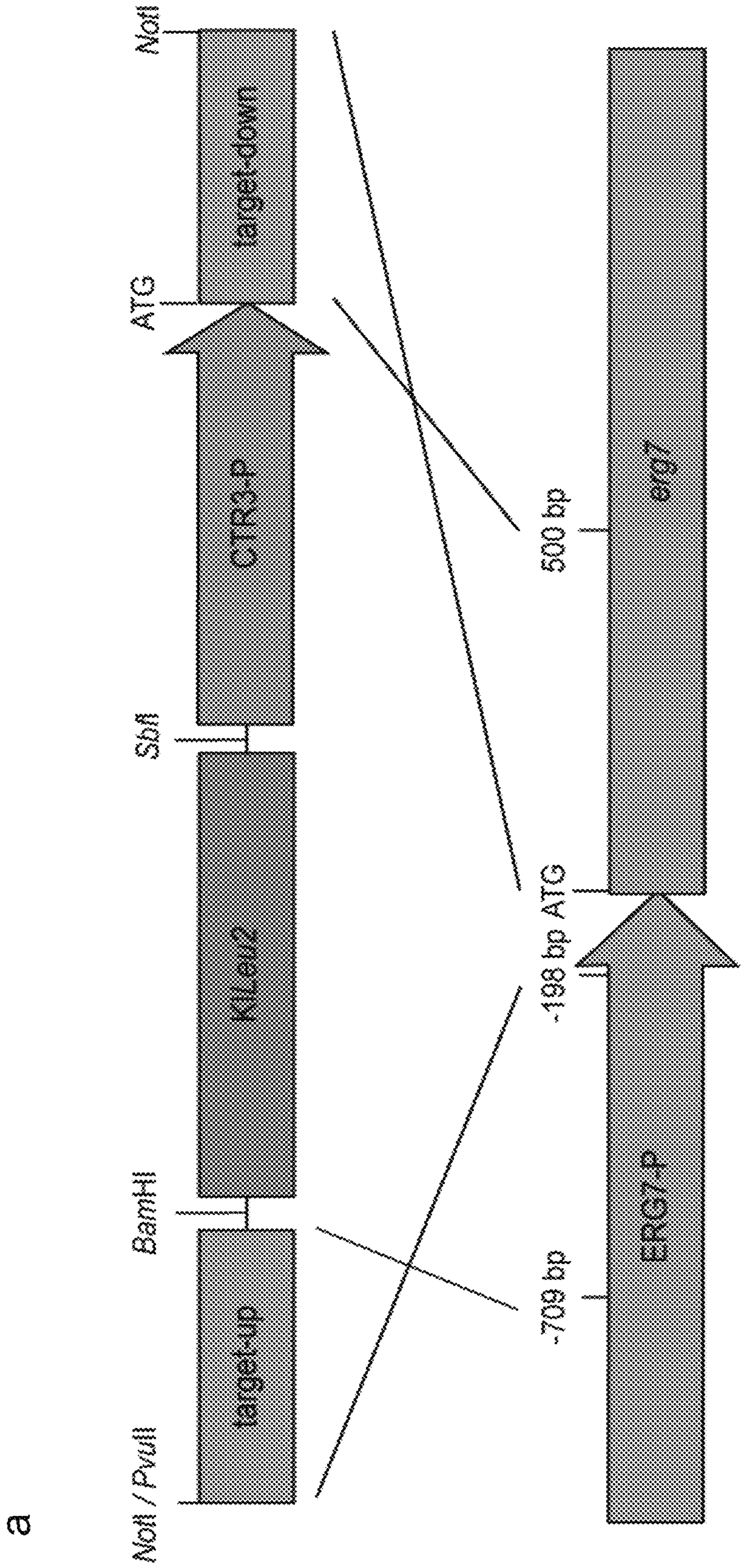
FIG. 8 shows that repression of ERG7 (SEQ ID NO: 20) leads to 2,3-oxidosqualene accumulation.
Figure 8:
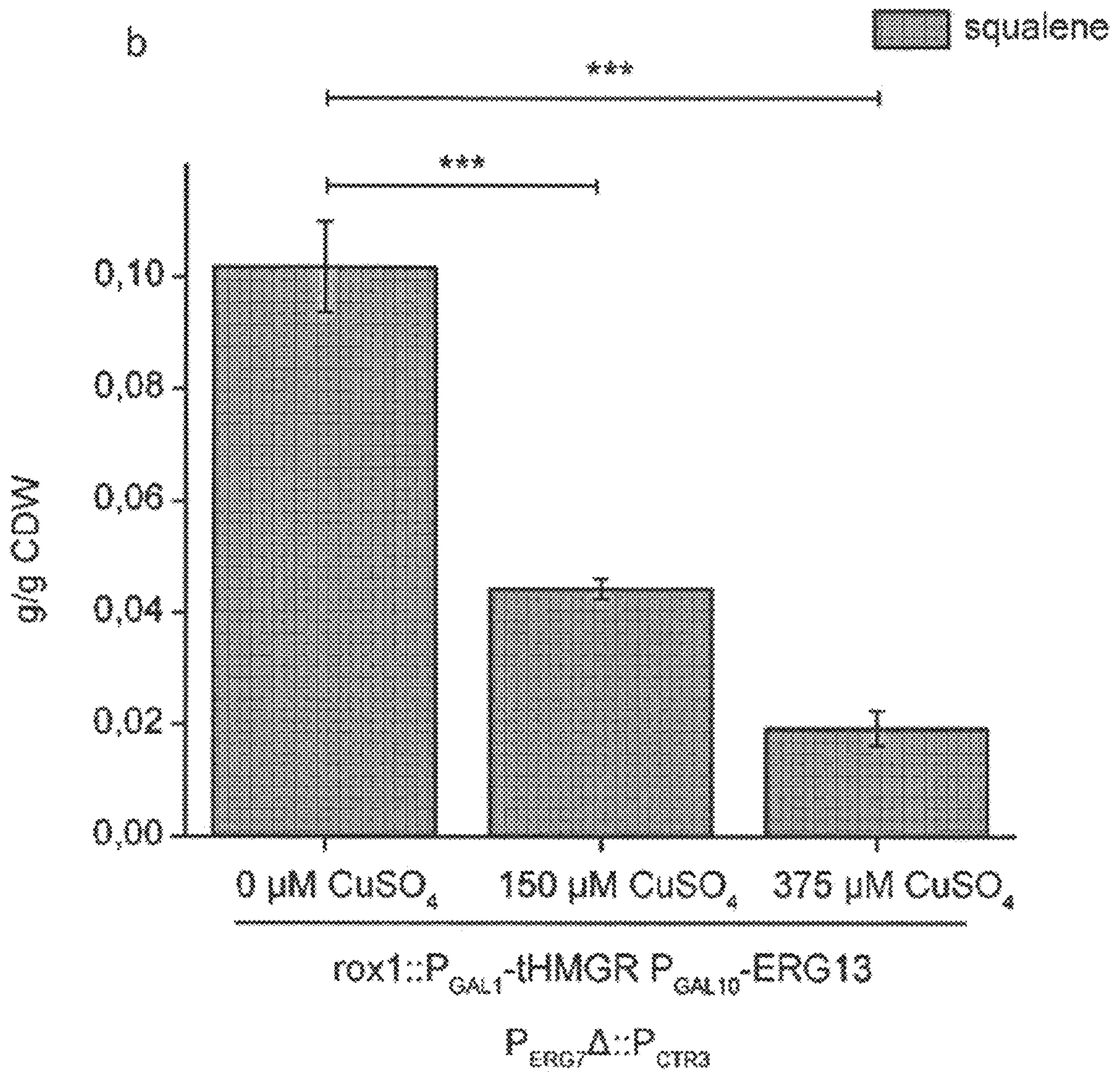
Figure 8:
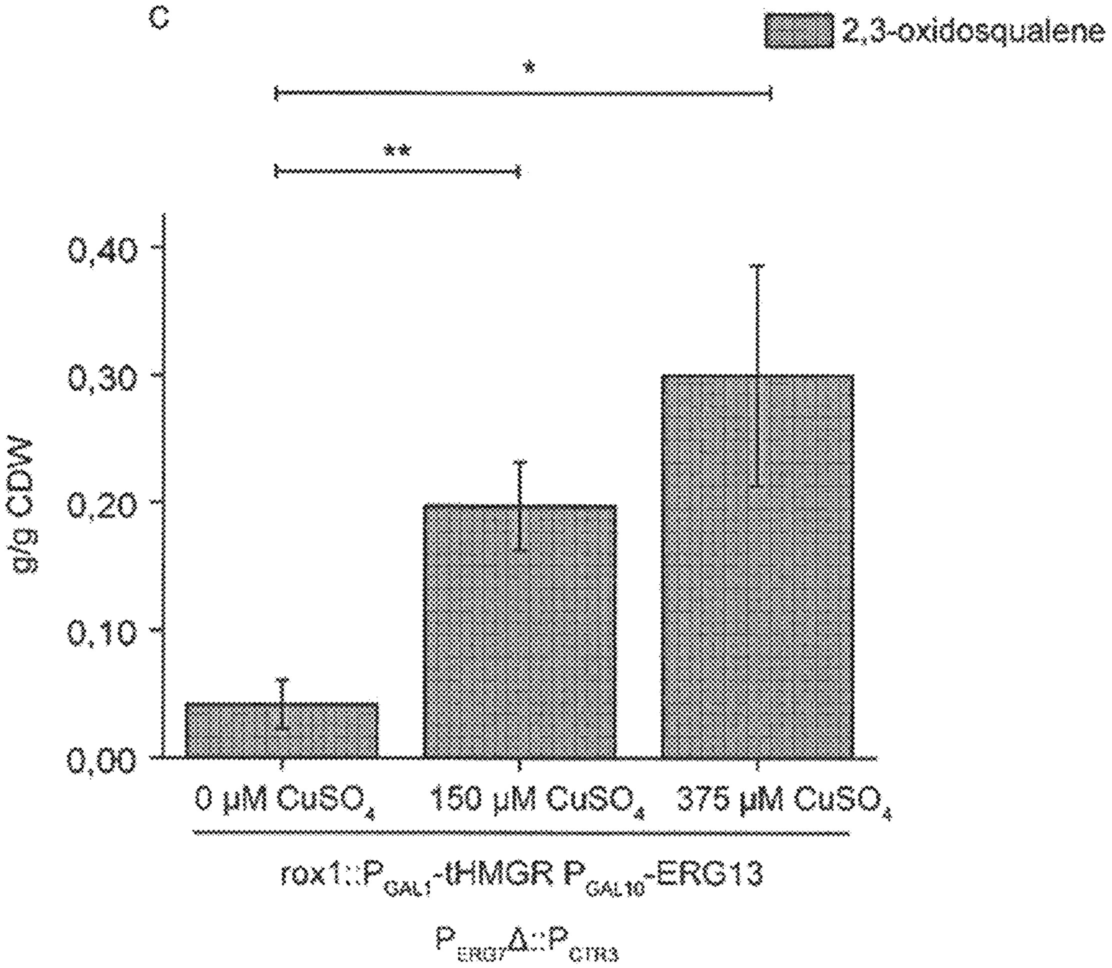

Example 6: Repression of ERG7 (SEQ ID NO: 20) Via CTR3 Promoter Leads to the Accumulation of 2,3-Oxidosqualene and a Further 7.6-Fold Enhanced Iupeol Accumulation As a knock out of the essential late sterol biosynthesis would result in a lethal yeast strain and the overexpression of ERG1 would not be sufficient to enhance 2,3-oxidosqualene accumulation for pentacyclic triterpene production, the inventors repressed ERG7 (SEQ ID NO: 20) to overcome the bottleneck of 2,3-oxidosqualene synthesis and thereby redirecting the metabolic flux from the late sterol biosynthesis into lupeol production. Therefore, we chose to insert a 735 bp promoter fragment of a copper transporter (CTR3) (SEQ ID NO: 42) infront of the endogenous ERG7 coding sequence (SEQ ID NO: 20) and, in the same step, delete a 196 bp fragment of the endogenous core-promoter (FIG. 8*a*). For the inserted CTR3 promoter fragment (SEQ ID NO: 42) it was shown that two cis-acting elements (TTTGCTC, copper responsive elements, short CuRE) are responsible for reduced gene expression in the presence of $CuSO_4$ (Labbé et al., 1997). Furthermore, a CTR3 promoter fragment (SEQ ID NO: 42) was used successfully to repress ERG9 (SEQ ID NO: 49) for an enhanced artemisinin production, thereby lowering the costs in this industrial process and indicating the equivalence to the MET3 promoter (SEQ ID NO: 50) that was used in previous studies of the authors (Paddon et al., 2013).

Figure 9:
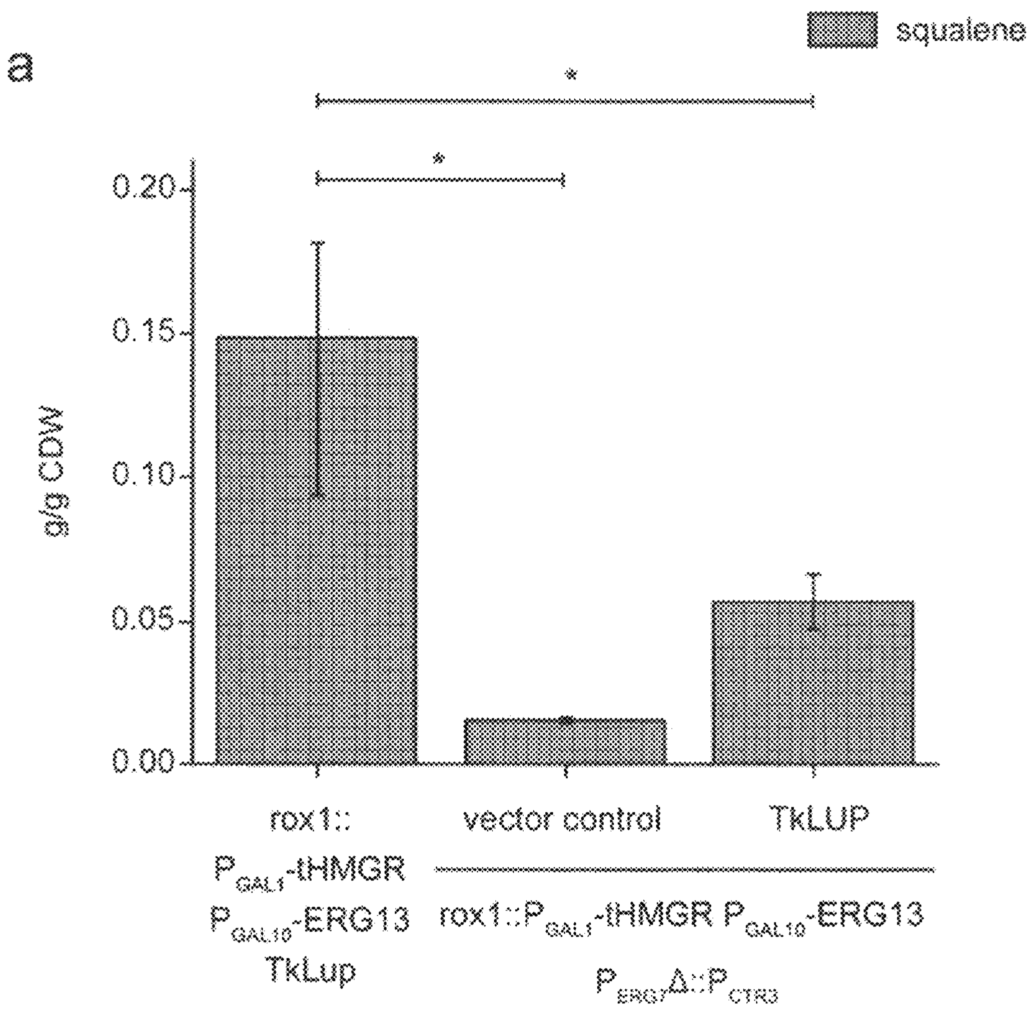
FIG. 9 shows that repression of ERG7 (SEQ ID NO: 20) leads to enhanced lupeol accumulation (FIG. 9*e*) and decreased sterol levels (FIGS. 9*c* and 9*d*). The accumulation of 2,3-oxidosqualene (FIG. 9*b*) and the reduction of squalene (FIG. 9*a*) could be observed in the yeast strain carrying the TkLUP sequence (SEQ ID NO: 12) in addition to the rox1::$P_{GA}$L1-tHMGR $P_{GAL}$1-ERG13 and the $P_{ERG7}$Δ::$P_{CTR3}$ modification after being exposed to 150 μM $CuSO_4$ during growth (rox1::$P_{GAL1}$-tHMGR $P_{GAL10}$-ERG13 $P_{ERG7}$Δ::$P_{CTR3}$ TkLUP) compared to its parental strain (rox1::$P_{GAL1}$-tHMGR $P_{GAL10}$-ERG13 TkLUP; p=0.04422 for squalene). As expected, sterol content was reduced, shown by the amount of lanosterol and ergosterol as representatives for sterol biosynthesis. The repression of ERG7 (SEQ ID NO: 20) resulted in a 6,5-fold decrease in lanosterol (p=0.02384) and a 3.9-fold decrease in ergosterol content (p=0.00941). Caused by the repression of sterol biosynthesis, the production of lupeol was enhanced 7.6-fold (p=0.00637), suggesting the redirection of the metabolic flux from sterol biosynthesis to lupeol production. Standard deviation was calculated from n=3 individual transformants. CDW=cell dry weight; *=p s 0.05; **=p s 0.01.
Figure 9:
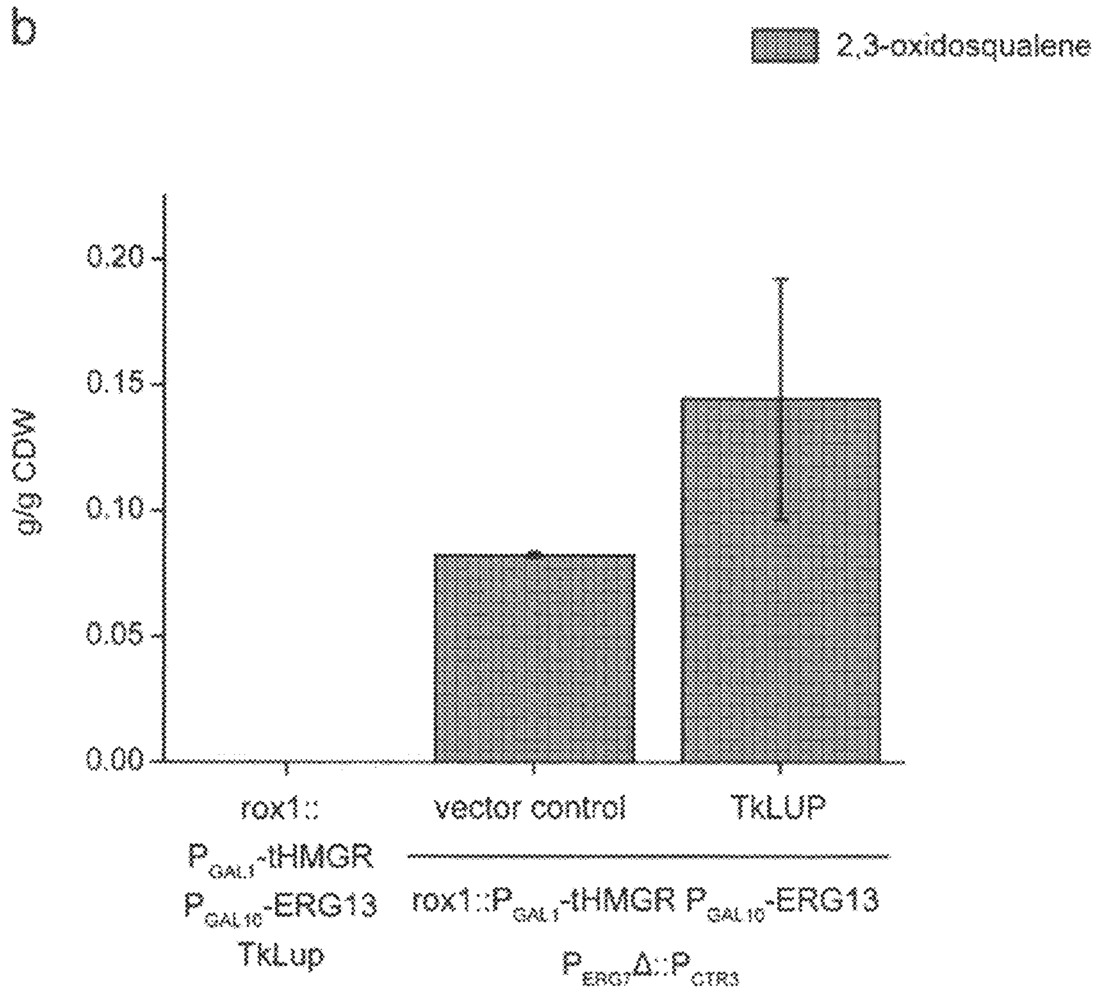
Figure 9:
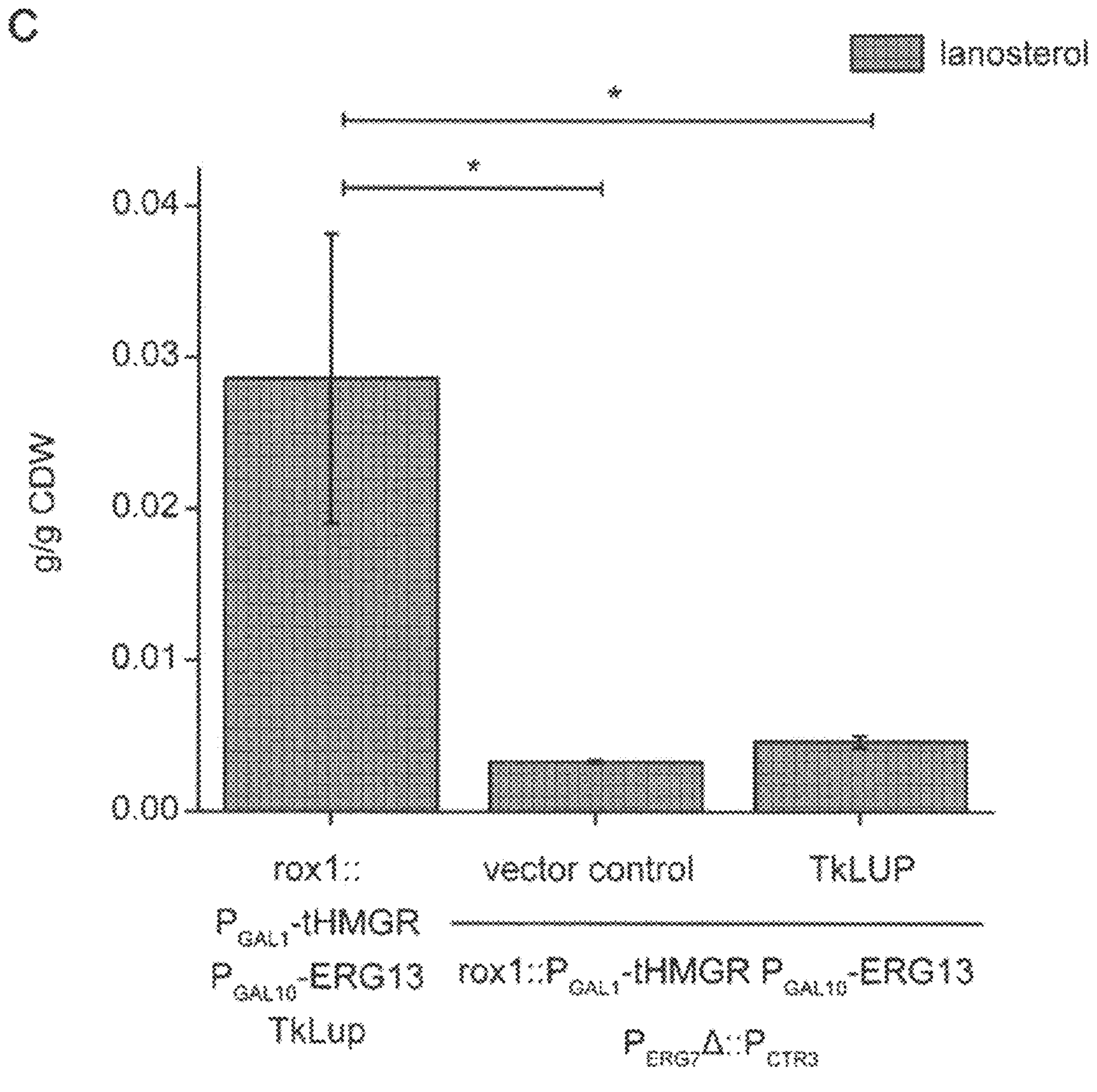
Figure 9:
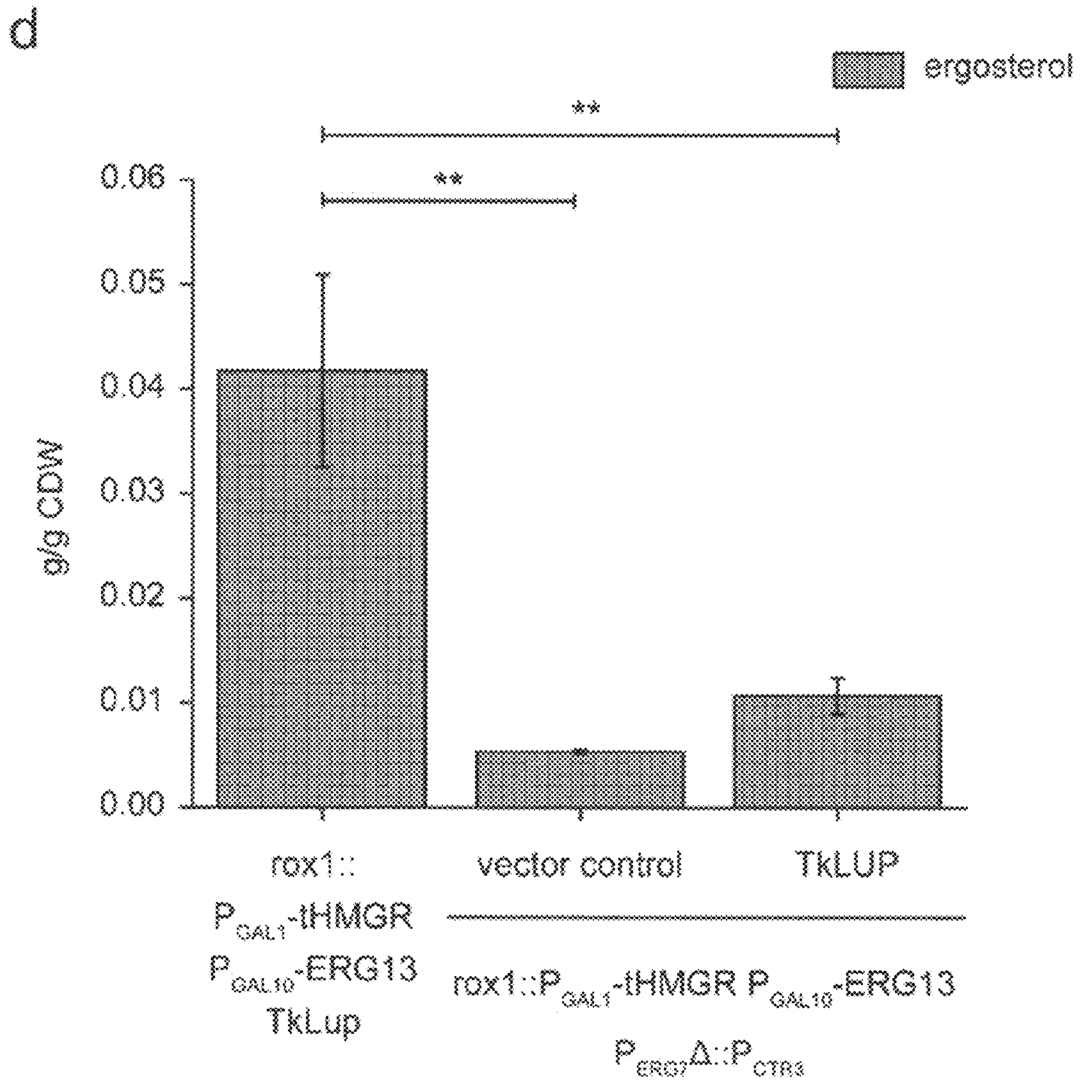
Figure 9:
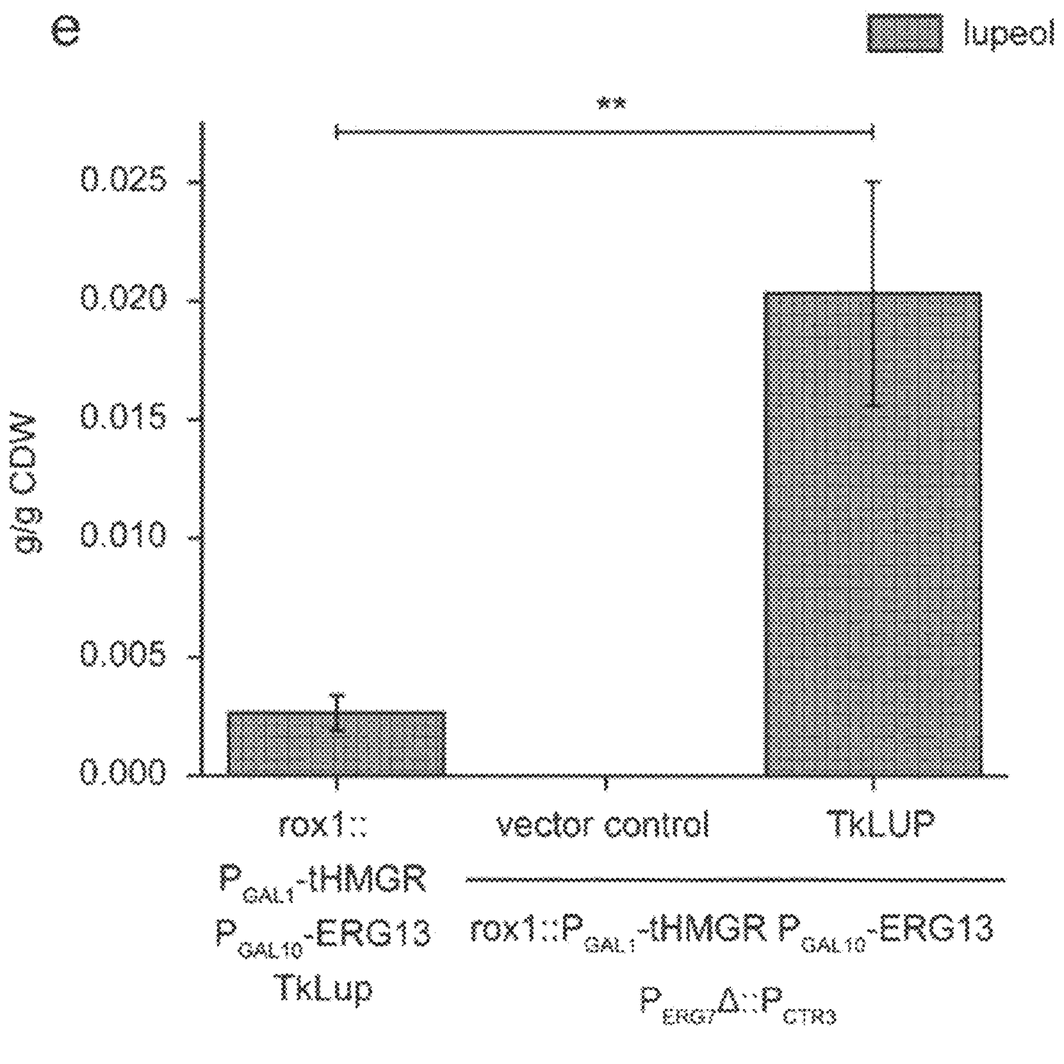

To test the effect of the construct we transformed the NotI digested fragment of pCFB255_ERG7-P_KILeu2_CTR3-P_ERG7 (SEQ ID NO: 10), containing KILeu2 as a selectable marker and the CTR3 promoter fragment (SEQ ID NO: 42), into the yeast strain harbouring the fragment of pCFB255_rox1_KIUra3_tHMGR/ERG13 (SEQ ID NO: 11). Positive transformants were cultured in the presence of 0 μM, 150 μM and 375 μM $CuSO_4$ and gene expression of tHMGR (SEQ ID NO: 32) and ERG13 (SEQ ID NO: 14) was induced with galactose, resulting in a shift from squalene to 2,3-oxidosqualene accumulation in yeast (FIG. 8*b*). Even in the absence of copper we could detect a slight accumulation of 2,3-oxidosqualene in the extracted GC-MS samples, indicating a weaker promoter activity of the CTR3 fragment (SEQ ID NO: 42) compared to the endogenous ERG7 promoter (SEQ ID NO: 45). This effect was even stronger on the yeast growing in the presence of 150 μM $CuSO_4$. The amount of squalene decreased significantly (p=0.00613) as the accumulation of 2,3-oxidosqualene was enhanced 4.7-fold (p=0.00507), which may be caused by the missing repression of ERG9 (SEQ ID NO: 49) and ERG1 (SEQ ID NO: 51) by ergosterol, as well as the enhanced induction of ERG1 (SEQ ID NO: 51) under limited lanosterol conditions (Table 1; M'Baya et al., 1989). A further significant decrease in squalene levels (p=0.00061) could be observed after cultivation of the yeast under an elevated copper concentration of 375 μM. However, we could not observe a significant change in 2,3-oxidosqualene, but the yeast showed a decreased growth rate, indicating the toxicity of high levels of $CuSO_4$ and a sufficient repression of ERG7 (SEQ ID NO: 20) in the presence of 150 μM $CuSO_4$ to overcome the bottleneck in 2,3-oxidosqualene synthesis. The inventors thus chose the concentration of 150 μM $CuSO_4$ as a sufficient amount of copper for the enhanced production of lupeol in a strain combining rox1::$P_{GAL1}$-tHMGR $P_{GAL10}$-ERG13 (SEQ ID NO: 11) $P_{erg7}\Delta$::$P_{CTR3}$ (SEQ ID NO: 10) and the coding sequence of TkLup (SEQ ID NO: 12), or the pAG424GAL1_ccdB empty plasmid serving as a control (FIG. 9).

As expected, the yeast strain harboring the three constructs and being cultivated in the presence of copper showed a shift in squalene and 2,3-oxidosqualene levels compared to its parental strain, lacking the CTR3 promoter fragment (SEQ ID NO: 42). Therefore, the accumulation of squalene was 2.6-fold lower (p=0.04422) and the accumulation of 2,3-oxidosqualene could be observed. Furthermore, we could detect decreased amounts of sterols, represented by lanosterol (6.5-fold; p=0.02384) and ergosterol (3.9-fold; p=0.00941), showing the functionality of copper repression, as well as the regulation of ERG9 (SEQ ID NO: 49) and ERG1 (SEQ ID NO: 51) by these compounds in the strain expressing TkLUP (SEQ ID NO: 12). Moreover, we could detect a further enhanced lupeol accumulation by the use of the copper repressible promoter and the identification of β-amyrin became possible as it can be seen in the comparison of the MS spectra of the measured sample (FIG. 10*a*) and the external β-amyrin standard (FIG. 10*b*). Lupeol levels increased 7.6-fold (p=0.00637), whereas the quantification of β-amyrin was still not possible. However, the accumulation of 2,3-oxidosqualene and lupeol, as well as the decreased amounts of sterols, prove the redirection of the metabolic flux from sterol biosynthesis to lupeol production in this engineered yeast strain.

TABLE 1

Metabolite levels in WT and engineered yeast strains in g/g CDW quantified via GC-MS

| | squalene | 2,3-oxido-squalene | lanosterol | ergosterol | lupeol |
|---|---|---|---|---|---|
| WT | 0.0248 (±0.0078) | n.d. | 0.01162 (±0.00567) | 0.0473 (±0.01844) | n.d. |
| vector control | 0.0168 (±0.0020) | n.d. | 0.009172 (±0.00203) | 0.0332 (±0.0061) | n.d. |
| TkLUP (SEQ ID NO: 12) | 0.0181 (±0.0030) | n.d. | 0.00803 (±0.00148) | 0.0289 (±0.0042) | 0.00016 (±0.00008) |
| rox1::$P_{GAL1}$-tHMGR $P_{GAL10}$-ERG13 (SEQ ID NO: 11) | 0.1539 (±0.0126) | n.d. | 0.03614 (±0.01597) | 0.0404 (±0.0038) | n.d. |
| rox1::$P_{GAL1}$-tHMGR $P_{GAL10}$ ERG13 vector control | 0.1037 (±0.0385) | n.d. | 0.03089 (±0.01019) | 0.0271 (±0.0061) | n.d. |
| rox1::$P_{GAL1}$-tHMGR $P_{GAL10}$-ERG13 TkLUP (SEQ ID NO: 11) (SEQ ID NO: 12) | 0.1486 (±0.0439) | n.d. | 0.02860 (±0.00954) | 0.0417 (±0.0092) | 0.00266 (±0.00074) |
| rox1::$P_{GAL1}$-tHMGR $P_{GAL10}$-ERG13 (SEQ ID NO: 11) $P_{ERG7}\Delta$::$P_{CTR3}$ (SEQ ID NO: 10) 0 μM $CuSO_4$ | 0.1018 (±0.0081) | 0.0418 (±0.0191) | 0.10514 (±0.03471) | 0.0416 (±0.0057) | n.d. |

TABLE 1-continued

| Metabolite levels in WT and engineered yeast strains in g/g CDW quantified via GC-MS | squalene | 2,3-oxido-squalene | lanosterol | ergosterol | lupeol |
|---|---|---|---|---|---|
| rox1::$P_{GAL1}$-tHMGR $P_{GAL10}$-ERG13 (SEQ ID NO: 11) $P_{ERG7}\Delta$::$P_{CTR3}$ (SEQ ID NO: 10) 150 μM $CuSO_4$ | 0.0442 (±0.0018) | 0.1974 (±0.0345) | 0.00645 (±0.00290) | 0.01765 (±0.0054) | n.d. |
| rox1::$P_{GAL1}$-tHMGR $P_{GAL10}$-ERG13 (SEQ ID NO: 11) $P_{ERG7}\Delta$::$P_{CTR3}$ (SEQ ID NO: 10) 375 μM $CuSO_4$ | 0.0194 (±0.0031) | 0.2996 (±0.0867) | 0.00098 (±0.00018) | 0.0027 (±0.0003) | n.d. |
| rox1::$P_{GAL1}$-tHMGR $P_{GAL10}$-ERG13 (SEQ ID NO: 11) $P_{ERG7}\Delta$::$P_{CTR3}$ (SEQ ID NO: 10) vector control 150 μM $CuSO_4$ | 0.0152 (±0.0009) | 0.0824 (±0.0011) | 0.00330 (±0.00012) | 0.0053 (±0.0002) | n.d. |
| rox1::$P_{GAL1}$-tHMGR $P_{GAL10}$-ERG13 (SEQ ID NO: 11) $P_{ERG7}\Delta$::$P_{CTR3}$ (SEQ ID NO: 10) TkLUP (SEQ ID NO: 12) 150 μM $CuSO_4$ | 0.057 (±0.0097) | 0.1443 (±0.0479) | 0.00463 (±0.00040) | 0.0107 (±0.0017) | 0.02032 (±0.00472) |

g/g CDW (±standard deviation);
standard deviation was calculated from n = 3 individual transformants via students t-test;
n.d. = not detectable;
CDW cell dry weight

Example 7: Triterpene Purification by HPLC

Semi-preparative HPLC was carried out using a Shimadzu LC20A HPLC system (Shimadzu, Duisburg, Germany) coupled to an UV detector (SPD-M20A) and a fraction collector (FRC-10A). The triterpenes were separated using an Ultra C18 column (250×21.2 mm, particle size: 5 μm, Restek GmbH, Bad Homburg, Germany) and methanol as solvent with a flow rate of 10 ml/min. The column oven temperature was set to 40° C. Detection was carried out at 205 nm and the triterpene fractions were collected, dried by using Rocket evaporator system (Thermo Fisher Scientific), dissolved in acetone and analyzed by GC-MS. As a second stationary phase an Ultra Biphenyl column was used (250×21.2 mm, particle size: 5 μm, Restek GmbH, Bad Homburg, Germany). The column oven temperature was set to 40° C. and the triterpenes were separated with a gradient of methanol (A) and water (B) at a flow rate of 8 ml/min using the following elution profile: 0-25 min, isocratic 90% A; 25-71 min, linear from 90% to 100% A; 71-75 min, isocratic 100% A; followed by column re-equilibration: 75-76 min, linear from 100% to 90% A; 76-85 min, isocratic 90% A.

Chemical Analysis

Triterpenes were quantified and identified by GC-MS as previously described (Pütter et al., 2017).

By the above described procedure, the inventors were able to carry out a detailed analysis of pentacyclic triterpenoid composition in acetone extracts of natural rubber from *T. koksaghyz* roots. The HPLC-based purification of single triterpenoids enabled the identification of a new pentacyclic triterpene, lup-19(21)-en-3-ol, with its corresponding pentacyclic triterpenoid, the ketone lup-19(21)-en-3-one.

*Taraxacum koksaghyz* natural rubber acetone extract reveals triterpene composition Beside the main component poly(cis-1,4-isoprene), natural rubber contains additional substances like proteins, fatty acids and triterpenes that influence the physical properties of the polymer (Xu et al., 2017). To gain a detailed overview about the single triterpenes that play a role in NR characteristics a lipid fraction was extracted from *T. koksaghyz* NR using acetone as a solvent. The acetone extract was separated on a C18 column by HPLC and seven main fractions could be observed using UV detection at 205 nm (FIG. 12*a*). They were collected and subsequently analyzed by GC-MS. In three of the seven fractions different pentacyclic triterpenes that are described to be highly abundant in the roots of *Taraxacum* spec. (Post et al. 2012) could be detected including lupeol (lup-20(29)-en-3-ol) in fraction F1, taraxasterol and R-amyrin in F4 and α-amyrin in F6. In addition to the alcohols, ketone derivatives of those four pentacyclic triterpenes were also identified in three fractions, namely lupenone (lup-20(29)-en-3-one) in F2, taraxasterone and β-amyrone in F5 and α-amyrone in F7. Furthermore, stigmasterol and sitosterol were detected in two fractions (F3 and F5), two sterol compounds that have been previously described to be present in root material of *Taraxacum* spec. (Post et al. 2012).

Using a second stationary phase for HPLC (biphenyl column), the inventors of the present invention were able to further separate the single triterpenes from each other as shown for F4 and F5 in FIG. 12*b*. In addition to taraxasterol and 3-amyrin a third so far unknown triterpene could be detected in F4 as well as the corresponding ketone in F5 (GC-MS data are exemplarily shown for β-amyrin, taraxasterol and their ketones in FIG. 12*c*). About 1.5 mg pure substance of the triterpene and 0.3 mg of the corresponding ketone was purified for NMR analysis resulting in the identification of a to date unknown pentacyclic triterpene, lup-19(21)-en-3-ol, and its corresponding pentacyclic triterpenoid, the ketone lup-19(21)-en-3-one (FIG. 12*d*).

All triterpenoids that could be found in the acetone extract are summarized in Table 2 below.

In the fractions F2, F3, F5, F6 and F7 further minor compounds could be detected and classified as triterpenoids due to their GC-MS profile but the detailed molecular structure of eight of those compounds is still unknown. Due to the limited amount of the single triterpenes NMR analysis could not be performed.

TABLE 2

Triterpenoids identified in NR acetone extracts, sorted according to their occurrence in C18 HPLC fractions

| C18 fraction | Triterpenoids |
|---|---|
| F1 | lupeol (lup-20(29)-en-3-ol) |
| F2 | lupenone (lup-20(29)-en-3-one) and two unidentified triterpenes |
| F3 | stigmasterol and two unidentified triterpenes |
| F4 | β-amyrin, lup-19(21)-en-3-ol, taraxasterol |
| F5 | sitosterol, β-amyrone, lup-19(21)-en-3-one, taraxasterone and one unidentified triterpene |
| F6 | α-amyrin and one unidentified triterpene |
| F7 | α-amyrone and two unidentified triterpenes |

Herein, the inventors of the present invention have established a new platform for the production of at least one of oxidosqualene, triterpenes and/or triterpenoids, for example, pentacyclic triterpenes in a heterologous system, such as yeast. Therefore, the lupeol synthase of *T. koksaghyz* (SEQ ID NO: 12) have been used as a model enzyme.

This platform was based on a push and pull strategy, that included for example the overexpression of mevalonate-pathway genes and preferably the deletion of a negative regulator of the pathway and late sterol biosynthesis. Furthermore, the inventors were able to enhance, for example, pentacyclic triterpene production by redirecting the metabolic flux from the late sterol biosynthesis—starting with the formation of lanosterol—into the production of the direct pentacyclic triterpene precursor 2,3-oxidosqualene by a copper regulated promoter.

In one embodiment, the inventors chose to overexpress the MVA-pathway genes ERG13 (SEQ ID NO: 14) and tHMGR (SEQ ID NO: 32). HMGR catalyses the key step of the pathway and is being used, as its deregulated form tHMGR, to enhance squalene accumulation and isoprenoid yield in different yeast platforms (Kirby et al., 2008; Asadohalli et al., 2010; Westfall et al., 2011; Scalcinati et al., 2012; Paddon et al., 2013; Lv et al., 2014; Yuan et al., 2014; and others). As an integration site for the described overexpression cassette, the rox1 (SEQ ID NO: 25) locus was chosen in one embodiment of the present invention, resulting in the knock out of this negative regulator of the mevalonate-pathway and late sterol biosynthesis (Henry et al., 2002; Montañés et al., 2011; Özaydin et al., 2013; Jakočiūnas et al., 2015). The knock out lead to the upregulation of the mevalonate pathway in general, as to a downgrade of squalene into the following parts of the pathway caused by the enhanced squalene consumption of the deregulated late sterol biosynthesis. With this strategy we were able to enhance the accumulation of squalene, lanosterol, ergosterol and lupeol (FIG. 7*b* and Table 1), proving the functionality of our strategy and our construct.

As we could not observe the accumulation of 2,3-oxidosqualene, the direct precursor molecule for pentacyclic triterpene synthesis, the inventors redirected the metabolic flux from the late sterol biosynthesis into the pentacyclic triterpene production, by replacing the endogenous ERG7 promoter (SEQ ID NO: 45) with the copper repressible CTR3-promoter (SEQ ID NO: 42) (Labbé et al., 1997). The missing accumulation of 2,3-oxidosqualene therefore may have two reasons. First, the lower capacity of ERG1 (SEQ ID NO: 52) compared to ERG9 (SEQ ID NO: 53) (as suggested by Asadohalli et al., 2010) and second, the rapid reaction towards lanosterol (Veen et al., 2003) by the consumption of ERG7 (SEQ ID NO: 9) and/or in our case pentacyclic triterpenes by the consumption of TkLUP (SEQ ID NO: 12).

The inventors of the present invention could detect in one embodiment of the present invention a decrease in squalene levels as well as the accumulation of 2,3-oxidosqualene upon the repression of endogenous ERG7 (SEQ ID NO: 20) in the used squalene and pentacyclic triterpene accumulating yeast strain. On the one hand this accumulation may occur due to the lower expression of ERG7 (SEQ ID NO: 20) itself, but the regulation mechanism of ERG1 (SEQ ID NO: 51) and ERG9 (SEQ ID NO: 49) may also contribute to our observations. As the inventors detected in this specific embodiment decreased levels of ergosterol and lanosterol, the deregulation of a described negative feedback loop may also contribute to an enhanced expression of ERG9 (SEQ ID NO: 49) and ERG1 (SEQ ID NO: 51), coding for yeast squalene synthase and squalene epoxidase. Therefore, the decreased amounts of sterols may lead to a missing repression of ERG9 (SEQ ID NO: 49) and ERG1 (SEQ ID NO: 51) due to limited ergosterol levels as well as an enhanced expression of ERG1 (SEQ ID NO: 51) due to missing lanosterol derived repression (M'Baya et al., 1989). However, by providing a bulk of the direct substrate of TkLUP (SEQ ID NO: 12) the inventors of the present invention were, for example, able to further enhance the accumulation of lupeol and in addition to identify a so far unknown peak in the respective GC-MS spectra as β-amyrin.

Taken together, the inventors of the present invention were able to enhance the productivity of at least one of oxidosqualene, triterpenes and/or triterpenoids, such as, for example, pentacyclic triterpene synthesis, up to 127-fold. In addition, the inventors were, for example, able to characterize a second pentacyclic triterpene (β-amyrin) synthesized by the model enzyme TkLUP (SEQ ID NO: 12) used in the present invention.

Further, the inventors of the present invention were, for example, also able to purify single triterpenes by using a C18 column in the first chromatography step and a biphenyl column in the second chromatography step, exemplary shown for a triterpene mixture from *T. koksaghyz* plant material.

REFERENCES

1. Alberti S, Gitler A D, Lindquist S (2007) A suite of Gateway cloning vectors for high-throughput genetic analysis in *Saccharomyces cerevisiae*. Yeast. 24:913-919
2. Arendt, P., Pollier, J., Callewaert, N., and Goossens, A. (2016). Synthetic biology for production of natural and new-to-nature terpenoids in photosynthetic organisms. Plant J. 87: 16-37
3. Arendt P, Miettinen K, Pollier J, De Rycke R, Callewaert N, Goossens A (2017) An endoplasmic reticulum-engineered yeast platform for overproduction of triterpenoids. Metab Eng. 40:165-175
4. Asadollahi M A, Maury J, Schalk M, Clark a, Nielsen J (2010) Enhancement of farnesyl diphosphate pool as direct precursor of sesquiterpenes through metabolic engineering of the mevalonate pathway in *Saccharomyces cerevisiae*. Biotechnol Bioeng. 106:89-96
5. Demierre M F, Higgings P D, Gruber S B, Hawk E, Lippmann S M (2005) Statins and cancer prevention. Nat Rev Cancer 5:930-42
6. Donald K A, Hampton R Y, Fritz I B (1997) Effects of overproduction of the catalytic domain of 3-hydroxy-3- methylglutaryl coenzyme A reductase on squalene synthesis in *Saccharomyces cerevisiae*. Appl Environ Microbiol. 63:3341-1

7. Gietz R D, Schiestl R H (2007) High-efficiency yeast transformation using the LiAC/S S carrier DNA/PEG method. Nat Protoc. 2:31-4
8. Hemmerlin A, Harwood J L, Bach T J (2012) A raison d'être for two distinct pathways in the early steps of plant isoprenoid biosynthesis. Prog Lipid Res. 51:95-148
9. Henry K W, Nickels J T, Edling T D (2002) ROX1 and ERG regulation in *Saccharomyces cerevisiae*: implications for antifungal susceptibility. Eukaryot Cell. 1:1041-4
10. Jakočiūnas T, Bonde I, Herrgård M, Harrison S J, Kristensen M, Pedersen L E, Jensen M K, Keasling J D (2015) Multiplex metabolic pathway engineering using CRISPR/Cas9 in *Saccharomyces cerevisiae*. Metab Eng. 28:213-22
11. Jamison McDaniels C P, Jensen L T, Srinivasan C, Winge D R, Tullius T D (1999) The yeast transcription factor Mac1 binds to DNA in a modular fashion. *J Biol Chem* 274(38):26962-7
12. Jensen N B, Strucko T, Kildegaard K R, David F, Maury J, Mortensen U H, Forster J, Nielsen J, Borodina I (2014) EasyClone: method for iterative chromosomal integration of multiple genes in *Saccharomyces cerevisiae*. FEMS Yeast Res. 14:238-48
13. Kirby J, Romanini D W, Paradise E M, Keasling J D (2008) Engineering triterpene production in *Saccharomyces cerevisiae*-beta-amyrin synthase from *Artemisia annua*. FEBS J. 275:1852-9
14. Labbé S, Zhu Z, Thiele D J (1997) Copper-specific transcriptional repression of yeast genes encoding critical components in the copper transport pathway. J Biol Chem. 272:1591-8
15. Liao P, Hemmerlin A, Bach T J, Chye M L (2016) The potential of the mevalonate pathway for enhanced isoprenoid production. Biotechnol Adv. 34:697-713
16. Lv X, Xie W, Lu W, Guo F, Gu J, Yu H, Ye L (2014) Enhanced isoprene biosynthesis in *Saccharomyces cerevisiae* by engineering of the native acetyl-CoA and mevalonic acid pathways with a push-pull-restrain strategy. J Biotechnol. 186:128-36
17. M'Baya B, Fequeur M, Servouse M, Karst F (1989) Regulation of squalene synthase and squalene epoxidase activities in *Saccharomyces cerevisiae*. Lipids. 24:1020-3
18. Martin V J, Pitera D J, Withers S T, Newman J D, Keasling J D (2003) Engineering a mevalonate pathway in *Escherichia coli* for the production of terpenoids. Nat Biotechnol. 21:796-802
19. Montañés F M Pascual-Ahuir A, Proft M (2011) Repression of ergosterol biosynthesis is essential for stress resistance and is mediated by the Hog1 MAP kinase and the Mot3 and Rox1 transcription factors. Mol Microbiol. 79:1008-23
20. Moses, T. and Pollier, J. (2013). Bioengineering of plant (tri) terpenoids: from metabolic engineering of plants to synthetic biology in vivo and in vitro. New Phytol. 200: 27-43
21. Özaydin B, Burd H, Lee T S, Keasling J D (2013) Carotenoid-based phenotypic screen of the yeast deletion collection reveals new genes with roles in isoprenoid production. Metab Eng. 15:1744-83
22. Paddon C J, Westfall P J, Pitera D J, Benjamin K, Fisher K, McPhee D, Leavell M D, Tai A, Main A, Eng D, Polichuk D R, Teoh K H, Reed D W, Treynor T, Lenihan J, Fleck M, Bajad S, Dang G, Dengrove D, Diola D, Dorin G, Ellens K W, Fickes S, Galazzo J, Gaucher S P, Geistlinger T, Henry R, Hepp M, Horning T, Iqbal T, Jiang H, Kizer L, Lieu B, Melis D, Moss N, Regentin R, Secrest S, Tsuruta H, Vazquez R, Westblade L F, Xu L, Yu M, Zhang Y, Zhao L, Lievense J, Covello P S, Keasling J D, Reiling K K, Renninger N S, Newman J D (2013) High-level semi-synthetic production of the potent antimalarial artemisinin. Nature. 496:528-32
23. Post, J., van Deenen, N., Fricke, J., Kowalski, N., Wurbs, D., Schaller, H., Eisenreich, W., Huber, C., Twyman, R. M., Prüfer, D., Schulze Gronover, C. (2012). Laticifer-Specific cis-Prenyltransferase Silencing Affects the Rubber, Triterpene, and Inulin Content of *Taraxacum brevicorniculatum*. American Society of Plant Biologists. pp. 111
24. Putter, K. M., van Deenen, N., Unland, K., Prüfer, D., and Schulze Gronover, C. (2017). Isoprenoid biosynthesis in dandelion latex is enhanced by the overexpression of three key enzymes involved in the mevalonate pathway. BMC Plant Biol. 17: 88
25. Ro D K, Paradise E M, Oulett M, Fisher K J, Newman, K L, Ndungu J M, Ho K A, Eachus R A, Ham T S, Kirby j, Chang M C, Withers S T, Shiba Y, Sarpong R, Keasling J D (2006) Production of the antimalarial drug precursor artemisinic acid in engineered yeast. Nature. 440:940-3
26. Rodriguez S, Kirby J, Denby C M, Keasling J D (2014) Production and quantification of sesquiterpenes in *Saccharomyces cerevisiae*, including extraction, detection and quantification of terpene products and key metabolites. Nat Protoc. 9:1980-96
27. Sanger F, Nicklen S, Coulson A R (1977) DNA sequencing with chain-terminating inhibitors. Proc Natl Acad Sci USA. 74:5463-5467
28. Sheng, H. and Sun, H. (2010). Synthesis, biology and clinical significance of pentacyclic triterpenes: a multi-target approach to prevention and treatment of metabolic and vascular diseases. Nat. Prod. Rep 28: 543-593
29. Scalcinati G, Partow S, Siewers V, Schalk M, Daviet L, Nielsen J (2012) Combinedmetabolic engineering of precursor and co-factor supply to increase α-santalene production by *Saccharomyces cerevisiae*. Microb Cell Fact. 31; 11:117
30. Shibuya M, Zhang H, Endo A, Shishikura K, Kushiro T, Ebizuka Y (1999) Two branches of the lupeol synthase gene in the molecular evolution of plant oxisqualene cyclases. Eur J Biochem. 266:307-7
31. Vickers C E, Williams T C, Peng B, Cherry J (2017) Recent advances in synthetic biology for engineered isoprenoid production in yeast. Corr Opin Chem Biol. 40:47-56
32. Veen M, Stahl U, Lang C (2003) Combined overexpression of genes of the ergosterol biosynthetic pathway leads to accumulation of sterols in *Saccharomyces cerevisiae*. FEMS Yeast Res. 2003 4:87-95
33. Westfall P J, Pitera D J, Lenihan J R, Eng D, Woolard F X, Regentin R, Horning T, Tsuruta H, Melis D J, Owens A, Fickes S, Diola D, Benjamin K R, Keasling J D, Leavell M D, McPhee D J, Renninger N S, Newman J D, Paddon C J (2012) Production of amorphadiene in yeast, and its conversion to dihydroartemisinic acid, precursor to the antimalarial agent artemisinin. Proc Natl Acad Sci USA. 109:E111-8
34. Yamaguchi-Iwai Y, Serpe M, Haile D, Yang W, Kosman D J, Klausner R D, Dancis A (1997) Homeostatic regulation of copper uptake in yeast via direct binding of MAC1 protein to upstream regulatory sequences of FRE1 and CTR1. J Biol Chem 272(28):17711-8
35. Xu, R., Fazio, G. C., and Matsuda, S. P. T. (2004). On the origins of triterpenoid skeletal diversity. Phytochemistry 65: 261-291

The invention claimed is:

1. A recombinant host cell for manufacturing one or more of oxidosqualene(s), triterpene(s) and triterpenoid(s), wherein the host cell is engineered to overexpress a 3-hydroxy-3-methylglutaryl-coenzyme A reductase comprising the amino acid sequence as shown in SEQ ID NO: 1, and to overexpress a protein comprising at least one amino acid sequence selected from the group consisting of SEQ ID NOs: 2, 3, 4, 5, 6, 7 and 8, and wherein the one or more of oxidosqualene(s), triterpene(s) and triterpenoid(s) is/are selected from the group consisting of an oxidosqualene, a sterol, a pentacyclic triterpene, an acylated triterpene, β-amyrin, α-amyrin, taraxasterol, a triterpene acetate, an acylated triterpene, taraxerol, taraxerone, α-amyrone, β-amyrone, taraxasterone, friedelin, betulin, betulinic acid, cholesterol, ergosterol, lanosterol, a glucocorticoid, a mineralocorticoid, an estrogen, a gestagen, a cardenolide, a bufadienolide, and a steroidalkaloid, wherein the host cell comprises a knock out of at least one locus selected from the group consisting of ROX1 (SEQ ID NO: 25), BTS1 (SEQ ID NO: 54), YPL062W (SEQ ID NO: 55), DOS2 (SEQ ID NO: 56), YER134C (SEQ ID NO: 57), VBA5 (SEQ ID NO: 58), YNR063W (SEQ ID NO: 59), YJL064W (SEQ ID NO: 60) and YGR259C (SEQ ID NO: 61).

2. The host cell of claim 1, wherein the host cell is selected from the group consisting of *Saccharomyces cerevisiae, Nicotiana benthamiana, Pichia pastoris, Pichia methanolica, Schizosaccharomyces pombe, Kluyveromyces lactis, Kluyveromyces marxianus, Pichia stipitis, Candida albicans, Candida utilis* and BY2 cells.

3. The host cell of claim 1, wherein the host cell is engineered to overexpress the protein comprising the SEQ ID NO: 3.

4. The host cell of claim 1, wherein the host cell is further engineered to repress the lanosterolsynthase having an amino acid sequence as shown in SEQ ID NO: 9, optionally by the insertion of the CTR3-promoter and/or the addition of copper sulfate ($CuSO_4$).

5. The host cell of claim 1, wherein ROX1 of SEQ ID NO: 25 is knocked out.

6. The host cell of claim 1, wherein the one or more of oxidosqualene(s), triterpene(s) and triterpenoid(s) is/are selected from the group consisting of 2,3-oxidosqualene, sigmasterol, sitosterol, and lupeol.

7. The host cell of claim 1, wherein the at least one heterologous protein producing the one or more of oxidosqualene(s), triterpene(s) and/or triterpenoid(s) is selected from the group consisting of lupeol synthases, oxidosqualene cyclases (OSC), β-amyrin synthases, and terpene cyclases, optionally wherein the lupeol synthase is from *Taraxacum koksaghyz,* optionally wherein the oxidosqualene cyclase is TkOSC1-6 from *Taraxacum koksaghyz,* optionally wherein the β-amyrin synthase is from *Arabidopsis thaliana* or from *Artemisia annua*, or optionally wherein the terpene cyclase is from *Glycyrrhiza uralensis* (GuLUP1).

8. The host cell of claim 1, wherein the one or more of oxidosqualene(s), triterpene(s) and triterpenoid(s) is/are selected from the group consisting of lup-19(21)-en-3-ol, lup-20(29)-en-3-ol, lup-19(21)-en-3-one, and lup-20(29)-en-3-one.

9. A method of producing one or more of oxidosqualene(s), triterpene(s), and triterpenoid(s) in a host cell comprising culturing the host cell of claim 1 under conditions to produce the one or more of oxidosqualene(s), triterpene(s), and triterpenoid(s), and wherein the one or more of oxidosqualene(s), triterpene(s) and triterpenoid(s) is/are selected from the group consisting of an oxidosqualene, a sterol, a pentacyclic triterpene, an acylated triterpene, β-amyrin, α-amyrin, taraxasterol, a triterpene acetate, an acylated triterpene, taraxerol, taraxerone, α-amyrone, β-amyrone, taraxasterone, friedelin, betulin, betulinic acid, cholesterol, ergosterol, lanosterol, a glucocorticoid, a mineralocorticoid, an estrogen, a gestagen, a cardenolide, a bufadienolide, and a steroidalkaloid.

10. The method of claim 9, wherein culturing comprises using a culture medium comprising copper sulfate ($CuSO_4$).

11. The method of claim 10, wherein $CuSO_4$ is present in the culture medium in an amount of at least 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370 or 375 mM $CuSO_4$, optionally at least 150 mM $CuSO_4$.

12. The method of claim 9, further comprising purifying the one or more of oxidosqualene(s), triterpene(s), and triterpenoid(s).

13. The method of claim 12, wherein purification is carried out by at least two chromatography steps, optionally using a C18 column in a first chromatography step and using a biphenyl column in a second chromatography step.

14. The method of claim 9, wherein the yield of more than one of the one or more of oxidosqualene(s), triterpene(s), and triterpenoid(s) is increased.

15. A method of making a recombinant host cell that manufactures one or more of oxidosqualene(s), triterpene(s), and triterpenoid(s), comprising a step of engineering a host cell to:

overexpress a 3-hydroxy-3-methylglutaryl-coenzyme A reductase comprising SEQ ID NO: 1, overexpress a protein comprising at least one amino acid sequence selected from the group consisting of SEQ ID NOs: 2, 3, 4, 5, 6, 7, and 8, and knock out at least one locus selected from the group consisting of ROX1 of SEQ ID NO: 25, BTS1 of SEQ ID NO: 54, YPL062W of SEQ ID NO: 55, DOS2 of SEQ ID NO: 56, YER134C of SEQ ID NO: 57, VBA5 of SEQ ID NO: 58, YNR063W of SEQ ID NO: 59, YJL064W of SEQ ID NO: 60 and YGR259C of SEQ ID NO: 61, and wherein the one or more of oxidosqualene(s), triterpene(s) and triterpenoid(s) is/are selected from the group consisting of an oxidosqualene, a sterol, a pentacyclic triterpene, an acylated triterpene, β-amyrin, α-amyrin, taraxasterol, a triterpene acetate, an acylated triterpene, taraxerol, taraxerone, α-amyrone, β-amyrone, taraxasterone, friedelin, betulin, betulinic acid, cholesterol, ergosterol, lanosterol, a glucocorticoid, a mineralocorticoid, an estrogen, a gestagen, a cardenolide, a bufadienolide, and a steroidalkaloid.

16. The method of claim 15, wherein the host cell is selected from the group consisting of *Saccharomyces cerevisiae, Nicotiana benthamiana, Pichia pastoris, Pichia methanolica, Schizosaccharomyces pombe, Kluyveromyces lactis, Kluyveromyces marxiams, Pichia stipitis, Candida albicans, Candida utilis* and BY2 cells.

17. The method of claim 15, comprising engineering the host cell to overexpress the protein comprising the SEQ ID NO: 3.

18. The method of claim 15, comprising engineering the host cell to repress the lanosterolsynthase having an amino acid sequence as shown in SEQ ID NO: 9, optionally by insertion of the CTR3-promoter.

19. The method of claim 15, comprising engineering the host cell to knock out ROX1 of SEQ ID NO: 25.

* * * * *

SEQUENCE LISTING

<160> NUMBER OF SEQ ID NOS: 67

<210> SEQ ID NO 1
<211> LENGTH: 502
<212> TYPE: PRT
<213> ORGANISM: Saccharomyces cerevisiae

<400> SEQUENCE: 1

```
Met Val Leu Thr Asn Lys Thr Val Ile Ser Gly Ser Lys Val Lys Ser
1               5                   10                  15

Leu Ser Ser Ala Gln Ser Ser Ser Ser Gly Pro Ser Ser Ser Ser Glu
            20                  25                  30

Glu Asp Asp Ser Arg Asp Ile Glu Ser Leu Asp Lys Lys Ile Arg Pro
        35                  40                  45

Leu Glu Glu Leu Glu Ala Leu Leu Ser Ser Gly Asn Thr Lys Gln Leu
    50                  55                  60

Lys Asn Lys Glu Val Ala Ala Leu Val Ile His Gly Lys Leu Pro Leu
65                  70                  75                  80

Tyr Ala Leu Glu Lys Lys Leu Gly Asp Thr Thr Arg Ala Val Ala Val
                85                  90                  95

Arg Arg Lys Ala Leu Ser Ile Leu Ala Glu Ala Pro Val Leu Ala Ser
            100                 105                 110

Asp Arg Leu Pro Tyr Lys Asn Tyr Asp Tyr Asp Arg Val Phe Gly Ala
        115                 120                 125

Cys Cys Glu Asn Val Ile Gly Tyr Met Pro Leu Pro Val Gly Val Ile
    130                 135                 140

Gly Pro Leu Val Ile Asp Gly Thr Ser Tyr His Ile Pro Met Ala Thr
145                 150                 155                 160

Thr Glu Gly Cys Leu Val Ala Ser Ala Met Arg Gly Cys Lys Ala Ile
                165                 170                 175

Asn Ala Gly Gly Gly Ala Thr Thr Val Leu Thr Lys Asp Gly Met Thr
            180                 185                 190

Arg Gly Pro Val Val Arg Phe Pro Thr Leu Lys Arg Ser Gly Ala Cys
        195                 200                 205

Lys Ile Trp Leu Asp Ser Glu Glu Gly Gln Asn Ala Ile Lys Lys Ala
    210                 215                 220

Phe Asn Ser Thr Ser Arg Phe Ala Arg Leu Gln His Ile Gln Thr Cys
225                 230                 235                 240

Leu Ala Gly Asp Leu Leu Phe Met Arg Phe Arg Thr Thr Thr Gly Asp
                245                 250                 255

Ala Met Gly Met Asn Met Ile Ser Lys Gly Val Glu Tyr Ser Leu Lys
            260                 265                 270

Gln Met Val Glu Glu Tyr Gly Trp Glu Asp Met Glu Val Val Ser Val
        275                 280                 285

Ser Gly Asn Tyr Cys Thr Asp Lys Lys Pro Ala Ala Ile Asn Trp Ile
    290                 295                 300

Glu Gly Arg Gly Lys Ser Val Val Ala Glu Ala Thr Ile Pro Gly Asp
305                 310                 315                 320

Val Val Arg Lys Val Leu Lys Ser Asp Val Ser Ala Leu Val Glu Leu
                325                 330                 335

Asn Ile Ala Lys Asn Leu Val Gly Ser Ala Met Ala Gly Ser Val Gly
```

```
            340                 345                 350

Gly Phe Asn Ala His Ala Ala Asn Leu Val Thr Ala Val Phe Leu Ala
        355                 360                 365

Leu Gly Gln Asp Pro Ala Gln Asn Val Glu Ser Ser Asn Cys Ile Thr
    370                 375                 380

Leu Met Lys Glu Val Asp Gly Asp Leu Arg Ile Ser Val Ser Met Pro
385                 390                 395                 400

Ser Ile Glu Val Gly Thr Ile Gly Gly Gly Thr Val Leu Glu Pro Gln
                405                 410                 415

Gly Ala Met Leu Asp Leu Leu Gly Val Arg Gly Pro His Ala Thr Ala
            420                 425                 430

Pro Gly Thr Asn Ala Arg Gln Leu Ala Arg Ile Val Ala Cys Ala Val
        435                 440                 445

Leu Ala Gly Glu Leu Ser Leu Cys Ala Ala Leu Ala Ala Gly His Leu
    450                 455                 460

Val Gln Ser His Met Thr His Asn Arg Lys Pro Ala Glu Pro Thr Lys
465                 470                 475                 480

Pro Asn Asn Leu Asp Ala Thr Asp Ile Asn Arg Leu Lys Asp Gly Ser
                485                 490                 495

Val Thr Cys Ile Lys Ser
            500


<210> SEQ ID NO 2
<211> LENGTH: 398
<212> TYPE: PRT
<213> ORGANISM: Saccharomyces cerevisiae

<400> SEQUENCE: 2

Met Ser Gln Asn Val Tyr Ile Val Ser Thr Ala Arg Thr Pro Ile Gly
1               5                   10                  15

Ser Phe Gln Gly Ser Leu Ser Ser Lys Thr Ala Val Glu Leu Gly Ala
            20                  25                  30

Val Ala Leu Lys Gly Ala Leu Ala Lys Val Pro Glu Leu Asp Ala Ser
        35                  40                  45

Lys Asp Phe Asp Glu Ile Ile Phe Gly Asn Val Leu Ser Ala Asn Leu
    50                  55                  60

Gly Gln Ala Pro Ala Arg Gln Val Ala Leu Ala Ala Gly Leu Ser Asn
65                  70                  75                  80

His Ile Val Ala Ser Thr Val Asn Lys Val Cys Ala Ser Ala Met Lys
                85                  90                  95

Ala Ile Ile Leu Gly Ala Gln Ser Ile Lys Cys Gly Asn Ala Asp Val
            100                 105                 110

Val Val Ala Gly Gly Cys Glu Ser Met Thr Asn Ala Pro Tyr Tyr Met
        115                 120                 125

Pro Ala Ala Arg Ala Gly Ala Lys Phe Gly Gln Thr Val Leu Val Asp
    130                 135                 140

Gly Val Glu Arg Asp Gly Leu Asn Asp Ala Tyr Asp Gly Leu Ala Met
145                 150                 155                 160

Gly Val His Ala Glu Lys Cys Ala Arg Asp Trp Asp Ile Thr Arg Glu
                165                 170                 175

Gln Gln Asp Asn Phe Ala Ile Glu Ser Tyr Gln Lys Ser Gln Lys Ser
            180                 185                 190

Gln Lys Glu Gly Lys Phe Asp Asn Glu Ile Val Pro Val Thr Ile Lys
        195                 200                 205
```

-continued

```
Gly Phe Arg Gly Lys Pro Asp Thr Gln Val Thr Lys Asp Glu Glu Pro
    210                 215                 220

Ala Arg Leu His Val Glu Lys Leu Arg Ser Ala Arg Thr Val Phe Gln
225                 230                 235                 240

Lys Glu Asn Gly Thr Val Thr Ala Ala Asn Ala Ser Pro Ile Asn Asp
                245                 250                 255

Gly Ala Ala Ala Val Ile Leu Val Ser Glu Lys Val Leu Lys Glu Lys
            260                 265                 270

Asn Leu Lys Pro Leu Ala Ile Ile Lys Gly Trp Gly Glu Ala Ala His
        275                 280                 285

Gln Pro Ala Asp Phe Thr Trp Ala Pro Ser Leu Ala Val Pro Lys Ala
    290                 295                 300

Leu Lys His Ala Gly Ile Glu Asp Ile Asn Ser Val Asp Tyr Phe Glu
305                 310                 315                 320

Phe Asn Glu Ala Phe Ser Val Val Gly Leu Val Asn Thr Lys Ile Leu
                325                 330                 335

Lys Leu Asp Pro Ser Lys Val Asn Val Tyr Gly Gly Ala Val Ala Leu
            340                 345                 350

Gly His Pro Leu Gly Cys Ser Gly Ala Arg Val Val Val Thr Leu Leu
        355                 360                 365

Ser Ile Leu Gln Gln Glu Gly Gly Lys Ile Gly Val Ala Ala Ile Cys
    370                 375                 380

Asn Gly Gly Gly Gly Ala Ser Ser Ile Val Ile Glu Lys Ile
385                 390                 395


<210> SEQ ID NO 3
<211> LENGTH: 491
<212> TYPE: PRT
<213> ORGANISM: Saccharomyces cerevisiae

<400> SEQUENCE: 3

Met Lys Leu Ser Thr Lys Leu Cys Trp Cys Gly Ile Lys Gly Arg Leu
1               5                   10                  15

Arg Pro Gln Lys Gln Gln Gln Leu His Asn Thr Asn Leu Gln Met Thr
            20                  25                  30

Glu Leu Lys Lys Gln Lys Thr Ala Glu Gln Lys Thr Arg Pro Gln Asn
        35                  40                  45

Val Gly Ile Lys Gly Ile Gln Ile Tyr Ile Pro Thr Gln Cys Val Asn
    50                  55                  60

Gln Ser Glu Leu Glu Lys Phe Asp Gly Val Ser Gln Gly Lys Tyr Thr
65                  70                  75                  80

Ile Gly Leu Gly Gln Thr Asn Met Ser Phe Val Asn Asp Arg Glu Asp
                85                  90                  95

Ile Tyr Ser Met Ser Leu Thr Val Leu Ser Lys Leu Ile Lys Ser Tyr
            100                 105                 110

Asn Ile Asp Thr Asn Lys Ile Gly Arg Leu Glu Val Gly Thr Glu Thr
        115                 120                 125

Leu Ile Asp Lys Ser Lys Ser Val Lys Ser Val Leu Met Gln Leu Phe
    130                 135                 140

Gly Glu Asn Thr Asp Val Glu Gly Ile Asp Thr Leu Asn Ala Cys Tyr
145                 150                 155                 160

Gly Gly Thr Asn Ala Leu Phe Asn Ser Leu Asn Trp Ile Glu Ser Asn
                165                 170                 175

Ala Trp Asp Gly Arg Asp Ala Ile Val Val Cys Gly Asp Ile Ala Ile
            180                 185                 190
```

Tyr Asp Lys Gly Ala Ala Arg Pro Thr Gly Gly Ala Gly Thr Val Ala
195 200 205

Met Trp Ile Gly Pro Asp Ala Pro Ile Val Phe Asp Ser Val Arg Ala
210 215 220

Ser Tyr Met Glu His Ala Tyr Asp Phe Tyr Lys Pro Asp Phe Thr Ser
225 230 235 240

Glu Tyr Pro Tyr Val Asp Gly His Phe Ser Leu Thr Cys Tyr Val Lys
245 250 255

Ala Leu Asp Gln Val Tyr Lys Ser Tyr Ser Lys Lys Ala Ile Ser Lys
260 265 270

Gly Leu Val Ser Asp Pro Ala Gly Ser Asp Ala Leu Asn Val Leu Lys
275 280 285

Tyr Phe Asp Tyr Asn Val Phe His Val Pro Thr Cys Lys Leu Val Thr
290 295 300

Lys Ser Tyr Gly Arg Leu Leu Tyr Asn Asp Phe Arg Ala Asn Pro Gln
305 310 315 320

Leu Phe Pro Glu Val Asp Ala Glu Leu Ala Thr Arg Asp Tyr Asp Glu
325 330 335

Ser Leu Thr Asp Lys Asn Ile Glu Lys Thr Phe Val Asn Val Ala Lys
340 345 350

Pro Phe His Lys Glu Arg Val Ala Gln Ser Leu Ile Val Pro Thr Asn
355 360 365

Thr Gly Asn Met Tyr Thr Ala Ser Val Tyr Ala Ala Phe Ala Ser Leu
370 375 380

Leu Asn Tyr Val Gly Ser Asp Asp Leu Gln Gly Lys Arg Val Gly Leu
385 390 395 400

Phe Ser Tyr Gly Ser Gly Leu Ala Ala Ser Leu Tyr Ser Cys Lys Ile
405 410 415

Val Gly Asp Val Gln His Ile Ile Lys Glu Leu Asp Ile Thr Asn Lys
420 425 430

Leu Ala Lys Arg Ile Thr Glu Thr Pro Lys Asp Tyr Glu Ala Ala Ile
435 440 445

Glu Leu Arg Glu Asn Ala His Leu Lys Lys Asn Phe Lys Pro Gln Gly
450 455 460

Ser Ile Glu His Leu Gln Ser Gly Val Tyr Tyr Leu Thr Asn Ile Asp
465 470 475 480

Asp Lys Phe Arg Arg Ser Tyr Asp Val Lys Lys
485 490

<210> SEQ ID NO 4
<211> LENGTH: 443
<212> TYPE: PRT
<213> ORGANISM: Saccharomyces cerevisiae

<400> SEQUENCE: 4

Met Ser Leu Pro Phe Leu Thr Ser Ala Pro Gly Lys Val Ile Ile Phe
1 5 10 15

Gly Glu His Ser Ala Val Tyr Asn Lys Pro Ala Val Ala Ala Ser Val
20 25 30

Ser Ala Leu Arg Thr Tyr Leu Leu Ile Ser Glu Ser Ser Ala Pro Asp
35 40 45

Thr Ile Glu Leu Asp Phe Pro Asp Ile Ser Phe Asn His Lys Trp Ser
50 55 60

Ile Asn Asp Phe Asn Ala Ile Thr Glu Asp Gln Val Asn Ser Gln Lys

```
65                  70                  75                  80

Leu Ala Lys Ala Gln Gln Ala Thr Asp Gly Leu Ser Gln Glu Leu Val
                85                  90                  95

Ser Leu Leu Asp Pro Leu Leu Ala Gln Leu Ser Glu Ser Phe His Tyr
            100                 105                 110

His Ala Ala Phe Cys Phe Leu Tyr Met Phe Val Cys Leu Cys Pro His
        115                 120                 125

Ala Lys Asn Ile Lys Phe Ser Leu Lys Ser Thr Leu Pro Ile Gly Ala
    130                 135                 140

Gly Leu Gly Ser Ser Ala Ser Ile Ser Val Ser Leu Ala Leu Ala Met
145                 150                 155                 160

Ala Tyr Leu Gly Gly Leu Ile Gly Ser Asn Asp Leu Glu Lys Leu Ser
                165                 170                 175

Glu Asn Asp Lys His Ile Val Asn Gln Trp Ala Phe Ile Gly Glu Lys
            180                 185                 190

Cys Ile His Gly Thr Pro Ser Gly Ile Asp Asn Ala Val Ala Thr Tyr
        195                 200                 205

Gly Asn Ala Leu Leu Phe Glu Lys Asp Ser His Asn Gly Thr Ile Asn
    210                 215                 220

Thr Asn Asn Phe Lys Phe Leu Asp Asp Phe Pro Ala Ile Pro Met Ile
225                 230                 235                 240

Leu Thr Tyr Thr Arg Ile Pro Arg Ser Thr Lys Asp Leu Val Ala Arg
                245                 250                 255

Val Arg Val Leu Val Thr Glu Lys Phe Pro Glu Val Met Lys Pro Ile
            260                 265                 270

Leu Asp Ala Met Gly Glu Cys Ala Leu Gln Gly Leu Glu Ile Met Thr
        275                 280                 285

Lys Leu Ser Lys Cys Lys Gly Thr Asp Asp Glu Ala Val Glu Thr Asn
    290                 295                 300

Asn Glu Leu Tyr Glu Gln Leu Leu Glu Leu Ile Arg Ile Asn His Gly
305                 310                 315                 320

Leu Leu Val Ser Ile Gly Val Ser His Pro Gly Leu Glu Leu Ile Lys
                325                 330                 335

Asn Leu Ser Asp Asp Leu Arg Ile Gly Ser Thr Lys Leu Thr Gly Ala
            340                 345                 350

Gly Gly Gly Gly Cys Ser Leu Thr Leu Leu Arg Arg Asp Ile Thr Gln
        355                 360                 365

Glu Gln Ile Asp Ser Phe Lys Lys Lys Leu Gln Asp Asp Phe Ser Tyr
    370                 375                 380

Glu Thr Phe Glu Thr Asp Leu Gly Gly Thr Gly Cys Cys Leu Leu Ser
385                 390                 395                 400

Ala Lys Asn Leu Asn Lys Asp Leu Lys Ile Lys Ser Leu Val Phe Gln
                405                 410                 415

Leu Phe Glu Asn Lys Thr Thr Thr Lys Gln Gln Ile Asp Asp Leu Leu
            420                 425                 430

Leu Pro Gly Asn Thr Asn Leu Pro Trp Thr Ser
        435                 440
```

<210> SEQ ID NO 5
<211> LENGTH: 451
<212> TYPE: PRT
<213> ORGANISM: Saccharomyces cerevisiae

<400> SEQUENCE: 5

-continued

```
Met Ser Glu Leu Arg Ala Phe Ser Ala Pro Gly Lys Ala Leu Leu Ala
1               5                   10                  15

Gly Gly Tyr Leu Val Leu Asp Pro Lys Tyr Glu Ala Phe Val Val Gly
            20                  25                  30

Leu Ser Ala Arg Met His Ala Val Ala His Pro Tyr Gly Ser Leu Gln
        35                  40                  45

Glu Ser Asp Lys Phe Glu Val Arg Val Lys Ser Lys Gln Phe Lys Asp
    50                  55                  60

Gly Glu Trp Leu Tyr His Ile Ser Pro Lys Thr Gly Phe Ile Pro Val
65                  70                  75                  80

Ser Ile Gly Gly Ser Lys Asn Pro Phe Ile Glu Lys Val Ile Ala Asn
                85                  90                  95

Val Phe Ser Tyr Phe Lys Pro Asn Met Asp Asp Tyr Cys Asn Arg Asn
            100                 105                 110

Leu Phe Val Ile Asp Ile Phe Ser Asp Asp Ala Tyr His Ser Gln Glu
        115                 120                 125

Asp Ser Val Thr Glu His Arg Gly Asn Arg Arg Leu Ser Phe His Ser
    130                 135                 140

His Arg Ile Glu Glu Val Pro Lys Thr Gly Leu Gly Ser Ser Ala Gly
145                 150                 155                 160

Leu Val Thr Val Leu Thr Thr Ala Leu Ala Ser Phe Phe Val Ser Asp
                165                 170                 175

Leu Glu Asn Asn Val Asp Lys Tyr Arg Glu Val Ile His Asn Leu Ser
            180                 185                 190

Gln Val Ala His Cys Gln Ala Gln Gly Lys Ile Gly Ser Gly Phe Asp
        195                 200                 205

Val Ala Ala Ala Ala Tyr Gly Ser Ile Arg Tyr Arg Arg Phe Pro Pro
    210                 215                 220

Ala Leu Ile Ser Asn Leu Pro Asp Ile Gly Ser Ala Thr Tyr Gly Ser
225                 230                 235                 240

Lys Leu Ala His Leu Val Asn Glu Glu Asp Trp Asn Ile Thr Ile Lys
                245                 250                 255

Ser Asn His Leu Pro Ser Gly Leu Thr Leu Trp Met Gly Asp Ile Lys
            260                 265                 270

Asn Gly Ser Glu Thr Val Lys Leu Val Gln Lys Val Lys Asn Trp Tyr
        275                 280                 285

Asp Ser His Met Pro Glu Ser Leu Lys Ile Tyr Thr Glu Leu Asp His
    290                 295                 300

Ala Asn Ser Arg Phe Met Asp Gly Leu Ser Lys Leu Asp Arg Leu His
305                 310                 315                 320

Glu Thr His Asp Asp Tyr Ser Asp Gln Ile Phe Glu Ser Leu Glu Arg
                325                 330                 335

Asn Asp Cys Thr Cys Gln Lys Tyr Pro Glu Ile Thr Glu Val Arg Asp
            340                 345                 350

Ala Val Ala Thr Ile Arg Arg Ser Phe Arg Lys Ile Thr Lys Glu Ser
        355                 360                 365

Gly Ala Asp Ile Glu Pro Pro Val Gln Thr Ser Leu Leu Asp Asp Cys
    370                 375                 380

Gln Thr Leu Lys Gly Val Leu Thr Cys Leu Ile Pro Gly Ala Gly Gly
385                 390                 395                 400

Tyr Asp Ala Ile Ala Val Ile Ala Lys Gln Asp Val Asp Leu Arg Ala
                405                 410                 415

Gln Thr Ala Asp Asp Lys Arg Phe Ser Lys Val Gln Trp Leu Asp Val
```

```
            420                 425                 430

Thr Gln Ala Asp Trp Gly Val Arg Lys Glu Lys Asp Pro Glu Thr Tyr
        435                 440                 445

Leu Asp Lys
    450


<210> SEQ ID NO 6
<211> LENGTH: 396
<212> TYPE: PRT
<213> ORGANISM: Saccharomyces cerevisiae

<400> SEQUENCE: 6

Met Thr Val Tyr Thr Ala Ser Val Thr Ala Pro Val Asn Ile Ala Thr
1               5                   10                  15

Leu Lys Tyr Trp Gly Lys Arg Asp Thr Lys Leu Asn Leu Pro Thr Asn
            20                  25                  30

Ser Ser Ile Ser Val Thr Leu Ser Gln Asp Asp Leu Arg Thr Leu Thr
        35                  40                  45

Ser Ala Ala Thr Ala Pro Glu Phe Glu Arg Asp Thr Leu Trp Leu Asn
    50                  55                  60

Gly Glu Pro His Ser Ile Asp Asn Glu Arg Thr Gln Asn Cys Leu Arg
65                  70                  75                  80

Asp Leu Arg Gln Leu Arg Lys Glu Met Glu Ser Lys Asp Ala Ser Leu
                85                  90                  95

Pro Thr Leu Ser Gln Trp Lys Leu His Ile Val Ser Glu Asn Asn Phe
            100                 105                 110

Pro Thr Ala Ala Gly Leu Ala Ser Ser Ala Ala Gly Phe Ala Ala Leu
        115                 120                 125

Val Ser Ala Ile Ala Lys Leu Tyr Gln Leu Pro Gln Ser Thr Ser Glu
    130                 135                 140

Ile Ser Arg Ile Ala Arg Lys Gly Ser Gly Ser Ala Cys Arg Ser Leu
145                 150                 155                 160

Phe Gly Gly Tyr Val Ala Trp Glu Met Gly Lys Ala Glu Asp Gly His
                165                 170                 175

Asp Ser Met Ala Val Gln Ile Ala Asp Ser Ser Asp Trp Pro Gln Met
            180                 185                 190

Lys Ala Cys Val Leu Val Val Ser Asp Ile Lys Lys Asp Val Ser Ser
        195                 200                 205

Thr Gln Gly Met Gln Leu Thr Val Ala Thr Ser Glu Leu Phe Lys Glu
    210                 215                 220

Arg Ile Glu His Val Val Pro Lys Arg Phe Glu Val Met Arg Lys Ala
225                 230                 235                 240

Ile Val Glu Lys Asp Phe Ala Thr Phe Ala Lys Glu Thr Met Met Asp
                245                 250                 255

Ser Asn Ser Phe His Ala Thr Cys Leu Asp Ser Phe Pro Pro Ile Phe
            260                 265                 270

Tyr Met Asn Asp Thr Ser Lys Arg Ile Ile Ser Trp Cys His Thr Ile
        275                 280                 285

Asn Gln Phe Tyr Gly Glu Thr Ile Val Ala Tyr Thr Phe Asp Ala Gly
    290                 295                 300

Pro Asn Ala Val Leu Tyr Tyr Leu Ala Glu Asn Glu Ser Lys Leu Phe
305                 310                 315                 320

Ala Phe Ile Tyr Lys Leu Phe Gly Ser Val Pro Gly Trp Asp Lys Lys
                325                 330                 335
```

```
Phe Thr Thr Glu Gln Leu Glu Ala Phe Asn His Gln Phe Glu Ser Ser
            340                 345                 350

Asn Phe Thr Ala Arg Glu Leu Asp Leu Glu Leu Gln Lys Asp Val Ala
        355                 360                 365

Arg Val Ile Leu Thr Gln Val Gly Ser Gly Pro Gln Glu Thr Asn Glu
    370                 375                 380

Ser Leu Ile Asp Ala Lys Thr Gly Leu Pro Lys Glu
385                 390                 395


<210> SEQ ID NO 7
<211> LENGTH: 352
<212> TYPE: PRT
<213> ORGANISM: Saccharomyces cerevisiae

<400> SEQUENCE: 7

Met Ala Ser Glu Lys Glu Ile Arg Arg Glu Arg Phe Leu Asn Val Phe
1               5                   10                  15

Pro Lys Leu Val Glu Glu Leu Asn Ala Ser Leu Leu Ala Tyr Gly Met
            20                  25                  30

Pro Lys Glu Ala Cys Asp Trp Tyr Ala His Ser Leu Asn Tyr Asn Thr
        35                  40                  45

Pro Gly Gly Lys Leu Asn Arg Gly Leu Ser Val Val Asp Thr Tyr Ala
    50                  55                  60

Ile Leu Ser Asn Lys Thr Val Glu Gln Leu Gly Gln Glu Glu Tyr Glu
65                  70                  75                  80

Lys Val Ala Ile Leu Gly Trp Cys Ile Glu Leu Leu Gln Ala Tyr Phe
                85                  90                  95

Leu Val Ala Asp Asp Met Met Asp Lys Ser Ile Thr Arg Arg Gly Gln
            100                 105                 110

Pro Cys Trp Tyr Lys Val Pro Glu Val Gly Glu Ile Ala Ile Asn Asp
        115                 120                 125

Ala Phe Met Leu Glu Ala Ala Ile Tyr Lys Leu Leu Lys Ser His Phe
    130                 135                 140

Arg Asn Glu Lys Tyr Tyr Ile Asp Ile Thr Glu Leu Phe His Glu Val
145                 150                 155                 160

Thr Phe Gln Thr Glu Leu Gly Gln Leu Met Asp Leu Ile Thr Ala Pro
                165                 170                 175

Glu Asp Lys Val Asp Leu Ser Lys Phe Ser Leu Lys Lys His Ser Phe
            180                 185                 190

Ile Val Thr Phe Lys Thr Ala Tyr Tyr Ser Phe Tyr Leu Pro Val Ala
        195                 200                 205

Leu Ala Met Tyr Val Ala Gly Ile Thr Asp Glu Lys Asp Leu Lys Gln
    210                 215                 220

Ala Arg Asp Val Leu Ile Pro Leu Gly Glu Tyr Phe Gln Ile Gln Asp
225                 230                 235                 240

Asp Tyr Leu Asp Cys Phe Gly Thr Pro Glu Gln Ile Gly Lys Ile Gly
                245                 250                 255

Thr Asp Ile Gln Asp Asn Lys Cys Ser Trp Val Ile Asn Lys Ala Leu
            260                 265                 270

Glu Leu Ala Ser Ala Glu Gln Arg Lys Thr Leu Asp Glu Asn Tyr Gly
        275                 280                 285

Lys Lys Asp Ser Val Ala Glu Ala Lys Cys Lys Lys Ile Phe Asn Asp
    290                 295                 300

Leu Lys Ile Asp Gln Leu Tyr His Glu Tyr Glu Glu Ser Val Ala Lys
305                 310                 315                 320
```

```
Asp Leu Lys Ala Lys Ile Ser Gln Val Asp Glu Ser Arg Gly Phe Lys
                325                 330                 335

Ala Asp Val Leu Thr Ala Phe Leu Asn Lys Val Tyr Lys Arg Ser Lys
            340                 345                 350


<210> SEQ ID NO 8
<211> LENGTH: 288
<212> TYPE: PRT
<213> ORGANISM: Saccharomyces cerevisiae

<400> SEQUENCE: 8

Met Thr Ala Asp Asn Asn Ser Met Pro His Gly Ala Val Ser Ser Tyr
1               5                   10                  15

Ala Lys Leu Val Gln Asn Gln Thr Pro Glu Asp Ile Leu Glu Glu Phe
            20                  25                  30

Pro Glu Ile Ile Pro Leu Gln Gln Arg Pro Asn Thr Arg Ser Ser Glu
        35                  40                  45

Thr Ser Asn Asp Glu Ser Gly Glu Thr Cys Phe Ser Gly His Asp Glu
    50                  55                  60

Glu Gln Ile Lys Leu Met Asn Glu Asn Cys Ile Val Leu Asp Trp Asp
65                  70                  75                  80

Asp Asn Ala Ile Gly Ala Gly Thr Lys Lys Val Cys His Leu Met Glu
                85                  90                  95

Asn Ile Glu Lys Gly Leu Leu His Arg Ala Phe Ser Val Phe Ile Phe
            100                 105                 110

Asn Glu Gln Gly Glu Leu Leu Leu Gln Gln Arg Ala Thr Glu Lys Ile
        115                 120                 125

Thr Phe Pro Asp Leu Trp Thr Asn Thr Cys Cys Ser His Pro Leu Cys
    130                 135                 140

Ile Asp Asp Glu Leu Gly Leu Lys Gly Lys Leu Asp Asp Lys Ile Lys
145                 150                 155                 160

Gly Ala Ile Thr Ala Ala Val Arg Lys Leu Asp His Glu Leu Gly Ile
                165                 170                 175

Pro Glu Asp Glu Thr Lys Thr Arg Gly Lys Phe His Phe Leu Asn Arg
            180                 185                 190

Ile His Tyr Met Ala Pro Ser Asn Glu Pro Trp Gly Glu His Glu Ile
        195                 200                 205

Asp Tyr Ile Leu Phe Tyr Lys Ile Asn Ala Lys Glu Asn Leu Thr Val
    210                 215                 220

Asn Pro Asn Val Asn Glu Val Arg Asp Phe Lys Trp Val Ser Pro Asn
225                 230                 235                 240

Asp Leu Lys Thr Met Phe Ala Asp Pro Ser Tyr Lys Phe Thr Pro Trp
                245                 250                 255

Phe Lys Ile Ile Cys Glu Asn Tyr Leu Phe Asn Trp Trp Glu Gln Leu
            260                 265                 270

Asp Asp Leu Ser Glu Val Glu Asn Asp Arg Gln Ile His Arg Met Leu
        275                 280                 285


<210> SEQ ID NO 9
<211> LENGTH: 731
<212> TYPE: PRT
<213> ORGANISM: Saccharomyces cerevisiae

<400> SEQUENCE: 9

Met Thr Glu Phe Tyr Ser Asp Thr Ile Gly Leu Pro Lys Thr Asp Pro
1               5                   10                  15
```

```
Arg Leu Trp Arg Leu Arg Thr Asp Glu Leu Gly Arg Glu Ser Trp Glu
            20                  25                  30

Tyr Leu Thr Pro Gln Gln Ala Ala Asn Asp Pro Pro Ser Thr Phe Thr
        35                  40                  45

Gln Trp Leu Leu Gln Asp Pro Lys Phe Pro Gln Pro His Pro Glu Arg
    50                  55                  60

Asn Lys His Ser Pro Asp Phe Ser Ala Phe Asp Ala Cys His Asn Gly
65                  70                  75                  80

Ala Ser Phe Phe Lys Leu Leu Gln Glu Pro Asp Ser Gly Ile Phe Pro
                85                  90                  95

Cys Gln Tyr Lys Gly Pro Met Phe Met Thr Ile Gly Tyr Val Ala Val
            100                 105                 110

Asn Tyr Ile Ala Gly Ile Glu Ile Pro Glu His Glu Arg Ile Glu Leu
        115                 120                 125

Ile Arg Tyr Ile Val Asn Thr Ala His Pro Val Asp Gly Gly Trp Gly
    130                 135                 140

Leu His Ser Val Asp Lys Ser Thr Val Phe Gly Thr Val Leu Asn Tyr
145                 150                 155                 160

Val Ile Leu Arg Leu Leu Gly Leu Pro Lys Asp His Pro Val Cys Ala
                165                 170                 175

Lys Ala Arg Ser Thr Leu Leu Arg Leu Gly Gly Ala Ile Gly Ser Pro
            180                 185                 190

His Trp Gly Lys Ile Trp Leu Ser Ala Leu Asn Leu Tyr Lys Trp Glu
        195                 200                 205

Gly Val Asn Pro Ala Pro Pro Glu Thr Trp Leu Leu Pro Tyr Ser Leu
    210                 215                 220

Pro Met His Pro Gly Arg Trp Trp Val His Thr Arg Gly Val Tyr Ile
225                 230                 235                 240

Pro Val Ser Tyr Leu Ser Leu Val Lys Phe Ser Cys Pro Met Thr Pro
                245                 250                 255

Leu Leu Glu Glu Leu Arg Asn Glu Ile Tyr Thr Lys Pro Phe Asp Lys
            260                 265                 270

Ile Asn Phe Ser Lys Asn Arg Asn Thr Val Cys Gly Val Asp Leu Tyr
        275                 280                 285

Tyr Pro His Ser Thr Thr Leu Asn Ile Ala Asn Ser Leu Val Val Phe
    290                 295                 300

Tyr Glu Lys Tyr Leu Arg Asn Arg Phe Ile Tyr Ser Leu Ser Lys Lys
305                 310                 315                 320

Lys Val Tyr Asp Leu Ile Lys Thr Glu Leu Gln Asn Thr Asp Ser Leu
                325                 330                 335

Cys Ile Ala Pro Val Asn Gln Ala Phe Cys Ala Leu Val Thr Leu Ile
            340                 345                 350

Glu Glu Gly Val Asp Ser Glu Ala Phe Gln Arg Leu Gln Tyr Arg Phe
        355                 360                 365

Lys Asp Ala Leu Phe His Gly Pro Gln Gly Met Thr Ile Met Gly Thr
    370                 375                 380

Asn Gly Val Gln Thr Trp Asp Cys Ala Phe Ala Ile Gln Tyr Phe Phe
385                 390                 395                 400

Val Ala Gly Leu Ala Glu Arg Pro Glu Phe Tyr Asn Thr Ile Val Ser
                405                 410                 415

Ala Tyr Lys Phe Leu Cys His Ala Gln Phe Asp Thr Glu Cys Val Pro
            420                 425                 430
```

-continued

Gly Ser Tyr Arg Asp Lys Arg Lys Gly Ala Trp Gly Phe Ser Thr Lys
435 440 445

Thr Gln Gly Tyr Thr Val Ala Asp Cys Thr Ala Glu Ala Ile Lys Ala
450 455 460

Ile Ile Met Val Lys Asn Ser Pro Val Phe Ser Glu Val His His Met
465 470 475 480

Ile Ser Ser Glu Arg Leu Phe Glu Gly Ile Asp Val Leu Leu Asn Leu
485 490 495

Gln Asn Ile Gly Ser Phe Glu Tyr Gly Ser Phe Ala Thr Tyr Glu Lys
500 505 510

Ile Lys Ala Pro Leu Ala Met Glu Thr Leu Asn Pro Ala Glu Val Phe
515 520 525

Gly Asn Ile Met Val Glu Tyr Pro Tyr Val Glu Cys Thr Asp Ser Ser
530 535 540

Val Leu Gly Leu Thr Tyr Phe His Lys Tyr Phe Asp Tyr Arg Lys Glu
545 550 555 560

Glu Ile Arg Thr Arg Ile Arg Ile Ala Ile Glu Phe Ile Lys Lys Ser
565 570 575

Gln Leu Pro Asp Gly Ser Trp Tyr Gly Ser Trp Gly Ile Cys Phe Thr
580 585 590

Tyr Ala Gly Met Phe Ala Leu Glu Ala Leu His Thr Val Gly Glu Thr
595 600 605

Tyr Glu Asn Ser Ser Thr Val Arg Lys Gly Cys Asp Phe Leu Val Ser
610 615 620

Lys Gln Met Lys Asp Gly Gly Trp Gly Glu Ser Met Lys Ser Ser Glu
625 630 635 640

Leu His Ser Tyr Val Asp Ser Glu Lys Ser Leu Val Val Gln Thr Ala
645 650 655

Trp Ala Leu Ile Ala Leu Leu Phe Ala Glu Tyr Pro Asn Lys Glu Val
660 665 670

Ile Asp Arg Gly Ile Asp Leu Leu Lys Asn Arg Gln Glu Glu Ser Gly
675 680 685

Glu Trp Lys Phe Glu Ser Val Glu Gly Val Phe Asn His Ser Cys Ala
690 695 700

Ile Glu Tyr Pro Ser Tyr Arg Phe Leu Phe Pro Ile Lys Ala Leu Gly
705 710 715 720

Met Tyr Ser Arg Ala Tyr Glu Thr His Thr Leu
725 730

<210> SEQ ID NO 10
<211> LENGTH: 4293
<212> TYPE: DNA
<213> ORGANISM: artificial sequence
<220> FEATURE:
<223> OTHER INFORMATION: nucleotide sequence of Perg7::PCTR3-construct

<400> SEQUENCE: 10
gcggccgcaa tctgctgcta ttcgtgatta ctgttacaac ctaacggttt aaatgaaacc 60
tggttctgaa gggtcatttt ataacttcaa gttcccttag cctttcgatt cattttgatt 120
atgccatttc tagaccgtgt tataggcgct ggcgtttaat ttggtgtagc ttggtttagt 180
caagagttgt attagtgttc ctcgataaag tcgatgtttc cggatattgt gttaaaattt 240
caagtatgct actaatgggg taaagttgca tgattagcag agacatatgg cttgttatgg 300
ttcggcttcc tcatttttca tgcttagttt ttgtccatct cattgtacat ttctgaatcc 360

-continued

```
taatgcatga ctccctaaca ttactattaa attctcaata gtgaagaata agcaaaatgg    420
gaaccatgat aatttctagc tttctctcca cccctatttt aatttgcaat catatatagt    480
actttcaata gcatcttttc tagatttgat atctgcggag aatcctcagc actagtcctg    540
caggggtaac gccagggttt tcccagtcac gacgttgtaa aacgacggcc agtgagcgcg    600
cgtaatacga ctcactatag ggcgaattgg gtgcataggc cactagtgga tctgatatca    660
cctaataact tcgtatagca tacattatac gaagttatat taagggttct cgagagctcg    720
ctgtgaagat cccagcaaag gcttacaaag tgttatctct tttgagactt gttgagttga    780
acactggtgt tttcatcaaa cttaccaagg acgtgtaccc attgttgaaa cttgtatcac    840
catatattgt tatcggacaa ccttcacttg catctatccg ttctttaatc caaaagagat    900
ctagaataat gtggcaaagg ccagaagata aagaaccaaa agagataatc ttgaatgaca    960
acaatatcgt tgaagagaaa ttaggtgatg aaggtgtcat ttgtatcgag gatatcatcc   1020
atgagatttc gacgttgggc gaaaatttct cgaaatgtac tttcttccta ttaccattca   1080
aattgaacag agaagtcagt ggattcggtg ccatctcccg tttgaataaa ctgaaaatgc   1140
gcgaacaaaa caagaagact cgtcaaattt caaacgctgc cacggctcca gttatccaag   1200
tagatatcga ctcaatgatt tccaagttga attgattaac tataaaagga aaatatctgt   1260
acaatagaca tcgggctccc attggcccta cccacatatg tagaaataca ttactctatt   1320
cactactgca tttagttatg tttaacattt gatatagcag actaccgcca ggcacaatat   1380
attccccttc cctcttgcca ttcgctgtac ttgtggtgga ttccaattca gcgcagtcac   1440
gtgctagtaa tcaccgcatt tttttctttt cctttcaggc taaaaccggt tccgggcctg   1500
atccctgcac tcattttcta acggaaaacc ttcagaagca taactaccca ttccagttta   1560
gagtcatgac aggttcaaca tcagatgctt catatacttt tatatattga attatataaa   1620
tatatctatg tactctaagt aagtacatct gctttaacgc attcctacat ttgcttcgat   1680
ttatttttat tgttgatacc tatttgaaga agtaaaaagt atcccacact acacagatta   1740
taccatgtct aagaatatcg ttgtcctacc gggtgatcac gtcggtaaag aagttactga   1800
cgaagctatt aaggtcttga atgccattgc tgaagtccgt ccagaaatta agttcaattt   1860
ccaacatcac ttgatcgggg gtgctgccat cgatgccact ggcactcctt taccagatga   1920
agctctagaa gcctctaaga aagccgatgc tgtcttacta ggtgctgttg gtggtccaaa   1980
atggggtacg ggcgcagtta gaccagaaca aggtctattg aagatcagaa aggaattggg   2040
tctatacgcc aacttgagac catgtaactt tgcttctgat tctttactag atctttctcc   2100
tttgaagcct gaatatgcaa agggtaccga tttcgtcgtc gttagagaat tggttggtgg   2160
tatctacttt ggtgaaagaa aagaagatga aggtgacgga gttgcttggg actctgagaa   2220
atacagtgtt cctgaagttc aaagaattac aagaatggct gctttcttgg cattgcaaca   2280
aaacccacca ttaccaatct ggtctcttga caaggctaac gtgcttgcct cttccagatt   2340
gtggagaaag actgttgaag aaaccatcaa gactgagttc ccacaattaa ctgttcagca   2400
ccaattgatc gactctgctg ctatgatttt ggttaaatca ccaactaagc taaacggtgt   2460
tgttattacc aacaacatgt ttggtgatat tatctccgat gaagcctctg ttattccagg   2520
ttctttgggt ttattacctt ctgcatctct agcttcccta cctgacacta acaaggcatt   2580
cggtttgtac gaaccatgtc atggttctgc cccagattta ccagcaaaca aggttaaccc   2640
aattgctacc atcttatctg cagctatgat gttgaagtta tccttggatt tggttgaaga   2700
aggtagggct cttgaagaag ctgttagaaa tgtcttggat gcaggtgtca gaaccggtga   2760
```

ccttggtggt tctaactcta ccactgaggt tggcgatgct atcgccaagg ctgtcaagga 2820
aatcttggct taaagagtct tttgtaacga ccccgtctcc accaacttgg tatgcttgaa 2880
atctcaaggc cattacacat tcagttatgt gaacgaaagg tctttattta acgtagcata 2940
aactaaataa tacaggttcc ggttagcctg cggatctcta gacctaataa cttcgtatag 3000
catacattat acgaagttat attaagggtt gtcgacctgc agcgggatcc ggtattccaa 3060
tgagaatcgc tagaaatgct ttaccagaac tagactactt gtcgcagatc acttttgaac 3120
tgtatgagag tacggatgct tctggtcaaa aatcgcattc cattagactg aaaatgtctc 3180
ctgggtgtca tactcaagat ccgttagatg ttcaattaga tgacaggcat tatattagtt 3240
gtattccaaa gatttccctg acgaagcatt tggatatgga ctacgttcaa cagaaattga 3300
gaaacaaatt taccagggtc attatgcctc cgaaatttac accagtaaac attacgagcc 3360
ccaacttgag tttccagaaa cgcaaaacca gaagaaagtc ggtatctgtt gagaagttga 3420
agcttcctgc ctcgtccgga tcttcatcat ctacctccgt taacaagaca ttagattagt 3480
gatcacaccc aatttttaat ttagcaaccc aaaataaata agtatttact caactttttt 3540
ttaataaaaa aaaacttaat tgaattttgc tcgcgatctt taggtccggg gttttcgttg 3600
aacccttaga cgagcaaatt agcgccataa ggatatacgt cagagcacat taattagtga 3660
catataccta tataaagagc aaccttctcc gatagacttg taatttatct tatttcattt 3720
cctaacactt tggtcgaaga agagggataa gaacagacga aaacacattt aagggctata 3780
caaagatgac agaattttat tctgacacaa tcggtctacc aaagacagat ccacgtcttt 3840
ggagactgag aactgatgag ctaggccgag aaagctggga atatttaacc cctcagcaag 3900
ccgcaaacga cccaccatcc actttcacgc agtggcttct tcaagatccc aaatttcctc 3960
aacctcatcc agaaagaaat aagcattcac cagatttttc agccttcgat gcgtgtcata 4020
atggtgcatc ttttttcaaa ctgcttcaag agcctgactc aggtattttt ccgtgtcaat 4080
ataaaggacc catgttcatg acaatcggtt acgtagccgt aaactatatc gccggtattg 4140
aaattcctga gcatgagaga atagaattaa ttagatacat cgtcaataca gcacatccgg 4200
ttgatggtgg ctggggtcta cattctgttg acaaatccac cgtgtttggt acagtattga 4260
actatgtaat cttacgttta ttggggcggc cgc 4293

<210> SEQ ID NO 11
<211> LENGTH: 7256
<212> TYPE: DNA
<213> ORGANISM: artificial sequence
<220> FEATURE:
<223> OTHER INFORMATION: nucleotide sequence of rox1::PGal1-tHMGR;
PGal10-ERG13-construct

<400> SEQUENCE: 11
gcggccgcat gaatcctaaa tcctctacac ctaagattcc aagacccaag aacgcattta 60
ttctgttcag acagcactac cacaggatct taatagacga atggaccgct caaggtgtgg 120 aaataccccca taattcaaac atttctaaaa ttattggtac gaagtggaag ggcttacaac 180
cggaagataa ggcacactgg gaaaatctag cggagaagga gaaactagaa cataaaagga 240
agtatcctga atacaaatac aagccggtaa gaaagtctaa gaagaagcaa ctacttttga 300
aggaaatcga gcaacagcag cagcaacaac agaaagaaca gcagcagcag aaacagtcac 360
aaccgcaatt acaacagccc tttaacaaca atatagttct tatgaaaaga gcacattctc 420
tttcaccatc ttcctcggtg tcaagctcga acagctatca gttccaattg aacaatgatc 480

-continued

```
ttaagaggtt gcctattcct tctgttaata cttctaacta tatggtctcc agatcttcag    540
cactagtcct gcaggggtaa cgccagggtt ttcccagtca cgacgttgta aaacgacggc    600
cagtgagcgc gcgtaatacg actcactata gggcgaattg ggtgcatagg ccactagtgg    660
atctgatatc acctaataac ttcgtatagc atacattata cgaagttata ttaagggttc    720
tcgagagctc gttttattta ggttctatcg aggagaaaaa gcgacaagaa gagatagacc    780
atggataaac tgattatgtt ctaaacactc ctcagaagct catcgaactg tcatcctgcg    840
tgaagattaa aatccaactt agaaatttcg agcttacgga gacaatcata tgggagaagc    900
aattggaaga tagaaaaaag gtactcggta cataaatata tgtgattctg ggtagaagat    960
cggtctgcat tggatggtgg taacgcattt ttttacacac attacttgcc tcgagcatca   1020
aatggtggtt attcgtggat ctatatcacg tgatttgctt aagaattgtc gttcatggtg   1080
acacttttag ctttgacatg attaagctca tctcaattga tgttatctaa agtcatttca   1140
actatctaag atgtggttgt gattgggcca ttttgtgaaa gccagtacgc cagcgtcaat   1200
acactcccgt caattagttg caccatgtcc acaaaatcat ataccagtag agctgagact   1260
catgcaagtc cggttgcatc gaaactttta cgtttaatgg atgaaaagaa gaccaatttg   1320
tgtgcttctc ttgacgttcg ttcgactgat gagctattga aacttgttga aacgttgggt   1380
ccatacattt gccttttgaa aacacacgtt gatatcttgg atgatttcag ttatgagggt   1440
actgtcgttc cattgaaagc attggcagag aaatacaagt tcttgatatt tgaggacaga   1500
aaattcgccg atatcggtaa cacagtcaaa ttacaatata catcgggcgt ttaccgtatc   1560
gcagaatggt ctgatatcac caacgcccac ggggttactg gtgctggtat tgttgctggc   1620
ttgaaacaag gtgcgcaaga ggtcaccaaa gaaccaaggg gattattgat gcttgctgaa   1680
ttgtcttcca agggttctct agcacacggt gaatatacta agggtaccgt tgatattgca   1740
aagagtgata aagatttcgt tattgggttc attgctcaga acgatatggg aggaagagaa   1800
gaagggtttg attggctaat catgacccca ggtgtaggtt tagacgacaa aggcgatgca   1860
ttgggtcagc agtacagaac cgtcgacgaa gttgtaagtg gtggatcaga tatcatcatt   1920
gttggcagag gacttttcgc caagggtaga gatcctaagg ttgaaggtga aagatacaga   1980
aatgctggat gggaagcgta ccaaaagaga atcagcgctc cccattaatt atacaggaaa   2040
cttaatagaa caaatcacat atttaatcta atagccacct gcattggcac ggtgcaacac   2100
tacttcaact tcatcttaca aaaagatcac gtgatctgtt gtattgggat ctctagacct   2160
aataacttcg tatagcatac attatacgaa gttatattaa gggttgtcga cctgcagcgt   2220
acgaagcttc agctgacgcg atgaatgcgt gcgatgagcg acctcatgct atacctgaga   2280
aagcaacctg acctacagga aagagttact caagaataag aattttcgtt ttaaaaccta   2340
agagtcactt taaaatttgt atacacttat ttttttata acttatttaa taataaaaat    2400
cataaatcat aagaaattcg cttatttaga agtgtcaaca acgtatctac caacgatttg   2460
acccttttcc atcttttcgt aaatttctgg caaggtagac aagccgacaa ccttgattgg   2520
agacttgacc aaacctctgg cgaagaattg ttaattaaga gctcagatct tatcgtcgtc   2580
atccttgtaa tccatcgata ctagtgcggc cgcttatttt ttaacatcgt aagatcttct   2640
aaatttgtca tcgatgttgg tcaagtagta aacaccactt tgcaaatgct caatggaacc   2700
ttgaggtttg aagttcttct tcaaatgggc attttctctc aattcgatgg cagcttcgta   2760
atcctttgga gtttcggtga ttctcttggc taatttgtta gtaatatcta attccttgat   2820
```

-continued aatatgttgg acgtcaccaa caattttgca agaatataga gatgcagcta aaccggaacc 2880
gtaagaaaat aaaccaacac gcttgccttg taagtcgtca gatccaacat agtttaatag 2940
agatgcaaag gcggcataaa cagatgcggt gtacatgtta cctgtgtttg ttggaacaat 3000
caaagattgg gcaactctct ctttgtggaa tggcttagca acattaacaa aagtttttc 3060
aatgttctta tcggttaaag attcgtcata atcgcgagta gctaattcgg cgtcaacttc 3120
tgggaacaat tgaggattgg ctctgaaatc gttatatagt aatctaccgt atgattttgt 3180
gaccaattta caggttggaa catggaaaac gttgtagtcg aaatatttca aaacgttcaa 3240
agcatccgaa ccagcgggat cgctaaccaa ccctttagaa atagccttct tggaataact 3300
cttgtaaact tgatcaagag ccttgacgta acaagttaat gaaaaatgac catcgacgta 3360
aggatattcg ctggtgaaat ctggcttgta aaaatcgtag gcgtgttcca tgtaagaagc 3420
tcttacagag tcaaatacaa ttggagcatc aggaccgatc cacatagcaa cagtaccggc 3480
accaccggtt ggtcttgcgg cacccttatc gtagatggca atatcaccgc aaactacaat 3540
ggcgtctcta ccatcccatg cgttagattc aatccagttc aaagagttga acaacgcgtt 3600
ggtaccaccg taacaggcat taagcgtgtc aataccttcg acgtcagtgt tttcaccaaa 3660
caattgcatc aagacagact tgacagactt ggacttgtca atcagagttt cagtaccgac 3720
ttctaatcta ccaattttgt tggtgtcgat gttgtaactc ttgatcaact tagacaaaac 3780
agttagggac atcgagtaga tatcttctct gtcattgaca aaagacatgt tggtttggcc 3840
cagaccaatt gtgtatttac cttgagaaac gccatcaaat ttctctagct cagattggtt 3900
gacacattga gttgggatgt aaatttggat acctttaata ccgacatttt gaggtctggt 3960
tttttgttca gcggtctttt gttttttag ttcagtcatt tgcaagtttg tattgtgtaa 4020
ttgttgttgc ttttgcggcc taagtcttcc tttaatacca caccaacaaa gtttagttga 4080
gagtttcata aaaaagaatt cgaattttca aaaattctta cttttttttt ggatggacgc 4140
aaagaagttt aataatcata ttacatggca ttaccaccat atacatatcc atatacatat 4200
ccatatctaa tcttacttat atgttgtgga aatgtaaaga gccccattat cttagcctaa 4260
aaaaaccttc tctttggaac tttcagtaat acgcttaact gctcattgct atattgaagt 4320
acggattaga agccgccgag cgggtgacag ccctccgaag gaagactctc ctccgtgcgt 4380
cctcgtcttc accggtcgcg ttcctgaaac gcagatgtgc ctcgcgccgc actgctccga 4440
acaataaaga ttctacaata ctagctttta tggttatgaa gaggaaaaat tggcagtaac 4500
ctggccccac aaaccttcaa atgaacgaat caaattaaca accataggat gataatgcga 4560
ttagtttttt agccttattt ctggggtaat taatcagcga agcgatgatt tttgatctat 4620
taacagatat ataaatgcaa aaactgcata accactttaa ctaatacttt caacattttc 4680
ggtttgtatt acttcttatt caaatgtaat aaaagtatca acaaaaaatt gttaatatac 4740
ctctatactt taacgtcaag gagaaaaaac cccggatcct tttttatggt tttaaccaat 4800
aaaacagtca tttctggatc gaaagtcaaa agtttatcat ctgcgcaatc gagctcatca 4860
ggaccttcat catctagtga ggaagatgat tcccgcgata ttgaaagctt ggataagaaa 4920
atacgtcctt tagaagaatt agaagcatta ttaagtagtg gaaatacaaa acaattgaag 4980
aacaaagagg tcgctgcctt ggttattcac ggtaagttac ctttgtacgc tttggagaaa 5040
aaattaggtg atactacgag agcggttgcg gtacgtagga aggctctttc aattttggca 5100
gaagctcctg tattagcatc tgatcgttta ccatataaaa attatgacta cgaccgcgta 5160
tttggcgctt gttgtgaaaa tgttataggt tacatgcctt tgcccgttgg tgttataggc 5220
cccttggtta tcgatggtac atcttatcat ataccaatgg caactacaga gggttgtttg 5280
gtagcttctg ccatgcgtgg ctgtaaggca atcaatgctg gcggtggtgc aacaactgtt 5340
ttaactaagg atggtatgac aagaggccca gtagtccgtt tcccaacttt gaaaagatct 5400
ggtgcctgta agatatggtt agactcagaa gagggacaaa acgcaattaa aaaagctttt 5460
aactctacat caagatttgc acgtctgcaa catattcaaa cttgtctagc aggagattta 5520
ctcttcatga gatttagaac aactactggt gacgcaatgg gtatgaatat gatttctaaa 5580
ggtgtcgaat actcattaaa gcaaatggta gaagagtatg gctgggaaga tatggaggtt 5640
gtctccgttt ctggtaacta ctgtaccgac aaaaaaccag ctgccatcaa ctggatcgaa 5700
ggtcgtggta agagtgtcgt cgcagaagct actattcctg gtgatgttgt cagaaaagtg 5760
ttaaaaagtg atgtttccgc attggttgag ttgaacattg ctaagaattt ggttggatct 5820
gcaatggctg ggtctgttgg tggatttaac gcacatgcag ctaatttagt gacagctgtt 5880
ttcttggcat taggacaaga tcctgcacaa aatgttgaaa gttccaactg tataacattg 5940
atgaaagaag tggacggtga tttgagaatt tccgtatcca tgccatccat cgaagtaggt 6000
accatcggtg gtggtactgt tctagaacca caaggtgcca tgttggactt attaggtgta 6060
agaggcccgc atgctaccgc tcctggtacc aacgcacgtc aattagcaag aatagttgcc 6120
tgtgccgtct tggcaggtga attatcctta tgtgctgccc tagcagccgg ccatttggtt 6180
caaagtcata tgacccacaa caggaaacct gctgaaccaa caaaacctaa caatttggac 6240
gccactgata taaatcgttt gaaagatggg tccgtcacct gcattaaatc ctagtcgaca 6300
tggaacagaa gttgatttcc gaagaagacc tcgagtaagc ttggtaccgc ggctagctaa 6360
gatccgctct aaccgaaaag gaaggagtta gacaacctga agtctaggtc cctatttatt 6420
tttttatagt tatgttagta ttaagaacgt tatttatatt tcaaattttt cttttttttc 6480
tgtacagacg cgtgtacgca tgtaacatta tactgaaaac cttgcttgag aaggttttgg 6540
gacgctcgaa gcgcgtgcat tcttattctt gagtaactct ttcctgtagg tcaggttgct 6600
ttctcaggta tagcatgagg tcgctcatcg cacgcattcc atgcgagctc gctgaggact 6660
taaagatctt taagtggact acctttgacg catgataaga cggcaagaga cctaccacag 6720
ctgtcatctc aactaaattc tattccatat tactcagctc cacacgaccc ttcaacgaga 6780
catcattacc tcaacgtcgc tcaagctcaa ccaagggcta actcgacccc tcaattgccc 6840
tttatttcat ccattatcaa caacagcagt caaacaccgg taactacaac taccacatcc 6900
acaacaactg cgacatcttc tcctgggaaa ttctcctctt ctccgaactc ctctgtactg 6960
gagaacaaca gattaaacag tatcaacaat tcaaatcaat atttacctcc ccctctatta 7020
ccttctctgc aagattttca actggatcag taccagcagc taaagcagat gggaccaact 7080
tatattgtca aaccactgtc tcacaccagg aacaatctat tgtccacaac tacccctacg 7140
catcatcaca ttcctcatat accaaaccaa aacattcctc tacatcaaat tataaactca 7200
agcaacactg aggtcaccgc taaaactagc ctagtttctc cgaaatgagc ggccgc 7256

<210> SEQ ID NO 12
<211> LENGTH: 2277
<212> TYPE: DNA
<213> ORGANISM: unknown
<220> FEATURE:
<223> OTHER INFORMATION: lupeol synthase of the Russian dandelion
Taraxacum koksaghyz

<400> SEQUENCE: 12

```
atgtggaagc tgaaaatagc agaaggtagt gatgatgagt ggctgaccac caccaacaac     60
cacgtcggcc gtcagcactg gcagtttgat ccggatgctg gaaccgaaga ggaacgtgct    120
cagattgaaa agattcgtct caacttcaaa cttaatcgtt ttcaattcaa acaaagtgcc    180
gacttgttaa tgcgtactca actaagaaaa gagaacccaa tcaataaaat accggatgca    240
ataaaattga atgaaacaga agaagtgaca aatgacgcag tgtcaactac actcaaaaga    300
gccattagct tttactccac cattcaagcc catgatgggc actggccagc tgagtctgct    360
ggcccctttgt tcttccttcc tccattggta atagcactat atgtgactgg agcaatgaat    420
gatattctaa cacccgcaca tcagctagaa ataaaacgtt acatatacaa tcatcagaat    480
gaagatggag gttggggatt acatatagag ggtcatagca caatatttgg atcagtactt    540
agttacataa ctttaagatt acttggggaa gaagctgata gtgttgcaga ggacatggct    600
ttggttaagg ggcgtaaatg gatccttgac catggtggtg cagttgggat tccttcgtgg    660
ggaaagtttt ggcttacgat acttggagta tacgaatggg gaggctgtaa tcctatgcca    720
cccgaatttt ggctcatgcc taagtttttc ccaattcatc caggcaaaat gttgtgttat    780
tgtcgcttag tttacatgcc catgtcgtac ttatacggca aaagatttgt gggaaaaata    840
accgagttgg ttcgcgacct aaggcaagag ctttatacag acccttatga tgagattaat    900
tggaataaag cacgaaacac gtgtgcaaag gaagatctct actatccaca cccttttgtt    960
caagatatgg tatggggtgt acttcataat gtttttgaac ctgtattaac aagtcgtccg   1020
ctttccacac taagagaaaa ggctttgaaa gtcgcaatgg atcatgttca ctatgaagat   1080
aagagtagta gatatctttg cattggatgt gtggaaaagg tgttatgctt gattgcaacg   1140
tgggtggaag atccaaatgg tgatgcatat aaacgtcatc ttgctagaat tcctgactac   1200
ttttgggttg ctgaagatgg gatgaaaatg cagagttttg gatgtcaaat gtgggatgcg   1260
gcctttgcta ttcaagctat tttatctagt aatctagccg aagaatacgg cccgactctt   1320
aaaaaagcac acgagtttgt aaaagcatca caggttcgtg ataatccgcc gggagatttc   1380
agtaaaatgt acagacacac ttctaagggt gcatggacat tttccataca agatcatggt   1440
tggcaagtct ctgattgtac ggctgaaggc ttgaaggttg cacttttgta ctcccaaatg   1500
agcccagaac ttgtgggcga aaaacttgaa actgagcatc tctacgatgc tgtcaatgtc   1560
attctttcat tacaaagtga aaacggtggc tttcctgctt gggaaccaca aagggcgtat   1620
gcttggttgg agaaattcaa cccgactgaa ttctttgaag atgtgttgat cgaacgagag   1680
tatgttgaat gcacttcatc tgcaatccaa ggtttgacac tcttcaagaa gttgcaccca   1740
gggcacagaa ccaaggagat cgagcattgt atatcaagag ctataaagta cgtcgaagac   1800
acacaagaaa gtgatggttc atggtatggt tgttggggaa tttgctacac ctatggtaca   1860
tggtttgcgg tagatgcgct agtagcttgt ggtaagaact atcataactc tcccgccctt   1920
caaaaagcat gcaaatttct gttatccaaa caacttccgg atggtggatg ggagaaaagt   1980
tatctttcga gctcaaataa ggtgtatacg aatttggagg gaaatcgttc gaatttagtg   2040
catacatcat gggctttaat atcacttatt aaagcgggac aggctgaaat tgatcctaca   2100
ccaatatcta atggcgtacg gcttctcatc aattcacaaa tggaagaagg ggactttcct   2160
caacaggaaa tcacaggagt gttcatgaag aactgtaacc tcaattactc atcatatcga   2220
aatatttttc ccatatgggc acttggtgaa tatcgtcgta ttgttcaaaa tatatga      2277
```

<210> SEQ ID NO 13

<211> LENGTH: 1197
<212> TYPE: DNA
<213> ORGANISM: Saccharomyces cerevisiae

<400> SEQUENCE: 13
atgtctcaga acgtttacat tgtatcgact gccagaaccc caattggttc attccagggt 60
tctctatcct ccaagacagc agtggaattg ggtgctgttg ctttaaaagg cgccttggct 120
aaggttccag aattggatgc atccaaggat tttgacgaaa ttatttttgg taacgttctt 180
tctgccaatt tgggccaagc tccggccaga caagttgctt tggctgccgg tttgagtaat 240
catatcgttg caagcacagt taacaaggtc tgtgcatccg ctatgaaggc aatcattttg 300
ggtgctcaat ccatcaaatg tggtaatgct gatgttgtcg tagctggtgg ttgtgaatct 360
atgactaacg caccatacta catgccagca gcccgtgcgg gtgccaaatt tggccaaact 420
gttcttgttg atggtgtcga aagagatggg ttgaacgatg cgtacgatgg tctagccatg 480
ggtgtacacg cagaaaagtg tgcccgtgat tgggatatta ctagagaaca acaagacaat 540
tttgccatcg aatcctacca aaaatctcaa aaatctcaaa aggaaggtaa attcgacaat 600
gaaattgtac ctgttaccat taagggattt agaggtaagc ctgatactca agtcacgaag 660
gacgaggaac ctgctagatt acacgttgaa aaattgagat ctgcaaggac tgttttccaa 720
aaagaaaacg gtactgttac tgccgctaac gcttctccaa tcaacgatgg tgctgcagcc 780
gtcatcttgg tttccgaaaa agttttgaag gaaaagaatt tgaagccttt ggctattatc 840
aaaggttggg gtgaggccgc tcatcaacca gctgatttta catgggctcc atctcttgca 900
gttccaaagg ctttgaaaca tgctggcatc gaagacatca attctgttga ttactttgaa 960
ttcaatgaag ccttttcggt tgtcggtttg gtgaacacta agattttgaa gctagaccca 1020
tctaaggtta atgtatatgg tggtgctgtt gctctaggtc acccattggg ttgttctggt 1080
gctagagtgg ttgttacact gctatccatc ttacagcaag aaggaggtaa gatcggtgtt 1140
gccgccattt gtaatggtgg tggtggtgct tcctctattg tcattgaaaa gatatga 1197

<210> SEQ ID NO 14
<211> LENGTH: 1476
<212> TYPE: DNA
<213> ORGANISM: Saccharomyces cerevisiae

<400> SEQUENCE: 14
atgaaactct caactaaact ttgttggtgt ggtattaaag gaagacttag gccgcaaaag 60
caacaacaat tacacaatac aaacttgcaa atgactgaac taaaaaaaca aaagaccgct 120
gaacaaaaaa ccagacctca aaatgtcggt attaaaggta tccaaattta catcccaact 180
caatgtgtca accaatctga gctagagaaa tttgatggcg tttctcaagg taaatacaca 240
attggtctgg gccaaaccaa catgtctttt gtcaatgaca gagaagatat ctactcgatg 300
tccctaactg ttttgtctaa gttgatcaag agttacaaca tcgacaccaa caaaattggt 360
agattagaag tcggtactga aactctgatt gacaagtcca agtctgtcaa gtctgtcttg 420
atgcaattgt ttggtgaaaa cactgacgtc gaaggtattg acacgcttaa tgcctgttac 480
ggtggtacca acgcgttgtt caactctttg aactggattg aatctaacgc atgggatggt 540
agagacgcca ttgtagtttg cggtgatatt gccatctacg ataagggtgc cgcaagacca 600
accggtggtg ccggtactgt tgctatgtgg atcggtcctg atgctccaat tgtatttgac 660
tctgtaagag cttcttacat ggaacacgcc tacgattttt acaagccaga tttcaccagc 720
gaatatcctt acgtcgatgg tcatttttca ttaacttgtt acgtcaaggc tcttgatcaa 780

```
gtttacaaga gttattccaa gaaggctatt tctaaagggt tggttagcga tcccgctggt    840

tcggatgctt tgaacgtttt gaaatatttc gactacaacg ttttccatgt tccaacctgt    900

aaattggtca caaaatcata cggtagatta ctatataacg atttcagagc caatcctcaa    960

ttgttcccag aagttgacgc cgaattagct actcgcgatt atgacgaatc tttaaccgat   1020

aagaacattg aaaaaacttt tgttaatgtt gctaagccat tccacaaaga gagagttgcc   1080

caatctttga ttgttccaac aaacacaggt aacatgtaca ccgcatctgt ttatgccgcc   1140

tttgcatctc tattaaacta tgttggatct gacgacttac aaggcaagcg tgttggttta   1200

ttttcttacg gttccggttt agctgcatct ctatattctt gcaaaattgt tggtgacgtc   1260

caacatatta tcaaggaatt agatattact aacaaattag ccaagagaat caccgaaact   1320

ccaaaggatt acgaagctgc catcgaattg agagaaaatg cccatttgaa gaagaacttc   1380

aaacctcaag gttccattga gcatttgcaa agtggtgttt actacttgac caacatcgat   1440

gacaaattta gaagatctta cgatgttaaa aaataa                             1476
```

<210> SEQ ID NO 15
<211> LENGTH: 1332
<212> TYPE: DNA
<213> ORGANISM: Saccharomyces cerevisiae

<400> SEQUENCE: 15

```
atgtcattac cgttcttaac ttctgcaccg ggaaaggtta ttatttttgg tgaacactct     60

gctgtgtaca acaagcctgc cgtcgctgct agtgtgtctg cgttgagaac ctacctgcta    120

ataagcgagt catctgcacc agatactatt gaattggact tcccggacat tagctttaat    180

cataagtggt ccatcaatga tttcaatgcc atcaccgagg atcaagtaaa ctcccaaaaa    240

ttggccaagg ctcaacaagc caccgatggc ttgtctcagg aactcgttag tcttttggat    300

ccgttgttag ctcaactatc cgaatccttc cactaccatg cagcgttttg tttcctgtat    360

atgtttgttt gcctatgccc ccatgccaag aatattaagt tttctttaaa gtctacttta    420

cccatcggtg ctgggttggg ctcaagcgcc tctatttctg tatcactggc cttagctatg    480

gcctacttgg gggggttaat aggatctaat gacttggaaa agctgtcaga aaacgataag    540

catatagtga atcaatgggc cttcataggt gaaaagtgta ttcacggtac cccttcagga    600

atagataacg ctgtggccac ttatggtaat gccctgctat ttgaaaaaga ctcacataat    660

ggaacaataa acacaaacaa ttttaagttc ttagatgatt tcccagccat tccaatgatc    720

ctaacctata ctagaattcc aaggtctaca aaagatcttg ttgctcgcgt tcgtgtgttg    780

gtcaccgaga aatttcctga agttatgaag ccaattctag atgccatggg tgaatgtgcc    840

ctacaaggct tagagatcat gactaagtta agtaaatgta aaggcaccga tgacgaggct    900

gtagaaacta ataatgaact gtatgaacaa ctattggaat tgataagaat aaatcatgga    960

ctgcttgtct caatcggtgt ttctcatcct ggattagaac ttattaaaaa tctgagcgat   1020

gatttgagaa ttggctccac aaaacttacc ggtgctggtg gcggcggttg ctctttgact   1080

ttgttacgaa gagacattac tcaagagcaa attgacagtt tcaaaaagaa attgcaagat   1140

gattttagtt acgagacatt tgaaacagac ttgggtggga ctggctgctg tttgttaagc   1200

gcaaaaaatt tgaataaaga tcttaaaatc aaatccctag tattccaatt atttgaaaat   1260

aaaactacca caaagcaaca aattgacgat ctattattgc caggaaacac gaatttacca   1320

tggacttcat aa                                                       1332
```

<210> SEQ ID NO 16
<211> LENGTH: 1356
<212> TYPE: DNA
<213> ORGANISM: Saccharomyces cerevisiae

<400> SEQUENCE: 16
atgtcagagt tgagagcctt cagtgcccca gggaaagcgt tactagctgg tggatattta 60
gttttagatc cgaaatatga agcatttgta gtcggattat cggcaagaat gcatgctgta 120
gcccatcctt acggttcatt gcaagagtct gataagtttg aagtgcgtgt gaaaagtaaa 180
caatttaaag atggggagtg gctgtaccat ataagtccta aaactggctt cattcctgtt 240
tcgataggcg gatctaagaa ccctttcatt gaaaaagtta tcgctaacgt atttagctac 300
tttaagccta acatggacga ctactgcaat agaaacttgt tcgttattga tattttctct 360
gatgatgcct accattctca ggaggacagc gttaccgaac atcgtggcaa cagaagattg 420
agttttcatt cgcacagaat tgaagaagtt cccaaaacag ggctgggctc ctcggcaggt 480
ttagtcacag ttttaactac agctttggcc tcctttttg tatcggacct ggaaaataat 540
gtagacaaat atagagaagt tattcataat ttatcacaag ttgctcattg tcaagctcag 600
ggtaaaattg gaagcgggtt tgatgtagcg gcggcagcat atggatctat cagatataga 660
agattcccac ccgcattaat ctctaatttg ccagatattg gaagtgctac ttacggcagt 720
aaactggcgc atttggttaa tgaagaagac tggaatataa cgattaaaag taaccattta 780
ccttcgggat taactttatg gatgggcgat attaagaatg gttcagaaac agtaaaactg 840
gtccagaagg taaaaaattg gtatgattcg catatgccgg aaagcttgaa aatatataca 900
gaactcgatc atgcaaattc tagatttatg gatggactat ctaaactaga tcgcttacac 960
gagactcatg acgattacag cgatcagata tttgagtctc ttgagaggaa tgactgtacc 1020
tgtcaaaagt atcctgagat cacagaagtt agagatgcag ttgccacaat tagacgttcc 1080
tttagaaaaa taactaaaga atctggtgcc gatatcgaac ctcccgtaca aactagctta 1140
ttggatgatt gccagacctt aaaaggagtt cttacttgct taatacctgg tgctggtggt 1200
tatgacgcca ttgcagtgat tgctaagcaa gatgttgatc ttagggctca aaccgctgat 1260
gacaaaagat tttctaaggt tcaatggctg gatgtaactc aggctgactg gggtgttagg 1320
aaagaaaaag atccggaaac ttatcttgat aaataa 1356

<210> SEQ ID NO 17
<211> LENGTH: 1191
<212> TYPE: DNA
<213> ORGANISM: Saccharomyces cerevisiae

<400> SEQUENCE: 17
atgaccgttt acacagcatc cgttaccgca cccgtcaaca tcgcaaccct taagtattgg 60
gggaaaaggg acacgaagtt gaatctgccc accaattcgt ccatatcagt gactttatcg 120
caagatgacc tcagaacgtt gacctctgcg gctactgcac ctgagtttga acgcgacact 180
ttgtggttaa atggagaacc acacagcatc gacaatgaaa gaactcaaaa ttgtctgcgc 240
gacctacgcc aattaagaaa ggaaatggaa tcgaaggacg cctcattgcc cacattatct 300
caatggaaac tccacattgt ctccgaaaat aactttccta cagcagctgg tttagcttcc 360
tccgctgctg gctttgctgc attggtctct gcaattgcta agttatacca attaccacag 420
tcaacttcag aaatatctag aatagcaaga aaggggtctg gttcagcttg tagatcgttg 480
tttggcggat acgtggcctg ggaaatggga aaagctgaag atggtcatga ttccatggca 540

```
gtacaaatcg cagacagctc tgactggcct cagatgaaag cttgtgtcct agttgtcagc    600
gatattaaaa aggatgtgag ttccactcag ggtatgcaat tgaccgtggc aacctccgaa    660
ctatttaaag aaagaattga acatgtcgta ccaaagagat ttgaagtcat gcgtaaagcc    720
attgttgaaa aagatttcgc cacctttgca aaggaaacaa tgatggattc caactctttc    780
catgccacat gtttggactc tttccctcca atattctaca tgaatgacac ttccaagcgt    840
atcatcagtt ggtgccacac cattaatcag ttttacggag aaacaatcgt tgcatacacg    900
tttgatgcag gtccaaatgc tgtgttgtac tacttagctg aaaatgagtc gaaactcttt    960
gcatttatct ataaattgtt tggctctgtt cctggatggg acaagaaatt tactactgag   1020
cagcttgagg ctttcaacca tcaatttgaa tcatctaact ttactgcacg tgaattggat   1080
cttgagttgc aaaaggatgt tgccagagtg attttaactc aagtcggttc aggcccacaa   1140
gaaacaaacg aatctttgat tgacgcaaag actggtctac caaaggaata a            1191
```

<210> SEQ ID NO 18
<211> LENGTH: 1059
<212> TYPE: DNA
<213> ORGANISM: Saccharomyces cerevisiae

<400> SEQUENCE: 18

```
atggcttcag aaaaagaaat taggagagag agattcttga acgttttccc taaattagta     60
gaggaattga acgcatcgct tttggcttac ggtatgccta aggaagcatg tgactggtat    120
gcccactcat tgaactacaa cactccaggc ggtaagttaa atagaggttt gtccgttgtg    180
gacacgtatg ctattctctc caacaagacc gttgaacaat tggggcaaga agaatacgaa    240
aaggttgcta ttctaggttg gtgcattgag ttgttgcagg cttacttctt ggtcgccgat    300
gatatgatgg acaagtccat taccagaaga ggccaaccat gttggtacaa ggttcctgaa    360
gttggggaaa ttgccatcaa tgacgcattc atgttagagg ctgctatcta caagcttttg    420
aaatctcact tcagaaacga aaaatactac atagatatca ccgaattgtt ccatgaagtc    480
accttccaaa ccgaattggg ccaattgatg gacttaatca ctgcacctga agacaaagtc    540
gacttgagta agttctccct aaagaagcac tccttcatag ttactttcaa gactgcttac    600
tattctttct acttgcctgt cgcattggct atgtacgttg ccggtatcac agatgaaaag    660
gatttgaaac aagccagaga tgtcttgatt ccattgggtg aatatttcca aattcaagat    720
gactacttag actgcttcgg taccccagaa cagatcggta agatcggtac agatatccaa    780
gataacaaat gttcttgggt aatcaacaag gcattagaac ttgcttccgc agaacaaaga    840
aagactttag acgaaaatta cggtaagaag gactcagtcg cagaagccaa atgcaaaaag    900
attttcaatg acttgaaaat cgaccagtta taccacgaat atgaagagtc tgttgccaag    960
gatttgaagg ccaagatctc ccaagtcgac gagtctcgtg gcttcaaagc cgacgtctta   1020
actgcgtttt tgaacaaggt ttacaagaga agtaaataa                         1059
```

<210> SEQ ID NO 19
<211> LENGTH: 867
<212> TYPE: DNA
<213> ORGANISM: Saccharomyces cerevisiae

<400> SEQUENCE: 19

```
atgactgccg acaacaatag tatgccccat ggtgcagtat ctagttacgc caaattagtg     60
caaaaccaaa cacctgaaga cattttggaa gagtttcctg aaattattcc attacaacaa    120
```

-continued

```
agacctaata cccgatctag tgagacgtca aatgacgaaa gcggagaaac atgtttttct    180

ggtcatgatg aggagcaaat taagttaatg aatgaaaatt gtattgtttt ggattgggac    240

gataatgcta ttggtgccgg taccaagaaa gtttgtcatt taatggaaaa tattgaaaag    300

ggtttactac atcgtgcatt ctccgtcttt attttcaatg aacaaggtga attactttta    360

caacaaagag ccactgaaaa aataactttc cctgatcttt ggactaacac atgctgctct    420

catccactat gtattgatga cgaattaggt ttgaagggta agctagacga taagattaag    480

ggcgctatta ctgcggcggt gagaaaacta gatcatgaat taggtattcc agaagatgaa    540

actaagacaa ggggtaagtt tcacttttta aacagaatcc attacatggc accaagcaat    600

gaaccatggg gtgaacatga aattgattac atcctatttt ataagatcaa cgctaaagaa    660

aacttgactg tcaacccaaa cgtcaatgaa gttagagact tcaaatgggt ttcaccaaat    720

gatttgaaaa ctatgtttgc tgacccaagt tacaagttta cgccttggtt taagattatt    780

tgcgagaatt acttattcaa ctggtgggag caattagatg acctttctga agtggaaaat    840

gacaggcaaa ttcatagaat gctataa                                        867
```

<210> SEQ ID NO 20
<211> LENGTH: 2196
<212> TYPE: DNA
<213> ORGANISM: Saccharomyces cerevisiae

<400> SEQUENCE: 20

```
atgacagaat tttattctga cacaatcggt ctaccaaaga cagatccacg tctttggaga     60

ctgagaactg atgagctagg ccgagaaagc tgggaatatt taacccctca gcaagccgca    120

aacgacccac catccacttt cacgcagtgg cttcttcaag atcccaaatt tcctcaacct    180

catccagaaa gaaataagca ttcaccagat tttcagcct tcgatgcgtg tcataatggt    240

gcatcttttt tcaaactgct tcaagagcct gactcaggta tttttccgtg tcaatataaa    300

ggacccatgt tcatgacaat cggttacgta gccgtaaact atatcgccgg tattgaaatt    360

cctgagcatg agagaataga attaattaga tacatcgtca atacagcaca tccggttgat    420

ggtggctggg gtctacattc tgttgacaaa tccaccgtgt ttggtacagt attgaactat    480

gtaatcttac gtttattggg tctacccaag gaccacccgg tttgcgccaa ggcaagaagc    540

acattgttaa ggttaggcgg tgctattgga tcccctcact ggggaaaaat ttggctaagt    600

gcactaaact tgtataaatg ggaaggtgtg aaccctgccc ctcctgaaac ttggttactt    660

ccatattcac tgcccatgca tccggggaga tggtgggttc atactagagg tgtttacatt    720

ccggtcagtt acctgtcatt ggtcaaattt tcttgcccaa tgactcctct tcttgaagaa    780

ctgaggaatg aaatttacac taaaccgttt gacaagatta acttctccaa gaacaggaat    840

accgtatgtg gagtagacct atattacccc cattctacta ctttgaatat tgcgaacagc    900

cttgtagtat tttacgaaaa atacctaaga aaccggttca tttactctct atccaagaag    960

aaggtttatg atctaatcaa aacggagtta cagaatactg attccttgtg tatagcacct   1020

gttaaccagg cgttttgcgc acttgtcact cttattgaag aaggggtaga ctcggaagcg   1080

ttccagcgtc tccaatatag gttcaaggat gcattgttcc atggtccaca gggtatgacc   1140

attatgggaa caaatggtgt gcaaacctgg gattgtgcgt ttgccattca atactttttc   1200

gtcgcaggcc tcgcagaaag acctgaattc tataacacaa ttgtctctgc ctataaattc   1260

ttgtgtcatg ctcaatttga caccgagtgc gttccaggta gttataggga taagagaaag   1320

ggggcttggg gcttctcaac aaaaacacag ggctatacag tggcagattg cactgcagaa   1380
```

```
gcaattaaag ccatcatcat ggtgaaaaac tctcccgtct ttagtgaagt acaccatatg   1440

attagcagtg aacgtttatt tgaaggcatt gatgtgttat tgaacctaca aaacatcgga   1500

tcttttgaat atggttcctt tgcaacctat gaaaaaatca aggccccact agcaatggaa   1560

accttgaatc ctgctgaagt ttttggtaac ataatggtag aatacccata cgtggaatgt   1620

actgattcat ccgttctggg gttgacatat tttcacaagt acttcgacta taggaaagag   1680

gaaatacgta cacgcatcag aatcgccatc gaattcataa aaaaatctca attaccagat   1740

ggaagttggt atggaagctg gggtatttgt tttacatatg ccggtatgtt tgcattggag   1800

gcattacaca ccgtggggga gacctatgag aattcctcaa cggtaagaaa aggttgcgac   1860

ttcttggtca gtaaacagat gaaggatggc ggttgggggg aatcaatgaa gtccagtgaa   1920

ttacatagtt atgtggatag tgaaaaatcg ctagtcgttc aaaccgcatg ggcgctaatt   1980

gcacttcttt tcgctgaata tcctaataaa gaagtcatcg accgcggtat tgacctttta   2040

aaaaatagac aagaagaatc cggggaatgg aaatttgaaa gtgtagaagg tgttttcaac   2100

cactcttgtg caattgaata cccaagttat cgattcttat tccctattaa ggcattaggt   2160

atgtacagca gggcatatga aacacatacg ctttaa                             2196
```

<210> SEQ ID NO 21
<211> LENGTH: 757
<212> TYPE: PRT
<213> ORGANISM: Nicotiana tabacum

<400> SEQUENCE: 21

```
Met Trp Lys Leu Lys Ile Ala Glu Gly Gly Asn Pro Trp Leu Arg Thr
1               5                   10                  15

Thr Asn Asn His Val Gly Arg Glu Leu Trp Glu Phe Asp Pro Glu Leu
            20                  25                  30

Gly Ser Pro Glu Asp Arg Ala Glu Ile Asp Lys Phe Arg Glu His Phe
        35                  40                  45

His Lys His Arg Phe Glu Gln Lys His Ser Ala Asp Leu Ile Met Arg
    50                  55                  60

Tyr Gln Leu Ser Lys Glu Asn Pro Gly Ile Thr Ile Leu Pro Gln Val
65                  70                  75                  80

Lys Val Gln Gly Asn Glu Asp Ile Thr Glu Asp Thr Val Ala Thr Thr
                85                  90                  95

Leu Arg Arg Ala Leu Ser Phe Tyr Ser Thr Leu Gln Thr His Asp Gly
            100                 105                 110

His Trp Ala Gly Asp Tyr Gly Gly Pro Met Phe Leu Met Pro Gly Met
        115                 120                 125

Val Ile Ala Leu Ser Val Thr Gly Ala Leu Asn Ala Val Leu Thr Ser
    130                 135                 140

Glu His Lys Arg Glu Met Ile Arg Tyr Leu Tyr Asn His Gln Asn Ser
145                 150                 155                 160

Asp Gly Gly Trp Gly Leu His Ile Glu Gly His Ser Thr Met Phe Gly
                165                 170                 175

Ser Val Leu Ser Tyr Val Thr Leu Arg Leu Leu Gly Glu Gly Ala Asn
            180                 185                 190

Asp Gly Glu Gly Ala Met Glu Lys Gly Arg Lys Trp Ile Leu Asp His
        195                 200                 205

Gly Ser Ala Thr Ala Ile Thr Ser Trp Gly Lys Met Trp Leu Thr Val
    210                 215                 220
```

-continued

Leu Gly Ala Phe Asp Trp Ser Gly Asn Asn Pro Leu Pro Pro Glu Ile
225 230 235 240

Trp Leu Leu Pro Tyr Phe Leu Pro Ile His Pro Gly Arg Met Trp Cys
245 250 255

His Cys Arg Met Val Tyr Leu Pro Met Cys Tyr Leu Tyr Gly Lys Arg
260 265 270

Phe Val Gly Pro Ile Thr Pro Thr Val Leu Ser Leu Arg Lys Glu Leu
275 280 285

Phe Thr Val Pro Tyr His Glu Ile Asp Trp Asn Lys Ala Arg Asn Glu
290 295 300

Cys Ala Lys Glu Asp Leu Tyr Tyr Pro His Pro Leu Val Gln Asp Ile
305 310 315 320

Leu Trp Ala Ser Leu His Lys Val Val Glu Pro Ile Leu Met His Trp
325 330 335

Pro Gly Lys Arg Leu Arg Glu Lys Ala Leu Arg Ile Val Met Glu His
340 345 350

Ile His Tyr Glu Asp Glu Asn Thr Arg Tyr Ile Cys Ile Gly Pro Val
355 360 365

Asn Lys Ile Leu Asn Met Leu Cys Cys Trp Val Glu Asp Pro Asn Ser
370 375 380

Glu Ala Phe Lys Leu His Leu Pro Arg Ile His Asp Tyr Met Trp Val
385 390 395 400

Ala Glu Asp Gly Met Lys Ile Lys Gly Tyr Asn Gly Ser Gln Ser Trp
405 410 415

Asp Thr Ser Phe Ala Ile Gln Ala Ile Ile Ala Thr Glu Leu Gly Glu
420 425 430

Glu Tyr Gly Ser Ala Leu Arg Lys Ala His Ser Phe Ile Lys Asn Thr
435 440 445

Gln Val Leu Asp Asp Cys Pro Gly Asn Leu Asp Phe Trp Tyr Arg His
450 455 460

Ile Ser Lys Gly Ala Trp Pro Phe Ser Thr Ala Asp His Gly Trp Pro
465 470 475 480

Ile Ser Asp Cys Thr Ala Glu Gly Leu Lys Ala Thr Leu Leu Leu Ser
485 490 495

Lys Leu Pro Ser Glu Ile Val Gly Asp Pro Leu Asp Ala Lys Arg Phe
500 505 510

Tyr Asp Ala Val Asn Val Leu Leu Ser Leu Gln Asn Ser Gly Gly Gly
515 520 525

Phe Ala Thr Tyr Glu Leu Ser Arg Ser Tyr Pro Trp Leu Glu Ile Ile
530 535 540

Asn Pro Ala Glu Thr Phe Gly Asp Ile Val Ile Asp Tyr Pro Tyr Val
545 550 555 560

Glu Cys Ser Ser Ala Ala Ile Gln Ala Leu Thr Ala Phe Lys Lys Leu
565 570 575

Tyr Pro Gly His Arg Lys Glu Glu Val Glu Arg Cys Ile Ala Lys Ala
580 585 590

Ala Ala Phe Ile Glu Lys Ile Gln Glu Ala Asp Gly Ser Trp Tyr Gly
595 600 605

Ser Trp Ala Val Cys Phe Thr Tyr Gly Thr Trp Phe Gly Val Leu Gly
610 615 620

Leu Leu Ala Ala Gly Arg Asn Tyr Thr Asn Ser Ser Ser Ile Arg Lys
625 630 635 640

Ala Cys Asp Phe Leu Leu Ser Lys Gln Ile Ser Ser Gly Gly Trp Gly

```
                645                 650                 655

Glu Ser Tyr Leu Ser Cys Gln Asn Lys Val Tyr Thr Asn Leu Glu Gly
            660                 665                 670

Asn Arg Tyr His Val Val Asn Thr Ser Trp Ala Met Leu Thr Leu Ile
        675                 680                 685

Ala Ala Gly Gln Ala Glu Arg Asn Pro Thr Pro Leu His His Ala Ala
    690                 695                 700

Lys Ala Leu Ile Asn Ala Gln Leu Glu Asn Gly Asp Phe Pro Gln Gln
705                 710                 715                 720

Glu Ile Ser Gly Val Phe Asn Arg Asn Cys Met Ile Ser Tyr Ser Ala
                725                 730                 735

Tyr Arg Asn Ile Phe Pro Ile Trp Ala Leu Gly Glu Tyr Arg Ser Arg
            740                 745                 750

Val Leu Lys Ala Lys
        755


<210> SEQ ID NO 22
<211> LENGTH: 2274
<212> TYPE: DNA
<213> ORGANISM: Nicotiana tabacum

<400> SEQUENCE: 22

atgtggaagt tgaagatagc agaaggaggg aatccatggc ttagaacaac aaacaatcat     60

gtaggtaggg aactatggga gtttgatcca gaactcggat ctccggaaga tcgagcggag    120

atcgacaagt ttcgcgagca tttccacaaa catcgctttg agcaaaagca tagtgctgat    180

ctcattatgc gttatcagct atcaaaggag aatccaggaa ttactatttt gccccaagtc    240

aaagtacaag gcaatgaaga tattacagaa gatactgtag ctaccacgct cagaagagca    300

ctaagttttt attccactct acaaactcat gatggtcatt gggctggaga ttatggaggg    360

ccgatgtttc taatgcctgg catggtcatt gctctatctg ttacgggggc actcaatgca    420

gtattaacaa gcgaacataa acgtgaaatg attcgatatc tttataacca tcagaacagt    480

gatggtggat ggggcttgca cattgagggc cacagcacca tgtttggttc tgttttgagc    540

tatgttactc taaggttact tggagaagga gctaatgatg gagaaggggc catggagaag    600

ggccgtaaat ggattctgga tcatggtagt gccacggcca ttacttcatg gggaaaaatg    660

tggctcacag tgcttggagc attcgactgg tctgggaaca atccactccc tccggaaata    720

tggcttcttc cctacttcct tccaattcat cctggaagaa tgtggtgtca ctgcaggatg    780

gtttatcttc ctatgtgcta cctgtatggt aaaaggttcg ttggcccaat cacgccaaca    840

gttttatctt tgagaaagga gctctttaca gtgccttatc atgagataga ttggaataaa    900

gcacgcaatg agtgcgcaaa ggaagacctt tactacccgc accctctagt acaagatatc    960

ctgtgggctt cacttcacaa ggttgtggaa cctattctga tgcattggcc agggaaaaga   1020

ttgagagaaa aagctctccg catagtgatg gagcacattc attatgaaga tgaaaacact   1080

cgttacatat gcataggacc tgtaaacaag attttaaata tgctttgctg ctgggttgaa   1140

gatcctaatt cagaagcttt caagttgcac cttccaagaa ttcatgacta tatgtgggtt   1200

gctgaagatg gcatgaaaat taagggatac aatggaagtc aatcttggga tacttcattt   1260

gcaattcaag caatcattgc aacagagctt ggcgaggaat atggttcagc attgagaaaa   1320

gcgcattcat tcataaaaaa tacacaggtg ttagatgatt gcccaggcaa tctagatttc   1380

tggtaccgtc atatttcaaa aggtgcttgg ccctttttcaa ctgcagatca cggatggccc   1440
```

```
atttcagatt gtactgcaga gggacttaaa gcaactcttc tattatcaaa actaccatca   1500

gagatagtcg gtgatccatt ggatgcaaag cgtttctatg atgctgtaaa tgttttgctt   1560

tctttacaga atagtggtgg tggctttgca acatatgaac tatcgaggtc atatccgtgg   1620

ttagagataa tcaatcctgc tgagactttt ggagatattg ttattgatta cccttatgta   1680

gagtgttcct cagctgcaat tcaagcttta acagcattta agaaattata ccctggtcat   1740

cgcaaagaag aagtggaacg ctgtattgct aaagctgctg ccttcattga aaagattcaa   1800

gaagcagatg gctcctggta tggctcttgg gcagtttgct tcacctatgg cacttggttt   1860

ggggtgcttg gcttactagc tgcaggaagg aactacacta attcttccag catccgtaag   1920

gcttgtgact ttttgttgtc caaacaaatc tcatctggtg gctgggggga gagttacctg   1980

tcttgtcaaa acaaggtgta tacaaatctt gaaggcaaca gatatcatgt tgtaaataca   2040

tcatgggcta tgctgactct aattgctgct ggacaggctg agagaaatcc cacaccatta   2100

caccatgcag caaaagcatt aataaatgct cagctagaaa atggagattt tcctcagcag   2160

gagatcagcg gggtcttcaa caggaattgc atgatatcct attctgcata taggaacatt   2220

ttcccaattt gggcactggg agaatatcgt tctcgtgtac tcaaggctaa gtaa         2274
```

```
<210> SEQ ID NO 23
<211> LENGTH: 36
<212> TYPE: DNA
<213> ORGANISM: artificial sequence
<220> FEATURE:
<223> OTHER INFORMATION: oligonucleotide primer TkLUP fw

<400> SEQUENCE: 23

aaagtcgact aaaaaaatgt ggaagctgaa aatagc                               36


<210> SEQ ID NO 24
<211> LENGTH: 29
<212> TYPE: DNA
<213> ORGANISM: artificial sequence
<220> FEATURE:
<223> OTHER INFORMATION: oligonucleotide primer TkLUP bw

<400> SEQUENCE: 24

aaactcgaga tatattttga acaatacga                                      29


<210> SEQ ID NO 25
<211> LENGTH: 1107
<212> TYPE: DNA
<213> ORGANISM: Saccharomyces cerevisiae

<400> SEQUENCE: 25

atgaatccta aatcctctac acctaagatt ccaagaccca agaacgcatt tattctgttc     60

agacagcact accacaggat cttaatagac gaatggaccg ctcaaggtgt ggaaataccc    120

cataattcaa acatttctaa aattattggt acgaagtgga agggcttaca accggaagat    180

aaggcacact gggaaaatct agcggagaag gagaaactag aacataaaag gaagtatcct    240

gaatacaaat acaagccggt aagaaagtct aagaagaagc aactactttt gaaggaaatc    300

gagcaacagc agcagcaaca acagaaagaa cagcagcagc agaaacagtc acaaccgcaa    360

ttacaacagc cctttaacaa caatatagtt cttatgaaaa gagcacattc tctttcacca    420

tcttcctcgg tgtcaagctc gaacagctat cagttccaat tgaacaatga tcttaagagg    480

ttgcctattc cttctgttaa tacttctaac tatatggtct ccagatcttt aagtggacta    540

cctttgacgc atgataagac ggcaagagac ctaccacagc tgtcatctca actaaattct    600
```

attccatatt actcagctcc acacgaccct tcaacgagac atcattacct caacgtcgct 660
caagctcaac caagggctaa ctcgacccct caattgccct ttatttcatc cattatcaac 720
aacagcagtc aaacaccggt aactacaact accacatcca caacaactgc gacatcttct 780
cctgggaaat tctcctcttc tccgaactcc tctgtactgg agaacaacag attaaacagt 840
atcaacaatt caaatcaata tttacctccc cctctattac cttctctgca agattttcaa 900
ctggatcagt accagcagct aaagcagatg ggaccaactt atattgtcaa accactgtct 960
cacaccagga acaatctatt gtccacaact acccctacgc atcatcacat tcctcatata 1020
ccaaaccaaa acattcctct acatcaaatt ataaactcaa gcaacactga ggtcaccgct 1080
aaaactagcc tagtttctcc gaaatga 1107

<210> SEQ ID NO 26
<211> LENGTH: 31
<212> TYPE: DNA
<213> ORGANISM: artificial sequence
<220> FEATURE:
<223> OTHER INFORMATION: oligonucleotide primer rox1 fw

<400> SEQUENCE: 26
aaagcggccg catgaatcct aaatcctcta c 31

<210> SEQ ID NO 27
<211> LENGTH: 30
<212> TYPE: DNA
<213> ORGANISM: artificial sequence
<220> FEATURE:
<223> OTHER INFORMATION: oligonucleotide primer rox1 bw

<400> SEQUENCE: 27
aaagcggccg ctcatttcgg agaaactagg 30

<210> SEQ ID NO 28
<211> LENGTH: 31
<212> TYPE: DNA
<213> ORGANISM: artificial sequence
<220> FEATURE:
<223> OTHER INFORMATION: oligonucleotide primer pESC-Ura_NotI fw

<400> SEQUENCE: 28
aaagcggccg cccagctgca ttaatgaatc g 31

<210> SEQ ID NO 29
<211> LENGTH: 32
<212> TYPE: DNA
<213> ORGANISM: artificial sequence
<220> FEATURE:
<223> OTHER INFORMATION: oligonucleotide primer pESC-Ura_NotI bw

<400> SEQUENCE: 29
aaagcggccg cgaagttcct attctctaga aa 32

<210> SEQ ID NO 30
<211> LENGTH: 1520
<212> TYPE: DNA
<213> ORGANISM: Saccharomyces cerevisiae

<400> SEQUENCE: 30
ataacttcgt atagcataca ttatacgaag ttatattaag ggttctcgag agctcgtttt 60
atttaggttc tatcgaggag aaaaagcgac aagaagagat agaccatgga taaactgatt 120

-continued

```
atgttctaaa cactcctcag aagctcatcg aactgtcatc ctgcgtgaag attaaaatcc    180

aacttagaaa tttcgagctt acggagacaa tcatatggga gaagcaattg gaagatagaa    240

aaaaggtact cggtacataa atatatgtga ttctgggtag aagatcggtc tgcattggat    300

ggtggtaacg catttttta cacacattac ttgcctcgag catcaaatgg tggttattcg    360

tggatctata tcacgtgatt tgcttaagaa ttgtcgttca tggtgacact tttagctttg    420

acatgattaa gctcatctca attgatgtta tctaaagtca tttcaactat ctaagatgtg    480

gttgtgattg ggccattttg tgaaagccag tacgccagcg tcaatacact cccgtcaatt    540

agttgcacca tgtccacaaa atcatatacc agtagagctg agactcatgc aagtccggtt    600

gcatcgaaac ttttacgttt aatggatgaa aagaagacca atttgtgtgc ttctcttgac    660

gttcgttcga ctgatgagct attgaaactt gttgaaacgt tgggtccata catttgcctt    720

ttgaaaacac acgttgatat cttggatgat ttcagttatg agggtactgt cgttccattg    780

aaagcattgg cagagaaata caagttcttg atatttgagg acagaaaatt cgccgatatc    840

ggtaacacag tcaaattaca atatacatcg ggcgtttacc gtatcgcaga atggtctgat    900

atcaccaacg cccacggggt tactggtgct ggtattgttg ctggcttgaa acaaggtgcg    960

caagaggtca ccaaagaacc aaggggatta ttgatgcttg ctgaattgtc ttccaagggt   1020

tctctagcac acggtgaata tactaagggt accgttgata ttgcaaagag tgataaagat   1080

ttcgttattg ggttcattgc tcagaacgat atgggaggaa gagaagaagg gtttgattgg   1140

ctaatcatga ccccaggtgt aggtttagac gacaaaggcg atgcattggg tcagcagtac   1200

agaaccgtcg acgaagttgt aagtggtgga tcagatatca tcattgttgg cagaggactt   1260

ttcgccaagg gtagagatcc taaggttgaa ggtgaaagat acagaaatgc tggatgggaa   1320

gcgtaccaaa agagaatcag cgctccccat taattataca ggaaacttaa tagaacaaat   1380

cacatattta atctaatagc cacctgcatt ggcacggtgc aacactactt caacttcatc   1440

ttacaaaaag atcacgtgat ctgttgtatt gggatctcta gacctaataa cttcgtatag   1500

catacattat acgaagttat                                                1520
```

<210> SEQ ID NO 31
<211> LENGTH: 16
<212> TYPE: DNA
<213> ORGANISM: artificial sequence
<220> FEATURE:
<223> OTHER INFORMATION: AsiSI/Nb.BsmI USER cassette

<400> SEQUENCE: 31

```
cgtgcgatcg cgtgca                                                      16
```

<210> SEQ ID NO 32
<211> LENGTH: 1509
<212> TYPE: DNA
<213> ORGANISM: Saccharomyces cerevisiae

<400> SEQUENCE: 32

```
atggttttaa ccaataaaac agtcatttct ggatcgaaag tcaaaagttt atcatctgcg     60

caatcgagct catcaggacc ttcatcatct agtgaggaag atgattcccg cgatattgaa    120

agcttggata agaaaatacg tcctttagaa gaattagaag cattattaag tagtggaaat    180

acaaaacaat tgaagaacaa agaggtcgct gccttggtta ttcacggtaa gttacctttg    240

tacgctttgg agaaaaaatt aggtgatact acgagagcgg ttgcggtacg taggaaggct    300

ctttcaattt tggcagaagc tcctgtatta gcatctgatc gtttaccata taaaaattat    360
```

gactacgacc gcgtatttgg cgcttgttgt gaaaatgtta taggttacat gcctttgccc 420
gttggtgtta taggcccctt ggttatcgat ggtacatctt atcatatacc aatggcaact 480
acagagggtt gtttggtagc ttctgccatg cgtggctgta aggcaatcaa tgctggcggt 540
ggtgcaacaa ctgttttaac taaggatggt atgacaagag gcccagtagt ccgtttccca 600
actttgaaaa gatctggtgc ctgtaagata tggttagact cagaagaggg acaaaacgca 660
attaaaaaag cttttaactc tacatcaaga tttgcacgtc tgcaacatat tcaaacttgt 720
ctagcaggag atttactctt catgagattt agaacaacta ctggtgacgc aatgggtatg 780
aatatgattt ctaaaggtgt cgaatactca ttaaagcaaa tggtagaaga gtatggctgg 840
gaagatatgg aggttgtctc cgtttctggt aactactgta ccgacaaaaa accagctgcc 900
atcaactgga tcgaaggtcg tggtaagagt gtcgtcgcag aagctactat tcctggtgat 960
gttgtcagaa aagtgttaaa aagtgatgtt tccgcattgg ttgagttgaa cattgctaag 1020
aatttggttg gatctgcaat ggctgggtct gttggtggat ttaacgcaca tgcagctaat 1080
ttagtgacag ctgttttctt ggcattagga caagatcctg cacaaaatgt tgaaagttcc 1140
aactgtataa cattgatgaa agaagtggac ggtgatttga gaatttccgt atccatgcca 1200
tccatcgaag taggtaccat cggtggtggt actgttctag aaccacaagg tgccatgttg 1260
gacttattag gtgtaagagg cccgcatgct accgctcctg gtaccaacgc acgtcaatta 1320
gcaagaatag ttgcctgtgc cgtcttggca ggtgaattat ccttatgtgc tgccctagca 1380
gccggccatt tggttcaaag tcatatgacc cacaacagga aacctgctga accaacaaaa 1440
cctaacaatt tggacgccac tgatataaat cgtttgaaag atgggtccgt cacctgcatt 1500
aaatcctaa 1509

<210> SEQ ID NO 33
<211> LENGTH: 35
<212> TYPE: DNA
<213> ORGANISM: artificial sequence
<220> FEATURE:
<223> OTHER INFORMATION: oligonucleotide primer tHMGR fw

<400> SEQUENCE: 33
aaaggatcca aaaaaatggt tttaaccaat aaaac 35

<210> SEQ ID NO 34
<211> LENGTH: 30
<212> TYPE: DNA
<213> ORGANISM: artificial sequence
<220> FEATURE:
<223> OTHER INFORMATION: oligonucleotide primer tHMGR bw

<400> SEQUENCE: 34
aaagtcgact taggatttaa tgcaggtgac 30

<210> SEQ ID NO 35
<211> LENGTH: 38
<212> TYPE: DNA
<213> ORGANISM: artificial sequence
<220> FEATURE:
<223> OTHER INFORMATION: oligonucleotide primer ERG13-fw

<400> SEQUENCE: 35
aaagaattca aaaaaatgaa actctcaact aaactttg 38

<210> SEQ ID NO 36

<211> LENGTH: 34
<212> TYPE: DNA
<213> ORGANISM: artificial sequence
<220> FEATURE:
<223> OTHER INFORMATION: oligonucleotide primer ERG13-bw

<400> SEQUENCE: 36
aaagcggccg cttatttttt aacatcgtaa gatc 34

<210> SEQ ID NO 37
<211> LENGTH: 30
<212> TYPE: DNA
<213> ORGANISM: artificial sequence
<220> FEATURE:
<223> OTHER INFORMATION: expression cassette fw-primer
<220> FEATURE:
<221> NAME/KEY: misc_feature
<222> LOCATION: (8)..(8)
<223> OTHER INFORMATION: n is uracil

<400> SEQUENCE: 37
cgtgcgantc agagcgacct catgctatac 30

<210> SEQ ID NO 38
<211> LENGTH: 27
<212> TYPE: DNA
<213> ORGANISM: artificial sequence
<220> FEATURE:
<223> OTHER INFORMATION: expression cassette bw-primer
<220> FEATURE:
<221> NAME/KEY: misc_feature
<222> LOCATION: (8)..(8)
<223> OTHER INFORMATION: n is uracil

<400> SEQUENCE: 38
cacgcganct tcgagcgtcc caaaacc 27

<210> SEQ ID NO 39
<211> LENGTH: 533
<212> TYPE: DNA
<213> ORGANISM: Saccharomyces cerevisiae

<400> SEQUENCE: 39
cacatttaag ggctatacaa agatgacaga attttattct gacacaatcg gtctaccaaa 60
gacagatcca cgtctttgga gactgagaac tgatgagcta ggccgagaaa gctgggaata 120
tttaacccct cagcaagccg caaacgaccc accatccact ttcacgcagt ggcttcttca 180
agatcccaaa tttcctcaac ctcatccaga aagaaataag cattcaccag atttttcagc 240
cttcgatgcg tgtcataatg gtgcatcttt tttcaaactg cttcaagagc ctgactcagg 300
tatttttccg tgtcaatata aaggacccat gttcatgaca atcggttacg tagccgtaaa 360
ctatatcgcc ggtattgaaa ttcctgagca tgagagaata gaattaatta gatacatcgt 420
caatacagca catccggttg atggtggctg gggtctacat tctgttgaca aatccaccgt 480
gtttggtaca gtattgaact atgtaatctt acgtttattg gggcggccgc ttt 533

<210> SEQ ID NO 40
<211> LENGTH: 44
<212> TYPE: DNA
<213> ORGANISM: artificial sequence
<220> FEATURE:
<223> OTHER INFORMATION: oligonucleotide primer ERG7 fragment fw

<400> SEQUENCE: 40
cacatttaag ggctatacaa agatgacaga attttattct gaca 44

<210> SEQ ID NO 41
<211> LENGTH: 32
<212> TYPE: DNA
<213> ORGANISM: artificial sequence
<220> FEATURE:
<223> OTHER INFORMATION: oligonucleotide primer ERG7 fragment-bw

<400> SEQUENCE: 41
aaagcggccg ccccaataaa cgtaagatta ca 32

<210> SEQ ID NO 42
<211> LENGTH: 735
<212> TYPE: DNA
<213> ORGANISM: Saccharomyces cerevisiae

<400> SEQUENCE: 42
ggtattccaa tgagaatcgc tagaaatgct ttaccagaac tagactactt gtcgcagatc 60
acttttgaac tgtatgagag tacggatgct tctggtcaaa aatcgcattc cattagactg 120
aaaatgtctc ctgggtgtca tactcaagat ccgttagatg ttcaattaga tgacaggcat 180
tatattagtt gtattccaaa gatttccctg acgaagcatt tggatatgga ctacgttcaa 240
cagaaattga gaaacaaatt taccagggtc attatgcctc cgaaatttac accagtaaac 300
attacgagcc ccaacttgag tttccagaaa cgcaaaacca gaagaaagtc ggtatctgtt 360
gagaagttga agcttcctgc ctcgtccgga tcttcatcat ctacctccgt taacaagaca 420
ttagattagt gatcacaccc aatttttaat ttagcaaccc aaaataaata agtatttact 480
caactttttt ttaataaaaa aaaacttaat tgaattttgc tcgcgatctt taggtccggg 540
gttttcgttg aacccttaga cgagcaaatt agcgccataa ggatatacgt cagagcacat 600
taattagtga catataccta tataaagagc aaccttctcc gatagacttg taatttatct 660
tatttcattt cctaacactt tggtcgaaga agagggataa gaacagacga aaacacattt 720
aagggctata caaag 735

<210> SEQ ID NO 43
<211> LENGTH: 45
<212> TYPE: DNA
<213> ORGANISM: artificial sequence
<220> FEATURE:
<223> OTHER INFORMATION: ologonucleotide primer CTR promoter fragment-fw

<400> SEQUENCE: 43
aaagcggccg ccagctgaag gatccggtat tccaatgaga atcgc 45

<210> SEQ ID NO 44
<211> LENGTH: 43
<212> TYPE: DNA
<213> ORGANISM: artificial sequence
<220> FEATURE:
<223> OTHER INFORMATION: oligonucleotide primer CTR promoter fragment-bw

<400> SEQUENCE: 44
tgtcagaata aaattctgtc atctttgtat agcccttaaa tgt 43

<210> SEQ ID NO 45
<211> LENGTH: 510
<212> TYPE: DNA
<213> ORGANISM: Saccharomyces cerevisiae

<400> SEQUENCE: 45

-continued

```
aatctgctgc tattcgtgat tactgttaca acctaacggt ttaaatgaaa cctggttctg     60

aagggtcatt ttataacttc aagttccctt agcctttcga ttcattttga ttatgccatt    120

tctagaccgt gttataggcg ctggcgttta atttggtgta gcttggttta gtcaagagtt    180

gtattagtgt tcctcgataa agtcgatgtt tccggatatt gtgttaaaat ttcaagtatg    240

ctactaatgg ggtaaagttg catgattagc agagacatat ggcttgttat ggttcggctt    300

cctcattttt catgcttagt ttttgtccat ctcattgtac atttctgaat cctaatgcat    360

gactccctaa cattactatt aaattctcaa tagtgaagaa taagcaaaat gggaaccatg    420

ataatttcta gctttctctc cacccctatt ttaatttgca atcatatata gtactttcaa    480

tagcatcttt tctagatttg atatctgcgg                                      510
```

<210> SEQ ID NO 46
<211> LENGTH: 27
<212> TYPE: DNA
<213> ORGANISM: artificial sequence
<220> FEATURE:
<223> OTHER INFORMATION: oligonucleotide primer ERG7 promoter fragment-fw

<400> SEQUENCE: 46

```
aaacagctga atctgctgct attcgtg                                          27
```

<210> SEQ ID NO 47
<211> LENGTH: 34
<212> TYPE: DNA
<213> ORGANISM: artificial sequence
<220> FEATURE:
<223> OTHER INFORMATION: oligonucleotide primer ERG7 promoter fragment-bw

<400> SEQUENCE: 47

```
aaaggatccc ctgcaggcgc tgcaggtcga caac                                  34
```

<210> SEQ ID NO 48
<211> LENGTH: 2519
<212> TYPE: DNA
<213> ORGANISM: Saccharomyces cerevisiae

<400> SEQUENCE: 48

```
aaacctgcag ggtaacgcc agggttttcc cagtcacgac gttgtaaaac gacggccagt      60

gagcgcgcgt aatacgactc actatagggc gaattgggtg cataggccac tagtggatct    120

gatatcacct aataacttcg tatagcatac attatacgaa gttatattaa gggttctcga    180

gagctcgctg tgaagatccc agcaaaggct tacaaagtgt tatctctttt gagacttgtt    240

gagttgaaca ctggtgtttt catcaaactt accaaggacg tgtacccatt gttgaaactt    300

gtatcaccat atattgttat cggacaacct tcacttgcat ctatccgttc tttaatccaa    360

aagagatcta gaataatgtg gcaaaggcca gaagataaag aaccaaaaga gataatcttg    420

aatgacaaca atatcgttga agagaaatta ggtgatgaag gtgtcatttg tatcgaggat    480

atcatccatg agatttcgac gttgggcgaa aatttctcga aatgtacttt cttcctatta    540

ccattcaaat tgaacagaga agtcagtgga ttcggtgcca tctcccgttt gaataaactg    600

aaaatgcgcg aacaaaacaa gaagactcgt caaatttcaa acgctgccac ggctccagtt    660

atccaagtag atatcgactc aatgatttcc aagttgaatt gattaactat aaaaggaaaa    720

tatctgtaca atagacatcg ggctcccatt ggccctaccc acatatgtag aaatacatta    780

ctctattcac tactgcattt agttatgttt aacatttgat atagcagact accgccaggc    840
```

acaatatatt ccccttccct cttgccattc gctgtacttg tggtggattc caattcagcg 900
cagtcacgtg ctagtaatca ccgcattttt ttcttttcct ttcaggctaa aaccggttcc 960
gggcctgatc cctgcactca ttttctaacg gaaaaccttc agaagcataa ctacccattc 1020
cagtttagag tcatgacagg ttcaacatca gatgcttcat atacttttat atattgaatt 1080
atataaatat atctatgtac tctaagtaag tacatctgct ttaacgcatt cctacatttg 1140
cttcgattta tttttattgt tgatacctat ttgaagaagt aaaaagtatc ccacactaca 1200
cagattatac catgtctaag aatatcgttg tcctaccggg tgatcacgtc ggtaaagaag 1260
ttactgacga agctattaag gtcttgaatg ccattgctga agtccgtcca gaaattaagt 1320
tcaatttcca acatcacttg atcgggggtg ctgccatcga tgccactggc actcctttac 1380
cagatgaagc tctagaagcc tctaagaaag ccgatgctgt cttactaggt gctgttggtg 1440
gtccaaaatg gggtacgggc gcagttagac cagaacaagg tctattgaag atcagaaagg 1500
aattgggtct atacgccaac ttgagaccat gtaactttgc ttctgattct ttactagatc 1560
tttctccttt gaagcctgaa tatgcaaagg gtaccgattt cgtcgtcgtt agagaattgg 1620
ttggtggtat ctactttggt gaaagaaaag aagatgaagg tgacggagtt gcttgggact 1680
ctgagaaata cagtgttcct gaagttcaaa gaattacaag aatggctgct ttcttggcat 1740
tgcaacaaaa cccaccatta ccaatctggt ctcttgacaa ggctaacgtg cttgcctctt 1800
ccagattgtg gagaaagact gttgaagaaa ccatcaagac tgagttccca caattaactg 1860
ttcagcacca attgatcgac tctgctgcta tgattttggt taaatcacca actaagctaa 1920
acggtgttgt tattaccaac aacatgtttg gtgatattat ctccgatgaa gcctctgtta 1980
ttccaggttc tttgggttta ttaccttctg catctctagc ttccctacct gacactaaca 2040
aggcattcgg tttgtacgaa ccatgtcatg gttctgcccc agatttacca gcaaacaagg 2100
ttaacccaat tgctaccatc ttatctgcag ctatgatgtt gaagttatcc ttggatttgg 2160
ttgaagaagg tagggctctt gaagaagctg ttagaaatgt cttggatgca ggtgtcagaa 2220
ccggtgacct tggtggttct aactctacca ctgaggttgg cgatgctatc gccaaggctg 2280
tcaaggaaat cttggcttaa agagtctttt gtaacgaccc cgtctccacc aacttggtat 2340
gcttgaaatc tcaaggccat tacacattca gttatgtgaa cgaaaggtct ttatttaacg 2400
tagcataaac taaataatac aggttccggt tagcctgcgg atctctagac ctaataactt 2460
cgtatagcat acattatacg aagttatatt aagggttgtc gacctgcagc ggatccaaa 2519

<210> SEQ ID NO 49
<211> LENGTH: 1335
<212> TYPE: DNA
<213> ORGANISM: Saccharomyces cerevisiae

<400> SEQUENCE: 49
atgggaaagc tattacaatt ggcattgcat ccggtcgaga tgaaggcagc tttgaagctg 60
aagttttgca gaacaccgct attctccatc tatgatcagt ccacgtctcc atatctcttg 120
cactgtttcg aactgttgaa cttgacctcc agatcgtttg ctgctgtgat cagagagctg 180
catccagaat tgagaaactg tgttactctc ttttatttga ttttaagggc tttggatacc 240
atcgaagacg atatgtccat cgaacacgat ttgaaaattg acttgttgcg tcacttccac 300
gagaaattgt tgttaactaa atggagtttc gacggaaatg cccccgatgt gaaggacaga 360
gccgttttga cagatttcga atcgattctt attgaattcc acaaattgaa accagaatat 420

-continued caagaagtca tcaaggagat caccgagaaa atgggtaatg gtatggccga ctacatcttg 480
gatgaaaatt acaacttgaa tgggttgcaa accgtccacg actacgacgt gtactgtcac 540
tacgtagctg gtttggtcgg tgatggtttg acccgtttga ttgtcattgc caagtttgcc 600
aacgaatctt tgtattctaa tgagcaattg tatgaaagca tgggtctttt cctacaaaaa 660
accaacatca tcagagacta caatgaagat ttggtcgatg gtagatcctt ctggcccaag 720
gaaatctggt cacaatacgc tcctcagttg aaggacttca tgaaacctga aaacgaacaa 780
ctggggttgg actgtataaa ccacctcgtc ttaaacgcat tgagtcatgt tatcgatgtg 840
ttgacttatt tggccagtat ccacgagcaa tccactttcc aattttgtgc cattccccaa 900
gttatggcca ttgcaacctt ggctttggta ttcaacaacc gtgaagtgct acatggcaat 960
gtaaagattc gtaagggtac tacctgctat ttaattttga aatcaaggac tttgcgtggc 1020
tgtgtcgaga tttttgacta ttacttacgt gatatcaaat ctaaattggc tgtgcaagat 1080
ccaaatttct taaaattgaa cattcaaatc tccaagatcg aacaattcat ggaagaaatg 1140
taccaggata aattacctcc taacgtgaag ccaaatgaaa ctccaatttt cttgaaagtt 1200
aaagaaagat ccagatacga tgatgaattg gtcccaaccc aacaagaaga agagtacaag 1260
ttcaatatgg ttttatctat catcttgtcc gttcttcttg ggttttatta tatatacact 1320
ttacacagag cgtga 1335

<210> SEQ ID NO 50
<211> LENGTH: 493
<212> TYPE: DNA
<213> ORGANISM: unknown
<220> FEATURE:
<223> OTHER INFORMATION: MET3 promoter

<400> SEQUENCE: 50
tttagtacta acagagactt ttgtcacaac tacatataag tgtacaaata tagtacagat 60
atgacacact tgtagcgcca acgcgcatcc tacggattgc tgacagaaaa aaaggtcacg 120
tgaccagaaa agtcacgtgt aattttgtaa ctcaccgcat tctagcggtc cctgtcgtgc 180
acactgcact caacaccata aaccttagca acctccaaag gaaatcaccg tataacaaag 240
ccacagtttt acaacttagt ctcttatgaa gttacttacc aatgagaaat agaggctctt 300
tctcgagaaa tatgaatatg gatatatata tatatatata tatatatata tatatatatg 360
taaacttggt tctttttag cttgtgatct ctagcttggg tctctctctg tcgtaacagt 420
tgtgatatcg tttcttaaca attgaaaagg aactaagaaa gtataataat aacaagaata 480
aagtataatt aac 493

<210> SEQ ID NO 51
<211> LENGTH: 1491
<212> TYPE: DNA
<213> ORGANISM: Saccharomyces cerevisiae

<400> SEQUENCE: 51
atgtctgctg ttaacgttgc acctgaattg attaatgccg acaacacaat tacctacgat 60
gcgattgtca tcggtgctgg tgttatcggt ccatgtgttg ctactggtct agcaagaaag 120
ggtaagaaag ttcttatcgt agaacgtgac tgggctatgc ctgatagaat tgttggtgaa 180
ttgatgcaac caggtggtgt tagagcattg agaagtctgg gtatgattca atctatcaac 240
aacatcgaag catatcctgt taccggttat accgtctttt tcaacggcga acaagttgat 300
attccatacc cttacaaggc cgatatccct aaagttgaaa aattgaagga cttggtcaaa 360

```
gatggtaatg acaaggtctt ggaagacagc actattcaca tcaaggatta cgaagatgat    420

gaaagagaaa ggggtgttgc ttttgttcat ggtagattct tgaacaactt gagaaacatt    480

actgctcaag agccaaatgt tactagagtg caaggtaact gtattgagat attgaaggat    540

gaaaagaatg aggttgttgg tgccaaggtt gacattgatg gccgtggcaa ggtggaattc    600

aaagcccact tgacatttat ctgtgacggt atcttttcac gtttcagaaa ggaattgcac    660

ccagaccatg ttccaactgt cggttcttcg tttgtcggta tgtctttgtt caatgctaag    720

aatcctgctc ctatgcacgg tcacgttatt cttggtagtg atcatatgcc aatcttggtt    780

taccaaatca gtccagaaga aacaagaatc ctttgtgctt acaactctcc aaaggtccca    840

gctgatatca agagttggat gattaaggat gtccaacctt tcattccaaa gagtctacgt    900

ccttcatttg atgaagccgt cagccaaggt aaatttagag ctatgccaaa ctcctacttg    960

ccagctagac aaaacgacgt cactggtatg tgtgttatcg gtgacgctct aaatatgaga   1020

catccattga ctggtggtgg tatgactgtc ggtttgcatg atgttgtctt gttgattaag   1080

aaaataggtg acctagactt cagcgaccgt gaaaaggttt tggatgaatt actagactac   1140

catttcgaaa gaaagagtta cgattccgtt attaacgttt tgtcagtggc tttgtattct   1200

ttgttcgctg ctgacagcga taacttgaag gcattacaaa aaggttgttt caaatatttc   1260

caaagaggtg gcgattgtgt caacaaaccc gttgaatttc tgtctggtgt cttgccaaag   1320

cctttgcaat tgaccagggt ttcttcgct gtcgcttttt acaccattta cttgaacatg   1380

gaagaacgtg gtttcttggg attaccaatg gctttattgg aaggtattat gattttgatc   1440

acagctatta gagtattcac cccatttttg tttggtgagt tgattggtta a            1491
```

```
<210> SEQ ID NO 52
<211> LENGTH: 496
<212> TYPE: PRT
<213> ORGANISM: Saccharomyces cerevisiae

<400> SEQUENCE: 52

Met Ser Ala Val Asn Val Ala Pro Glu Leu Ile Asn Ala Asp Asn Thr
1               5                   10                  15

Ile Thr Tyr Asp Ala Ile Val Ile Gly Ala Gly Val Ile Gly Pro Cys
            20                  25                  30

Val Ala Thr Gly Leu Ala Arg Lys Gly Lys Lys Val Leu Ile Val Glu
        35                  40                  45

Arg Asp Trp Ala Met Pro Asp Arg Ile Val Gly Glu Leu Met Gln Pro
    50                  55                  60

Gly Gly Val Arg Ala Leu Arg Ser Leu Gly Met Ile Gln Ser Ile Asn
65                  70                  75                  80

Asn Ile Glu Ala Tyr Pro Val Thr Gly Tyr Thr Val Phe Phe Asn Gly
                85                  90                  95

Glu Gln Val Asp Ile Pro Tyr Pro Tyr Lys Ala Asp Ile Pro Lys Val
            100                 105                 110

Glu Lys Leu Lys Asp Leu Val Lys Asp Gly Asn Asp Lys Val Leu Glu
        115                 120                 125

Asp Ser Thr Ile His Ile Lys Asp Tyr Glu Asp Asp Glu Arg Glu Arg
    130                 135                 140

Gly Val Ala Phe Val His Gly Arg Phe Leu Asn Asn Leu Arg Asn Ile
145                 150                 155                 160

Thr Ala Gln Glu Pro Asn Val Thr Arg Val Gln Gly Asn Cys Ile Glu
                165                 170                 175
```

```
Ile Leu Lys Asp Glu Lys Asn Glu Val Val Gly Ala Lys Val Asp Ile
            180                 185                 190

Asp Gly Arg Gly Lys Val Glu Phe Lys Ala His Leu Thr Phe Ile Cys
        195                 200                 205

Asp Gly Ile Phe Ser Arg Phe Arg Lys Glu Leu His Pro Asp His Val
    210                 215                 220

Pro Thr Val Gly Ser Ser Phe Val Gly Met Ser Leu Phe Asn Ala Lys
225                 230                 235                 240

Asn Pro Ala Pro Met His Gly His Val Ile Leu Gly Ser Asp His Met
                245                 250                 255

Pro Ile Leu Val Tyr Gln Ile Ser Pro Glu Glu Thr Arg Ile Leu Cys
            260                 265                 270

Ala Tyr Asn Ser Pro Lys Val Pro Ala Asp Ile Lys Ser Trp Met Ile
        275                 280                 285

Lys Asp Val Gln Pro Phe Ile Pro Lys Ser Leu Arg Pro Ser Phe Asp
    290                 295                 300

Glu Ala Val Ser Gln Gly Lys Phe Arg Ala Met Pro Asn Ser Tyr Leu
305                 310                 315                 320

Pro Ala Arg Gln Asn Asp Val Thr Gly Met Cys Val Ile Gly Asp Ala
                325                 330                 335

Leu Asn Met Arg His Pro Leu Thr Gly Gly Gly Met Thr Val Gly Leu
            340                 345                 350

His Asp Val Val Leu Leu Ile Lys Lys Ile Gly Asp Leu Asp Phe Ser
        355                 360                 365

Asp Arg Glu Lys Val Leu Asp Glu Leu Leu Asp Tyr His Phe Glu Arg
    370                 375                 380

Lys Ser Tyr Asp Ser Val Ile Asn Val Leu Ser Val Ala Leu Tyr Ser
385                 390                 395                 400

Leu Phe Ala Ala Asp Ser Asp Asn Leu Lys Ala Leu Gln Lys Gly Cys
                405                 410                 415

Phe Lys Tyr Phe Gln Arg Gly Gly Asp Cys Val Asn Lys Pro Val Glu
            420                 425                 430

Phe Leu Ser Gly Val Leu Pro Lys Pro Leu Gln Leu Thr Arg Val Phe
        435                 440                 445

Phe Ala Val Ala Phe Tyr Thr Ile Tyr Leu Asn Met Glu Glu Arg Gly
    450                 455                 460

Phe Leu Gly Leu Pro Met Ala Leu Leu Glu Gly Ile Met Ile Leu Ile
465                 470                 475                 480

Thr Ala Ile Arg Val Phe Thr Pro Phe Leu Phe Gly Glu Leu Ile Gly
                485                 490                 495


<210> SEQ ID NO 53
<211> LENGTH: 444
<212> TYPE: PRT
<213> ORGANISM: Saccharomyces cerevisiae

<400> SEQUENCE: 53

Met Gly Lys Leu Leu Gln Leu Ala Leu His Pro Val Glu Met Lys Ala
1               5                   10                  15

Ala Leu Lys Leu Lys Phe Cys Arg Thr Pro Leu Phe Ser Ile Tyr Asp
            20                  25                  30

Gln Ser Thr Ser Pro Tyr Leu Leu His Cys Phe Glu Leu Leu Asn Leu
        35                  40                  45

Thr Ser Arg Ser Phe Ala Ala Val Ile Arg Glu Leu His Pro Glu Leu
```

-continued

```
    50                  55                  60

Arg Asn Cys Val Thr Leu Phe Tyr Leu Ile Leu Arg Ala Leu Asp Thr
65                  70                  75                  80

Ile Glu Asp Asp Met Ser Ile Glu His Asp Leu Lys Ile Asp Leu Leu
                85                  90                  95

Arg His Phe His Glu Lys Leu Leu Leu Thr Lys Trp Ser Phe Asp Gly
            100                 105                 110

Asn Ala Pro Asp Val Lys Asp Arg Ala Val Leu Thr Asp Phe Glu Ser
        115                 120                 125

Ile Leu Ile Glu Phe His Lys Leu Lys Pro Glu Tyr Gln Glu Val Ile
    130                 135                 140

Lys Glu Ile Thr Glu Lys Met Gly Asn Gly Met Ala Asp Tyr Ile Leu
145                 150                 155                 160

Asp Glu Asn Tyr Asn Leu Asn Gly Leu Gln Thr Val His Asp Tyr Asp
                165                 170                 175

Val Tyr Cys His Tyr Val Ala Gly Leu Val Gly Asp Gly Leu Thr Arg
            180                 185                 190

Leu Ile Val Ile Ala Lys Phe Ala Asn Glu Ser Leu Tyr Ser Asn Glu
        195                 200                 205

Gln Leu Tyr Glu Ser Met Gly Leu Phe Leu Gln Lys Thr Asn Ile Ile
    210                 215                 220

Arg Asp Tyr Asn Glu Asp Leu Val Asp Gly Arg Ser Phe Trp Pro Lys
225                 230                 235                 240

Glu Ile Trp Ser Gln Tyr Ala Pro Gln Leu Lys Asp Phe Met Lys Pro
                245                 250                 255

Glu Asn Glu Gln Leu Gly Leu Asp Cys Ile Asn His Leu Val Leu Asn
            260                 265                 270

Ala Leu Ser His Val Ile Asp Val Leu Thr Tyr Leu Ala Ser Ile His
        275                 280                 285

Glu Gln Ser Thr Phe Gln Phe Cys Ala Ile Pro Gln Val Met Ala Ile
    290                 295                 300

Ala Thr Leu Ala Leu Val Phe Asn Asn Arg Glu Val Leu His Gly Asn
305                 310                 315                 320

Val Lys Ile Arg Lys Gly Thr Thr Cys Tyr Leu Ile Leu Lys Ser Arg
                325                 330                 335

Thr Leu Arg Gly Cys Val Glu Ile Phe Asp Tyr Tyr Leu Arg Asp Ile
            340                 345                 350

Lys Ser Lys Leu Ala Val Gln Asp Pro Asn Phe Leu Lys Leu Asn Ile
        355                 360                 365

Gln Ile Ser Lys Ile Glu Gln Phe Met Glu Glu Met Tyr Gln Asp Lys
    370                 375                 380

Leu Pro Pro Asn Val Lys Pro Asn Glu Thr Pro Ile Phe Leu Lys Val
385                 390                 395                 400

Lys Glu Arg Ser Arg Tyr Asp Asp Glu Leu Val Pro Thr Gln Gln Glu
                405                 410                 415

Glu Glu Tyr Lys Phe Asn Met Val Leu Ser Ile Ile Leu Ser Val Leu
            420                 425                 430

Leu Gly Phe Tyr Tyr Ile Tyr Thr Leu His Arg Ala
        435                 440
```

<210> SEQ ID NO 54
<211> LENGTH: 1008
<212> TYPE: DNA
<213> ORGANISM: Saccharomyces cerevisiae

<400> SEQUENCE: 54
atggaggcca agatagatga gctgatcaat aatgatcctg tttggtccag ccaaaatgaa 60
agcttgattt caaaacctta taatcacatc cttttgaaac ctggcaagaa ctttagacta 120
aatttaatag ttcaaattaa cagagttatg aatttgccca aagaccagct ggccatagtt 180
tcgcaaattg ttgagctctt gcataattcc agccttttaa tcgacgatat agaagataat 240
gctcccttga gaaggggaca gaccacttct cacttaatct tcggtgtacc ctccactata 300
aacaccgcaa attatatgta tttcagagcc atgcaacttg tatcgcagct aaccacaaaa 360
gagcctttgt atcataattt gattacgatt ttcaacgaag aattgatcaa tctacatagg 420
ggacaaggct tggatatata ctggagagac tttctgcctg aaatcatacc tactcaggag 480
atgtatttga atatggttat gaataaaaca ggcggccttt tcagattaac gttgagactc 540
atggaagcgc tgtctccttc ctcacaccac ggccattcgt tggttccttt cataaatctt 600
ctgggtatta tttatcagat tagagatgat tacttgaatt tgaaagattt ccaaatgtcc 660
agcgaaaaag gctttgctga ggacattaca gaggggaagt tatcttttcc catcgtccac 720
gcccttaact tcactaaaac gaaaggtcaa actgagcaac acaatgaaat tctaagaatt 780
ctcctgttga ggacaagtga taaagatata aaactaaagc tgattcaaat actggaattc 840
gacaccaatt cattggccta caccaaaaat tttattaatc aattagtgaa tatgataaaa 900
aatgataatg aaaataagta tttacctgat ttggcttcgc attccgacac cgccaccaat 960
ttacatgacg aattgttata tataatagac cacttatccg aattgtga 1008

<210> SEQ ID NO 55
<211> LENGTH: 405
<212> TYPE: DNA
<213> ORGANISM: Saccharomyces cerevisiae

<400> SEQUENCE: 55
atgatagaat tggattatgt aaaaggtgaa gataccattg tagaagcaac cagcacgtcg 60
ccgtggctga tgaggtctcc tcttgcccgg gccgcagaaa agaggggcag tggcctgttt 120
ttcgacataa atgaggggca tggccagcac cgagacgtca ttgttgcata tggcgtatcc 180
aagccgaaac ggcgctcgcc tcatccccac gggaataagg cagccgacaa aagaaaaacg 240
accgaaaagg aaccagaaag aaaaaagagg gtgggcgcgc cgcggacgtg taaaaagata 300
tgcatccagc ttctatatcg ctttaacttt accgttttgg gcatcgggaa cgtatgtaac 360
attgatctcc tcttgggaac ggtgagtgca acgaatgcga tatag 405

<210> SEQ ID NO 56
<211> LENGTH: 957
<212> TYPE: DNA
<213> ORGANISM: Saccharomyces cerevisiae

<400> SEQUENCE: 56
atggaattct tttatgaaga gcaagtagct tgtatcgaag atgataaaat aaacgactct 60
cataccaagg aaactggatc aacagaaaac actgaaaata acgaacttca gagccgagat 120
gacaaaacaa atggggcctt ccaaaagtta gaagaggaag tcaataaacg atatgaaaag 180
actacaagtg cattcaaaaa gttagtaatc gaaaaagatg acggaattga gattaacttg 240
ccaattagca atgaaactac agagactgca caaaagtatt tgaagaaact agacgagaac 300
attcacagcg tggaaagtct agcccagtca tattggagca aaatgaaaac taagaatttt 360

-continued

```
tggtctggct tcagtagctt cgataatgct gcagaaaatg actctaatga caaggatgag    420

aattcgaaag aaaatgaaat tgctgtgggt ggaaatagaa cagaagccga actaaggaca    480

ttatctaaag ataaatcggt ttatttagac aataaaatgg atttgcaact ggacccgttt    540

gacgtggatg aaaaaactga ggagatatgt tctattttac agggcgacaa agatatctcc    600

aaattaatga acgacatcgt accccataaa atcagctata aagatttctg gcacatctat    660

ttcttacaaa gaaacaaaat tctagataaa gaaagtaaaa ggaaagaaat attgtccaaa    720

aaggaaaagg aaacggagga aaaagaagtt gagtgggatg acgaagaaga agatgatgat    780

gatgacaaag tagaagcagt agttgacaac aaatctaaag gagagacgaa agttgctgtg    840

tctcaagagg gattgaaaga tgttagtgac catgttggcc tcgccaacaa ggatgagagc    900

aaggacgacg acgacgacga cgacgacgac gacgacgacg atgatgactg ggaatga       957
```

<210> SEQ ID NO 57
<211> LENGTH: 537
<212> TYPE: DNA
<213> ORGANISM: Saccharomyces cerevisiae

<400> SEQUENCE: 57

```
atgactggat accctgacgt ggccgccttc gatttggact acaccatttg gccctgctat     60

tgtgataccc atttgcacgg tccctttaag ccagttaaaa gtagtaatgg cgaagttctc    120

acaattatat gtagagatgg ttacgagctc acaatctaca aagatatccc acgtatacta    180

ggtgatctta aagataatgg agttaagtta atgaccgcgt cacgaacgtg ggcacctgag    240

attgcccagg aaatactgaa aatattcaag gtcaagtatg ctggtgtcgt aaccccgttg    300

gccaacctgt tcgatgaatt tcagtgggga gaaagaagta aaattggcca tttaagggac    360

ggtttgaaag atctttataa taccagcgat ttaaaatcga aaaagatttg tttatttgat    420

gatgaaagta gaaacaaaga agtggagaaa tacggagtga agtttgttta tgtaagagac    480

ccagagaatg gaccatcttg gaaactttat caagattacc tgagtggaaa ggtttga       537
```

<210> SEQ ID NO 58
<211> LENGTH: 1749
<212> TYPE: DNA
<213> ORGANISM: Saccharomyces cerevisiae

<400> SEQUENCE: 58

```
atggaggaaa ctaagtactc ttcgcagcag gagatagaag gagcatgtgg ttcagacgct     60

tcattgaatg ctagaggtag caatgattct ccaatgggac tttccttgta cctctgcctg    120

gcttcgttaa ctcttgtact attcataact gcactggata ttttgatagt gggaactatt    180

attgacgtgg tcgcagaaca gttcggaaac tactccaaaa caggttggct cgttacaggc    240

tacagtttac caaatgctat tctgagtctc atttggggaa gattcgcatc tatcataggt    300

ttccagcata gtctcatttt agcaatactt atttttgaag ccggatccct aattgctgcc    360

cttgcctctt caatgaatat gctcattttc ggtagagttg ttgctggtgt tgggggaagc    420

ggactccaaa cgctttgctt tgttattggt tgtacgatgg ttggtgaaag gtcacgtcca    480

ttggtgattt ccatcctaag ttgtgcattt gctgtagctg ctatcgttgg tcctataatc    540

ggaggtgcct ttacaaccca tgttacctgg aggtggtgct tctatatcaa tcttcctatc    600

ggtggtcttg ccattattat gtttttactc acatataagg ccgagaataa gggtatactt    660

caacaaatta aagatgctat aggaacaatc tcgagcttta cttttagtaa gttcagacac    720

caagttaatt ttaaaagact tatgaatggc ataatcttca agtttgactt ctttggtttt    780
```

gccctctgct ctgcagggct ggtccttttc ctactggggc taacctttgg tggtaataaa 840
tatagttgga actctggcca agtcatcgca tatttggttt tgggtgtctt actttttatt 900
ttttcattgg tgtacgattt cttcctattc gataaattca acccggaacc tgataatata 960
tcctacaggc ctctccttct aagaagattg gtagcaaaac cagccataat aatagtaaac 1020
atggtaacat ttctattatg taccggttac aatgggcaaa tgatatactc tgtccagttt 1080
ttccaactta tatttgcgtc gagtgcatgg aaagccggtc ttcacttgat accaatcgtt 1140
attaccaacg ttattgcggc cattgcaagt ggtgtgatta ccaaaaagct cggtttagtt 1200
aaaccactct taatatttgg aggcgttctt ggggtaattg gagcagggct tatgacactt 1260
atgacaaata cgtccacgaa gtcaactcaa attggtgttt tgctattacc ggggttttcc 1320
cttggatttg ctctacaagc atcgctcatg agtgcacagc ttcaaattac caaagatcgt 1380
ccagaagctg ctatggactt tattgaagta acagctttca atacattcat gaagtcatta 1440
ggtacaactc ttggtggtgt gctttcaacc actgtttttt ccgcctcctt tcacaacaaa 1500
gtatcacgag ctcatctaga gccttacgaa ggaaaaacgg ttgatgacat gattttgtat 1560
cgtcttcaaa actacgacgg ttctcattcg actattggaa acattttaag cgactccatt 1620
aagaacgtat tttggatgga tctagggttt tatgccttag gatttttgtt ttgtagtttt 1680
tcatccaata agaaattaat cataccaaaa aaggacgata caccagaaga taatttagaa 1740
gacaagtag 1749

<210> SEQ ID NO 59
<211> LENGTH: 1824
<212> TYPE: DNA
<213> ORGANISM: Saccharomyces cerevisiae

<400> SEQUENCE: 59
atggacaggc ctaaggacgc tagaaagaga tctattagtt tggcctgtac tgtgtgtagg 60
aaacgaaagt tgaagtgcga tgggaacaag ccatgtggaa gatgtataag gctaaataca 120
ccaaaagaat gcatttatga tattgataaa aggaaagaca agagaaaaat caaaaacggg 180
tcgaaggttt ttttattcaa gaataatact atcgataacg ggaataactc tatactagag 240
aacaaaggac taaatgaaga cctttcttcc catatatatg agaaagaagc gccaaaattt 300
gattcagata ttgatatatc aagatttggc acaaatgatg ctgtgatttt taataatgac 360
gggtgggaca cttctcttcc gatcgatttt gatttcgatg agtttaacac tgagacaaca 420
gatttcgatg actttttaaa actattaggc gataattcac cttcaaagga acaaaaaagt 480
ctttcctatt ccccaactgc catagcctta agcggtgtgg ttaaagaaac tgagagcgaa 540
gataacgctc ctacgaggtc tcggctaatc gatgtcttgt ttgagaacga gcttcactcc 600
gtaccaggaa tatcaaaatg gcatctatat gagctggaat cccaataccc aaatttggaa 660
tgtacagaag gaaatagtga tgaaaagttt ttactttcaa ctgtattgtg cctggggtcg 720
ttgaccatac gaaaaaggga attattgaat cattcgaaca tagacaatag tccacttttg 780
ccagagaata gtatttcaaa actgaccgct gatgctttta agtactataa tgctgcgaaa 840
acgcttgttc ccgacttgtt atctcatccc acaatcgatg gattttgcgg cctcgttcta 900
atggcaaatt tcatgacgat gatgatatcc ttagagcacc aattatattt gagtataaat 960
gctttacaac ttgctgtggc tttaaacttg aacgacaata caaaatgcaa ggaattactt 1020
gagtcgaaca gcgacggaat tggtgtgatc ttgctttttt ggaacatttg gtgttcttct 1080
tgcatgttgg caacaattca tggaaaaaat ccttttatca ctttggaaca aattacaaca 1140
cctctgccgt gtgaaatatc cccccgcaat aaaaccaata aacttttgat agatttcatg 1200
caaatcagaa tcaagctagc cactctacaa agtaagattt ttcaacggct atatacttcc 1260
agcaccgcaa acgaggtacc attcgtaaac ttagaaagag aatttgagga agtttcactc 1320
cagattacca ggttaaaagg ctttccgata ttcgaagaac atctttttta caggagcaga 1380
gtcttaatgt tagagctatc atgtttaaga gctcaagctt cttttctatt atatcgtccg 1440
tatctgatca ctggagaatc cttacaagca gtaaccatgg caaaatcaat aattcacgaa 1500
atatggagtc aatacactaa acagtttccc gataacgaaa aggaaaggca tgaacgtttg 1560
gattggaatt tttgttatcc tttaagaaca gcgtcactga cattatgtat ttcatgtatt 1620
atactcctaa ggtataagca ggtggtgcag ttccttaaag gtactgaact atttgaatac 1680
attctagcat tggaaatatt gcaagattta gttcaggtac ttcctattga acaaaacctt 1740
attgatataa tcaaatatcc gatcagtcca gtacagctga gtggtgatag ctttgtcgaa 1800
ttttggggtc gcatacttta ctaa 1824

<210> SEQ ID NO 60
<211> LENGTH: 396
<212> TYPE: DNA
<213> ORGANISM: Saccharomyces cerevisiae

<400> SEQUENCE: 60
atgacacttg tagtatatct aactcggttt tcttccacta gaagcctcaa attctttgtt 60
gttggtatca catcattcaa aaactgcaga tggccgtcag aagagtgcac aattgcggca 120
gagatgtcat cgtacgacag cgtgagttca tctgggagcg gcggtacctg ttgttgttgc 180
tgctgctgtt gcctatgtag ggactcatgt gtcagcacct ggacgaagaa ttctgtagca 240
aacgctgtgg ctacgaatgc gtcatccgaa gtgtccatat attctggatc attcttggct 300
attctctgca ctttttctac aggtaacttg ggcgaacaca gaggtgcaga cgccgtttct 360
ttaccactag tctcgttgtt cattgtgtta gcctga 396

<210> SEQ ID NO 61
<211> LENGTH: 441
<212> TYPE: DNA
<213> ORGANISM: Saccharomyces cerevisiae

<400> SEQUENCE: 61
atggggtcga aaagaacata cgtcgcgaaa aaaactgtga cacatgtgtt atattgcgtt 60
cctacaaggt ggatatcctt ggatagacct gcaacttctg cgttaccaat attcgattta 120
tccaggttag aaaggaaata tagcatcccc ataagaggaa tcaagtatat atccattttg 180
cgcaagacac gcttttccat tggatgggaa ggggagggga tgccgtcatc atccgtggta 240
gtagccataa tttcccgttc ggtggcaagt tccgacttct tgtcatggct gcgattatgc 300
aagctagcgt catggccttc atcttcctgg aacgtgactt ccgtaggctt ttcttctgat 360
ccatcattgg tgggtgatat gaaaagcaca tcatccacca aatgcttagg tgactccatt 420
gtaaatttgt tgctcatcta g 441

<210> SEQ ID NO 62
<211> LENGTH: 728
<212> TYPE: PRT
<213> ORGANISM: Pichia stipitis

<400> SEQUENCE: 62

```
Met Tyr Tyr Ser Asp Lys Leu Gly Ile Pro Lys Thr Asp Pro Ser Leu
1               5                   10                  15

Trp Arg Leu Arg Thr Thr Glu Leu Gly Arg Glu Thr Trp His Tyr Leu
            20                  25                  30

Thr Pro Gln Glu Ala Glu His Glu Pro Gln Thr Ser Tyr Val Lys Tyr
        35                  40                  45

Leu Leu Gln Thr Lys Asp Phe Gln Ala Pro Ala Glu Glu Lys Ile Thr
    50                  55                  60

Ser Pro Phe His Ala Ala Glu Lys Gly Ala Gln Phe Leu Glu Leu Leu
65                  70                  75                  80

Gln Asp Glu Ser Gly Ile Phe Pro Cys Gln Tyr Lys Gly Pro Met Phe
                85                  90                  95

Met Thr Ile Gly Tyr Val Val Ala Asn Tyr Tyr Ser Gly Asn Glu Ile
            100                 105                 110

Pro Glu Pro Tyr Arg His Glu Met Ile Arg Tyr Ile Val Asn Ser Ala
        115                 120                 125

His Pro Val Asp Gly Gly Trp Gly Leu His Ser Ile Asp Lys Ser Thr
    130                 135                 140

Cys Phe Gly Thr Ala Ile Asn Tyr Ile Val Leu Arg Leu Leu Gly Leu
145                 150                 155                 160

Glu Ala Asp His Pro Val Cys Ala Lys Ala Arg Lys Thr Leu His Ser
                165                 170                 175

Leu Gly Gly Ala Ile Lys Val Pro His Trp Gly Lys Ala Trp Leu Ser
            180                 185                 190

Ile Leu Ser Leu Tyr Glu Trp Glu Gly Val Asn Pro Ala Pro Pro Glu
        195                 200                 205

Leu Trp Ala Leu Pro Tyr Ser Leu Pro Ile His Pro Gly Arg Trp Trp
    210                 215                 220

Val His Thr Arg Ala Ile Tyr Leu Pro Leu Gly Phe Val Ser Ser Asn
225                 230                 235                 240

Arg Ile His Cys Lys Leu Asp Pro Leu Leu Glu Gln Leu Arg Thr Glu
                245                 250                 255

Ile Tyr Leu Pro Arg Gln Leu Pro Tyr Thr Ser Ile Asp Phe Ser Gln
            260                 265                 270

His Arg Asn Asp Val Cys Gly Ile Asp Leu Tyr Tyr Pro His Thr Lys
        275                 280                 285

Val Leu Asn Met Ala Asn Tyr Val Leu Ser Lys Tyr Glu Gly Trp Arg
    290                 295                 300

Pro Lys Trp Val Leu Asp Trp Ile Asn Lys Arg Ala Tyr Asp Leu Ile
305                 310                 315                 320

Leu Lys Glu Tyr His Asn Thr Glu Tyr Leu Cys Ile Ala Pro Val Asn
                325                 330                 335

Phe Ala Phe Asn Met Val Val Thr His Phe Tyr Glu Gly Pro Lys Ser
            340                 345                 350

Glu Asn Phe Ala Lys Leu Gln Ala Arg Met Asn Asp Val Leu Phe His
        355                 360                 365

Gly Pro Gln Gly Met Thr Val Met Gly Thr Asn Gly Val Gln Val Trp
    370                 375                 380

Asp Ala Ala Phe Met Val Gln Tyr Phe Phe Met Ala Gly Leu Ala Asp
385                 390                 395                 400

Leu Pro Arg Tyr His Asp Met Ile Arg Lys Ser Tyr Met Phe Leu Val
                405                 410                 415
```

-continued

```
Arg Ser Gln Phe Thr Glu Asp Cys Val Asp Gly Ser Phe Arg Asp Lys
            420                 425                 430

Arg Lys Gly Ala Trp Pro Phe Ser Thr Lys Glu Gln Gly Tyr Thr Val
        435                 440                 445

Ser Asp Cys Thr Ala Glu Ala Leu Lys Ala Ile Ile Met Val Arg Asn
    450                 455                 460

His Pro Ala Phe Ala Asp Leu Val Asp Glu Ile Lys Glu Glu Asp Leu
465                 470                 475                 480

Phe Asn Ala Val Asp Val Leu Leu Asn Ile Gln Asn Val Gly Asn Phe
                485                 490                 495

Glu Phe Gly Ser Phe Ser Ala Tyr Glu Lys Ile Arg Ser Thr Leu Leu
            500                 505                 510

Leu Glu Lys Leu Asn Pro Ala Glu Val Phe Asn Asn Ile Met Val Glu
        515                 520                 525

Tyr Pro Tyr Val Glu Cys Thr Asp Ser Ser Val Leu Gly Leu Thr Phe
    530                 535                 540

Phe Ala Lys Tyr Tyr Pro Asn His Lys Pro Glu Val Ile Ser Thr Ala
545                 550                 555                 560

Ile Glu Arg Ala Ile Lys Tyr Ile Ile Ser Ala Gln Asp Glu Ile Asp
                565                 570                 575

Gly Ser Trp Tyr Gly Ala Trp Gly Ile Cys Tyr Thr Tyr Ala Ser Met
            580                 585                 590

Phe Ala Leu Glu Ala Leu Asn Thr Val Gly Leu Asn Tyr Glu Asn Ser
        595                 600                 605

Ala Thr Val Lys Arg Gly Cys Asp Phe Leu Ile Ser Lys Gln Leu Pro
    610                 615                 620

Asp Gly Gly Trp Ser Glu Ser Met Lys Ala Cys Glu Thr His Ser Tyr
625                 630                 635                 640

Val Asn Gly Asp Lys Ser Tyr Val Val Gln Thr Ala Trp Ala Val Ile
                645                 650                 655

Gly Leu Ile Leu Gly Gly Tyr Pro Asp Gln Glu Pro Ile Arg Lys Gly
            660                 665                 670

Ile Gln Leu Leu Met Gln Arg Gln Leu Pro Thr Gly Glu Trp Lys Phe
        675                 680                 685

Glu Glu Val Glu Gly Val Phe Asn His Ser Cys Ala Ile Glu Tyr Pro
    690                 695                 700

Ser Tyr Lys Phe Leu Phe Pro Ile Lys Ala Leu Gly Leu Tyr His Gln
705                 710                 715                 720

Lys Phe Gly Asn Glu Pro Ile Val
                725


<210> SEQ ID NO 63
<211> LENGTH: 721
<212> TYPE: PRT
<213> ORGANISM: Schizosaccharomyces pombe

<400> SEQUENCE: 63

Met Glu Ala Cys Arg Val Arg Pro Glu Leu Ser Lys Thr Val Glu Gln
1               5                   10                  15

Ile Asp Lys Ser Leu Trp Arg Leu Asn Ile Asp Ser Ala Gly Gly Glu
            20                  25                  30

Thr Trp Glu Tyr Val Thr Lys Glu Glu Ala Glu Lys Arg Pro Leu Thr
        35                  40                  45

Ile Ala Glu Lys Tyr Phe Leu Gly Phe Asp Leu Asp Leu Pro Lys Arg
    50                  55                  60
```

```
Pro Pro Ala Lys Thr Pro Leu Glu Ser Ala Glu Tyr Gly Tyr Glu Phe
65                  70                  75                  80

Phe Arg Arg Leu Gln Leu Pro Asp Gly His Trp Ala Ser Pro Tyr Glu
                85                  90                  95

Gly Pro Met Phe Leu Ile Cys Gly Ala Val Phe Ala Phe Tyr Ile Ser
            100                 105                 110

Gln Thr Pro Phe Pro Lys Gly Trp Ala Pro Glu Ile Ile Gln Tyr Leu
        115                 120                 125

Ile Asn His Thr Asn Asp Asp Gly Gly Trp Gly Ile His Thr Glu Gly
    130                 135                 140

Val Ser Thr Val Phe Gly Thr Ser Met Asn Tyr Val Val Leu Arg Ile
145                 150                 155                 160

Leu Gly Met Asp Ala Gly His Pro Val Ala Thr Arg Ala Arg Asn Arg
                165                 170                 175

Leu His Glu Leu Gly Gly Ala Ile Gly Cys Pro His Trp Gly Lys Phe
            180                 185                 190

Trp Leu Ala Thr Leu Asn Cys Tyr Asp Trp Asp Gly Val Asn Pro Ile
        195                 200                 205

Pro Pro Glu Leu Trp Leu Leu Pro Asp Trp Ile Pro Phe His Pro Gly
    210                 215                 220

Lys Trp Trp Cys His Val Arg Leu Val Tyr Leu Pro Met Gly Tyr Met
225                 230                 235                 240

Tyr Gly Glu Arg Leu Lys Cys Pro Lys Asp Ser Leu Ile Met Gln Leu
                245                 250                 255

Arg Lys Glu Leu Tyr Val Glu Asn Tyr Asp Ser Ile Asn Phe Ala Asp
            260                 265                 270

His Arg Asn Thr Ile Ser Asp Val Asp Leu Tyr Phe Pro His Thr Gln
        275                 280                 285

Ile Leu Asp Arg Leu Asn Trp Ile Leu Glu Lys Tyr Phe Thr Tyr Leu
    290                 295                 300

Arg Pro Ser Trp Leu Lys Lys Leu Gly Thr Arg Arg Ala Tyr Glu Leu
305                 310                 315                 320

Ile Lys Ile Glu Asp Gln Asn Thr Asp Tyr Ser Cys Ile Gly Pro Val
                325                 330                 335

Asn Ala Ala Met Asn Thr Val Cys Val Tyr Phe His Glu Gly Pro Ser
            340                 345                 350

Ser Lys Ala Phe Gln Lys His Ile Gln Arg Leu His Asp Phe Met Trp
        355                 360                 365

Val Gln Pro Glu Gly Met Leu Met Arg Gly Thr Asn Gly Leu Gln Val
    370                 375                 380

Trp Glu Thr Ser Phe Thr Leu Gln Ala Leu Val Glu Ser Gly Leu Tyr
385                 390                 395                 400

Glu Lys Glu Ala Phe Lys Pro Asp Ile Ala Lys Ala Leu Glu Phe Leu
                405                 410                 415

Asp Arg Gln Gln Ile Arg Thr Gln Tyr Glu Gly Ser Gly Tyr Arg Tyr
            420                 425                 430

Asn Ser Leu Gly Ala Trp Pro Phe Ser Asn Ile Thr Gln Gly Tyr Thr
        435                 440                 445

Val Ser Asp Thr Thr Ser Glu Ala Leu Arg Ala Val Leu Leu Val Gln
    450                 455                 460

Ser Leu Pro Asp Phe Glu Lys Leu Val Asp Ile Pro Arg Leu Arg Leu
465                 470                 475                 480
```

```
Ser Val Asp Val Ile Leu Gly Met Gln Asn Glu Asn Leu Gly Phe Ala
                485                 490                 495

Ser Tyr Glu Pro Ala Arg Thr Gly Glu Trp Met Glu Leu Leu Asn Pro
            500                 505                 510

Ala Glu Val Phe Gly Asn Ile Met Val Glu Tyr Ser Tyr Pro Glu Cys
        515                 520                 525

Thr Thr Ser Val Ile Leu Ala Leu Arg Ala Phe Thr Lys Tyr Asp Pro
    530                 535                 540

Gly Tyr Arg Arg Asp Glu Ile Glu Asn Thr Ile Glu Asn Ala Leu Glu
545                 550                 555                 560

Tyr Val Val Lys Met Gln Arg Pro Asp Gly Ser Trp Tyr Gly Ser Trp
                565                 570                 575

Ala Ile Cys Phe Thr Tyr Ala Ala Met Phe Ala Thr Gly Ser Leu Ala
            580                 585                 590

Ser Ala Gly Arg Tyr Tyr Glu Asn Cys Pro Val Gln Lys Lys Ala Cys
        595                 600                 605

Glu Phe Leu Leu Ser Lys Gln Arg Pro Asp Gly Gly Trp Ser Glu Ser
    610                 615                 620

Tyr Met Ala Cys Val Thr Gly Val Tyr Thr Glu Thr Glu Ser Ser Leu
625                 630                 635                 640

Val Thr Gln Thr Gly Trp Ala Leu Asp Ala Leu Ile Asn Ala Lys Tyr
                645                 650                 655

Pro Asp Arg Lys Pro Ile Glu Lys Gly Ile Lys Phe Leu Met Ala Ser
            660                 665                 670

Gln Lys Ser Asp Gly Ser Trp Gln Gln Lys Ser Met Glu Gly Ile Phe
        675                 680                 685

Asn Lys Asn Val Ala Ile Ala Tyr Pro Asn Tyr Lys Leu Tyr Phe Ser
    690                 695                 700

Ile Tyr Thr Leu Gly Lys Phe Ala Lys Gln Tyr Gly Asn Tyr Leu Thr
705                 710                 715                 720

Ile


<210> SEQ ID NO 64
<211> LENGTH: 721
<212> TYPE: PRT
<213> ORGANISM: Pichia pastoris

<400> SEQUENCE: 64

Met Thr Val Tyr Tyr Ser Glu Lys Ile Gly Leu Pro Lys Thr Asp Pro
1               5                   10                  15

Gln Arg Trp Arg Leu Arg Val Asn Glu Leu Gly Arg Gln Tyr Trp Asp
            20                  25                  30

Tyr Ile Glu Lys Glu Asp Leu Lys Asn Asp Pro Gln Thr Pro Tyr Val
        35                  40                  45

Gln Tyr Leu Leu Lys Gly Asp Glu Phe Glu Cys Pro Ile Pro Glu Lys
    50                  55                  60

Pro Gln Ser Ala Phe Glu Ser Ala Arg Asn Cys Ala Asp Phe Leu Ala
65                  70                  75                  80

Leu Ile Gln Asp Glu Ser Gly Val Phe Pro Cys Gln Tyr Lys Gly Pro
                85                  90                  95

Met Phe Met Ser Ile Gly Tyr Val Val Ala Cys Tyr Phe Thr Asn Thr
            100                 105                 110

Pro Ile Pro Asp His Val Arg Thr Glu Met Ile Arg Tyr Val Val Asn
        115                 120                 125
```

```
Thr Ala His Pro Val Asp Gly Gly Trp Gly Leu His Glu Trp Asp Lys
    130                 135                 140

Ser Thr Cys Phe Gly Thr Cys Met Asn Tyr Val Val Leu Arg Leu Leu
145                 150                 155                 160

Gly Leu Pro Lys Asp Asn Pro Val Cys Ile Lys Ala Arg Lys Val Leu
                165                 170                 175

His Ala Leu Gly Gly Ala Leu Ala Thr Pro Tyr Trp Gly Lys Ala Trp
            180                 185                 190

Leu Ser Leu Leu Asn Val Tyr Lys Trp Glu Gly Val Asn Pro Ala Pro
        195                 200                 205

Pro Glu Met Trp Asn Leu Pro Tyr Ser Leu Lys Ile His Pro Cys Arg
    210                 215                 220

Trp Trp Val His Thr Arg Ala Ile Ala Leu Pro Leu Ser Tyr Ile Ser
225                 230                 235                 240

Ser Tyr Lys Ser Gln Met Pro Leu Thr Pro Leu Leu Lys Glu Leu Arg
                245                 250                 255

Asn Glu Ile Phe Leu Gln Asp Phe Asp Thr Ile Asp Phe Ser Lys His
            260                 265                 270

Arg Asn Asn Val Cys Gly Ile Asp Leu Tyr Tyr Pro His Thr Ser Leu
        275                 280                 285

Leu Asp Phe Ala Asn Ser Ile Leu Val Gly Tyr Asp Lys Ile Arg Pro
    290                 295                 300

Thr Trp Leu Leu Lys Glu Ser Asn Asp Ala Val Tyr Glu Leu Ile Lys
305                 310                 315                 320

Lys Glu Leu Ala Asn Thr Glu His Leu Cys Ile Ala Pro Val Asn Ala
                325                 330                 335

Ala Phe Asn Thr Ile Val Ala Tyr Leu Glu Glu Gly Pro Glu Ser Tyr
            340                 345                 350

Asn Phe Lys Arg Leu Gln Glu Arg Phe Lys Asp Val Ile Phe His Gly
        355                 360                 365

Pro Gln Gly Met Thr Thr Met Gly Thr Asn Gly Thr Gln Val Trp Asp
    370                 375                 380

Thr Ser Phe Cys Leu Gln Tyr Phe Phe Met Ala Gly Leu Ala Asp Leu
385                 390                 395                 400

Asp Glu Tyr Glu Glu Leu Ile Ile Arg Cys Phe Lys Phe Leu Ile Arg
                405                 410                 415

Ser Gln Phe Thr Thr Asp Thr Val Asp Gly Ser Tyr Arg Asp Lys Arg
            420                 425                 430

Ile Gly Cys Phe Pro Phe Ser Thr Lys Glu Gln Gly Tyr Thr Val Ser
        435                 440                 445

Asp Cys Thr Ala Glu Ala Ile Lys Ala Ile Leu Met Val Lys Asn His
    450                 455                 460

Pro Lys Phe Ala Tyr Leu Gly Asp Tyr Ile Asp Glu Asp Leu Leu Lys
465                 470                 475                 480

Lys Gly Ile Asp Gly Leu Leu Ser Leu Gln Asn Val Gly Ser Tyr His
                485                 490                 495

Phe Gly Ser Phe Ser Thr Tyr Glu Ser Thr Arg Ala Asn Pro Ala Leu
            500                 505                 510

Glu Lys Ile Asn Pro Ala Glu Val Phe Gly Asn Ile Met Val Glu Tyr
        515                 520                 525

Pro Tyr Val Glu Cys Thr Asp Ser Ser Val Leu Gly Leu Thr Tyr Phe
    530                 535                 540

Arg Glu His Trp Asp Tyr Arg Arg His Asp Ile Asp Thr Ala Ile Glu
```

545 550 555 560

Arg Gly Val Lys Phe Ile Cys Asp Ala Gln Gln Glu Asp Gly Ser Trp
565 570 575

Tyr Gly Cys Trp Gly Val Cys Phe Thr Tyr Ala Gly Met Phe Ala Leu
580 585 590

Glu Ala Leu Ala Ser Val Asn Gln Tyr Tyr Glu Thr Asn Glu Val Val
595 600 605

Arg Lys Gly Cys Asp Phe Leu Val Ser Lys Gln Met Ala Asp Gly Gly
610 615 620

Trp Ser Glu Ser Ile Lys Ser Cys Glu Thr His Thr Tyr Val Arg Gly
625 630 635 640

Lys Arg Gly Met Val Val Gln Thr Ser Trp Val Leu Ile Gly Leu Ile
645 650 655

Leu Ala Lys Tyr Pro His Lys Glu Val Ile Asp Arg Gly Val Gln Leu
660 665 670

Ile Met Ser Arg Gln Lys Thr Arg Gly Asp Phe Asp Phe Glu Ala Val
675 680 685

Glu Gly Ile Phe Asn His Ser Cys Gly Ile Glu Tyr Pro Asn Tyr Lys
690 695 700

Phe Leu Phe Pro Ile Lys Ala Leu Gly Leu Tyr Ser Lys Glu Tyr Glu
705 710 715 720

Gln

<210> SEQ ID NO 65
<211> LENGTH: 731
<212> TYPE: PRT
<213> ORGANISM: Kluyveromyces lactis

<400> SEQUENCE: 65

Met Pro Glu Leu Tyr Ser Glu Thr Ile Gly Leu Pro Arg Thr Asp Pro
1 5 10 15

Lys Arg Trp Arg Leu Ile Thr Asp Asp Leu Gly Arg Gln Thr Trp Glu
20 25 30

Tyr Leu Ser Glu Asn Asp Ser Lys Lys Val Pro Gln Ser Thr Phe Ala
35 40 45

Arg Trp Leu Leu Lys Cys Glu Asp Phe Pro Glu Pro His Pro Glu Ile
50 55 60

Asn Ser Lys Thr Ser Gly Phe Thr Ala Trp Asn Ala Ala His Asn Gly
65 70 75 80

Ala Lys Phe Phe Glu Leu Leu Gln Asp Pro Asp Ser Gly Thr Phe Pro
85 90 95

Cys Gln Tyr Lys Gly Pro Met Phe Met Thr Ile Gly Tyr Val Val Thr
100 105 110

Met Tyr Ile Ala Lys Ile Glu Ile Pro Glu His Glu Lys Ala Glu Met
115 120 125

Ile Arg Tyr Val Ala Asn Tyr Ala His Pro Val Asp Gly Gly Trp Gly
130 135 140

Leu His His Val Asp Lys Ser Thr Val Leu Gly Thr Val Leu Asn Tyr
145 150 155 160

Val Met Met Arg Leu Leu Gly Leu Pro Lys Asp His Glu Val Cys Val
165 170 175

Arg Ala Arg Asp Thr Leu Leu Arg Leu Gly Gly Ala Ile Ala Ser Pro
180 185 190

His Trp Ala Lys Ile Trp Leu Ser Ile Leu Asn Leu Tyr Lys Trp Glu

```
        195                 200                 205

Gly Val Asn Pro Ala Pro Pro Glu Leu Trp Met Leu Pro Tyr Gly Leu
    210                 215                 220

Asn Ile His Pro Ala Arg Trp Trp Val His Thr Arg Gly Ile Tyr Leu
225                 230                 235                 240

Pro Val Ser Tyr Leu Ser Ser Thr Gln Tyr Ser Cys Glu Leu Asp Pro
                245                 250                 255

Leu Leu Glu Glu Ile Arg Thr Glu Ile Tyr Thr Gln Pro Phe Glu Thr
            260                 265                 270

Ile Asp Phe Lys Lys His Arg Asn Thr Val Cys Gly Val Asp Leu Tyr
        275                 280                 285

Tyr Pro His Thr Lys Val Leu Asp Thr Met Asn Tyr Phe Ile Ser Lys
    290                 295                 300

Tyr Glu Arg Tyr Val Arg Pro Asn Trp Leu Leu Lys Lys Ser Thr Asn
305                 310                 315                 320

Arg Val Tyr Glu Leu Val Lys Lys Glu Ile Ala Asn Thr Asp Tyr Leu
                325                 330                 335

Cys Ile Ala Pro Val Asn Asn Ala Phe Cys Ala Ile Val Thr Leu Ile
            340                 345                 350

Glu Glu Gly Lys Asp Ser Glu Glu Phe Gly Arg Phe Leu Tyr Arg Phe
        355                 360                 365

Lys Asp Val Leu Phe His Gly Pro Gln Gly Leu Thr Val Met Gly Thr
    370                 375                 380

Asn Gly Val Gln Val Trp Asp Cys Ala Phe Tyr Ile Gln Tyr Met Phe
385                 390                 395                 400

Met Ala Gly Leu Ala Glu Leu Pro Glu Phe His Glu Thr Ile Val Arg
                405                 410                 415

Ser Phe Lys Phe Leu Cys Arg Ser Gln Phe Thr Glu Asp Cys Val Glu
            420                 425                 430

Gly Ser Phe Arg Asp Lys Arg Leu Gly Ala Trp Pro Phe Ser Thr Lys
        435                 440                 445

Thr Gln Gly Tyr Thr Val Ser Asp Cys Thr Ala Glu Ala Ile Lys Ala
    450                 455                 460

Ile Ile Met Val Leu Asn Ser Asp Lys Tyr Arg Asp Val Trp Gly Val
465                 470                 475                 480

Tyr Asp Thr Glu Lys Leu Lys Asn Gly Ile Asp Val Leu Leu Gly Leu
                485                 490                 495

Gln Asn Leu Ser Ser Phe Glu Tyr Gly Ser Phe Ala Thr Tyr Glu Lys
            500                 505                 510

Ile Lys Ala Pro Leu Leu Met Glu Lys Leu Asn Pro Ala Glu Val Phe
        515                 520                 525

Gly Asn Ile Met Val Glu Phe Pro Tyr Val Glu Cys Thr Asp Ser Ser
    530                 535                 540

Val Leu Gly Leu Thr Tyr Phe Arg Arg Tyr Phe Asn Tyr Arg Lys Lys
545                 550                 555                 560

Asp Ile Asp His Ala Ile Asp Ser Ala Ile Ala Tyr Ile Lys Lys Ser
                565                 570                 575

Gln Gln Pro Asn Gly Ser Trp Tyr Gly Cys Trp Gly Ile Cys Tyr Thr
            580                 585                 590

Tyr Ala Gly Met Phe Ala Leu Glu Ala Leu Asn Thr Ile Gly Glu Thr
        595                 600                 605

Tyr Glu Asn Ser Glu Val Val Arg Lys Gly Cys Asp Phe Phe Val Thr
    610                 615                 620
```

```
Lys Gln Leu Pro Asp Gly Gly Trp Ser Glu Lys Met Lys Ser Ser Glu
625                 630                 635                 640

Leu His Thr Tyr Val Ser Asp Lys Glu Ser Tyr Val Val Gln Thr Ala
                645                 650                 655

Trp Val Leu Ile Gly Leu Ile Leu Ala Lys Phe Pro Asp Lys Ser Val
            660                 665                 670

Ile Asp Arg Ala Ile Asn Leu Leu Lys Gln Arg Gln Gln Pro Ser Gly
        675                 680                 685

Glu Trp Lys Tyr Glu Ala Val Glu Gly Val Phe Asn His Ser Cys Ala
    690                 695                 700

Ile Glu Tyr Pro Ser Tyr Arg Phe Leu Phe Pro Ile Lys Ala Leu Gly
705                 710                 715                 720

Leu Tyr Val Lys Glu Tyr Gly His Ser Ala Ile
                725                 730


<210> SEQ ID NO 66
<211> LENGTH: 731
<212> TYPE: PRT
<213> ORGANISM: Kluyveromyces marxianus

<400> SEQUENCE: 66

Met Leu Glu Leu Tyr Ser Glu Lys Ile Lys Leu Pro Arg Thr Asp Pro
1               5                   10                  15

Thr Arg Trp Arg Leu His Thr Asp Asp Leu Gly Arg Glu Thr Trp Glu
            20                  25                  30

Tyr Leu Ser Val Glu Glu Ser Lys Lys Ile Pro Gln Ser Thr Phe Ala
        35                  40                  45

Gln Trp Leu Leu Gln Cys Glu Glu Phe Pro Glu Pro Gln Pro Gln Val
    50                  55                  60

Asn Ser Lys Thr Ser Asn Phe Thr Ala Trp Asn Ala Ala His Asn Gly
65                  70                  75                  80

Ala Lys Phe Phe Glu Leu Leu Gln Asp Pro Asn Ser Gly Ile Phe Pro
                85                  90                  95

Cys Gln Tyr Lys Gly Pro Met Phe Met Thr Ile Gly Tyr Val Ala Thr
            100                 105                 110

Met Tyr Leu Ala Lys Leu Glu Ile Pro Glu His Glu Arg Ile Glu Leu
        115                 120                 125

Ile Arg Tyr Ile Ala Asn Tyr Ala His Pro Val Asp Gly Gly Trp Gly
    130                 135                 140

Leu His Thr Thr Asp Lys Ser Thr Val Leu Gly Thr Val Leu Asn Tyr
145                 150                 155                 160

Val Ser Leu Arg Leu Leu Gly Leu Pro Lys Asp His Glu Val Cys Thr
                165                 170                 175

Arg Ala Arg Asp Thr Leu His Arg Leu Gly Gly Ala Ile Gly Ser Pro
            180                 185                 190

His Trp Ala Lys Ile Trp Leu Ser Ile Leu Asn Leu Tyr Lys Trp Glu
        195                 200                 205

Gly Val Asn Pro Ala Pro Pro Glu Leu Trp Met Phe Pro Tyr Ser Leu
    210                 215                 220

Pro Ile His Pro Ala Arg Trp Trp Val His Thr Arg Gly Ile Tyr Leu
225                 230                 235                 240

Pro Val Ser Tyr Leu Ser Ser Thr Arg Tyr Thr Cys Asp Leu Asp Pro
                245                 250                 255

Leu Leu Lys Glu Ile Arg Ser Glu Ile Tyr Ile Lys Pro Phe Glu Thr
```

-continued

```
            260                 265                 270

Ile Asn Phe Thr Glu His Arg Asn Thr Val Cys Gly Val Asp Leu Tyr
        275                 280                 285

Tyr Pro His Thr Lys Val Leu Asn Thr Val Asn Ala Met Met Thr Cys
    290                 295                 300

Tyr Glu Lys Tyr Ile Arg Pro Asn Trp Met Leu Lys Lys Ala Thr Lys
305                 310                 315                 320

Arg Val Tyr Glu Leu Val Lys Lys Glu Ile Ala Asn Thr Asp Tyr Leu
                325                 330                 335

Cys Ile Ala Pro Val Asn Met Ala Phe Cys Ala Ile Val Thr Leu Ile
            340                 345                 350

Glu Glu Gly Lys Asp Ser Thr Glu Phe Asn Ser Phe Leu Tyr Arg Phe
        355                 360                 365

Lys Asp Val Leu Phe His Gly Pro Gln Gly Leu Thr Val Met Gly Thr
    370                 375                 380

Asn Gly Val Gln Val Trp Asp Cys Ala Phe Phe Val Gln Tyr Met Phe
385                 390                 395                 400

Thr Ala Gly Leu Ala Glu Leu Pro Glu Phe His Asp Ser Val Ala Arg
                405                 410                 415

Ser Phe Lys Phe Leu Cys Arg Ser Gln Phe Thr Glu Asn Cys Ala Asp
            420                 425                 430

Gly Ser Phe Arg Asp Lys Arg Leu Gly Ala Trp Pro Phe Ser Thr Lys
        435                 440                 445

Thr Gln Gly Tyr Thr Val Ser Asp Cys Thr Ala Glu Ala Ile Lys Ala
    450                 455                 460

Ile Ile Met Val Leu Asn Ser Ala Ser Phe Lys Asp Val His Asp Tyr
465                 470                 475                 480

Tyr Asp Pro Lys Lys Leu Asn Asn Gly Ile Asp Val Leu Leu Ser Leu
                485                 490                 495

Gln Asn Val Ser Ser Phe Glu Tyr Gly Ser Phe Ser Thr Tyr Glu Lys
            500                 505                 510

Ile Lys Ala Thr Thr Leu Leu Glu Lys Leu Asn Pro Ala Glu Val Phe
        515                 520                 525

Gly Asn Ile Met Val Glu Tyr Pro Tyr Val Glu Cys Thr Asp Ser Ser
    530                 535                 540

Val Leu Gly Leu Thr Tyr Phe Arg Lys His Phe Asp Tyr Arg Lys Lys
545                 550                 555                 560

Asp Ile Asp Phe Ala Ile Lys Glu Ala Ile Ala Tyr Ile Lys Asn Val
                565                 570                 575

Gln Asn Glu Asp Gly Ser Trp Tyr Gly Cys Trp Gly Ile Cys Tyr Thr
            580                 585                 590

Tyr Ala Gly Met Phe Ala Leu Glu Ala Leu Tyr Thr Val Gly Glu Asn
        595                 600                 605

Tyr Glu Asn Ser Glu Val Val Arg Lys Gly Cys Asp Phe Leu Val Ser
    610                 615                 620

Lys Gln Leu Pro Asp Gly Gly Trp Ser Glu Thr Met Lys Ser Ser Glu
625                 630                 635                 640

Leu His Ser Tyr Val Ser Asp Lys Thr Ser Tyr Val Val Gln Thr Ala
                645                 650                 655

Trp Ala Ile Ile Gly Leu Ile Leu Ala Lys Tyr Pro Asn Lys His Val
            660                 665                 670

Ile Asp Arg Gly Ile Lys Leu Leu Lys Glu Arg Gln Gln Pro Ser Gly
        675                 680                 685
```

```
Glu Trp Lys Phe Glu Ala Val Glu Gly Val Phe Asn His Ser Cys Ala
    690                 695                 700

Ile Glu Tyr Pro Ser Tyr Arg Phe Leu Phe Pro Ile Lys Ala Leu Gly
705                 710                 715                 720

Leu Tyr Val Lys Glu Tyr Lys Asp Asn Ala Ile
                725                 730


<210> SEQ ID NO 67
<211> LENGTH: 728
<212> TYPE: PRT
<213> ORGANISM: Candida albicans

<400> SEQUENCE: 67

Met Tyr Tyr Ser Glu Glu Ile Gly Leu Pro Lys Thr Asp Ile Ser Arg
1               5                   10                  15

Trp Arg Leu Arg Ser Asp Ala Leu Gly Arg Glu Thr Trp His Tyr Leu
            20                  25                  30

Ser Gln Ser Glu Cys Glu Ser Glu Pro Gln Ser Thr Phe Val Gln Trp
        35                  40                  45

Leu Leu Glu Ser Pro Asp Phe Pro Ser Pro Pro Ser Ser Asp Ile His
    50                  55                  60

Thr Pro Asp Glu Ala Ala Arg Lys Gly Ala Asp Phe Leu Lys Leu Leu
65                  70                  75                  80

Gln Leu Asp Asn Gly Ile Phe Pro Cys Gln Tyr Lys Gly Pro Met Phe
                85                  90                  95

Met Thr Ile Gly Tyr Val Thr Ala Asn Tyr Tyr Ser Lys Thr Glu Ile
            100                 105                 110

Pro Glu Pro Tyr Arg Val Glu Met Ile Arg Tyr Ile Val Asn Thr Ala
        115                 120                 125

His Pro Val Asp Gly Gly Trp Gly Leu His Ser Val Asp Lys Ser Thr
    130                 135                 140

Cys Phe Gly Thr Thr Met Asn Tyr Val Cys Leu Arg Leu Leu Gly Met
145                 150                 155                 160

Glu Lys Asp His Pro Val Leu Val Lys Ala Arg Lys Thr Leu His Arg
                165                 170                 175

Leu Gly Gly Ala Ile Lys Asn Pro His Trp Gly Lys Ala Trp Leu Ser
            180                 185                 190

Ile Leu Asn Leu Tyr Glu Trp Glu Gly Val Asn Pro Ala Pro Pro Glu
        195                 200                 205

Leu Trp Arg Leu Pro Tyr Trp Leu Pro Ile His Pro Ala Lys Trp Trp
    210                 215                 220

Val His Thr Arg Ala Ile Tyr Leu Pro Leu Gly Tyr Thr Ser Ala Asn
225                 230                 235                 240

Arg Val Gln Cys Glu Leu Asp Pro Leu Leu Lys Glu Ile Arg Asn Glu
                245                 250                 255

Ile Tyr Val Pro Ser Gln Leu Pro Tyr Glu Ser Ile Lys Phe Gly Asn
            260                 265                 270

Gln Arg Asn Asn Val Cys Gly Val Asp Leu Tyr Tyr Pro His Thr Lys
        275                 280                 285

Ile Leu Asp Phe Ala Asn Ser Ile Leu Ser Lys Trp Glu Ala Val Arg
    290                 295                 300

Pro Lys Trp Leu Leu Asn Trp Val Asn Lys Lys Val Tyr Asp Leu Ile
305                 310                 315                 320

Val Lys Glu Tyr Gln Asn Thr Glu Tyr Leu Cys Ile Ala Pro Val Ser
```

-continued

```
                325                 330                 335

Phe Ala Phe Asn Met Val Val Thr Cys His Tyr Glu Gly Ser Glu Ser
            340                 345                 350

Glu Asn Phe Lys Lys Leu Gln Asn Arg Met Asn Asp Val Leu Phe His
        355                 360                 365

Gly Pro Gln Gly Met Thr Val Met Gly Thr Asn Gly Val Gln Val Trp
    370                 375                 380

Asp Ala Ala Phe Met Val Gln Tyr Phe Phe Met Thr Gly Leu Val Asp
385                 390                 395                 400

Asp Pro Lys Tyr His Asp Met Ile Arg Lys Ser Tyr Leu Phe Leu Val
                405                 410                 415

Arg Ser Gln Phe Thr Glu Asn Cys Val Asp Gly Ser Phe Arg Asp Arg
            420                 425                 430

Arg Lys Gly Ala Trp Pro Phe Ser Thr Lys Glu Gln Gly Tyr Thr Val
        435                 440                 445

Ser Asp Cys Thr Ala Glu Ala Met Lys Ala Ile Ile Met Val Arg Asn
    450                 455                 460

His Ala Ser Phe Ala Asp Ile Arg Asp Glu Ile Lys Asp Glu Asn Leu
465                 470                 475                 480

Phe Asp Ala Val Glu Val Leu Leu Gln Ile Gln Asn Val Gly Glu Trp
                485                 490                 495

Glu Tyr Gly Ser Phe Ser Thr Tyr Glu Gly Ile Lys Ala Pro Leu Leu
            500                 505                 510

Leu Glu Lys Leu Asn Pro Ala Glu Val Phe Asn Asn Ile Met Val Glu
        515                 520                 525

Tyr Pro Tyr Val Glu Cys Thr Asp Ser Ser Val Leu Gly Leu Thr Tyr
    530                 535                 540

Phe Ala Lys Tyr Tyr Pro Asp Tyr Lys Pro Glu Leu Ile Gln Lys Thr
545                 550                 555                 560

Ile Ser Ser Ala Ile Gln Tyr Ile Leu Asp Ser Gln Asp Asn Ile Asp
                565                 570                 575

Gly Ser Trp Tyr Gly Cys Trp Gly Ile Cys Tyr Thr Tyr Ala Ser Met
            580                 585                 590

Phe Ala Leu Glu Ala Leu His Thr Val Gly Leu Asp Tyr Glu Ser Ser
        595                 600                 605

Ser Ala Val Lys Lys Gly Cys Asp Phe Leu Ile Ser Lys Gln Leu Pro
    610                 615                 620

Asp Gly Gly Trp Ser Glu Ser Met Lys Gly Cys Glu Thr His Ser Tyr
625                 630                 635                 640

Val Asn Gly Glu Asn Ser Leu Val Val Gln Ser Ala Trp Ala Leu Ile
                645                 650                 655

Gly Leu Ile Leu Gly Asn Tyr Pro Asp Glu Glu Pro Ile Lys Arg Gly
            660                 665                 670

Ile Gln Phe Leu Met Lys Arg Gln Leu Pro Thr Gly Glu Trp Lys Tyr
        675                 680                 685

Glu Asp Ile Glu Gly Val Phe Asn His Ser Cys Ala Ile Glu Tyr Pro
    690                 695                 700

Ser Tyr Arg Phe Leu Phe Pro Ile Lys Ala Leu Gly Leu Tyr Lys Asn
705                 710                 715                 720

Lys Tyr Gly Asp Lys Val Leu Val
                725
```